United States Patent
Miao et al.

(10) Patent No.: US 8,124,584 B2
(45) Date of Patent: *Feb. 28, 2012

(54) MACROCYCLIC HEPATITIS C SERINE PROTEASE INHIBITORS

(75) Inventors: Zhenwei Miao, San Diego, CA (US); Ying Sun, Waltham, MA (US); Suanne Nakajima, Winchester, MA (US); Datong Tang, Newton, MA (US); Frank Wu, Shrewsbury, MA (US); Guoyou Xu, Framingham, MA (US); Yat Sun Or, Watertown, MA (US); Zhe Wang, Hockessin (DE)

(73) Assignee: Enanta Pharmaceuticals, Inc., Watertown, MA (US)

( * ) Notice: Subject to any disclaimer, the term of this patent is extended or adjusted under 35 U.S.C. 154(b) by 352 days.

This patent is subject to a terminal disclaimer.

(21) Appl. No.: 12/351,144

(22) Filed: Jan. 9, 2009

(65) Prior Publication Data

US 2009/0304629 A1    Dec. 10, 2009

Related U.S. Application Data

(62) Division of application No. 10/774,047, filed on Feb. 6, 2004, now Pat. No. 7,601,709.

(60) Provisional application No. 60/608,955, filed on Mar. 7, 2003, provisional application No. 60/509,069, filed on Feb. 13, 2003, provisional application No. 60/560,712, filed on Feb. 7, 2003.

(51) Int. Cl.
*A61K 38/00*   (2006.01)

(52) U.S. Cl. ........................................................ 514/3.7
(58) Field of Classification Search .................. None
See application file for complete search history.

(56) References Cited

OTHER PUBLICATIONS

Ettmayer P. et al. J. Med. Chem. (2004) 47(10), pp. 2393-2404.*
Singh, Yashveer et al, "Recent Trends in Targeted Anticancer Prodrug and Conjugate," DesignCurr Med Chem. 2008; 15(18): 1802-1826.*
Muller, Christa E. "Prodrug Approaches for Enhancing the Bioavailability of Drugs with Low Solubility," Chemistry & Biodiversity, vol. 6 (2009), pp. 2071-2083.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Han, H.-K.. AAPS Pharmsci. (2000) 2(1), Article 6, pp. 1-11.*
Testa Prodrug research: futile or fertile? Biochemical Pharmacology (2004) 2097-2106.*

* cited by examiner

*Primary Examiner* — Cecilia J Tsang
*Assistant Examiner* — Thomas Heard

(74) *Attorney, Agent, or Firm* — Edgar W. Harlan; Carolyn S. Elmore; Elmore Patent Law Group P.C.

(57) ABSTRACT

The present invention relates to compounds of Formula I, II or III, or a pharmaceutically acceptable salt, ester, or prodrug, thereof:

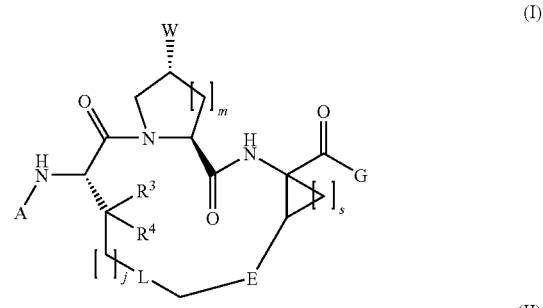

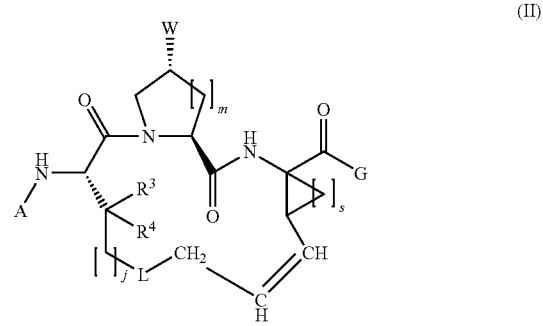

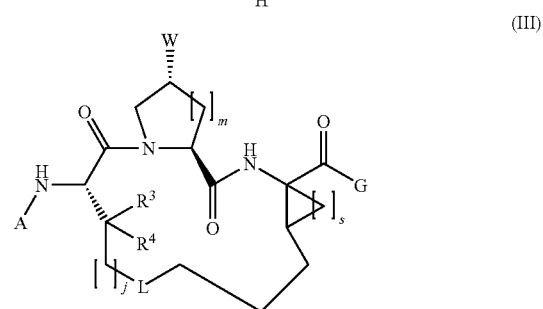

wherein W is a substituted or unsubstituted heterocyclic ring system. The compounds inhibit serine protease activity, particularly the activity of hepatitis c virus (HCV) NS3-NS4A protease. Consequently, the compounds of the present invention interfere with the life cycle of the hepatitis c virus and are also useful as antiviral agents. The present invention further relates to pharmaceutical compositions comprising the aforementioned compounds for administration to a subject suffering from HCV infection. The invention also relates to methods of treating an HCV infection in a subject by administering a pharmaceutical composition comprising the compounds of the present invention.

46 Claims, No Drawings

MACROCYCLIC HEPATITIS C SERINE PROTEASE INHIBITORS

CROSS-REFERENCE TO RELATED APPLICATIONS

This application is a divisional of U.S. Ser. No. 10/774,047 filed on Feb. 6, 2004 now U.S. Pat. No. 7,601,709, which claims benefit to U.S. provisional Ser. No. 60/509,069 (conversion of U.S. Ser. No. 10/365,854), filed Feb. 13, 2003; 60/560,712 (conversion of U.S. Ser. No. 10/360,947), filed Feb. 7, 2003; and 60/608,955 (conversion of U.S. Ser. No. 10/384,120), filed Mar. 7, 2003, each of which is hereby incorporated by reference in its entirety for any purpose.

TECHNICAL FIELD

The present invention relates to novel macrocycles having activity against hepatitis C virus (HCV) and useful in the treatment of HCV infections. More particularly, the invention relates to macrocyclic compounds, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon-related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug must possess significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3.4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov., 1, 867-881 (2002). More relevant patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999).

SUMMARY OF THE INVENTION

The present invention relates to novel macrocyclic compounds and methods of treating a hepatitis C infection in a subject in need of such therapy with said macrocyclic compounds. The present invention further relates to pharmaceutical compositions comprising the compounds of the present invention, or pharmaceutically acceptable salts, esters, or prodrugs thereof, in combination with a pharmaceutically acceptable carrier or excipient.

A compound having the Formula I or a pharmaceutically acceptable salt, ester or prodrug thereof:

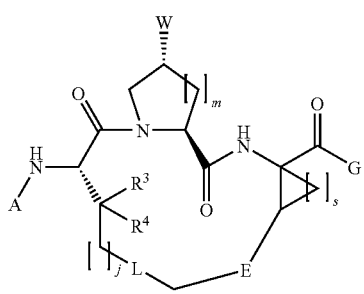

(I)

wherein:

A is selected from the group consisting of H, —(C═O)—$R^2$, —(C═O)—O—$R^1$, —C(═O)—NH—$R^2$, —C(═S)—NH—$R^2$, —S(O)$_2$—$R^2$, —(C═N$R^1$)—$R^1$, and —(C═N$R^1$)—NH—$R^1$;

G is selected from the group consisting of —OH, —O—($C_1$-$C_{12}$ alkyl), —NHS(O)$_2$—$R^1$, —(C═O)—$R^1$, —(C═O)—$R^2$, —(C═O)—O—$R^1$, —(C═O)—NH—$R^1$, and —(C═O)—NH—$R^2$;

L is selected from the group consisting of absent, —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C═O)—CH$_2$—, —CH(CH$_3$)CH$_2$—, —CFHCH$_2$—, —CF$_2$CH$_2$—, and —C$R_x$═C$R_x$— where $R_x$=H or halogen;

j is 0, 1, 2, 3, or 4;

m is 0, 1, or 2;

s is 0, 1 or 2;

$R^1$ is selected form the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

$R^2$ is selected from the group consisting of H, $C_1$-$C_6$ alkyl, $C_3$-$C_{12}$ cycloalkyl, alkylamino, dialkylamino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

$R^3$ and $R^4$ are each independently selected from the group consisting of hydrogen, OH, CH$_3$, CN, SH, halogen, NO$_2$, NH$_2$, amide, methoxy, trifluoromethoxy, and trifluoromethyl;

E represents either a single bond or a double bond between the two carbon atoms attached thereto; and W is a substituted or unsubstituted heterocyclic ring system.

In one embodiment of the present invention E represents a double bond, resulting in Formula II or pharmaceutically acceptable salts, esters, or prodrugs thereof:

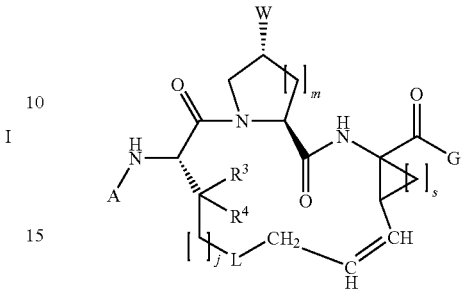

(II)

wherein the remaining substitutents are as described above.

In one embodiment of the present invention E represents a single bond, resulting in Formula III or pharmaceutically acceptable salts, esters, or prodrugs thereof:

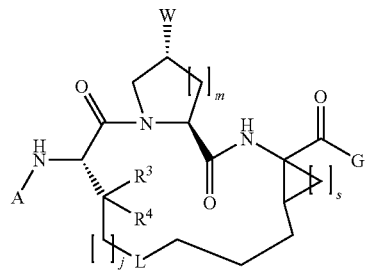

(III)

wherein the remaining substituents are as described above.

In one embodiment of the present invention there are disclosed compounds represented by Formulas II and III, or pharmaceutically acceptable salts, esters, or prodrugs thereof:

wherein

W is selected from the group consisting of:

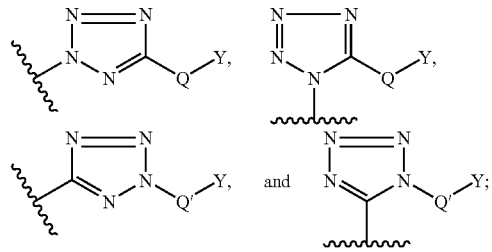

Q is selected from the group consisting of: absent, —CH$_2$—, —O—, —NH—, —N($R^1$)—, —S—, —S(O)$_2$—, and —(C═O)—;

Q' is selected from the group consisting of: absent, —CH$_2$—, and —NH—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

All other substituents are as defined above.

In one embodiment of the present invention there are disclosed compounds represented by Formulas II and III, or pharmaceutically acceptable salts, esters, or prodrugs thereof wherein;

W is selected from the group consisting of:

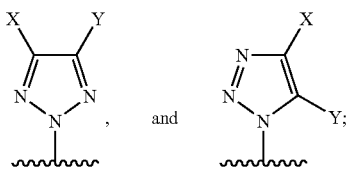
, and

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl;

All other substituents are as defined above.

In one embodiment of the present invention there are disclosed compounds represented by Formulas II and III, or pharmaceutically acceptable salts, esters, or prodrugs thereof wherein:

W is

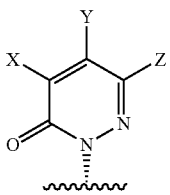

and

X, Y, and Z are independently selected from the group consisting of H, $N_3$, halogen, $C_1$-$C_6$ alkyl, $C_3$-$C_{12}$ cycloalkyl, alkylamino, dialkylamino, $C_1$-$C_6$ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or, in the alternative, X and Y or Y and Z taken together with the carbon atoms to which they are attached form an aryl, substituted aryl, heteroaryl, or substituted heteroaryl cyclic moiety.

Other aspects of the invention are:

A compound according to any of the formulae herein wherein W is substituted with one or more substituents, each of said substituents being independently selected from any of (a), (b), (c), (d) and (e):

(a) alkenyl; alkoxy; alkoxyalkyl; alkyl; alkylamino; alkylaryl; alkylsulfonyl; alkynyl; amide; amido optionally mono-substituted with $C_1$-$C_6$ alkyl; aryl; arylalkanoylalkyl; arylalkyl; arylaminoalkyl; aryloxyalkyl; arylsulfonyl; cycloalkoxy; cycloalkyl; dialkylamino; dialkylaminoalkyl; diarylaminoalkyl; haloalkyl; heteroaryl; heteroarylalkyl; heterocyclo; heterocycloalkyl; heterocycloalkylalkyl; thioalkyl; monoalkylaminoalkyl; sulfonyl; (lower alkyl)sulfonyl; haloalkyl; carboxyl; amide; (lower alkyl)amide; heterocyclo optionally substituted with $C_1$-$C_6$ alkyl; perhaloalkyl; sulfonyl; thioalkyl; urea, C(=O)—$R^{11}$; OC(=O)$R^{11}$; C(=O)O—$R^{11}$; C(=O)N($R^{11}$)$_2$; C(=S)N($R^{11}$)$_2$; SO$_2$$R^{11}$; NHS(O$_2$)$R^{11}$; N($R^{12}$)$_2$; N($R^{12}$)C(=O)$R^{11}$;

wherein each of the foregoing can be optionally be substituted with up to three groups selected from halogen, OH, alkoxy, perhaloalkyl;

(b) $C_7$-$C_{14}$ aralkyl; $C_2$-$C_7$cycloalkyl; $C_6$-$C_{10}$ aryl; heterocyclo; (lower alkyl)-heterocyclo;

wherein each aralkyl, cycloalkyl, aryl, heterocyclo or (lower alkyl)-heterocyclo may be optionally substituted with $R^6$, where $R^6$ is halogen, $C_1$-$C_6$ alkyl, $C_3$-$C_6$ cycloalkyl, $C_1$-$C_6$ alkoxy, $C_3$-$C_6$ cycloalkoxy, $NO_2$, N($R^7$)$_2$, NH—C(O)—$R^7$ or NH—C(O)—NH$R^7$; where $R^7$ is H, $C_1$-$C_6$ alkyl or $C_3$-$C_6$ cycloalkyl;

or $R^6$ is NH—C(O)—O$R^8$ where $R^8$ is $C_1$-$C_6$ alkyl or $C_3$-$C_6$ cycloalkyl;

(c) N($R^5$)$_2$, NH—C(O)—$R^5$, or NH—C(O)—NH—$R^5$ where $R^5$ is independently H, $C_1$-$C_6$ alkyl or $C_3$-$C_6$ cycloalkyl, $C_6$ or $C_{10}$ aryl, $C_7$-$C_{14}$ aralkyl, heterocyclo or (lower alkyl)-heterocyclo;

(d) NH—C(O)—O$R^8$ where $R^8$ is $C_1$-$C_6$ alkyl or $C_3$-$C_6$ cycloalkyl;

(e) formyl; halogen; hydroxy; $NO_2$; OH; SH; halo; CN;

Wherein;

each $R^{11}$ is independently H, OH, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroaryl, heteroarylalkyl, arylalkanoylalkyl, heterocycloalkylalkyl aryloxyalkyl, alkylamino, dialkylamino, monoalkylaminoalkyl, dialkylaminoalkyl, arylaminoalkyl, diarylaminoalkyl, wherein any of the foregoing can be optionally be substituted with up to three groups selected from halogen, OH, alkoxy and perhaloalkyl; and each $R^{12}$ is independently H, formyl, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroarylalkyl, heteroaryl, arylalkanoylalkyl, heterocycloalkylalkyl aryloxyalkyl, monoalkylaminoalkyl, dialkylaminoalkyl, arylaminoalkyl, or diarylaminoalkyl, wherein any of the foregoing can be optionally be substituted with up to three groups selected from halogen, OH, alkoxy and perhaloalkyl;

The compound of any of the formulae herein wherein W is selected from the group consisting of:

(a) an aliphatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl, $R^{10}$ and $R^{11}$; and (b) an aromatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl, and $R^{10}$;

wherein:

each $R^{10}$ is independently alkyl, alkenyl, alkynyl, perhaloalkyl, alkoxy, aryl, arylalkyl, alkylaryl, heterocyclo, heterocycloalkyl, alkylsulfonyl, arylsulfonyl, heretoaryl, heteroarylalkyl, arylalkanoylalkyl, heterocycloalkylalkyl aryloxyalkyl, alkylamino, dialkylamino, monoalkylaminoalkyl, dialkylaminoalkyl, arylaminoalkyl, diarylaminoalkyl, heteroaryl or urea, wherein any of the foregoing can be optionally be substituted with up to three groups selected from halogen, OH, alkoxy and perhaloalkyl; $C(\!=\!O)\!-\!R^{11}$, $OC(\!=\!O)R^{11}$, $C(\!=\!O)O\!-\!R^{11}$, $C(\!=\!O)N(R^{11})_2$, $C(\!=\!S)N(R^{11})_2$, $SO_2R^{11}$, $NHS(O_2)R^{11}$, $N(R^{12})_2$, and $N(R^{12})C(\!=\!O)R^{11}$;

each $R^{11}$ is independently H, OH, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroaryl, heteroarylalkyl, arylalkanoylalkyl, heterocycloalkylalkyl aryloxyalkyl, alkylamino, dialkylamino, monoalkylaminoalkyl, dialkylaminoalkyl, arylaminoalkyl, diarylaminoalkyl, wherein any of the foregoing can be optionally be substituted with up to three groups selected from halogen, OH, alkoxy and perhaloalkyl;

each $R^{12}$ is independently H, formyl, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroarylalkyl, heteroaryl, arylalkanoylalkyl, heterocycloalkylalkyl aryloxyalkyl, monoalkylaminoalkyl, dialkylaminoalkyl, arylaminoalkyl, or diarylaminoalkyl, wherein any of the foregoing can be optionally be substituted with up to three groups selected from halogen, OH, alkoxy and perhaloalkyl;

The compound of any of the formulae herein wherein W is an aliphatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl, $R_{10}$ and $R_{11}$;

The compound of any of the formulae herein wherein W is an aliphatic heteromonocyclic ring system having from five to seven ring atoms and up to four ring hetero atoms selected from O, N and S, wherein said ring system is optionally substituted with up to three ring substituents selected from the group consisting of OH, CN, halogen, formyl, $R^{10}$ and $R^{11}$;

The compound of any of the formulae wherein said optionally substituted aliphatic heteromonocyclic ring system has five ring atoms and 1 or 2 ring hetero atoms selected from O, N and S;

The compound of any of the formulae herein wherein said optionally substituted aliphatic heteromonocyclic ring system is selected from the group consisting of pyrrolidines, pyrazolidines, pyrrolines, tetrahydrothiophenes, dihydrothiophenes, tetrahydrofurans, dihydrofurans, imidazolines, tetrahydroimidazoles, dihydropyrazoles, tetrahydropyrazoles, and oxazolines;

The compound of any of the formulae herein wherein said optionally substituted aliphatic heteromonocyclic ring system has six ring atoms and 1 or 2 ring hetero atoms selected from O, N and S;

The compound of any of the formulae herein wherein said optionally substituted aliphatic heteromonocyclic ring system is selected from the group consisting of pyridines, piperidines, dihydropyridines, tetrahydropyridines, dihydropyrans, tetrahydropyrans, dioxanes, piperazines, dihydropyrimidines, tetrahydropyrimidines, perhydro pyrimidine, morpholine, thioxane, and thiomorpholine;

The compound of any of the formulae herein wherein said optionally substituted aliphatic heteromonocyclic ring system has seven ring atoms and 1 or 2 ring hetero atoms selected from O, N and S;

The compound of any of the formulae herein wherein said optionally substituted aliphatic heteromonocyclic ring system is selected from the group consisting of hexamethyleneimine, and hexamethylenesulfide;

The compound of any of the formulae herein wherein W is an aliphatic heterobicyclic ring system having from five to sixteen ring atoms and up to four ring hetero atoms selected from O, N and S, wherein said ring system is optionally substituted with up to three ring substituents selected from the group consisting of OH, CN, halogen, formyl and $R^{10}$.

The compound of any of the formulae herein wherein said optionally substituted aliphatic heterobicyclic ring system has eight to twelve ring atoms and 1 to 4 ring hetero atoms selected from O, N and S;

The compound of any of the formulae herein wherein said optionally substituted aliphatic heterobicyclic ring system eight to twelve ring atoms and 1 or 2 ring hetero atoms selected from O and N;

The compound of any of the formulae herein wherein W is an aromatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl and $R_{10}$;

The compound of any of the formulae herein wherein W is an aromatic heteromonocyclic ring system having from five to seven ring atoms and up to four ring hetero atoms selected from O, N and S, wherein said ring system is optionally substituted with up to three ring substituents selected from the group consisting of OH, CN, halogen, formyl and $R_{10}$;

The compound of any of the formulae herein wherein said optionally substituted aromatic heteromonocyclic ring system has five ring atoms and 1 or 2 ring hetero atoms selected from O, N and S;

The compound of any of the formulae herein wherein said optionally substituted aromatic heteromonocyclic ring system is selected from the group consisting of pyrroles, pyrazoles, porphyrins, furans, thiophenes, pyrazoles, imidazoles, oxazoles, oxadiazoles, isoxazoles, thiazoles, thiadiazoles, and isothiazoles;

The compound of any of the formulae herein wherein said optionally substituted aromatic heteromonocyclic ring system has six ring atoms and 1, 2 or 3 ring hetero atoms selected from O, N and S;

The compound of any of the formulae herein wherein said optionally substituted aromatic heteromonocyclic ring system is selected from the group consisting of pyridines, pyrimidines, pyrazines, pyrans, and triazines;

The compound of any of the formulae herein wherein said optionally substituted aromatic heteromonocyclic ring system has five ring atoms and 3 or 4 ring hetero atoms selected from O, N and S;

The compound of any of the formulae herein wherein said optionally substituted aromatic heteromonocyclic ring system is triazolyl or tetrazolyl;

The compound of any of the formulae herein wherein W is an aromatic heterobicyclic ring system having from eight to twelve ring atoms and up to four ring hetero atoms selected from O, N and S, wherein said ring system is optionally substituted with up to three ring substituents selected from the group consisting of OH, CN, halogen, formyl and $R_{10}$;

The compound of any of the formulae herein wherein said optionally substituted aromatic heterobicyclic ring system is selected from the group consisting of adenines, azabenzimidazoles, azaindoles, benzimidazoles, benzo isothiazoles, benzofurans, benzoisoxazoles, benzooxazoles, benzothiadiazoles, benzothiazoles, benzothienes, benzothiophenes, benzoxazoles, carbazoles, cinnolines, guanines, imidazopyridines, indazoles, indoles, isoindoles, isoquinolines, phthalazines, purines, pyrrolo pyridines, quinazolines, quinolines, quinoxalines, thianaphthenes, and xanthines;

The compound of any of the formulae herein wherein W is an aromatic heterotricyclic ring system having from ten to sixteen ring atoms and up to four ring hetero atoms selected from O, N and S, wherein said ring system is optionally substituted with up to three ring substituents selected from the group consisting of OH, CN, halogen, formyl, $R_{10}$ and $R_{11}$; and The compound of any of the formulae herein wherein said optionally substituted aromatic heterotricyclic ring system is selected from the group consisting of carbazoles, bibenzofurans, psoralens, dibenzothiophenes, phenazines, thianthrenes, phenanthrolines, phenanthridines.

Other embodiments are a compound of Formula II

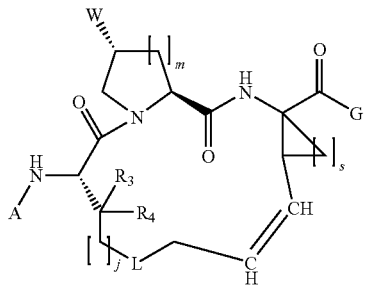

Formula II

Wherein:
A is selected from the group consisting of H, —(C=O)—R$^2$, —(C=O)—O—R$^1$, —C(=O)—NH—R$^1$, —C(=S)—NH—R$^2$, —S(O)$_2$—R$^2$, —(C=NR$^1$)—R$^1$, and —(C=NR$^1$)—NH—R$^1$;

G is selected from the group consisting of —OH, —O—(C$_1$-C$_{12}$ alkyl), —NHS(O)$_2$—R$^1$, —(C=O)—R$^2$, —(C=O)—O—R$^1$, and —(C=O)—NH—R$^2$;

L is selected from the group consisting of absent, —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, —CF$_2$CH$_2$—, and —CR$_x$=CR$_x$— where R$_x$=H or halogen;

W is selected from the group consisting of

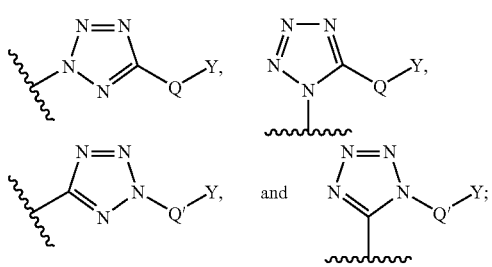

Q is selected from the group consisting of absent, —CH$_2$—, —O—, —NH—, —N(R$^1$)—, —S—, —S(O)$_2$—, and —(C=O)—;

Q' is selected from the group consisting of absent, —CH$_2$—, and —NH—;

Y is selected from the group consisting of H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

j=0, 1, 2, 3, or 4;
m=0, 1, or 2;
s=0, 1 or 2;

R$^1$ is selected from the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R$^2$ is selected from the group consisting of H, C$_1$-C$_6$ alkyl, C$_3$-C$_{12}$ cycloalkyl, substituted C$_3$-C$_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R$^3$ and R$^4$ are each independently selected from the group consisting of hydrogen and methyl;

A compound of the above formula II, wherein:
A is —(C=O)—O—R$^1$;
G is hydroxyl;
L is absent;
j=3;
m=s=1; and
R$^3$ and R$^4$ are hydrogen;

A compound of the above formula II, wherein:
A is —(C=O)—O-tert-butyl;
G is hydroxyl;
L is absent;
j=3;
m=s=1; and
R$^3$ and R$^4$ are hydrogen;

A compound of the above formula II, wherein:
A is —(C=O)—O—R$^1$,
G is hydroxyl;
L is absent;
W is

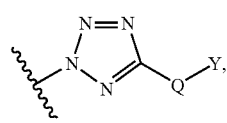

j=3;
m=s=1; and
R$^3$ and R$^4$ are hydrogen; and

A compound of the above formula II, wherein:
A is —(C=O)—O-tert-butyl;
G is hydroxyl;
L is absent;

W is

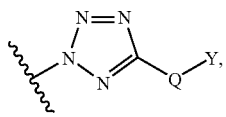

j=3;
m=s=1; and
R³ and R⁴ are hydrogen.
Other embodiments are:
A compound of Formula III:

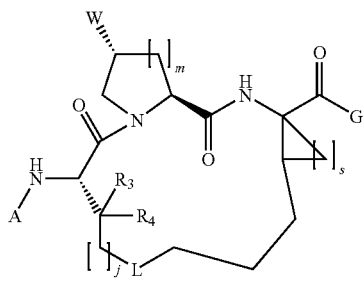

Formula III wherein
A is selected from the group consisting of H, —(C=O)—R², —(C=O)—O—R¹, —C(=O)—NH—R², —C(=S)—NH—R², —S(O)₂—R², —(C=NR¹)—R¹, and —(C=NR¹)—NH—R¹;
G is selected from the group consisting of —OH, —O—(C₁-C₁₂ alkyl), —NHS(O)₂—R¹, —(C=O)—R², —(C=O)—O—R¹, and —(C=O)—NH—R²;
L is selected from the group consisting of absent, —S—, —SCH₂—, —SCH₂CH₂—, —S(O)₂—, —S(O)₂CH₂CH₂—, —S(O)—, —S(O)CH₂CH₂—, —O—, —OCH₂—, —OCH₂CH₂—, —(C=O)—CH₂—, —CH(CH₃)CH₂—, —CFHCH₂—, —CF₂CH₂—, and —CRₓ=CRₓ— where Rₓ=H or halogen;
W is selected from the group consisting of

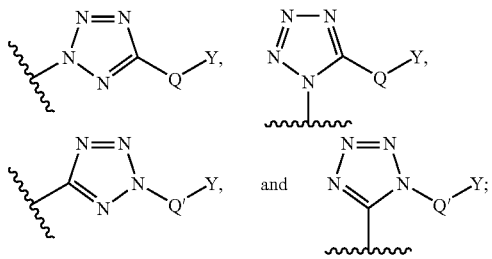

Q is selected from the group consisting of absent, —CH₂—, —O—, —NH—, —N(R¹)—, —S—, —S(O)₂—, and —(C=O)—;
Q' is selected from the group consisting of absent, —CH₂—, and —NH—;
Y is selected from the group consisting of H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

j=0, 1, 2, 3, or 4;
m=0, 1, or 2;
s=0, 1 or 2;
R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;
R² is selected from the group consisting of H, C₁-C₆ alkyl, C₃-C₁₂ cycloalkyl, substituted C₃-C₁₂ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and
R³ and R⁴ are each independently selected from the group consisting of hydrogen and methyl;
A compound according to formula III above, wherein:
A is —(C=O)—O—R¹;
G is hydroxyl;
L is absent;
j=3;
m=s=1; and
R³ and R⁴ are hydrogen;
A compound according to formula III above, wherein:
A is —(C=O)—O-tert-butyl;
G is hydroxyl;
L is absent;
j=3;
m=s=1; and
R³ and R⁴ are hydrogen;
A compound according to formula III above, wherein:
A is —(C=O)—O—R¹;
G is hydroxyl;
L is absent;
W is

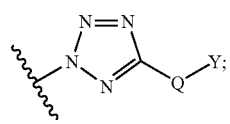

j=3;
m=s=1; and
R³ and R⁴ are hydrogen;
A compound according to formula III above, wherein:
A is —(C=O)—O-tert-butyl;
G is hydroxyl;
L is absent;
W is

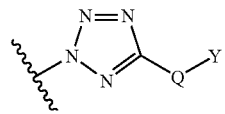

j=3;
m=s=1; and
R³ and R⁴ are hydrogen;

A compound of Formula II:

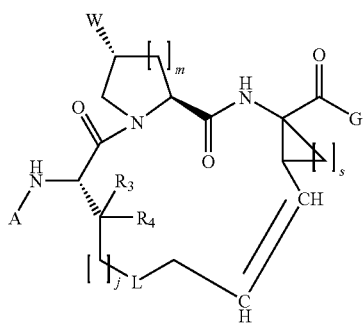

Formula II

Wherein;

A is selected from the group consisting of H, —(C=O)—R², —(C=O)—O—R¹, —C(=O)—NH—R², —C(=S)—NH—R², —S(O)₂—R², —(C=NR¹)—R¹, and —(C=NR¹)—NH—R¹;

G is selected from the group consisting of —OH, —O—(C₁-C₁₂ alkyl), —NHS(O)₂—R¹, —(C=O)—R², —(C=O)—O—R¹, and —(C=O)—NH—R²;

L is selected from the group consisting of absent, —S—, —SCH₂—, —SCH₂CH₂—, —S(O)₂—, —S(O)₂CH₂CH₂—, —S(O)—, —S(O)CH₂CH₂—, —O—, —OCH₂—, —OCH₂CH₂—, —(C=O)—CH₂—, —CH(CH₃)CH₂—, —CFHCH₂—, —CF₂CH₂—, and —CRₓ=CRₓ— where Rₓ=H or halogen;

W is selected from the group consisting of

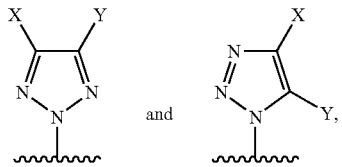

and where X and Y are independently selected from the group consisting of H, halogen, C₁-C₆ alkyl, C₃-C₁₂ cycloalkyl, —CH₂-alkylamino, —CH₂-dialkylamino, —CH₂-arylamino, —CH₂-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, for a cyclic moiety selected from the group consisting of aryl, substituted aryl, heteroaryl, and substituted heteroaryl;

j=0, 1, 2, 3, or 4;
m=0, 1, or 2;
s=0, 1 or 2;
R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;
R² is selected from the group consisting of H, C₁-C₆ alkyl, C₃-C₁₂ cycloalkyl, substituted C₃-C₁₂ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R³ and R⁴ are each independently selected from the group consisting of hydrogen and methyl;

A compound according to formula II above, wherein:
A is —(C=O)—O—R¹;
G is hydroxyl;
L is absent;
j=3;
m=s=1; and
R³ and R⁴ are hydrogen;

A compound according to formula II above, wherein:
A is —(C=O)—O-tert-butyl;
G is hydroxyl;
L is absent;
j=3;
m=s=1; and
R³ and R⁴ are hydrogen;

A compound according to formula II above, wherein:
A is —(C=O)—O—R¹;
G is hydroxyl;
L is absent;
W is

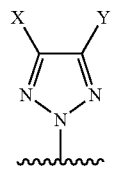

j=3;
m=s=1; and
R³ and R⁴ are hydrogen;

A compound according to formula II above, wherein:
A is —(C=O)—O-tert-butyl;
G is hydroxyl;
L is absent;
W is

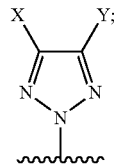

J=3;
M=s=1; and
R³ and R⁴ are hydrogen.

Other embodiments are a compound of Formula III:

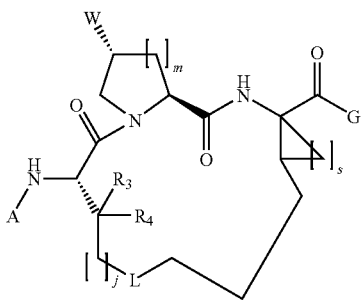

Formula III

Wherein;

A is selected from the group consisting of H, —(C=O)—R², —(C=O)—O—R¹, —C(=O)—NH—R², —C(=S)—NH—R², —S(O)₂—R², —(C=NR¹)—R¹, and —(C=NR¹)—NH—R¹;

G is selected from the group consisting of —OH, —O—(C₁-C₁₂ alkyl), —NHS(O)₂—R¹, —(C=O)—R², —(C=O)—O—R¹, and —(C=O)—NH—R²;

L is selected from the group consisting of absent, —S—, —SCH₂—, —SCH₂CH₂—, —S(O)₂—, —S(O)₂CH₂CH₂—, —O—, —OCH₂—, —OCH₂CH₂—, —(C=O)—CH₂—, —CH(CH₃)CH₂—, —CFHCH₂—, —CF₂CH₂—, and —CR$_x$=CR$_x$— where R$_x$=H or halogen;

from the group consisting of

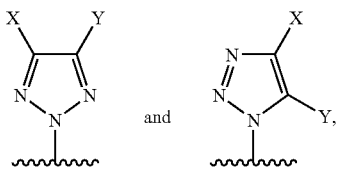

and where X and Y are independently selected from the group consisting of H, halogen, C₁-C₆ alkyl, C₃-C₁₂ cycloalkyl, —CH₂-alkylamino, —CH₂-dialkylamino, —CH₂-arylamino, —CH₂-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, for a cyclic moiety selected from the group consisting of aryl, substituted aryl, heteroaryl, and substituted heteroaryl;

j=0, 1, 2, 3, or 4;
m=0, 1, or 2;
s=0, 1 or 2;

R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R² is selected from the group consisting of H, C₁-C₆ alkyl, C₃-C₁₂ cycloalkyl, substituted C₃-C₁₂ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R³ and R⁴ are each independently selected from the group consisting of hydrogen and methyl;

A compound according to formula III above, wherein:
A is —(C=O)—O—R¹;
G is hydroxyl;
L is absent;
j=3;
m=s=1; and
R³ and R⁴ are hydrogen;

A compound according to formula III above, wherein:
A is —(C=O)—O-tert-butyl;
G is hydroxyl;
L is absent;
j=3;
m=s=1; and
R³ and R⁴ are hydrogen;

A compound according to formula III above, wherein:
A is —(C=O)—O—R¹;
G is hydroxyl;
L is absent;
W is

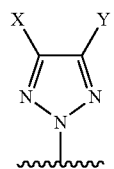

j=3;
m=s=1; and
R³ and R⁴ are hydrogen;

A compound according to formula III above, wherein:
A is —(C=O)—O-tert-butyl;
G is hydroxyl;
L is absent;
W is

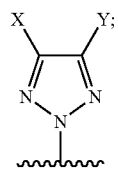

j=3;
m=s=1; and
R³ and R⁴ are hydrogen;

A compound of Formula IV:

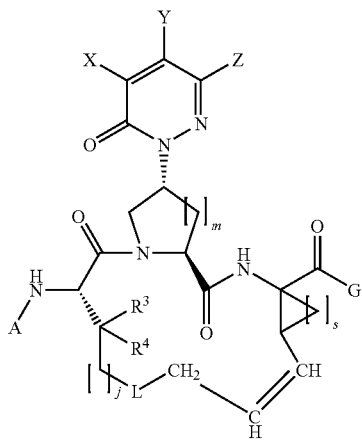

(IV)

Wherein;
A is hydrogen, —(C=O)—R$^1$, —(C=O)—O—R$^1$, —C(=O)—NH—R$^2$, —C(=S)—NH—R$^2$, —S(O)$_2$—R$^2$, —(C=NR$^1$)—R$^1$, or —(C=NR$^1$)—NH—R$^1$;
G is —OH, —O—(C$_1$-C$_{12}$ alkyl), —NHS(O)$_2$—R$^1$, —(C=O)—R$^2$, —(C=O)—O—R$^1$, or —(C=O)—NH—R$^2$;
L is —S—, —SCH$_2$—, —SCH$_2$CH$_2$—, —S(O)$^2$—, —S(O)$^2$CH$^2$CH$^2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, —CF$_2$CH$_2$—, or —CR$_x$=CR$_x$— where R$_x$=H or halogen;
X, Y, and Z are independently selected from the group consisting of hydrogen, N$_3$, halogen, C$_1$-C$_6$ alkyl, C$_3$-C$_{12}$ cycloalkyl, alkylamino, dialkylamino, C$_1$-C$_6$ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or,
in the alternative, X and Y or Y and Z taken together with the carbon atoms to which they are attached form an aryl, substituted aryl, heteroaryl, or substituted heteroaryl cyclic moiety;
j=0, 1, 2, 3, or 4;
m=0, 1, or 2;
s=0, 1 or 2;
R$^1$ is hydrogen, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;
R$^2$ is hydrogen, C$_1$-C$_6$ alkyl, C$_3$-C$_{12}$ cycloalkyl, substituted C$_3$-C$_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; and
R$^3$ and R$^4$ are each independently hydrogen or methyl;

A compound according to formula IV above, wherein:
A is —(C=O)—O—R$^1$;
G is hydroxyl;
L is absent;
j=3;
m=s=1; and
R$^3$ and R$^4$ are hydrogen;
A compound according to formula IV above, wherein:
A is —(C=O)—O-tert-butyl;
G is hydroxyl;
L is absent;
j=3;
m=s=1; and
R$^3$ and R$^4$ are hydrogen;
A compound of Formula V:

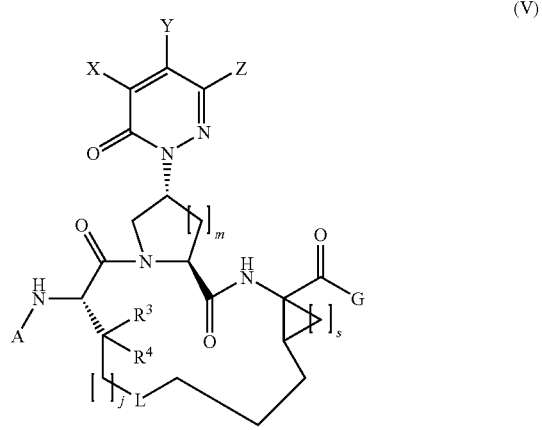

(V)

Wherein:
A is hydrogen, —(C=O)—R$^1$, —(C=O)—O—R$^1$, —C(=O)—NH—R$^2$, —C(=S)—NH—R$^2$, or —S(O)$_2$—R$^2$, —(C=NR$^1$)—R$^1$, or —(C=NR$^1$)—NH—R$^1$;
G is —OH, —O—(C$_1$-C$_{12}$ alkyl), —NHS(O)$_2$—R$^1$, —(C=O)—R$^2$, —(C=O)—O—R$^1$, or —(C=O)—NH—R$^2$;
L is absent, —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, —CF$_2$CH$_2$—, or —CR$_x$=CR$_x$— where R$_x$=H or halogen-;
X, Y, and Z are independently selected from the group consisting of hydrogen, N$_3$, halogen, C$_1$-C$_6$ alkyl, C$_3$-C$_{12}$ cycloalkyl, alkylamino, dialkylamino, C$_1$-C$_6$ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or,
in the alternative, X and Y or Y and Z taken together with the carbon atoms to which they are attached form an aryl, substituted aryl, heteroaryl, and substituted heteroaryl cyclic moiety;
j=0, 1, 2, 3, or 4;
m=0, 1, or 2;
s=0, 1 or 2;

$R^1$ is hydrogen, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;

$R^2$ is hydrogen, $C_1$-$C_6$ alkyl, $C_3$-$C_{12}$ cycloalkyl, substituted $C_3$-$C_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; and $R^3$ and $R^4$ are each independently hydrogen or methyl;

A compound according to formula V above, wherein:
A is —(C=O)—O—$R^1$;
G is hydroxyl;
L is absent;
j=3;
m=s=1; and
$R^3$ and $R^4$ are hydrogen; and A compound according to formula V above, wherein:
A is —(C=O)—O-tert-butyl;
G is hydroxyl;
L is absent;
j=3;
m=s=1; and
$R^3$ and $R^4$ are hydrogen.

Other embodiments are:
compounds of formulae II or III as delineated herein, wherein:
A is selected from the group consisting of: H, —(C=O)—$R^2$, —(C=O)—O—$R^1$, —C(=O)—NH—$R^2$, —C(=S)—NH—$R^2$, and —S(O)$_2$—$R^2$; G is selected from the group consisting of: —OH, —O—($C_1$-$C_{12}$ alkyl), —NHS(O)$_2$—$R^1$, —(C=O)—$R^1$, —(C=O)—O—$R^1$, and —(C=O)—NH—$R^1$; L is selected from the group consisting of: absent, —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, and —CF$_2$CH$_2$—; W is selected from the group consisting of:

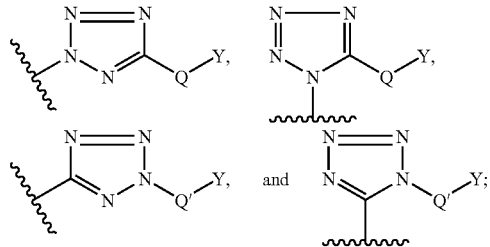

Q is selected from the group consisting of: absent, —CH$_2$—, —O—, —NH—, —N($R^1$)—, —S—, —S(O)$_2$—, and —(C=O)—; Q' is selected from the group consisting of: absent, —CH$_2$—, and —NH—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=0, 1, 2, 3, or 4; m=0, 1, or 2; s=0, 1 or 2; $R^1$ is selected from the group consisting of: H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; $R^2$ is selected from the group consisting of: H, $C_1$-$C_6$ alkyl, $C_3$-$C_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and $R^3$ and $R^4$ are each independently selected from the group consisting of hydrogen and methyl;

compounds of formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

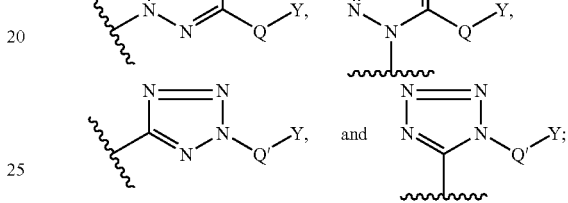

Q is selected from the group consisting of: absent, —CH$_2$—, —O—, —NH—, —N($R^1$)—, —S—, —S(O)$_2$—, and —(C=O)—; Q' is selected from the group consisting of: absent, —CH$_2$—, and —NH—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and $R^3$ and $R^4$ are hydrogen;

Compounds of formula II wherein A is —(C=O)—O-tert-butyl; G is hydroxyl; L is absent; W is

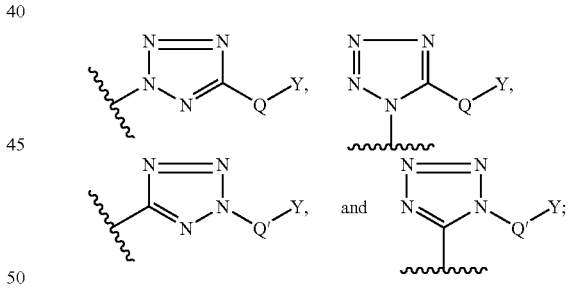

Q is selected from the group consisting of: absent, —CH$_2$—, —O—, —NH—, —N($R^1$)—, —S—, —S(O)$_2$—, and —(C=O)—; Q' is selected from the group consisting of: absent, —CH$_2$—, and —NH—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and $R^3$ and $R^4$ are hydrogen;

Compounds of Formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

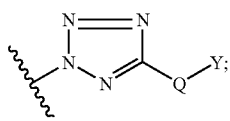

Q is selected from the group consisting of: absent, —CH₂—, —O—, —NH—, —N(R¹)—, —S—, —S(O)₂—, and —(C=O)—; Y is selected from the group consisting of: H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R³ and R⁴ are hydrogen;

Compounds of Formula II, wherein A is —(C=O)—O-tert-butyl; G is hydroxyl; L is absent; W is

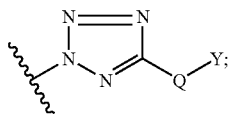

Q is selected from the group consisting of: absent, —CH₂—, —O—, —NH—, —N(R¹)—, —S—, —S(O)₂—, and —(C=O)—; Y is selected from the group consisting of: H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R³ and R⁴ are hydrogen;

Compounds of Formula III, wherein A is —(C=O)—O—R¹, R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

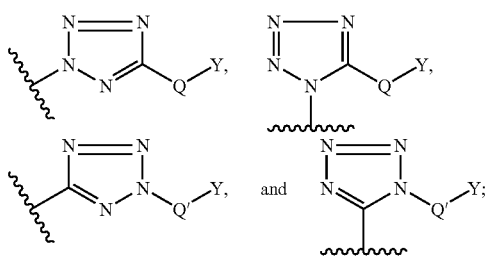

Q is selected from the group consisting of: absent, —CH₂—, —O—, —NH—, —N(R¹)—, —S—, —S(O)₂—, and —(C=O)—; Q' is selected from the group consisting of: absent, —CH₂—, and —NH—; Y is selected from the group consisting of: H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R³ and R⁴ are hydrogen;

Compounds of Formula III, wherein A is —(C=O)—O-tert-butyl; G is hydroxyl; L is absent; W is

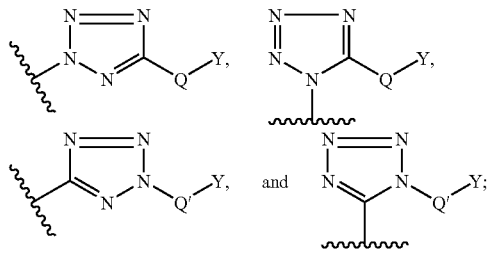

Q is selected from the group consisting of: absent, —CH₂—, —O—, —NH—, —N(R¹)—, —S—, —S(O)₂—, and —(C=O)—; Q' is selected from the group consisting of: absent, —CH₂—, and —NH—; Y is selected from the group consisting of: H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R³ and R⁴ are hydrogen;

Compounds of Formula III, wherein A is —(C=O)—O—R¹, R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

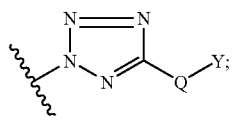

Q is selected from the group consisting of: absent, —CH₂—, —O—, —NH—, —N(R¹)—, —S—, —S(O)₂—, and —(C=O)—; Y is selected from the group consisting of: H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R³ and R⁴ are hydrogen; and Compounds of Formula III, wherein A is —(C=O)—O-tert-butyl; G is hydroxyl; L is absent; W is

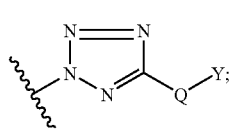

Q is selected from the group consisting of: absent, —CH₂—, —O—, —NH—, —N(R¹)—, —S—, —S(O)₂—, and —(C=O)—; Y is selected from the group consisting of: H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R³ and R⁴ are hydrogen.

Other embodiments are:

Compounds of formulae II or III wherein A is selected from the group consisting of: H, —(C=O)—R², —(C=O)—O—R¹, —C(=O)—NH—R², —C(=S)—NH—R², and —S(O)$_2$—R$^2$; G is selected from the group consisting of: —OH, —O—(C$_1$-C$_{12}$ alkyl), —NHS(O)$_2$—R$^1$, —(C=O)—R$^2$, —(C=O)—O—R$^1$, and —(C=O)—NH—R$^2$; L is selected from the group consisting of: absent, —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$— and —CF$_2$CH$_2$—; W is selected from the group consisting of:

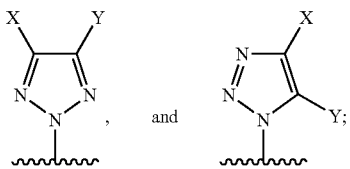

X and Y are independently selected from the group consisting of: H, halogen, C$_1$-C$_6$ alkyl, C$_3$-C$_{12}$ cycloalkyl, —CH$_2$-alkylamino, —CH$_2$-dialkylamino, —CH$_2$-arylamino, —CH$_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=0, 1, 2, 3, or 4; m=0, 1, or 2; s=0, 1, or 2; R$^1$ is selected from the group consisting of: H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; R$^2$ is selected from the group consisting of: H, C$_1$-C$_6$ alkyl, C$_3$-C$_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R$^3$ and R$^4$ are each independently selected from the group consisting of hydrogen and methyl;

A compound of Formula II, wherein A is —(C=O)—O—R$^1$, R$^1$ is selected from the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is selected from the group consisting of:

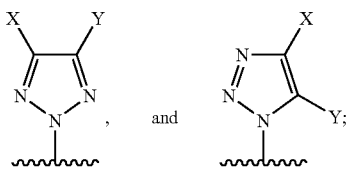

X and Y are independently selected from the group consisting of: H, halogen, C$_1$-C$_6$ alkyl, C$_3$-C$_{12}$ cycloalkyl, —CH$_2$-alkylamino, —CH$_2$-dialkylamino, —CH$_2$-arylamino, —CH$_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and R$^3$ and R$^4$ are hydrogen;

A compound of Formula II, wherein A is —(C=O)—O-tert-butyl; G is hydroxyl; L is absent; W is selected from the group consisting of:

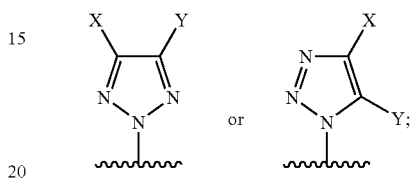

X and Y are independently selected from the group consisting of: H, halogen, C$_1$-C$_6$ alkyl, C$_3$-C$_{12}$ cycloalkyl, —CH$_2$-alkylamino, —CH$_2$-dialkylamino, —CH$_2$-arylamino, —CH$_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and R$^3$ and R$^4$ are hydrogen;

A compound of Formula II, wherein A is —(C=O)—O—R$^1$, R$^1$ is selected from the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

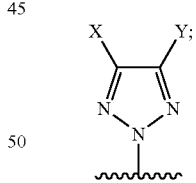

X and Y are independently selected from the group consisting of: H, halogen, C$_1$-C$_6$ alkyl, C$_3$-C$_{12}$ cycloalkyl, —CH$_2$-alkylamino, —CH$_2$-dialkylamino, —CH$_2$-arylamino, —CH$_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and R$^3$ and R$^4$ are hydrogen;

A compound of Formula II, wherein A is —(C═O)—O-tert-butyl; G is hydroxyl; L is absent; W is

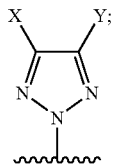

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C═O)-alkylamino, —(C═O)-dialkylamino, —(C═O)-arylamino, —(C═O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula III, wherein A is —(C═O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is selected from the group consisting of:

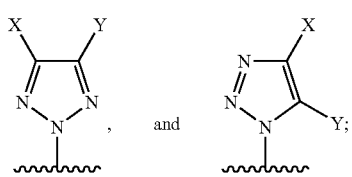

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C═O)-alkylamino, —(C═O)-dialkylamino, —(C═O)-arylamino, —(C═O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula III, wherein A is —(C═O)—O-tert-butyl; G is hydroxyl; L is absent; W is selected from the group consisting of:

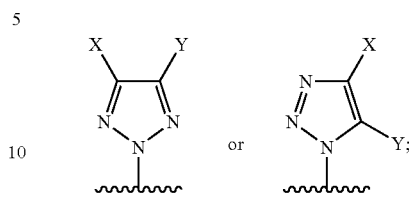

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C═O)-alkylamino, —(C═O)-dialkylamino, —(C═O)-arylamino, —(C═O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula III, wherein A is —(C═O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

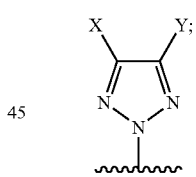

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C═O)-alkylamino, —(C═O)-dialkylamino, —(C═O)-arylamino, —(C═O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen; and A compound of Formula III, wherein A is —(C=O)—O-tert-butyl; G is hydroxyl; L is absent; W is

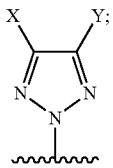

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen.

Other embodiments are compounds of formulae IV or V:

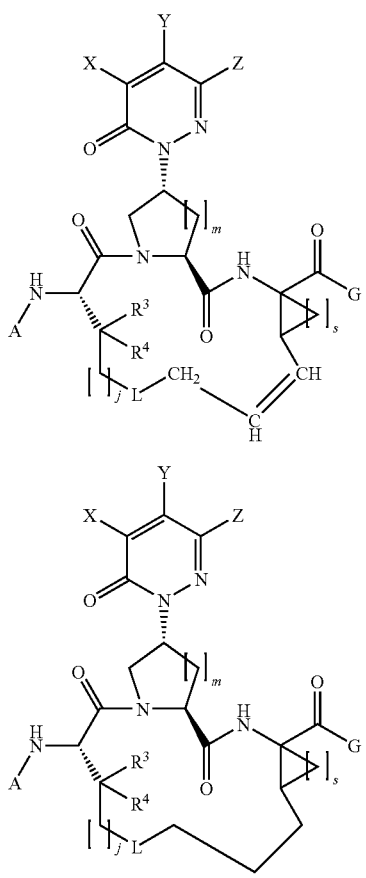

wherein A is H, —(C=O)—$R^2$, —(C=O)—O—$R^1$, —C(=O)—NH—$R^2$, —C(=S)—NH—$R^2$, or —S(O)$_2$—$R^2$; G is —OH, —O—($C_1$-$C_{12}$ alkyl), —NHS(O)$_2$—$R^1$, —(C=O)—$R^2$, —(C=O)—O—$R^1$, or —(C=O)—NH—$R^2$; L is absent, —S—, —$SCH_2$—, —$SCH_2CH_2$—, —S(O)$_2$—, —S(O)$_2CH_2CH_2$—, —S(O)—, —S(O)$CH_2CH_2$—, —O—, —$OCH_2$—, —$OCH_2CH_2$—, —(C=O)—$CH_2$—, —$CH(CH_3)CH_2$—, —$CFHCH_2$— or —$CF_2CH_2$—; X, Y, and Z are independently selected from the group consisting of H, $N_3$, halogen, $C_1$-$C_6$ alkyl, $C_3$-$C_{12}$ cycloalkyl, alkylamino, dialkylamino, $C_1$-$C_6$ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or, in the alternative, X and Y or Y and Z taken together with the carbon atoms to which they are attached form an aryl, substituted aryl, heteroaryl, or substituted heteroaryl cyclic moiety; j=0, 1, 2, 3, or 4; m=0, 1, or 2; s=0, 1, or 2; $R^1$ is H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; $R^2$ is H, $C_1$-$C_6$ alkyl, $C_3$-$C_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; and $R^3$ and $R^4$ are each independently hydrogen or methyl;

A compound of Formula IV, wherein A is —(C=O)—O—$R^1$; G is hydroxyl; L is absent; j=3; m=s=1; and $R^3$ and $R^4$ are hydrogen;

A compound of Formula IV, wherein A is —(C=O)—O-tert-butyl; G is hydroxyl; L is absent; j=3; m=s=1; and $R^3$ and $R^4$ are hydrogen;

A compound of Formula V, wherein A is —(C=O)—O—$R^1$; L is absent; j=3; m=s=1; and $R^3$ and $R^4$ are hydrogen; and A compound of Formula V, wherein A is —(C=O)—O-tert-butyl; G is hydroxyl; L is absent; j=3; m=s=1; and $R^3$ and $R^4$ are hydrogen.

Another aspect is a compound of formula I, wherein W is

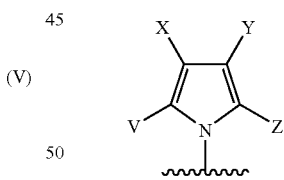

wherein V, X, Y, and Z are each independently selected from:
a) —$C_1$-$C_6$ alkyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
b) —$C_2$-$C_6$ alkenyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
c) —$C_2$-$C_6$ alkynyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
d) aryl;
e) substituted aryl;
f) heteroaryl;
g) substituted heteroaryl;
h) heterocycloalkyl; or
i) substituted heterocycloalkyl;
or in the alternative, V and X, X and Y, or Y and Z are taken together with the carbons to which they are attached to for a cyclic moiety selected from: aryl, substituted aryl, heteroaryl, substituted heteroaryl, heterocycloalkyl, or substituted heterocycloalkyl;

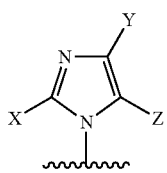

Another aspect is a compound of formula I, wherein W is
wherein X, Y, and Z are each independently selected from:
a) —$C_1$-$C_6$ alkyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
b) —$C_2$-$C_6$ alkenyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
c) —$C_2$-$C_6$ alkynyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
d) aryl;
e) substituted aryl;
f) heteroaryl;
g) substituted heteroaryl;
h) heterocycloalkyl; or
i) substituted heterocycloalkyl;
or in the alternative, Y and Z are taken together with the carbons to which they are attached to for a cyclic moiety selected from: aryl, substituted aryl, heteroaryl, substituted heteroaryl, heterocycloalkyl, or substituted heterocycloalkyl;
All remaining substituents are as listed above.
Another aspect is a method for making a compound of Formula I herein, comprising the steps of: (i) reacting a proline derivative of formula VI:

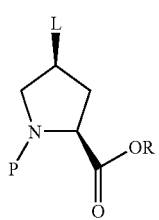

Wherein:
P is a nitrogen-protecting group (e.g., BOC);
L is a leaving group (e.g., halide, OMs);
R is optionally substituted alkyl, optionally substituted aralkyl, or optionally substituted heteroaralkyl;
with a nucleophilic heterocyclic compound; and (ii) converting the resulting compound to a compound of Formula I as delineated herein.

Another aspect is a method for making a compound of Formula I herein, comprising the steps of: (i) reacting a compound of formula VII:

Formula VII

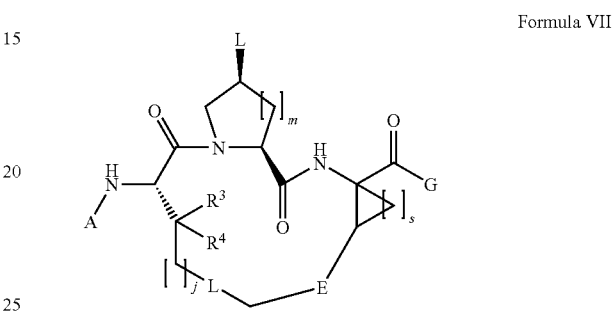

Wherein:
L is a leaving group (e.g., halide, OMs);
A is a nitrogen protecting group (e.g., BOC); and
the remaining variables are as defined for formula I;
with a nucleophilic heterocyclic compound; and (ii) converting the resulting compound to a compound of Formula I as delineated herein.

In other aspects, the invention relates to a method for making a compound of any of the formulae delineated herein (e.g., Formulae I to VII with substituent variables as defined anywhere herein) or a pharmaceutically acceptable salt, ester or prodrug thereof, comprising the steps of: (i) reacting a proline derivative described herein (including that having a mesylate substituent) with a nucleophilic form (e.g., protonated or corresponding metal salt form) of a heterocyclic compound; and (ii) converting the resulting compound to a compound of any of the formulae delineated herein. In other aspects the method includes reacting any one or more intermediate compounds as described herein, or includes any one or more steps or reagents or combination of transformations as specifically delineated in the examples and schemes herein.

In another aspect, the invention relates to a method of making a pharmaceutical composition comprising combining a compound of any of the formulae herein or a pharmaceutically acceptable salt, ester or prodrug thereof, with a pharmaceutically acceptable carrier.

Another aspect is a compound of formulae VI or VII wherein L is OMs and A and the remaining variables are as defined for any of the formulae (e.g., I, II, III) herein.

DETAILED DESCRIPTION OF THE INVENTION

A first embodiment of the invention is a compound represented by Formula I as described above, or a pharmaceutically acceptable salt, ester or prodrug thereof, in combination with a pharmaceutically acceptable carrier or excipient.

In some embodiments, the compounds may be of any of the formulae delineated herein (including any substituent variables as defined anywhere delineated herein) wherein W is selected from the following aromatics, which may optionally be substituted:

Aromatic

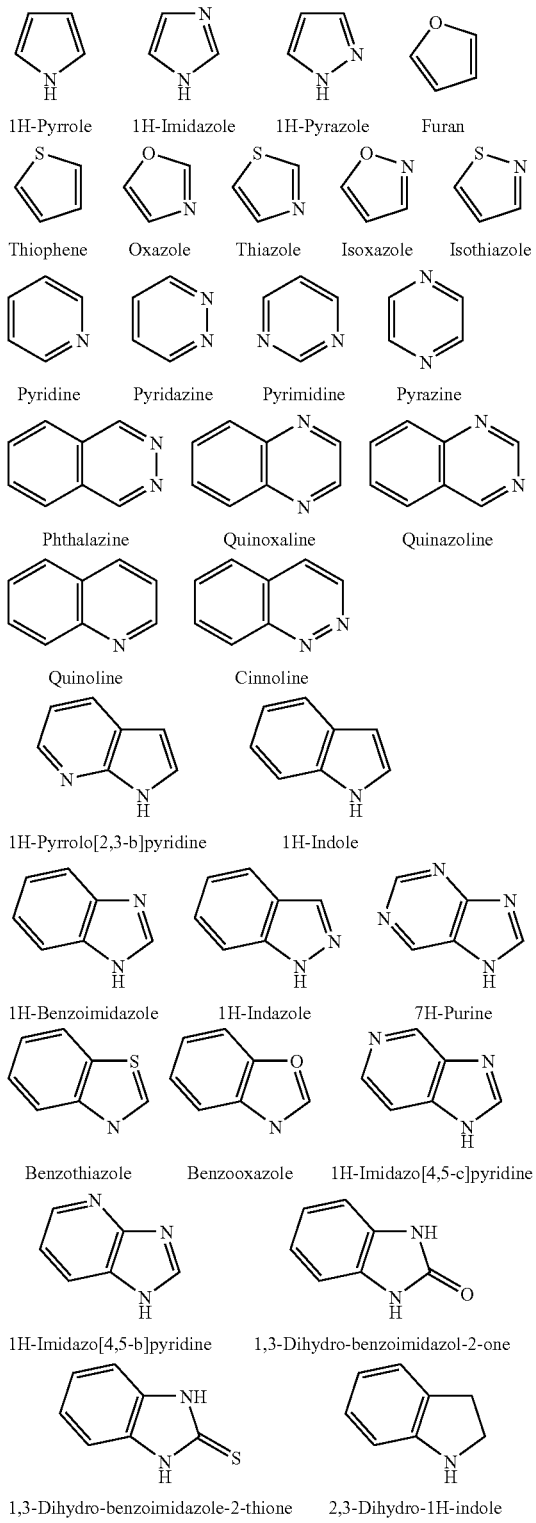

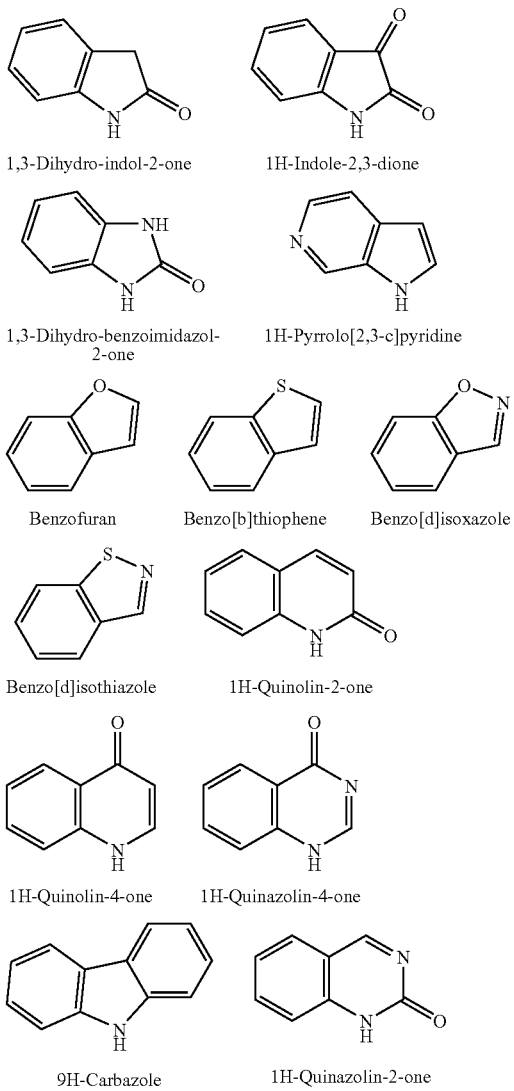

In other embodiments, the compounds may be of any of the formulae delineated herein (including any substituent variables as defined anywhere delineated herein) wherein W is selected from the following non-aromatics, which may be optionally substituted:

Non-Aromatic

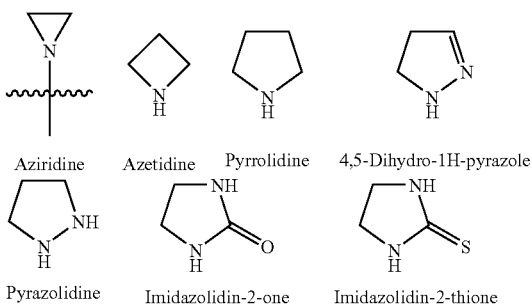

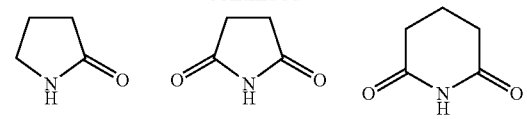

Pyrrolidin-2-one    Pyrrolidine-2,5-dione    Piperidine-2,6-dione

Piperidin-2-one    Piperazine-2,6-dione    Piperazin-2-one

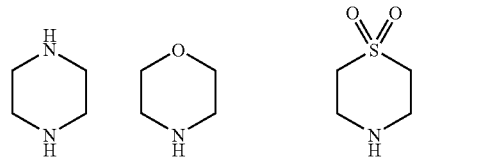

Piperazine    Morpholine    Thiomorpholine 1,1-dioxide

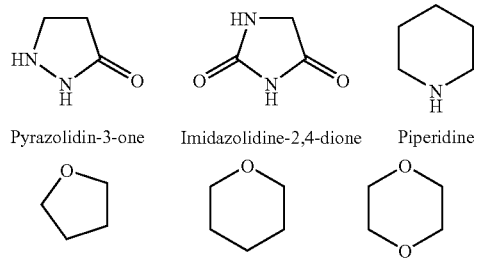

Pyrazolidin-3-one    Imidazolidine-2,4-dione    Piperidine

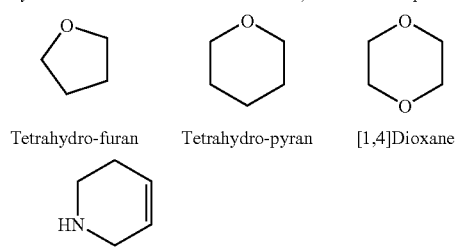

Tetrahydro-furan    Tetrahydro-pyran    [1,4]Dioxane


1,2,3,6-Tetrahydro-pyridine

Another embodiment of the invention is a compound, or a pharmaceutically acceptable salt, ester or prodrug thereof, represented by Formula II as described above where W is a tetrazole or derivative thereof, in combination with a pharmaceutically acceptable carrier or excipient.

Another embodiment of the invention is a compound, or a pharmaceutically acceptable salt, ester or prodrug thereof, represented by Formula III as described above wherein W is a tetrazole, or derivative thereof, in combination with a pharmaceutically acceptable carrier or excipient.

Exemplary tetrazolyl macrocyclic compounds and associated methods of the invention are disclosed in U.S. Provisional Patent application No. 60/509,069 (conversion of U.S. Ser. No. 10/365,854), filed Feb. 13, 2003. Representative subgenera of the invention include, but are not limited to:

Compounds of Formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

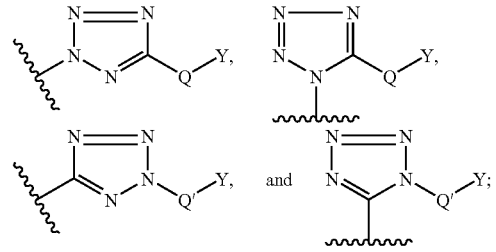

Q is selected from the group consisting of: absent, —$CH_2$—, —O—, —NH—, —N($R^1$)—, —S—, —S(O)$_2$—, and —(C=O)—; Q' is selected from the group consisting of: absent, —$CH_2$—, and —NH—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and $R^3$ and $R^4$ are hydrogen;

Compounds of Formula II, wherein A is —(C=O)—O-tert-butyl; G is hydroxyl; L is absent; W is

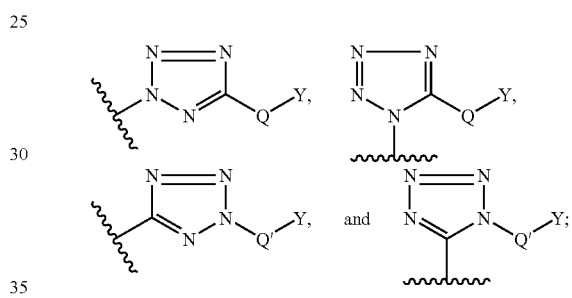

Q is selected from the group consisting of: absent, —$CH_2$—, —O—, —NH—, —N($R^1$)—, —S—, —S(O)$_2$—, and —(C=O)—; Q' is selected from the group consisting of: absent, —$CH_2$—, and —NH—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and $R^3$ and $R^4$ are hydrogen;

Compounds of Formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

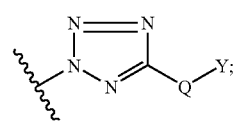

Q is selected from the group consisting of: absent, —$CH_2$—, —O—, —NH—, —N($R^1$)—, —S—, —S(O)$_2$—, and —(C=O)—; Y is selected from the group consisting of: H, $C_1$-$C_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and $R^3$ and $R^4$ are hydrogen;

Compounds of Formula II, wherein A is —(C=O)—O-tert-butyl; G is hydroxyl; L is absent; W is

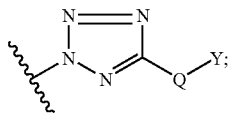

Q is selected from the group consisting of: absent, —CH$_2$—, —O—, —NH—, —N(R$^1$)—, —S—, —S(O)$_2$—, and —(C=O)—; Y is selected from the group consisting of: H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R$^3$ and R$^4$ are hydrogen;

Compounds of Formula III, wherein A is —(C=O)—O—R$^1$, R$^1$ is selected from the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

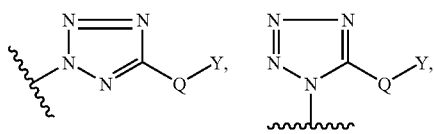

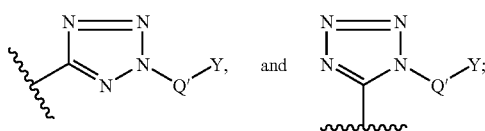

Q is selected from the group consisting of: absent, —CH$_2$—, —O—, —NH—, —N(R$^1$)—, —S—, —S(O)$_2$—, and —(C=O)—; Q' is selected from the group consisting of: absent, —CH$_2$—, and —NH—; Y is selected from the group consisting of: H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R$^3$ and R$^4$ are hydrogen;

Compounds of Formula III, wherein A is —(C=O)—O-tert-butyl; G is hydroxyl; L is absent; W is

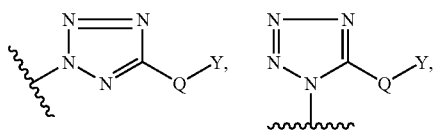

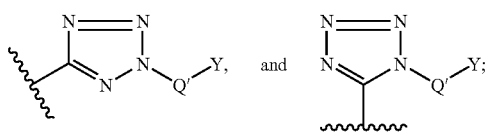

Q is selected from the group consisting of: absent, —CH$_2$—, —O—, —NH—, —N(R$^1$)—, —S—, —S(O)$_2$—, and —(C=O)—; Q' is selected from the group consisting of: absent, —CH$_2$—, and —NH—; Y is selected from the group consisting of: H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R$^3$ and R$^4$ are hydrogen;

Compounds of Formula III, wherein A is —(C=O)—O—R$^1$, R$^1$ is selected from the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

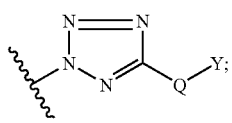

Q is selected from the group consisting of: absent, —CH$_2$—, —O—, —NH—, —N(R$^1$)—, —S—, —S(O)$_2$—, and —(C=O)—; Y is selected from the group consisting of: H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R$^3$ and R$^4$ are hydrogen; and Compounds of Formula III, wherein A is —(C=O)—O-tert-butyl; G is hydroxyl; L is absent; W is

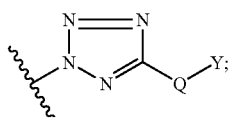

Q is selected from the group consisting of: absent, —CH$_2$—, —O—, —NH—, —N(R$^1$)—, —S—, —S(O)$_2$—, and —(C=O)—; Y is selected from the group consisting of: H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; j=3; m=s=1; and R$^3$ and R$^4$ are hydrogen.

Representative compounds of the invention include, but are not limited to, the following compounds:

TABLE 1

| A | G | L | W | Q | V | J | R³, R⁴ |
|---|---|---|---|---|---|---|---|
| Compounds of Formula II, where m = s = 1 | | | | | | | |
| tBOC | OH | Absent | tetrazole-C(Q-Y) | Absent | phenyl | 3 | R³ = R⁴ = H; |
| tBOC | OH | Absent | tetrazole-C(Q-Y) | Absent | 2-bromophenyl | 3 | R³ = R⁴ = H; |
| tBOC | OH | Absent | tetrazole-C(Q-Y) | Absent | 3-bromophenyl | 3 | R³ = R⁴ = H; |
| tBOC | OH | Absent | tetrazole-C(Q-Y) | Absent | 4-bromophenyl | 3 | R³ = R⁴ = H; |
| tBOC | OH | Absent | tetrazole-C(Q-Y) | Absent | 5-Bromo-2-thienyl | 3 | R³ = R⁴ = H; |
| TBOC | OH | Absent | tetrazole-C(Q-Y) | Absent | 2-bromo-4-pyridyl | 3 | R³ = R⁴ = H; |
| TBOC | OH | Absent | tetrazole-C(Q-Y) | Absent | 2-biphenyl | 3 | R³ = R⁴ = H; |
| TBOC | OH | Absent | tetrazole-C(Q-Y) | Absent | 3-biphenyl | 3 | R³ = R⁴ = H; |
| TBOC | OH | Absent | tetrazole-C(Q-Y) | Absent | 4-biphenyl | 3 | R³ = R⁴ = H; |
| TBOC | OH | Absent | tetrazole-C(Q-Y) | Absent | 3-(3-thienyl)phenyl | 3 | R³ = R⁴ = H; |
| TBOC | OH | Absent | tetrazole-C(Q-Y) | Absent | 3-(p-trifluoromethoxyphenyl)phenyl | 3 | R³ = R⁴ = H; |
| TBOC | OH | Absent | tetrazole-C(Q-Y) | Absent | 3-(p-cyanophenyl)phenyl | 3 | R³ = R⁴ = H; |
| TBOC | OH | Absent | tetrazole-C(Q-Y) | Absent | 4-(3-thienyl)phenyl | 3 | R³ = R⁴ = H; |
| TBOC | OH | Absent | tetrazole-C(Q-Y) | Absent | 4-(p-trifluoromethoxyphenyl)phenyl | 3 | R³ = R⁴ = H; |

TABLE 1-continued

| A | G | L | W | Q | V | J | R³, R⁴ |
|---|---|---|---|---|---|---|---|
| TBOC | OH | Absent | 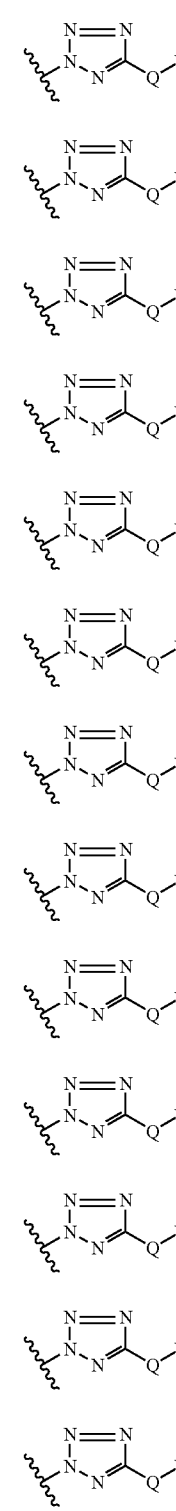 | Absent | 4-(p-cyanophenyl)phenyl | 3 | R³ = R⁴ = H; |
| TBOC | OH | Absent | 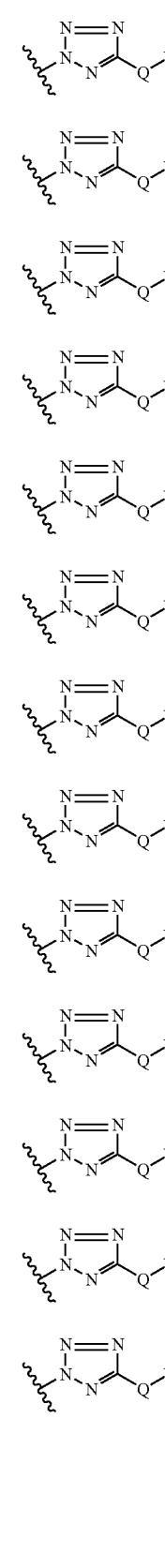 | Absent | 5-phenyl-2-thienyl | 3 | R³ = R⁴ = H; |
| TBOC | OH | Absent | 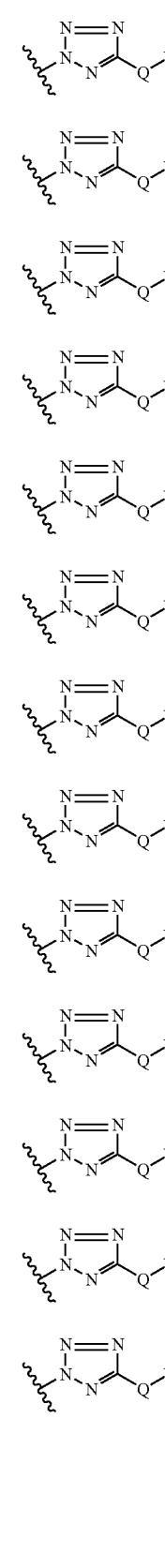 | Absent | 5-phenyl-3-pyridyl | 3 | R³ = R⁴ = H; |
| TBOC | OLt | Absent | 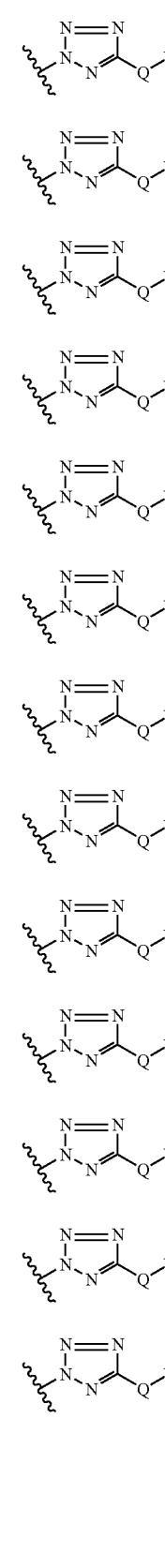 | Absent | 3-chloro-4-hydroxyphenyl | 3 | R³ = R⁴ = H; |
| TBOC | OH | Absent | 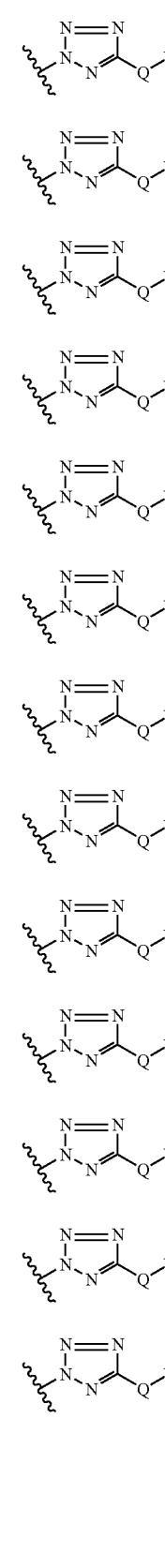 | Absent | 3-chloro-4-hydroxyphenyl | 3 | R³ = R⁴ = H; |
| TBOC | OH | Absent | 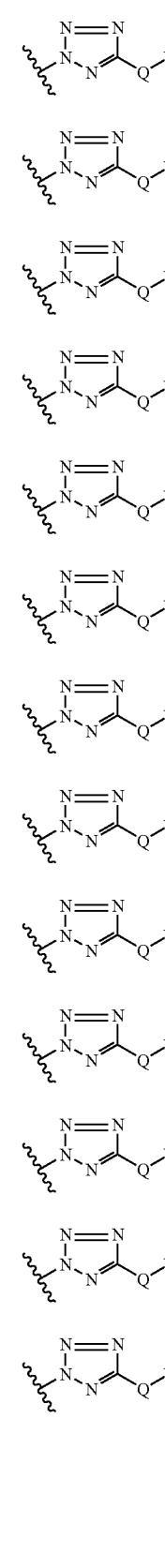 | Absent | 3-bromo-4-hydroxyphenyl | 3 | R³ = R⁴ = H; |
| TBOC | OH | Absent | 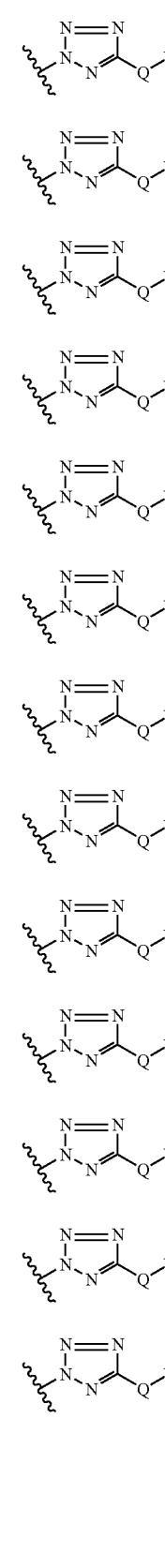 | Absent | 2-methyl-4-bromophenyl | 3 | R³ = R⁴ = H; |
| TBOC | OH | Absent | 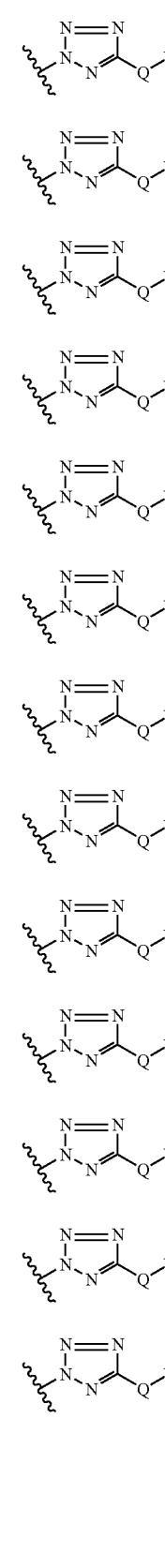 | Absent | 3-methyl-4-bromophenyl | 3 | R³ = R⁴ = H; |
| TBOC | OH | Absent | 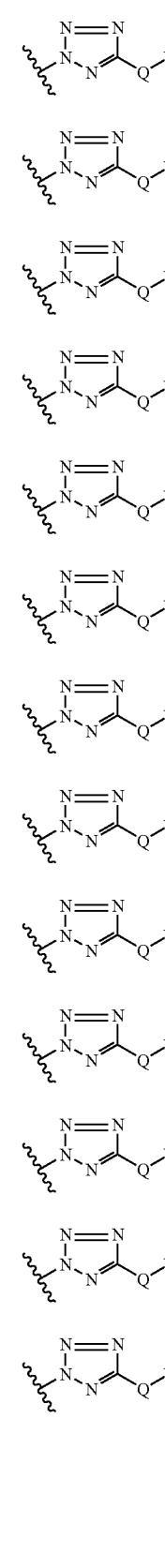 | Absent | n-propyl | 3 | R³ = R⁴ = H; |
| TBOC | OH | Absent | 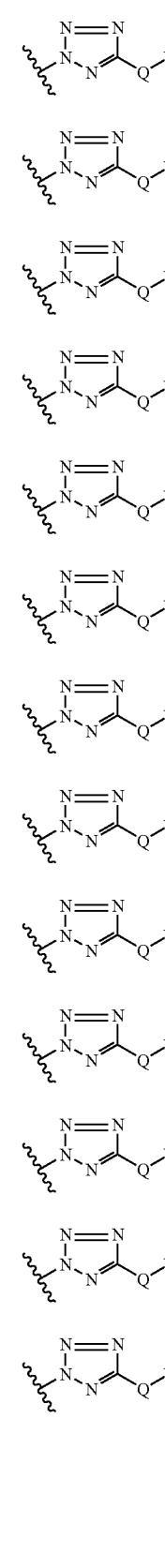 | Absent | n-butyl | 3 | R³ = R⁴ = H; |
| TBOC | OH | Absent | 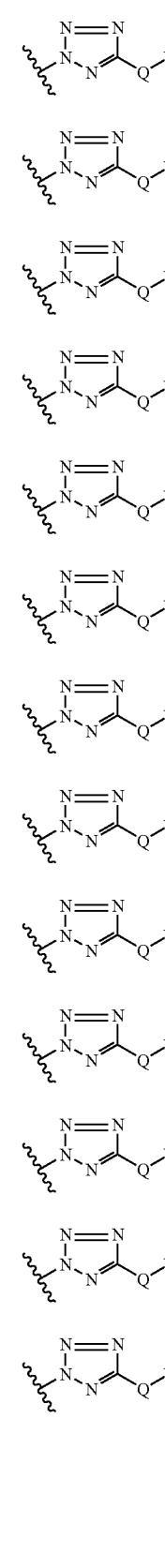 | Absent | 4-ethoxyphenyl | 3 | R³ = R⁴ = H; |
| TBOC | OH | Absent | 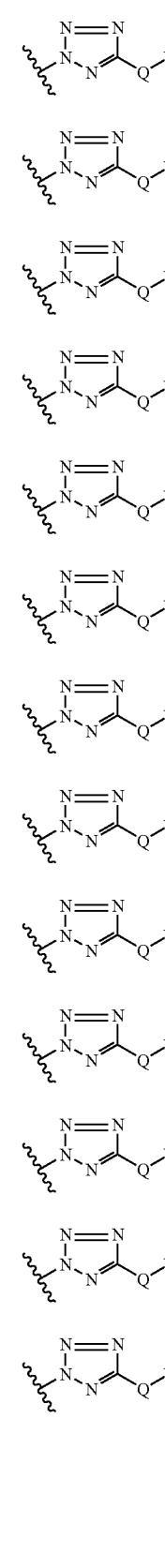 | Absent | 4-propoxyphenyl | 3 | R³ = R⁴ = H; |
| TBOC | OH | Absent | 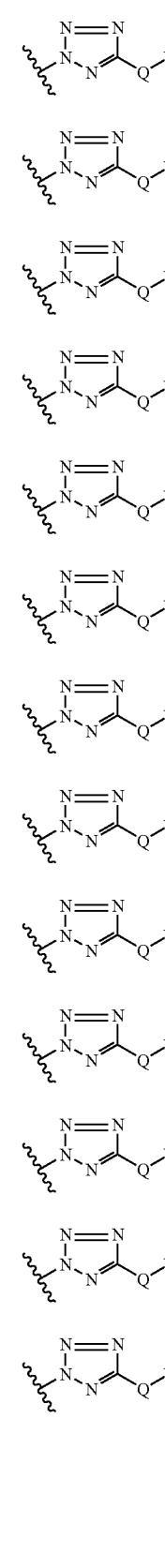 | Absent | 4-butoxyphenyl | 3 | R³ = R⁴ = H; |
| TBOC | OH | Absent | 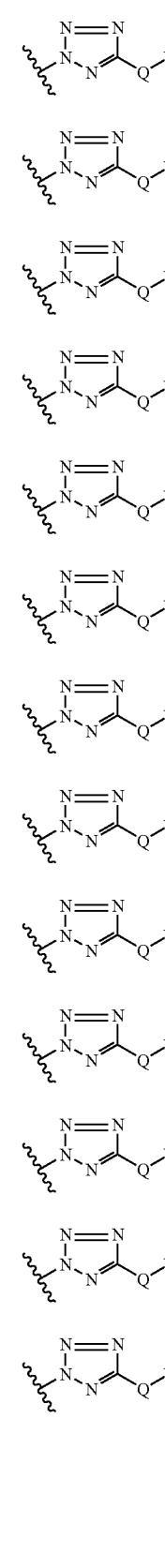 | Absent | 3-methoxyphenyl | 3 | R³ = R⁴ = H; |

TABLE 1-continued

| A | G | L | W | Q | V | J | R³, R⁴ |
|---|---|---|---|---|---|---|---|
| TBOC | OH | Absent | N=N / N-N-Q-Y (tetrazole) | Absent | 3,4-dimethoxyphenyl | 3 | R³ = R⁴ = H; |
| TBOC | OH | Absent | N=N / N-N-Q-Y | Absent | 4-methoxy-1-naphthyl | 3 | R³ = R⁴ = H; |
| TBOC | OH | Absent | N=N / N-N-Q-Y | Absent | 4-phenoxyphenyl | 3 | R³ = R⁴ = H; |
| TBOC | OH | Absent | N=N / N-N-Q-Y | Absent | benzyl | 3 | R³ = R⁴ = H; |
| TBOC | OH | Absent | N=N / N-N-Q-Y | Absent | p-phenylbenzyl | 3 | R³ = R⁴ = H; |
| TBOC | OH | Absent | N=N / N-N-Q-Y | Absent | 3-chlorophenyl | 3 | R³ = R⁴ = H; |
| TBOC | OH | Absent | N=N / N-N-Q-Y | Absent | 3-fluorophenyl | 3 | R³ = R⁴ = H; |
| TBOC | OH | Absent | N=N / N-N-Q-Y | Absent | 3-methoxyphenyl | 3 | R³ = R⁴ = H; |
| TBOC | OH | Absent | N=N / N-N-Q-Y | Absent | 3-phenoxyphenyl | 3 | R³ = R⁴ = H; |
| TBOC | OH | Absent | N=N / N-N-Q-Y | Absent | 3-benzyloxyphenyl | 3 | R³ = R⁴ = H; |
| TBOC | OH | Absent | N=N / N-N-Q-Y | Absent | 3-trifluormethyl-phenyl | 3 | R³ = R⁴ = H; |
| TBOC | OH | Absent | N=N / N-N-Q-Y | Absent | 4-bromophenyl | 3 | R³ = R⁴ = H; |
| TBOC | OH | Absent | N=N / N-N-Q-Y | Absent | 4-fluorophenyl | 3 | R³ = R⁴ = H; |
| TBOC | OH | Absent | N=N / N-N-Q-Y | Absent | 4-methoxyphenyl | 3 | R³ = R⁴ = H; |
| TBOC | OH | Absent | N=N / N-N-Q-Y | Absent | 4-ethoxyphenyl | 3 | R³ = R⁴ = H; |

TABLE 1-continued

| A | G | L | W | Q | V | J | R³, R⁴ |
|---|---|---|---|---|---|---|---|
| TBOC | OH | Absent | tetrazole-Q-Y | Absent | 4-trifluoro-methylphenyl | 3 | R³ = R⁴ = H; |
| TBOC | OH | Absent | tetrazole-Q-Y | Absent | 5-di(trifluoromethyl)phenyl | 3 | R³ = R⁴ = H; |
| TBOC | OH | Absent | tetrazole-Q-Y | Absent | 4-(N,N-dimethylamino)-3,5-di(trifluoromethyl)phenyl | 3 | R³ = R⁴ = H; |
| TBOC | OH | Absent | tetrazole-Q-Y | Absent | 2,4-dichlorophenyl | 3 | R³ = R⁴ = H; |
| TBOC | OH | Absent | tetrazole-Q-Y | Absent | 3,5-dichlorophenyl | 3 | R³ = R⁴ = H; |
| TBOC | OH | Absent | tetrazole-Q-Y | Absent | 3,4-dichlorophenyl | 3 | R³ = R⁴ = H; |
| TBOC | OH | Absent | tetrazole-Q-Y | Absent | 2-pyridyl | 3 | R³ = R⁴ = H; |
| TBOC | OH | Absent | tetrazole-Q-Y | Absent | 2-pyridyl | 3 | R³ = R⁴ = H; |
| TBOC | OH | Absent | tetrazole-Q-Y | Absent | 3-pyridyl | 3 | R³ = R⁴ = H; |
| TBOC | OH | Absent | tetrazole-Q-Y | Absent | 4-pyridyl | 3 | R³ = R⁴ = H; |
| TBOC | OH | Absent | tetrazole-Q-Y | Absent | 4-methoxy-3-bromophenyl | 3 | R³ = R⁴ = H; |
| TBOC | OH | Absent | tetrazole-Q-Y | Absent | 4-(methyl-cyclopropane)phenyl | 3 | R³ = R⁴ = H; |
| TBOC | OH | Absent | tetrazole-Q-Y | Absent | 3-chloro-4-(methyl-cyclopropane)phenyl | 3 | R³ = R⁴ = H; |
| TBOC | OH | Absent | tetrazole-Q-Y | Absent | 3-chloro-4-methoxyphenyl | 3 | R³ = R⁴ = H; |

TABLE 1-continued

| A | G | L | W | Q | V | J | R³, R⁴ |
|---|---|---|---|---|---|---|---|
| TBOC | OH | Absent | tetrazole-Q-Y | Absent | 3-chloro-4-ethoxyphenyl | 3 | R³ = R⁴ = H; |
| TBOC | OH | Absent | tetrazole-Q-Y | Absent | 3-bromo-4-ethoxyphenyl | 3 | R³ = R⁴ = H; |
| TBOC | OH | Absent | tetrazole-Q-Y | Absent | 3-chloro-4-(2-hydroxyethoxy)phenyl | 3 | R³ = R⁴ = H; |
| TBOC | OH | Absent | tetrazole-Q-Y | Absent | 3-bromo-4-(2-hydroxyethoxy)phenyl | 3 | R³ = R⁴ = H; |
| TBOC | OH | Absent | tetrazole-Q-Y | Absent | 3-chloro-4-(O-allyl)phenyl | 3 | R³ = R⁴ = H; |
| TBOC | OH | Absent | tetrazole-Q-Y | Absent | 3-bromo-4-(O-allyl)phenyl | 3 | R³ = R⁴ = H; |
| TBOC | OH | Absent | tetrazole-Q-Y | Absent | 3-chloro-4-(O—CH₂SCH₃)phenyl | 3 | R³ = R⁴ = H; |
| TBOC | OH | Absent | tetrazole-Q-Y | Absent | 3-chloro-4-(O—CH₂SCH₃)phenyl | 3 | R³ = R⁴ = H; |
| TBOC | OH | Absent | tetrazole-Q-Y | Q' = —CH₂— | biphenyl | 3 | R³ = R⁴ = H; |
| TBOC | OH | Absent | tetrazole-Q-Y | Q' = —CH₂— | biphenyl | 3 | R³ = R⁴ = H; |
| —(C=O)—O—R¹ wherein R¹ = cyclopentyl | OH | Absent | tetrazole-Q-Y | Absent | phenyl | 3 | R³ = R⁴ = H; |
| —(C=O)—O—R¹ wherein R¹ = cyclobutyl | OH | Absent | tetrazole-Q-Y | Absent | phenyl | 3 | R³ = R⁴ = H; |
| —(C=O)—O—R¹ wherein R¹ = cyclohexyl | OH | Absent | tetrazole-Q-Y | Absent | phenyl | 3 | R³ = R⁴ = H; |
| —(C=O)—O—R¹ wherein R¹ = tetrahydrofuranyl | OH | Absent | tetrazole-Q-Y | Absent | phenyl | 3 | R³ = R⁴ = H; |

TABLE 1-continued

| A | G | L | W | Q | V | J | R³, R⁴ |
|---|---|---|---|---|---|---|---|
| —(C=O)—O—R¹ wherein R¹ = 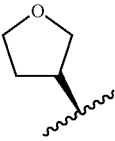 | OH | Absent | 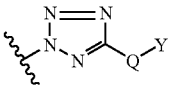 | Absent | phenyl | 3 | R³= R⁴ = H; |
| —(C=O)—O—R¹ wherein R¹ = 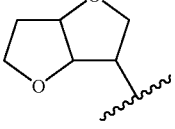 | OH | Absent | 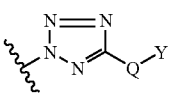 | Absent | phenyl | 3 | R³= R⁴ = H; |
| —(C=O)—R¹ wherein R¹= cyclopentyl | OH | Absent | 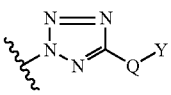 | Absent | phenyl | 3 | R³= R⁴ = H; |
| —(C=O)—NH—R¹ wherein R¹= cyclopentyl | OH | Absent | 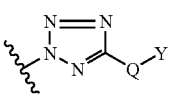 | Absent | phenyl | 3 | R³= R⁴ = H; |
| —(C=O)—NH—R¹ wherein R¹= cyclopentyl | OH | Absent | 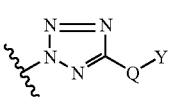 | Absent | phenyl | 3 | R³= R⁴ = H; |
| —S(O)₂—R¹ wherein R¹ = cyclopentyl | OH | Absent | 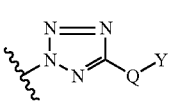 | Absent | phenyl | 3 | R³= R⁴ = H; |
| tBOC | —O—CH₂-cyclopentyl | Absent | 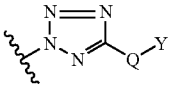 | Absent | phenyl | 3 | R3 = R4 = H; |
| tBOC | —NHS(O)₂—CH₂-cyclopentyl | Absent | 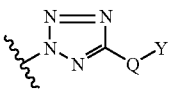 | Absent | phenyl | 3 | R³= R⁴ = H; |
| tBOC | —(C=O)—CH₂-cyclopentyl | Absent | 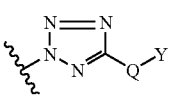 | Absent | phenyl | 3 | R³= R⁴ = H; |
| tBOC | —(C=O)—O—CH₂-cyclopentyl | Absent | 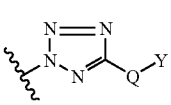 | Absent | phenyl | 3 | R³= R⁴ = H; |

TABLE 1-continued

| A | G | L | W | Q | V | J | R³, R⁴ |
|---|---|---|---|---|---|---|---|
| tBOC | —(C=O)—OH | Absent | 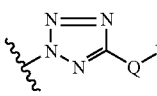 | Absent | phenyl | 3 | R³= R⁴ = H; |
| tBOC | —(C=O)—NH—CH₂-cyclopentyl | Absent | 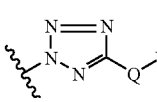 | Absent | phenyl | 3 | R³= R⁴ = H; |
| tBOC | OH | —(C=O)CH₂— | 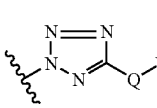 | Absent | phenyl | 1 | R³= R⁴ = H; |
| tBOC | OH | —CH(CH₃)CH₂— | 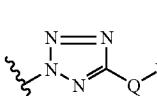 | Absent | phenyl | 1 | R³ = methyl, R⁴ = H; |
| tBOC | OH | —O— | 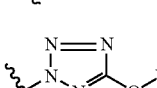 | Absent | phenyl | 0 | R³ = methyl, R⁴ = H; |
| tBOC | OH | —S— | 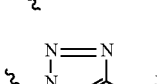 | Absent | phenyl | 0 | R³ = methyl, R⁴ = H; |
| tBOC | OH | —S(O)— | 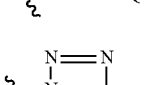 | Absent | phenyl | 0 | R³ = methyl, R⁴ = H; |
| tBOC | OH | —S(O)₂— | 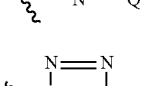 | Absent | phenyl | 0 | R³ = methyl, R⁴ = H; |
| tBOC | OH | —SCH₂CH₂— | 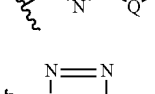 | Absent | phenyl | 0 | R³= R⁴ = CH₃; |
| tBOC | OH | —CF₂CH₂— | 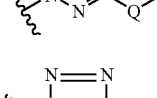 | Absent | phenyl | 1 | R³= R⁴ = H; |
| tBOC | OH | —CFHCH₂— | 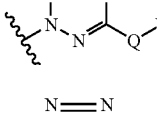 | Absent | phenyl | 1 | R³= R⁴ = H; |
| Compounds of Formula III, where m = s = 1 | | | | | | | |
| tBOC | OH | Absent | 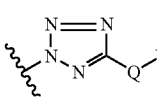 | Absent | phenyl | 3 | R³= R⁴ = H; |

The following additional tetrazolyl macrocyclic molecules of the invention were made by the methods and procedures described herein. While stereochemistry is shown, the invention is not limited to the stereochemistry depicted. Those of ordinary skill in the art will readily appreciate that other isomers of these compounds are also within the scope of the invention.

51
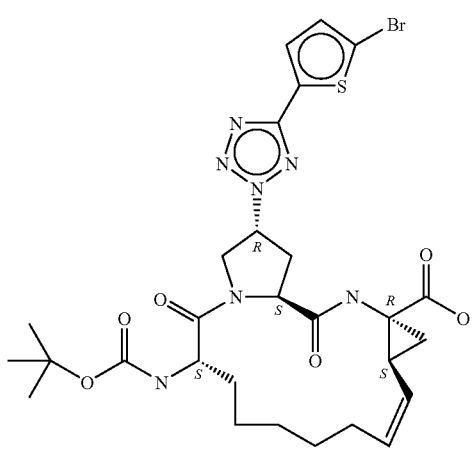
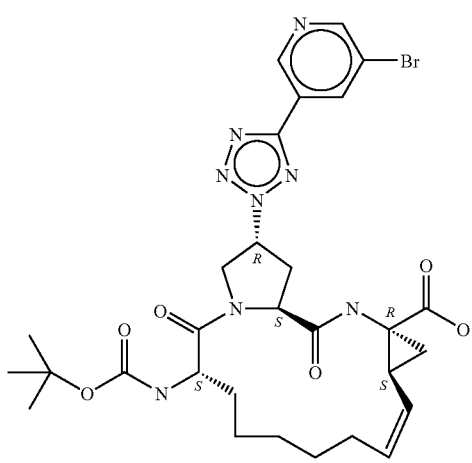
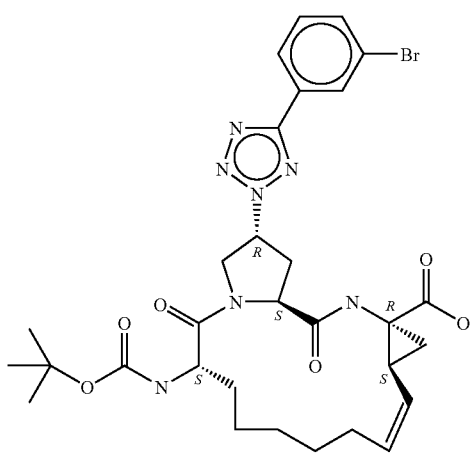
52
-continued
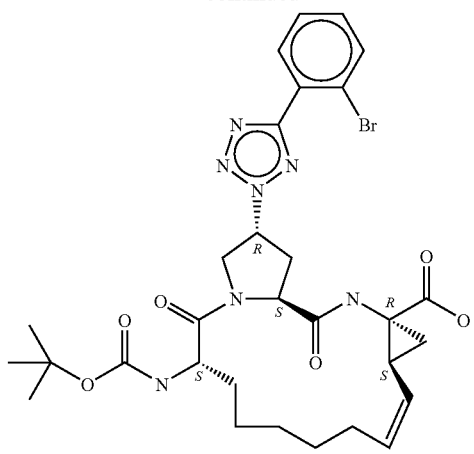
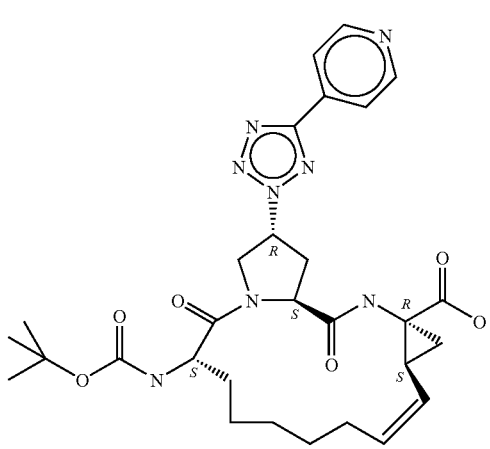
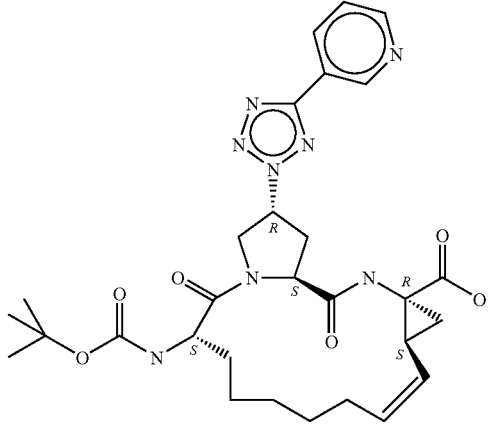

53
-continued
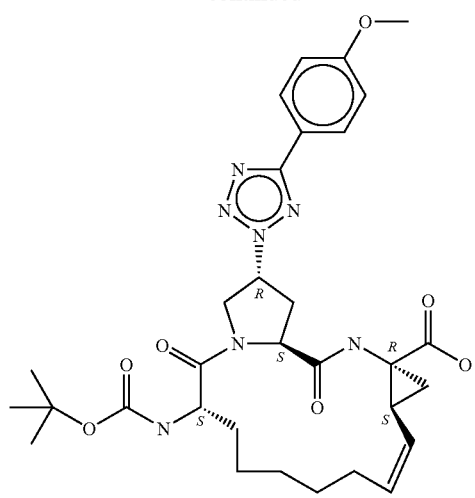
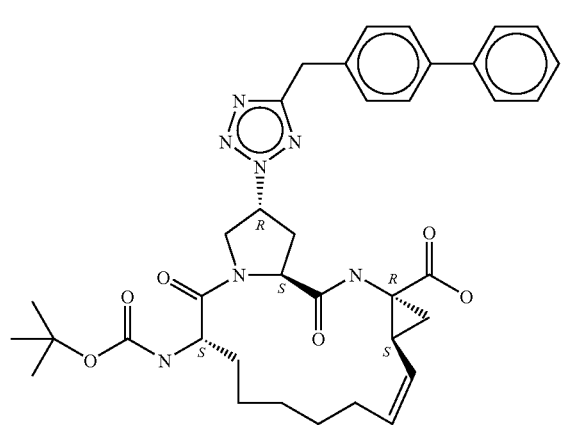
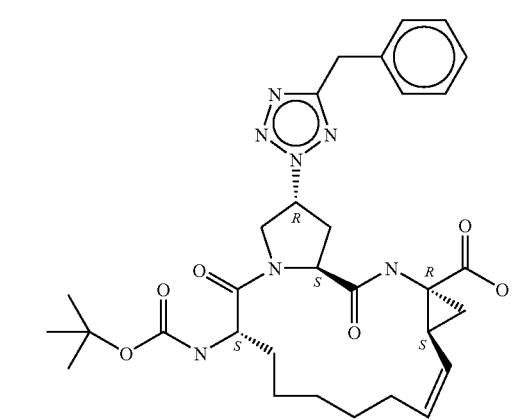
54
-continued
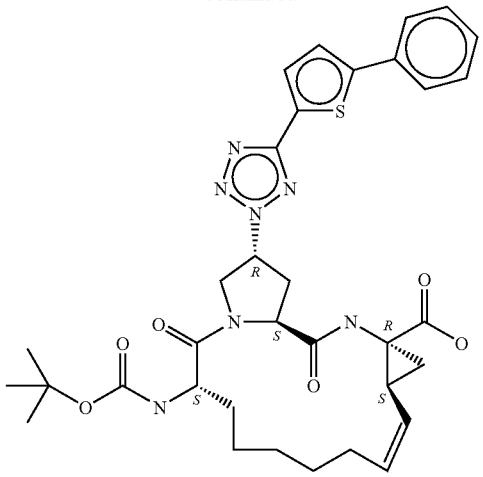
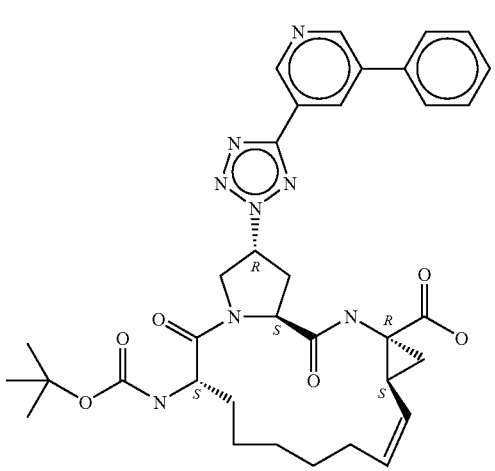
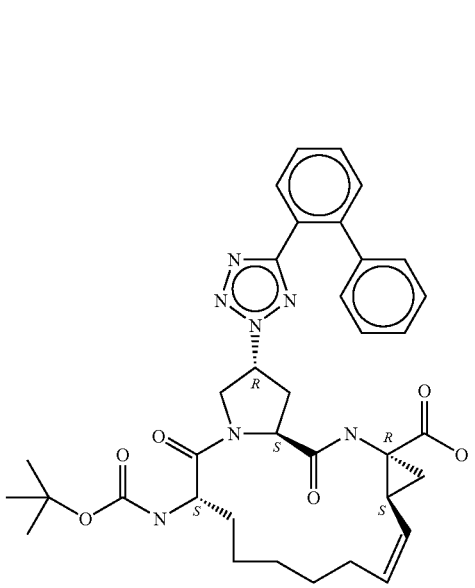

55
-continued
56
-continued
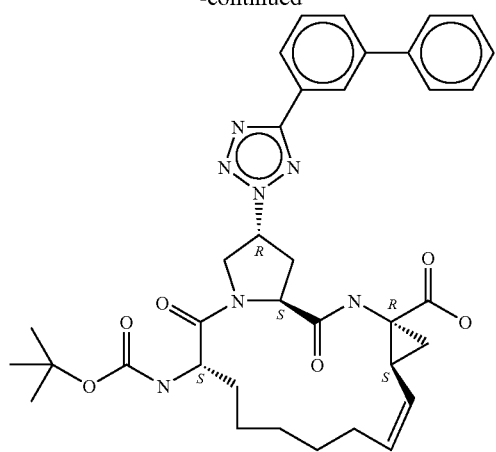
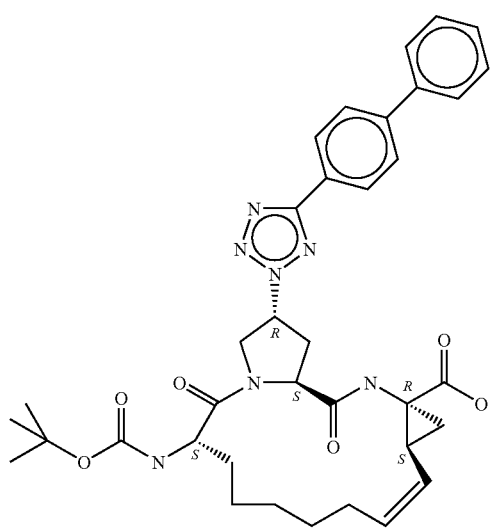
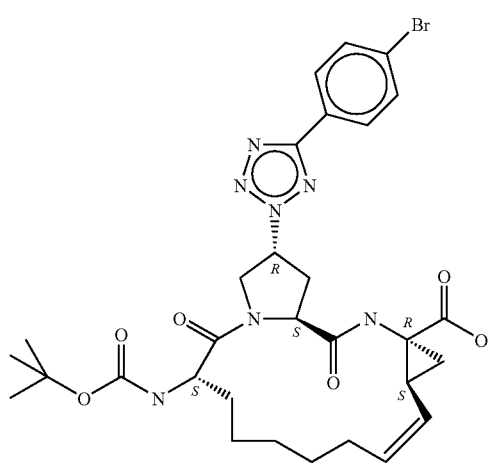
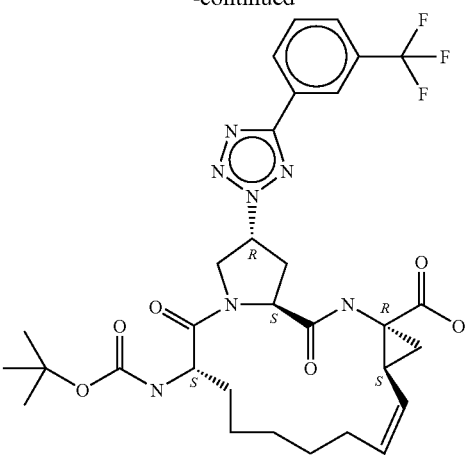
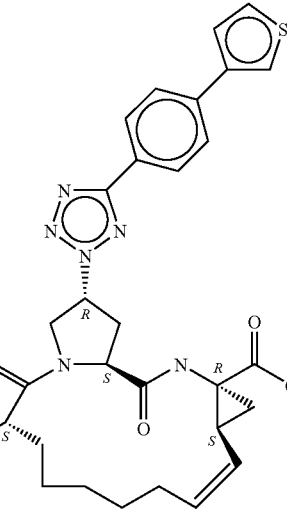
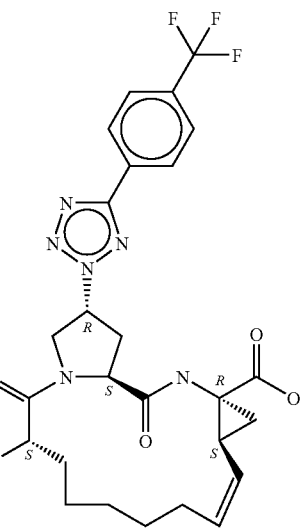

57
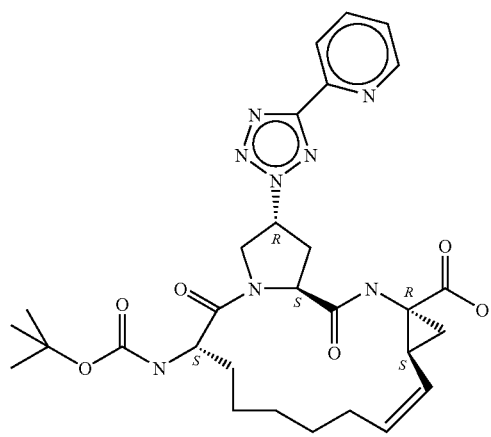
58
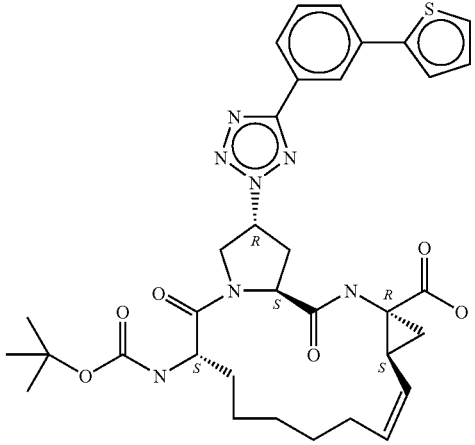
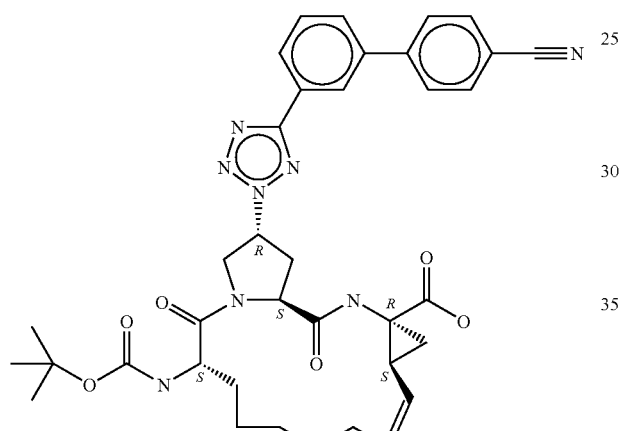
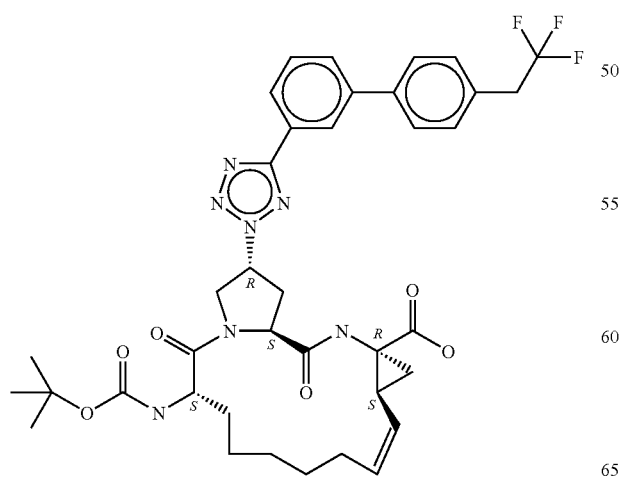
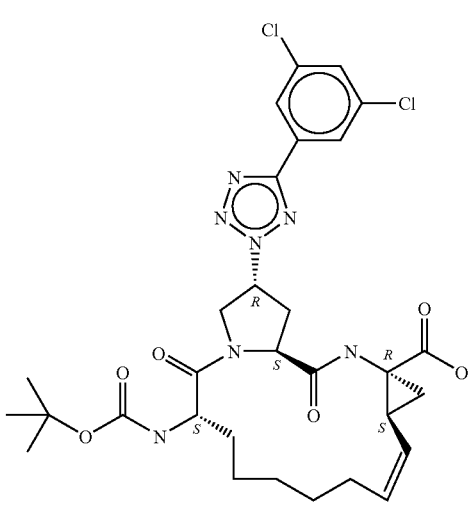

59
-continued
60
-continued
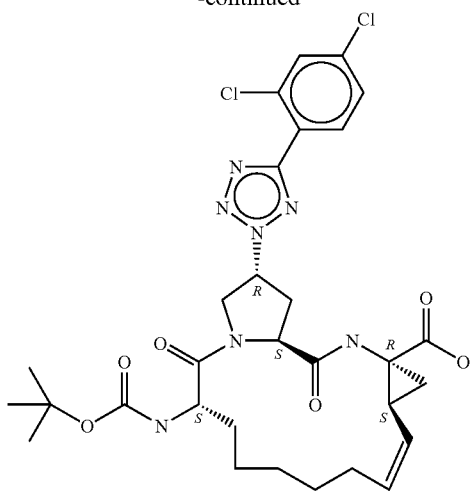
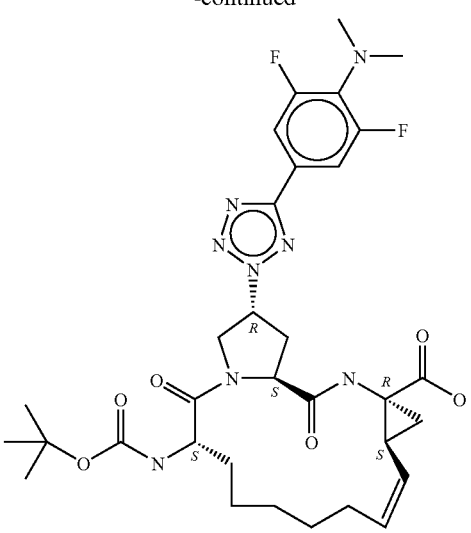

61

63
-continued
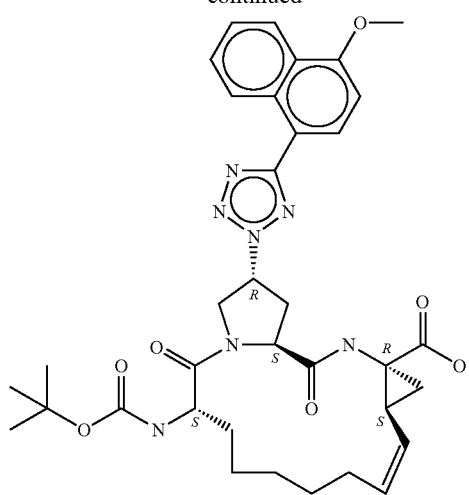
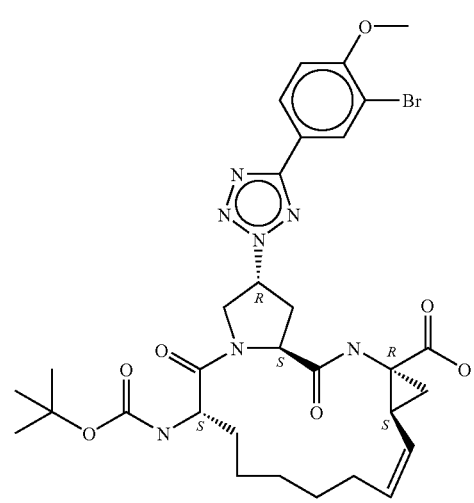
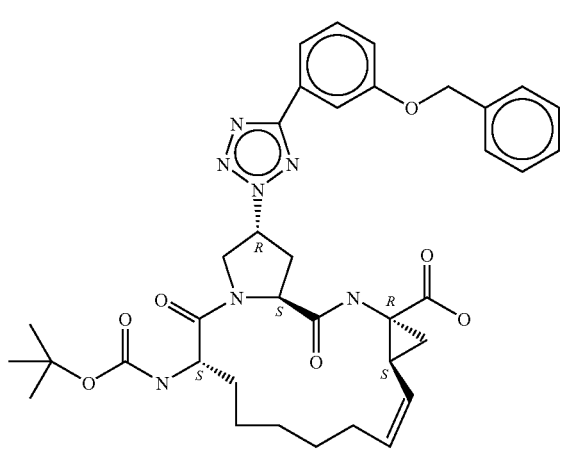
64
-continued
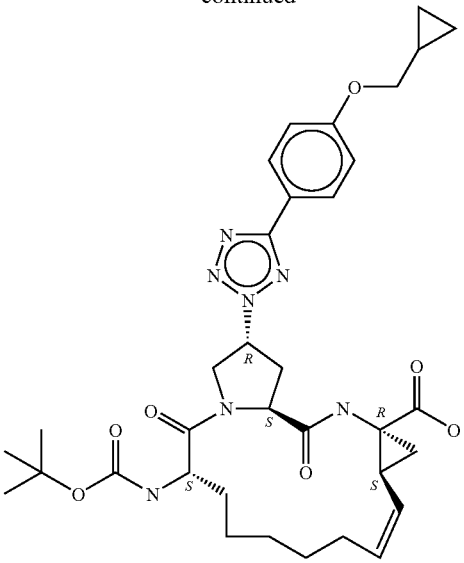
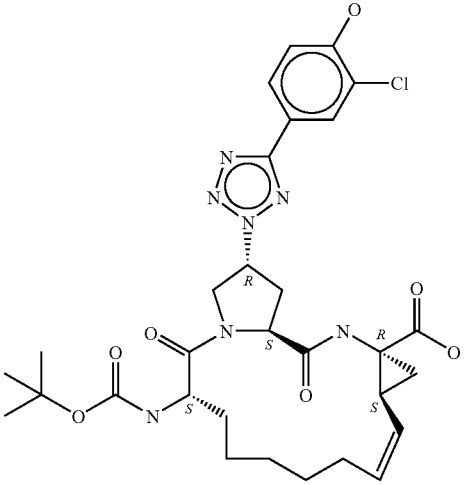

65
-continued
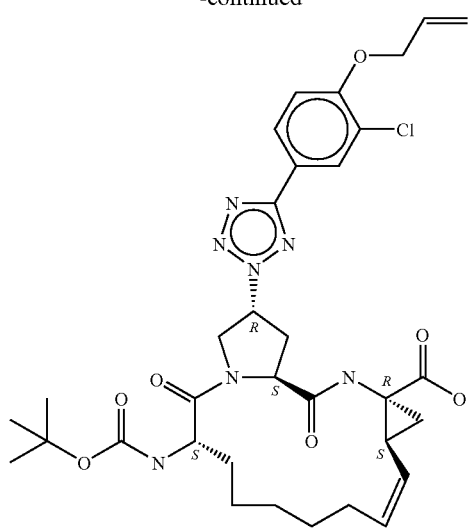
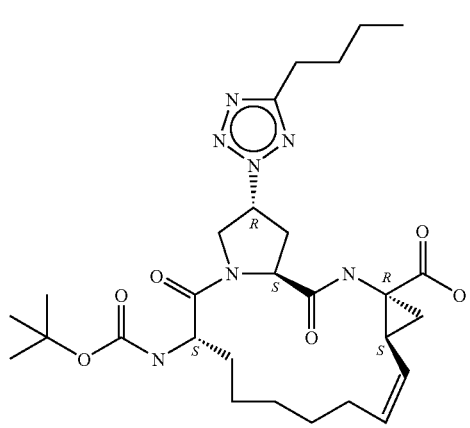
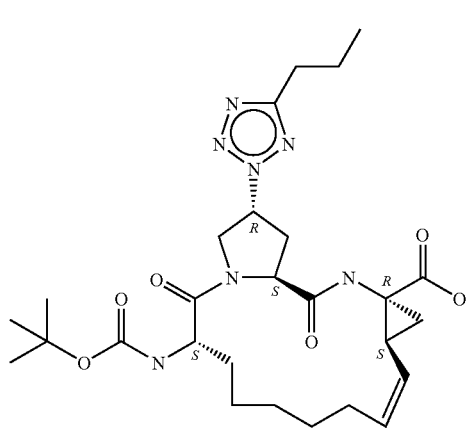
66
-continued
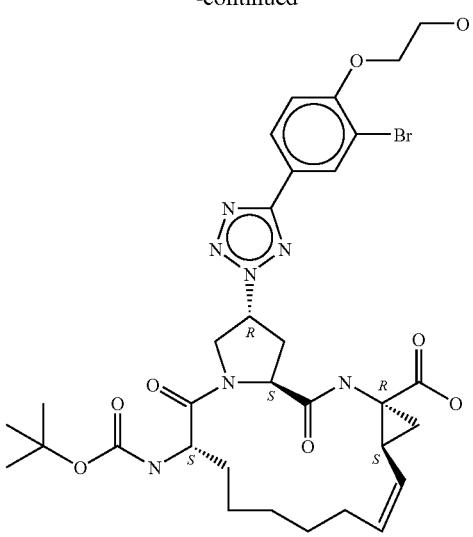
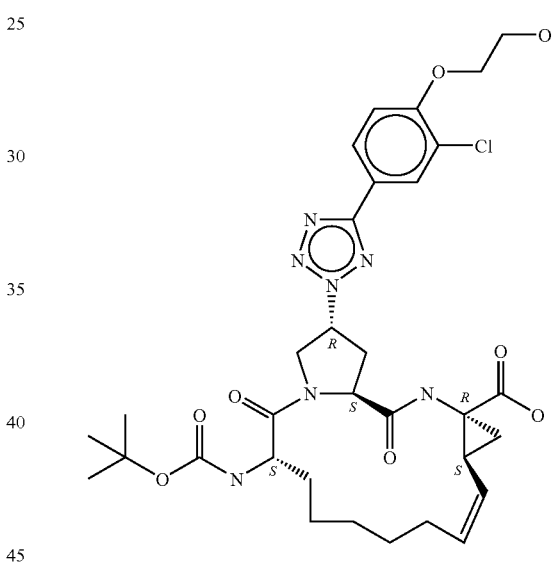
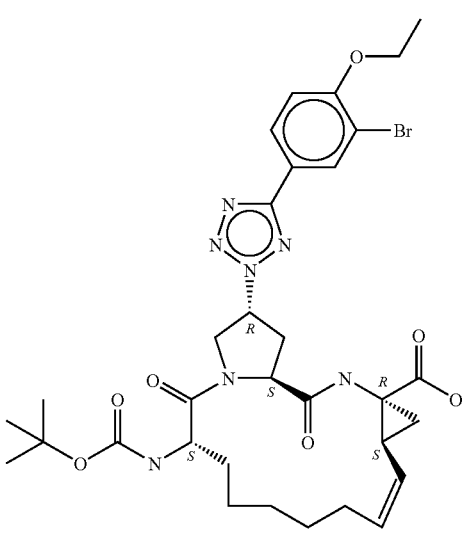

67
-continued
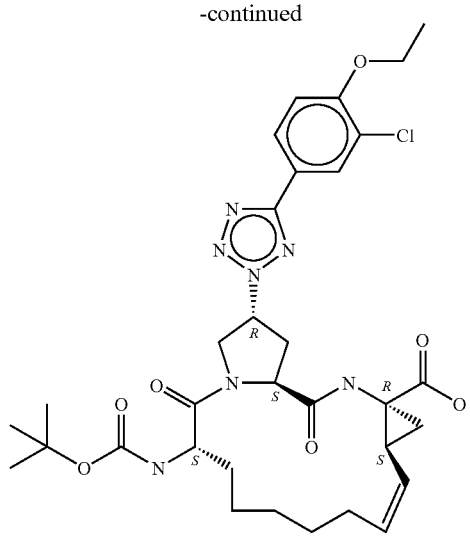
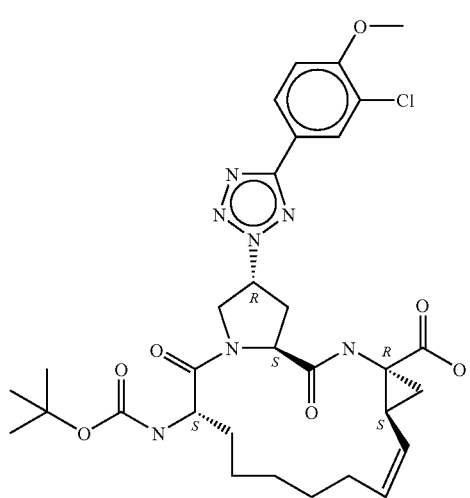
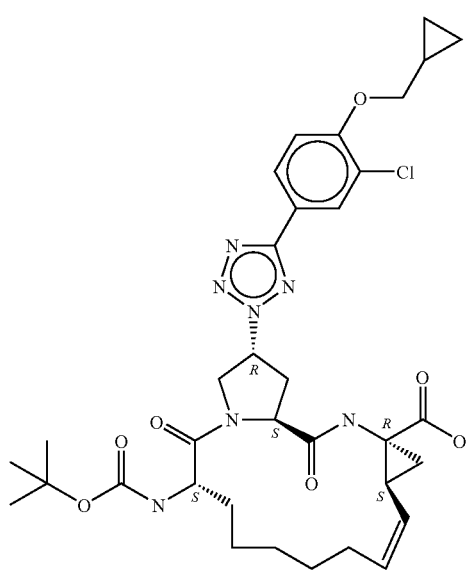
68
-continued
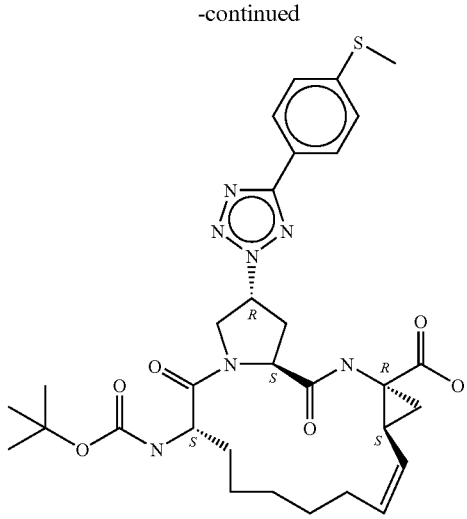
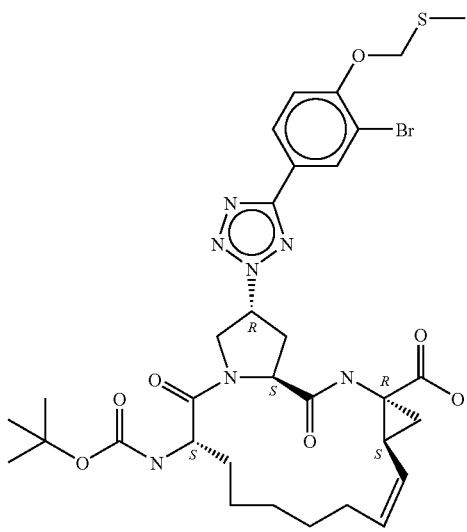
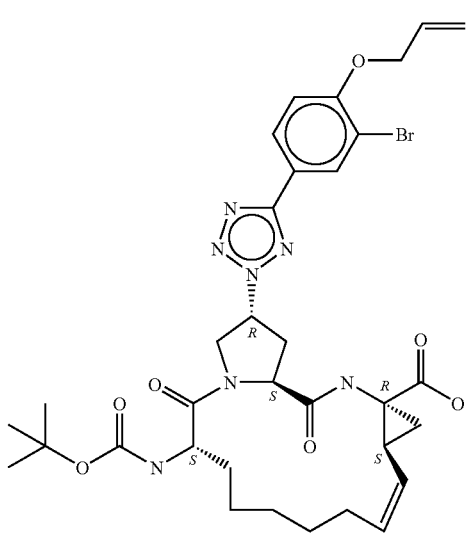

69
-continued
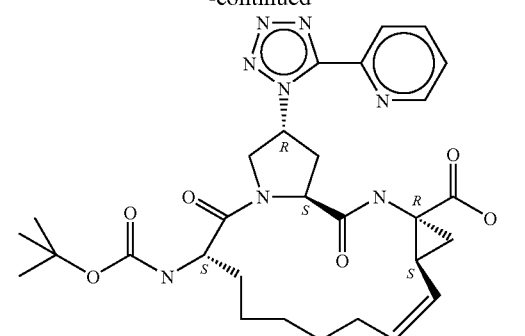
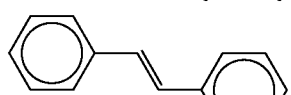
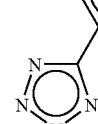
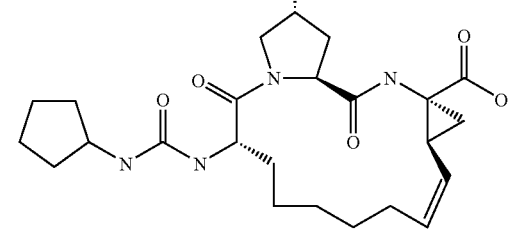
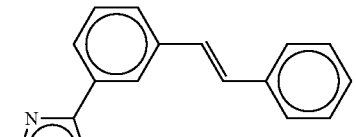
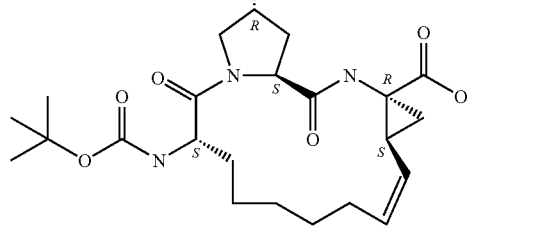
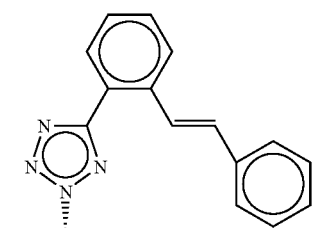
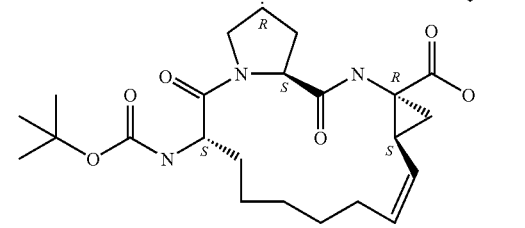
70
-continued
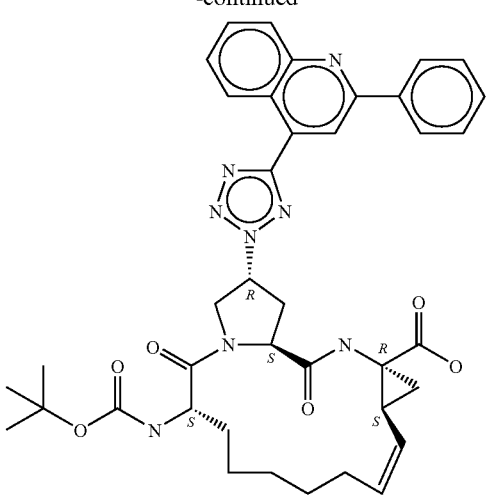
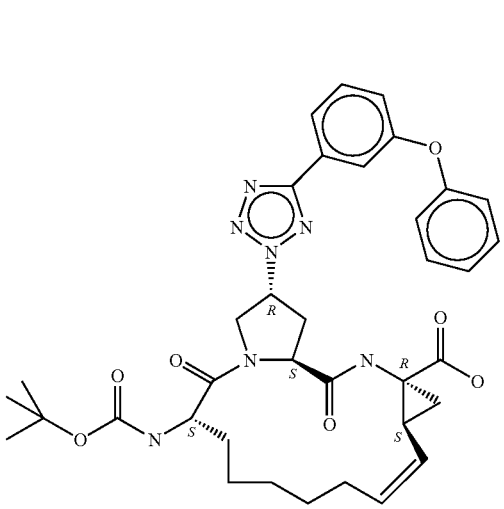

-continued

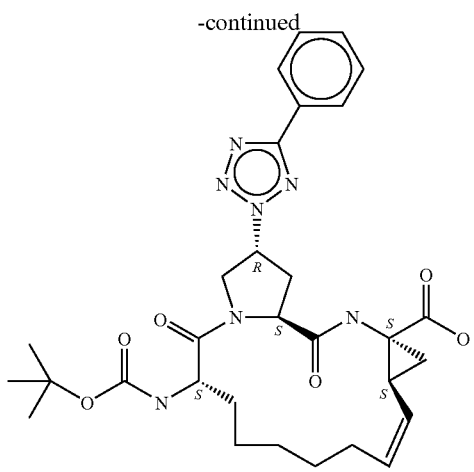

Another embodiment of the invention is a compound, or a pharmaceutically acceptable salt, ester or prodrug thereof, represented by Formula II as described above where W is a triazole or derivative thereof, in combination with a pharmaceutically acceptable carrier or excipient.

Another embodiment of the invention is a compound, or a pharmaceutically acceptable salt, ester or prodrug thereof, represented by Formula III as described above where W is a triazole or derivative thereof, in combination with a pharmaceutically acceptable carrier or excipient.

Exemplary triazole macrocyclic compounds and associated methods of the invention are disclosed in U.S. Provisional Patent application No. 60/560,712 (conversion of U.S. Ser. No. 10/360,947), filed Feb. 7, 2003. Representative subgenera of the invention include, but are not limited to:

A compound of Formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is selected from the group consisting of:

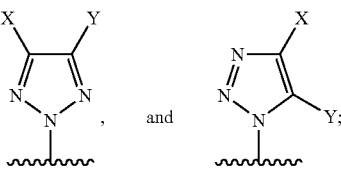

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula II, wherein A is —(C=O)—O-tert-butyl; G is hydroxyl; L is absent; W is selected from the group consisting of:

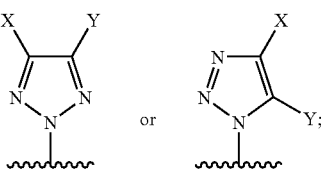

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

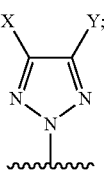

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula II, wherein A is —(C=O)—O-tert-butyl; G is hydroxyl; L is absent; W is

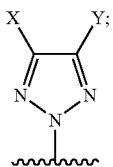

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula III, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is selected from the group consisting of:

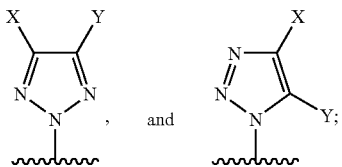

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula III, wherein A is —(C=O)—O-tert-butyl; G is hydroxyl; L is absent; W is selected from the group consisting of:

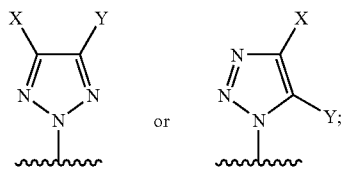

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen;

A compound of Formula II, wherein A is —(C=O)—O—$R^1$, $R^1$ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; G is hydroxyl; L is absent; W is

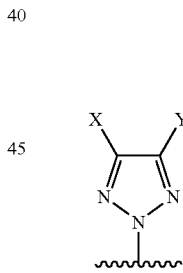

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen; and A compound of Formula II, wherein A is —(C=O)—O-tert-butyl; G is hydroxyl; L is absent; W is

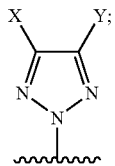

X and Y are independently selected from the group consisting of: H, halogen, $C_1$-$C_6$ alkyl, $C_3$-$C_{12}$ cycloalkyl, —$CH_2$-alkylamino, —$CH_2$-dialkylamino, —$CH_2$-arylamino, —$CH_2$-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, form a cyclic moiety selected from the group consisting of aryl, substituted aryl, heteroaryl, and substituted heteroaryl; j=3; m=s=1; and $R^3$ and $R^4$ are hydrogen.

Representative compounds of the invention include, but are not limited to, the following compounds:

TABLE 2

| Compounds of Formula II where m = s = 1 | | | | | |
|---|---|---|---|---|---|
| A | G | L | W | j | $R^3$, $R^4$ |
| tBOC | OH | absent | X = Y = phenyl (1,2,3-triazole, N2-linked) | 3 | $R^3 = R^4 =$ H; |
| tBOC | OH | absent | X = Y = phenyl (1,2,3-triazole, N1-linked) | 3 | $R^3 = R^4 =$ H. |
| tBOC | OH | absent | X = n-propyl; Y = phenyl | 3 | $R^3 = R^4 =$ H; |
| tBOC | OH | absent | X = m-methoxyphenyl; Y = p-methoxyphenyl | 3 | $R^3 = R^4 =$ H; |
| tBOC | OH | absent | X = m-bromophenyl; Y = p-methoxyphenyl | 3 | $R^3 = R^4 =$ H; |

TABLE 2-continued

| Compounds of Formula II where m = s = 1 | | | | | |
|---|---|---|---|---|---|
| A | G | L | W | j | R³, R⁴ |
| tBOC | OH | absent | 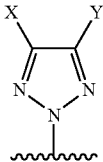<br>X = 1-napthyl;<br>Y = p-methoxyphenyl | 3 | R³ = R⁴ = H; |
| tBOC | OH | absent | 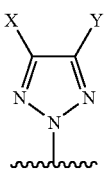<br>X = 2-thienyl;<br>Y = p-methoxyphenyl | 3 | R³ = R⁴ = H; |
| tBOC | OH | absent | 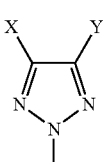<br>X = 3-thienyl;<br>Y = p-methoxyphenyl | 3 | R³ = R⁴ = H; |
| tBOC | OH | absent | 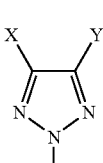<br>X = 4-pyrazolyl;<br>Y = p-methoxyphenyl | 3 | R³ = R⁴ = H; |
| tBOC | OH | absent | 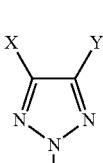<br>X = 3-pyridyl;<br>Y = p-methoxyphenyl | 3 | R³ = R⁴ = H; |
| tBOC | OH | absent | 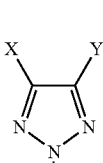<br>X = 2-pyridyl;<br>Y = p-methoxyphenyl | 3 | R³ = R⁴ = H; |

TABLE 2-continued

Compounds of Formula II where m = s = 1

| A | G | L | W | j | R³, R⁴ |
|---|---|---|---|---|---|
| tBOC | OH | absent | 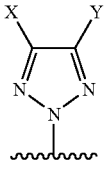<br>X = 2-thiazolyl;<br>Y = p-methoxyphenyl | 3 | R³ = R⁴ = H; |
| tBOC | OH | absent | 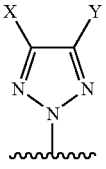<br>X = benzyl;<br>Y = phenyl | 3 | R³ = R⁴ = H; |
| tBOC | OH | absent | 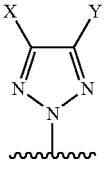<br>X = n-butyl;<br>Y = phenyl | 3 | R³ = R⁴ = H; |
| tBOC | OH | absent | 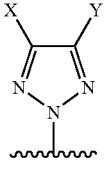<br>X = n-propyl;<br>Y = n-propyl | 3 | R³ = R⁴ = H; |
| tBOC | OH | absent | 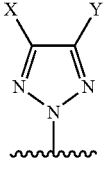<br>X = 4-(N,N-dimethylamino)phenyl;<br>Y = phenyl | 3 | R³ = R⁴ = H; |
| tBOC | OH | absent | 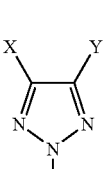<br>X = (N,N-diethylamino)methyl;<br>Y = phenyl | 3 | R³ = R⁴ = H; |

TABLE 2-continued

Compounds of Formula II where m = s = 1

| A | G | L | W | j | $R^3$, $R^4$ |
|---|---|---|---|---|---|
| tBOC | OH | absent | 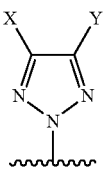<br>X = N,N-diethylaminocarbonyl;<br>Y = phenyl | 3 | $R^3 = R^4 =$ H; |
| tBOC | OH | absent | 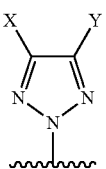<br>X = m-chlorophenyl;<br>Y = 4-ethoxyphenyl | 3 | $R^3 = R^4 =$ H; |
| tBOC | OH | absent | 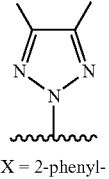<br>X = 2-phenyl-ethenyl;<br>Y = phenyl | 3 | $R^3 = R^4 =$ H; |
| tBOC | OH | absent | Benzotriazole | 3 | $R^3 = R^4 =$ H; |
| tBOC | OH | absent | 5,6-methylbenzotriazole | 3 | $R^3 = R^4 =$ H; and |
| tBOC | OH | absent | 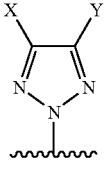<br>X = N-ethylamino-carbonyl;<br>Y = phenyl | 3 | $R^3 = R^4 =$ H; |
| —(CO=O)—O—$R^1$;<br>wherein $R^1$ = cyclopentyl | OH | absent | 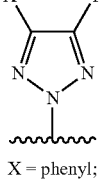<br>X = phenyl;<br>Y = phenyl | 3 | $R^3 = R^4 =$ H; |
| —(CO=O)—O—$R^1$;<br>wherein $R^1$ = cyclobutyl | OH | absent | 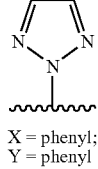<br>X = phenyl;<br>Y = phenyl | 3 | $R^3 = R^4 =$ H; |

TABLE 2-continued

| | | | Compounds of Formula II where m = s = 1 | | |
|---|---|---|---|---|---|
| A | G | L | W | j | $R^3, R^4$ |
| —(CO=O)—O—$R^1$; wherein $R^1$ = cyclohexyl | OH | absent | X—Y triazole (N-N-N), X = phenyl; Y = phenyl | 3 | $R^3 = R^4 =$ H; |
| —(C=O)—O—$R^1$; wherein $R^1$ = tetrahydrofuran-3-yl | OH | absent | X—Y triazole, X = phenyl; Y = phenyl | 3 | $R^3 = R^4 =$ H; |
| —(C=O)—O—$R^1$; wherein $R^1$ = tetrahydrofuran-3-yl | OH | absent | X—Y triazole, X = phenyl; Y = phenyl | 3 | $R^3 = R^4 =$ H; |
| —(C=O)—O—$R^1$; wherein $R^1$ = hexahydrofuro[3,2-b]furan-3-yl | OH | absent | X—Y triazole, X = phenyl; Y = phenyl | 3 | $R^3 = R^4 =$ H; |
| —(CO=O)—O—$R^1$; wherein $R^1$ = cyclopentyl | OH | absent | X—Y triazole, X = phenyl; Y = phenyl | 3 | $R^3 = R^4 =$ H; |
| —(CO=O)—O—NH—$R^2$; wherein $R^2$ = cyclopentyl | OH | absent | X—Y triazole, X = phenyl; Y = phenyl | 3 | $R^3 = R^4 =$ H; |

TABLE 2-continued

| | Compounds of Formula II where m = s = 1 | | | | | |
|---|---|---|---|---|---|---|
| A | G | L | W | j | R³, R⁴ | |
| wherein R² = cyclopentyl | OH | absent | triazole (X = phenyl; Y = phenyl) | 3 | R³ = R⁴ = H; |
| —S(O)₂—R²; wherein R² = cyclopentyl | OH | absent | triazole (X = phenyl; Y = phenyl) | 3 | R³ = R⁴ = H; |
| —(CO=O)—O—R¹; wherein R¹ = cyclopentyl | —O-phenethyl | absent | triazole (X = phenyl; Y = phenyl) | 3 | R3 = R4 = H |
| —(CO=O)—O—R¹; wherein R¹ = cyclopentyl | —NH-phenethyl | absent | triazole (X = phenyl; Y = phenyl) | 3 | R3 = R4 = H |
| —(CO=O)—O—R¹; wherein R¹ = cyclopentyl | —NHS(O)₂-phenethyl | absent | triazole (X = phenyl; Y = phenyl) | 3 | R3 = R4 = H |
| —(CO=O)—O—R¹; wherein R¹ = cyclopentyl | —(C=O)—OH | absent | triazole (X = phenyl; Y = phenyl) | 3 | R³ = R⁴ = H; |

TABLE 2-continued

| | | Compounds of Formula II where m = s = 1 | | | |
|---|---|---|---|---|---|
| A | G | L | W | j | $R^3, R^4$ |
| —(C=O)—O—$R^1$; wherein $R^1$ = cyclopentyl | —(C=O)—O-phenethyl | absent | 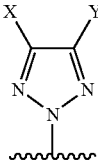<br>X = phenyl;<br>Y = phenyl | 3 | $R^3 = R^4 = H$ |
| —(C=O)—O—$R^1$; wherein $R^1$ = cyclopentyl | —(C=O)—NH-phenethy | absent | 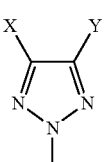<br>X = phenyl;<br>Y = phenyl | 3 | $R^3 = R^4 = H$; |
| —(C=O)—O—$R^1$; wherein $R^1$ = cyclopentyl | —(C=O)—NH—S(O)$_2$-benzyl | absent | 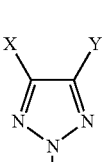<br>X = phenyl;<br>Y = phenyl | 3 | $R^3 = R^4 = H$; |
| tBOC | OH | —(C=O)CH$_2$— | 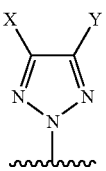<br>X = phenyl;<br>Y = phenyl | 1 | $R^3 = R^4 = H$; |
| tBOC | OH | —CH(CH$_3$)CH$_2$— | 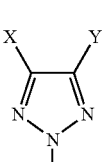<br>X = phenyl;<br>Y = phenyl | 1 | $R^3$ = methyl<br>$R^4$ = H |
| tBOC | OH | —O— | 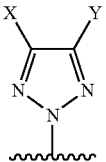<br>X = phenyl;<br>Y = phenyl | 0 | $R^3$ = methyl;<br>$R^4$ = H; |

TABLE 2-continued
Compounds of Formula II where m = s = 1
| A | G | L | W | j | R³, R⁴ |
|---|---|---|---|---|--------|
| tBOC | OH | —S— | 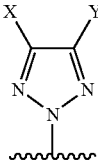 X = phenyl; Y = phenyl | 0 | R³ = methyl; R⁴ = H; |
| tBOC | OH | —S(O)— | 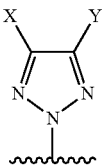 X = phenyl; Y = phenyl | 0 | R³ = methyl; R⁴ = H; |
| tBOC | OH | —S(O)₂— | 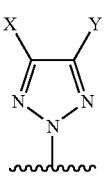 X = phenyl; Y = phenyl | 0 | R³ = methyl; R⁴ = H; |
| tBOC | OH | —SCH₂CH₂— | 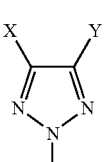 X = phenyl; Y = phenyl | 0 | R³ = R⁴ = CH₃; |
| tBOC | OH | —CF₂CH₂— | 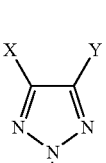 X = phenyl; Y = phenyl | 1 | R³ = R⁴ = H; |

TABLE 2-continued

| | | Compounds of Formula II where m = s = 1 | | | |
|---|---|---|---|---|---|
| A | G | L | W | j | R³, R⁴ |
| tBOC | OH | —CFHCH₂— | 4,5-diphenyl-2H-1,2,3-triazol-2-yl (X = phenyl; Y = phenyl) | 1 | R³ = R⁴ = H; |
| tBOC | OH | absent | 4,5-diphenyl-2H-1,2,3-triazol-2-yl (X = phenyl; Y = phenyl) | 3 | R³ = R⁴ = H; |
| tBOC | OH | absent | 5-bromo-4,6-dimethyl-2H-benzotriazol-2-yl | 3 | R³ = R⁴ = H; |
| tBOC | OH | absent | 4,5-dimethyl-6-(thiophen-3-yl)-2H-benzotriazol-2-yl | 3 | R³ = R⁴ = H; |
| tBOC | OH | absent | 2H-[1,2,3]triazolo[4,5-b]pyridin-2-yl | 3 | R³ = R⁴ = H. |

The following additional triazole macrocyclic molecules of the invention were made by the methods and procedures described herein. While stereochemistry is shown, the invention is not limited to the stereochemistry depicted. Those of ordinary skill in the art will readily appreciate that other isomers of these compounds are also within the scope of the invention.

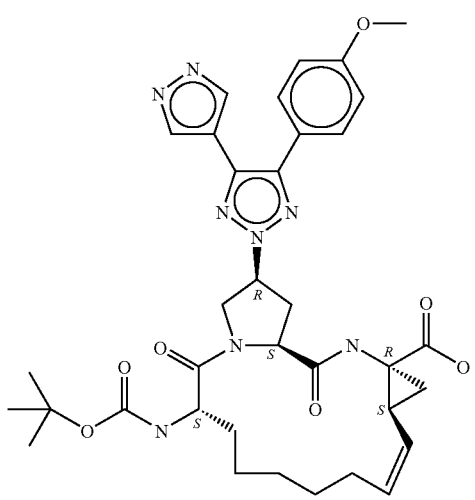

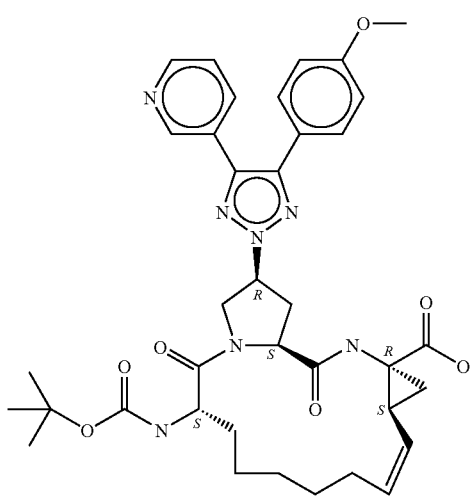

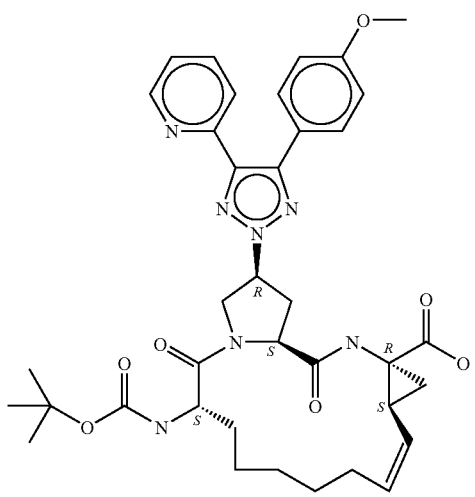

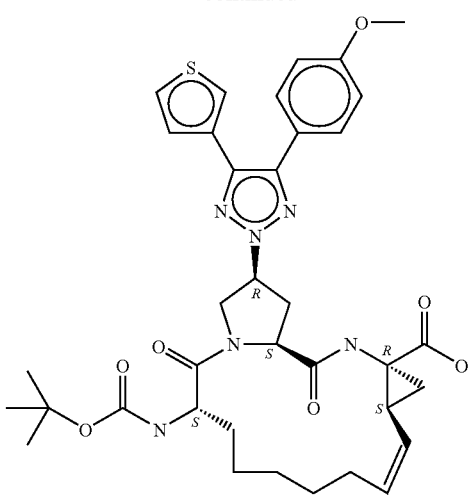

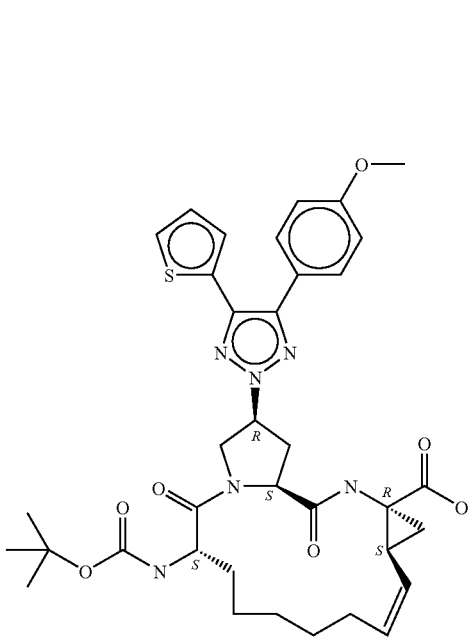

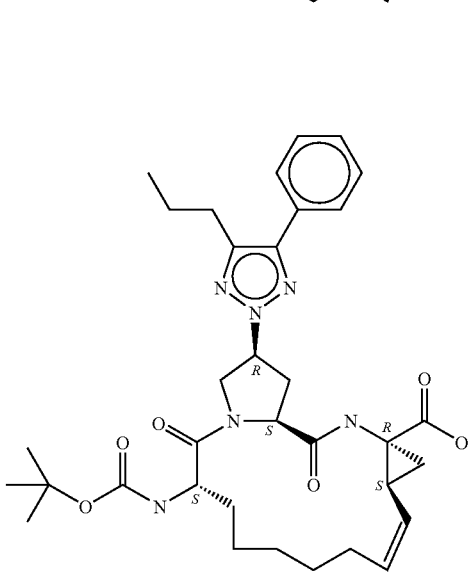

95
-continued
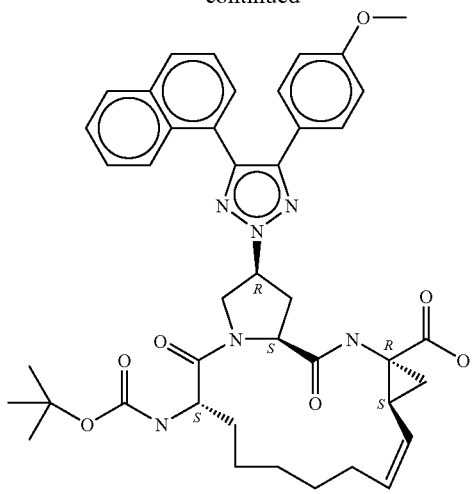
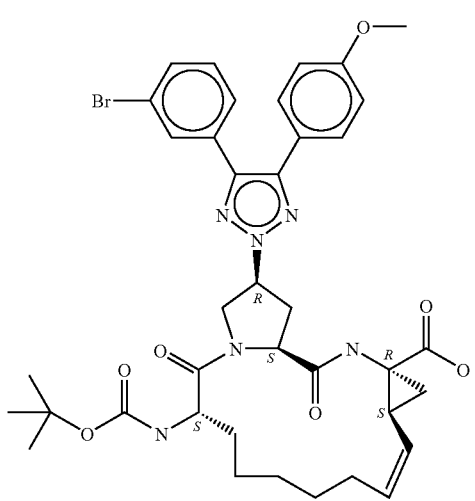
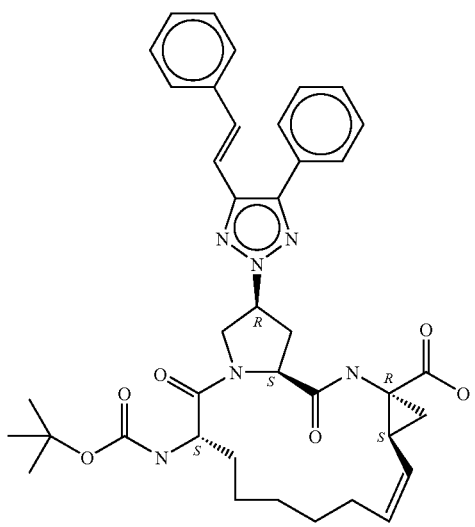
96
-continued
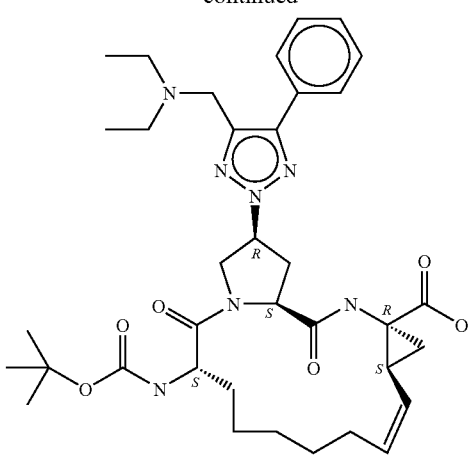
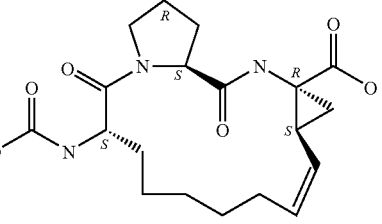
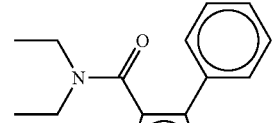
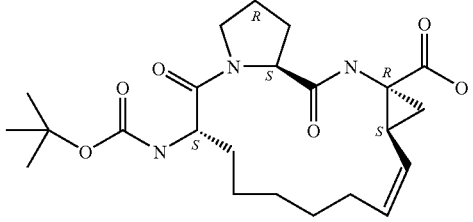

97
-continued
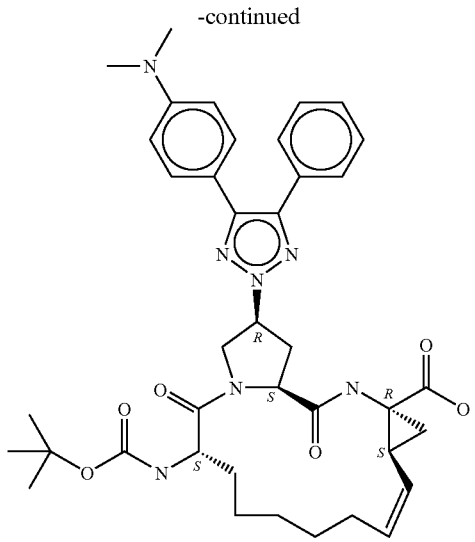
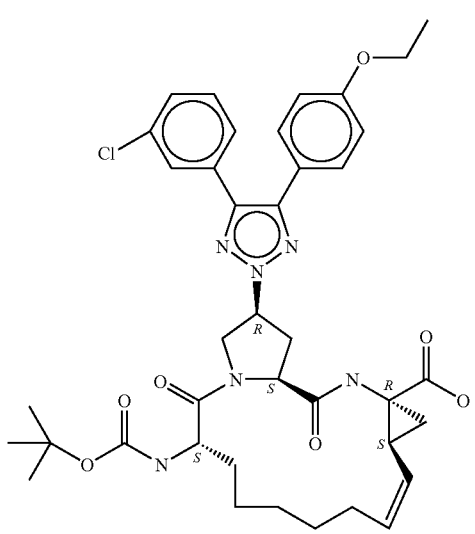
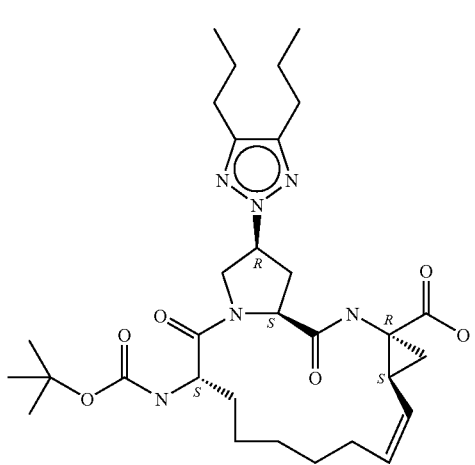
98
-continued
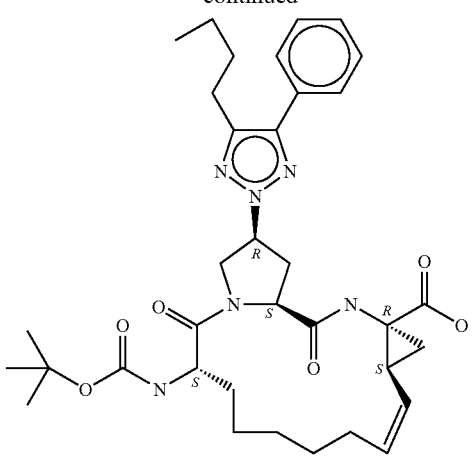
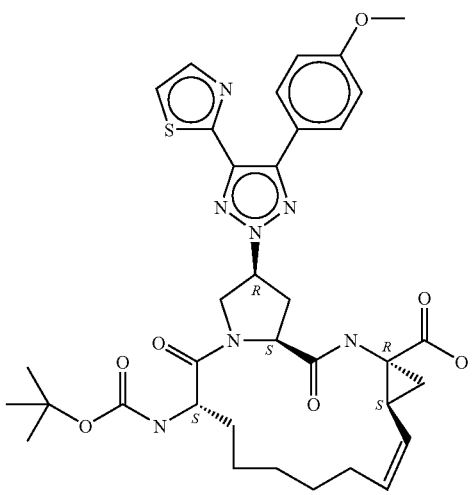
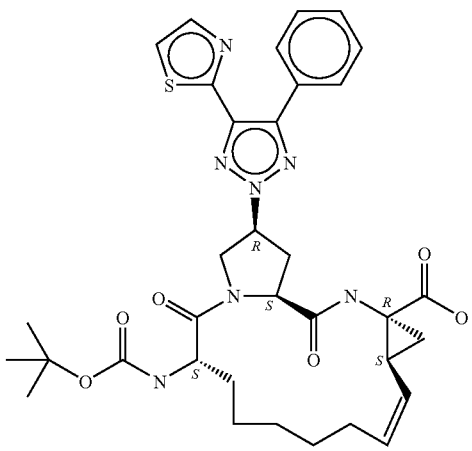

99
-continued
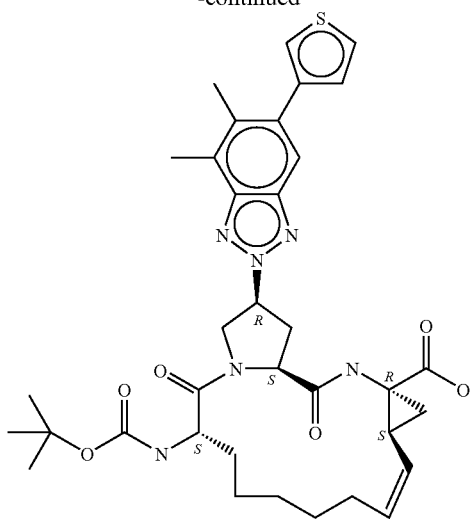
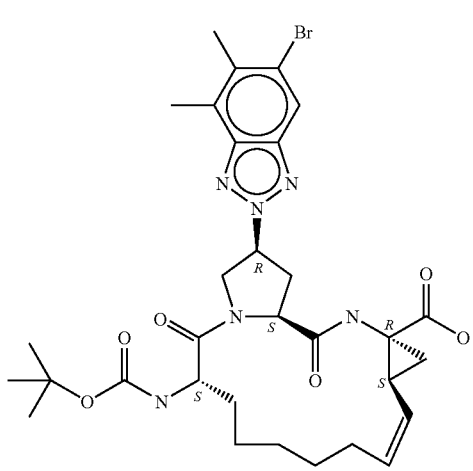
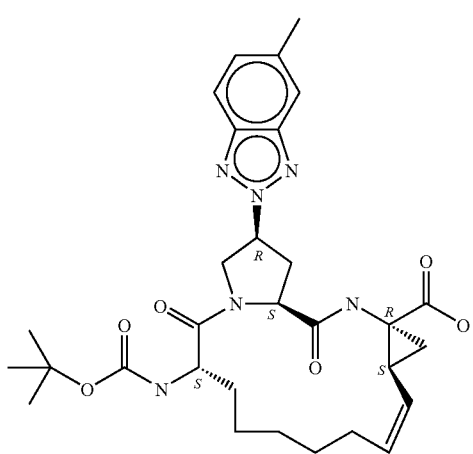
100
-continued
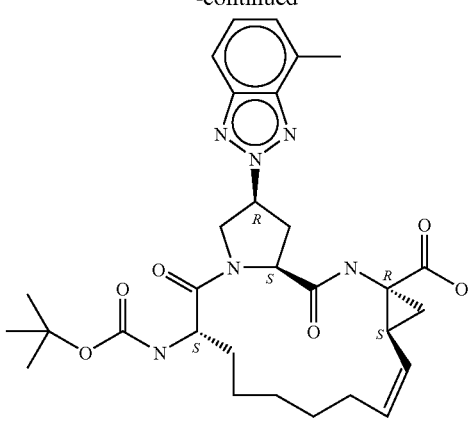
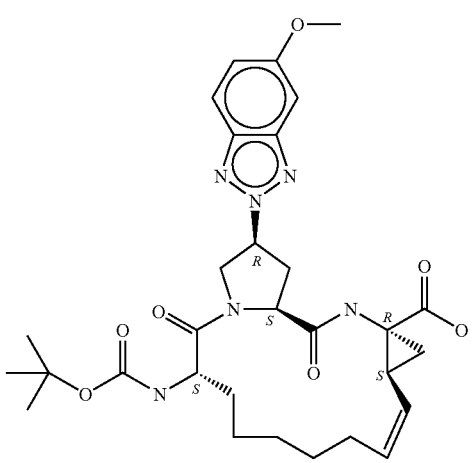
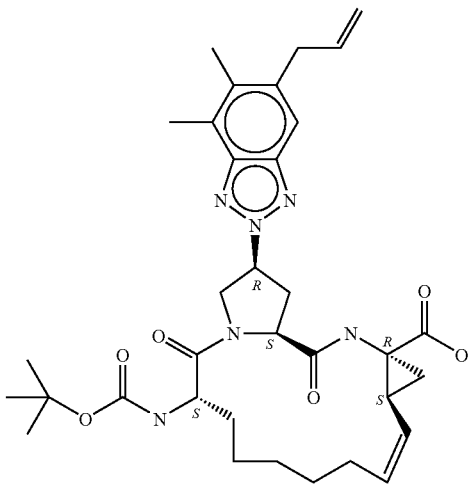

101
-continued
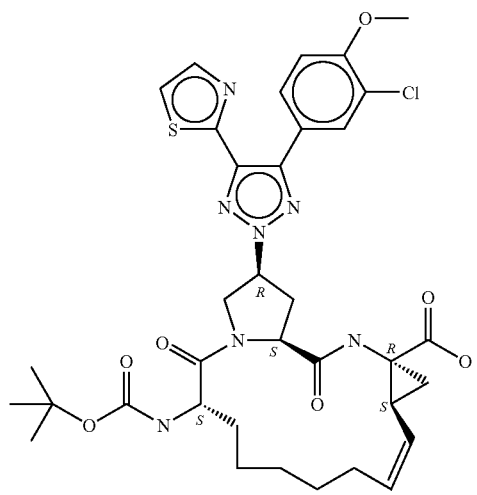
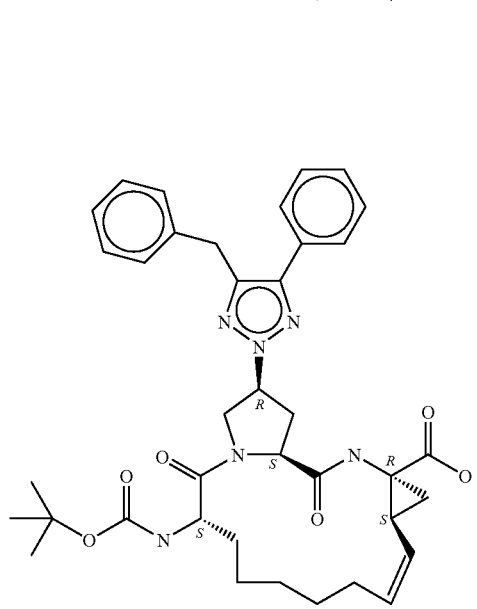
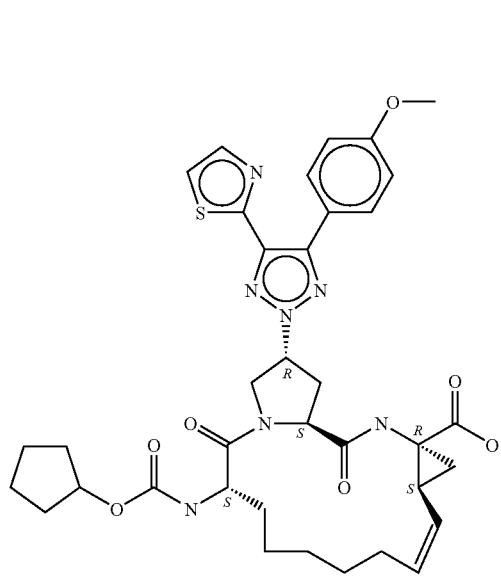
102
-continued
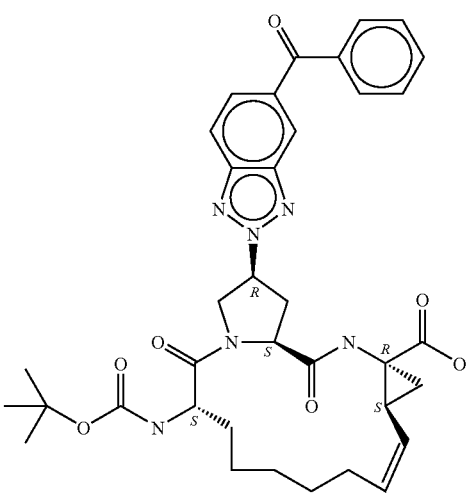
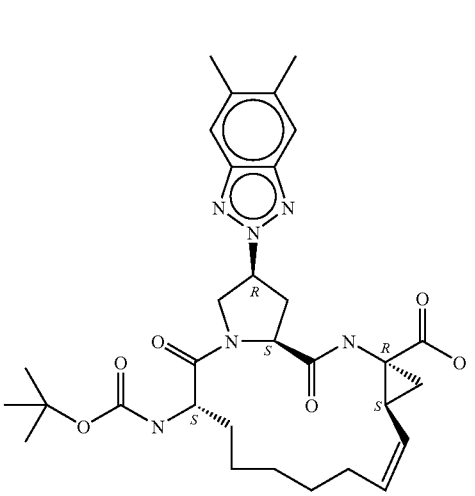
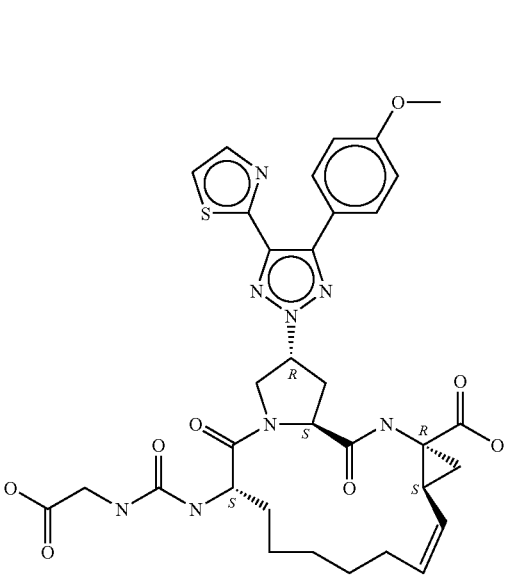

103
-continued
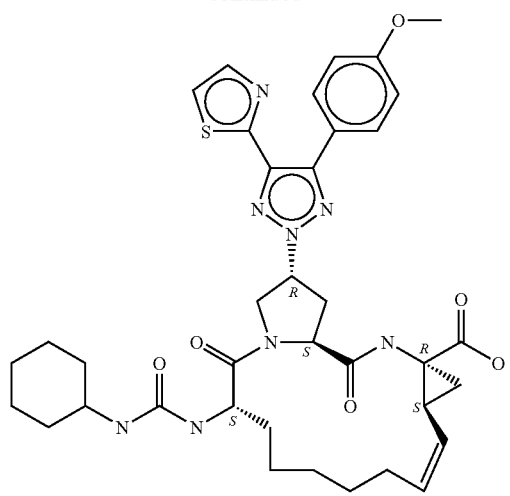
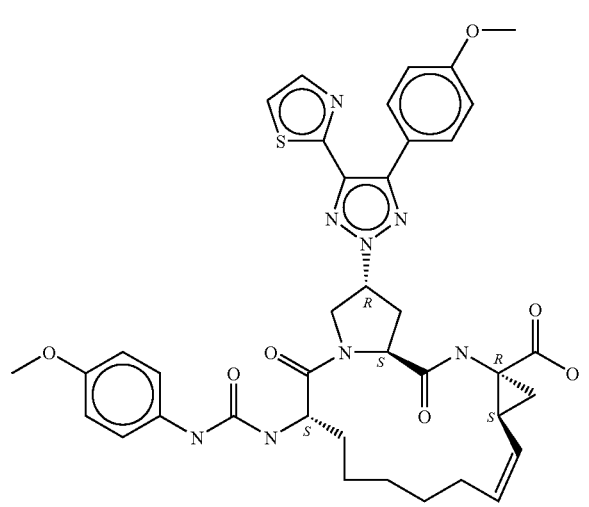
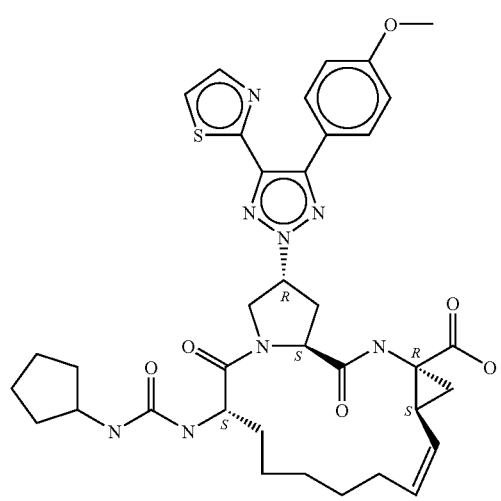
104
-continued
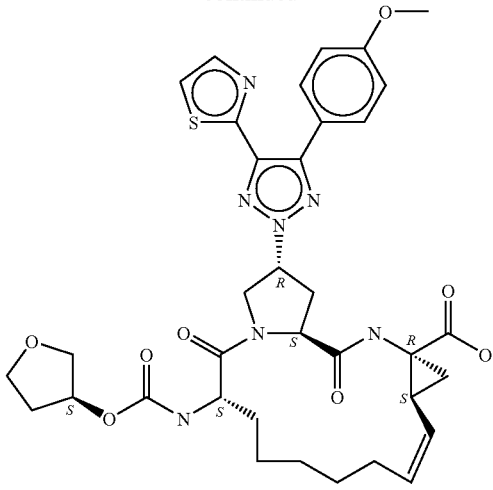
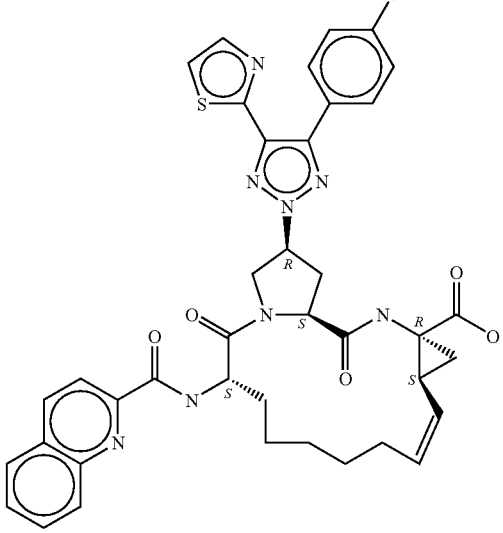
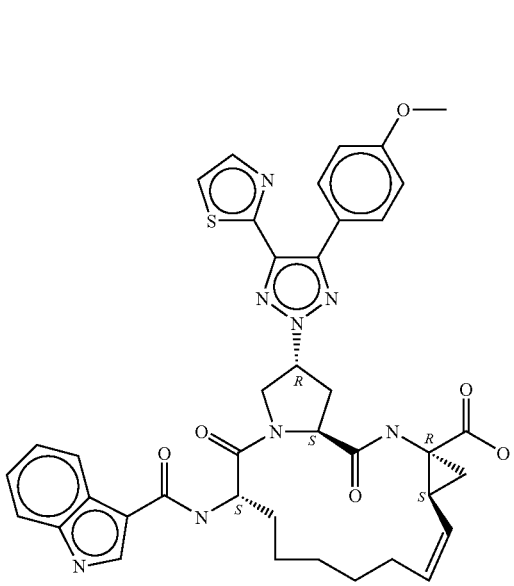

105
-continued
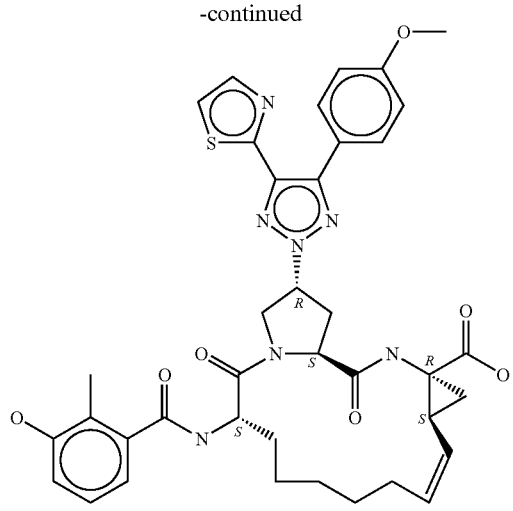
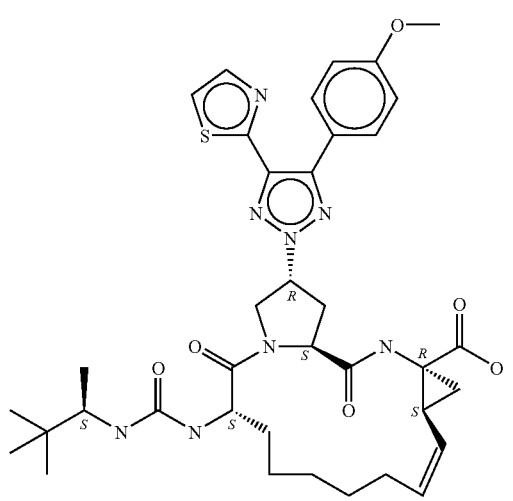
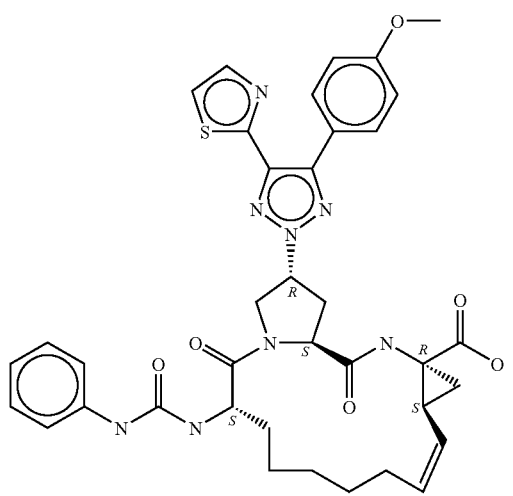
106
-continued
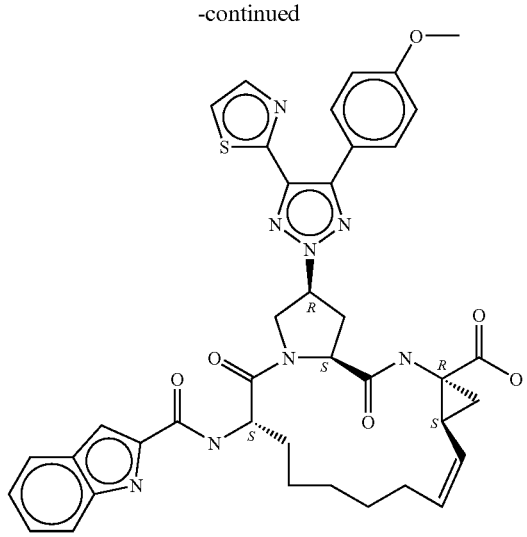
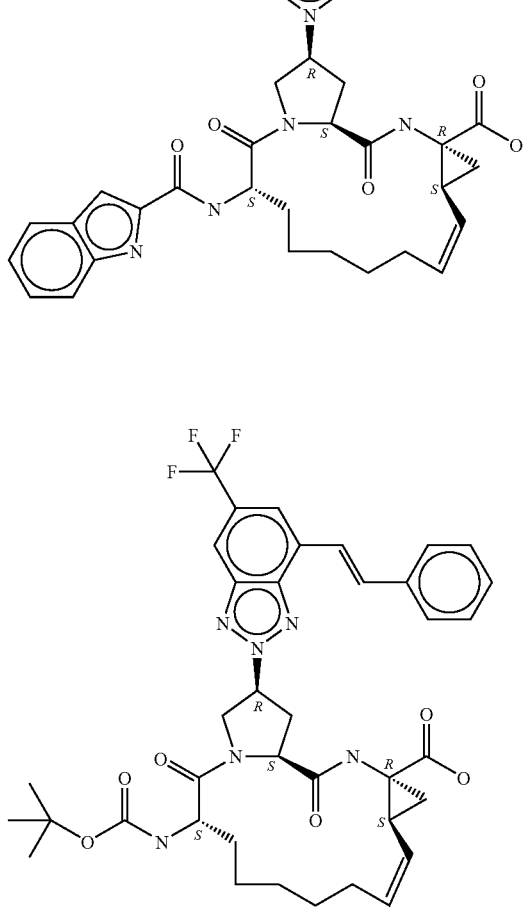
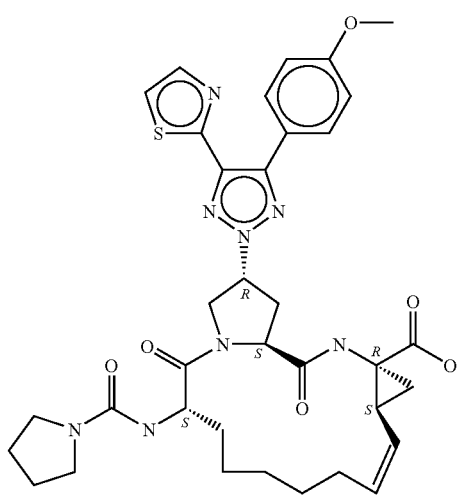

107
-continued
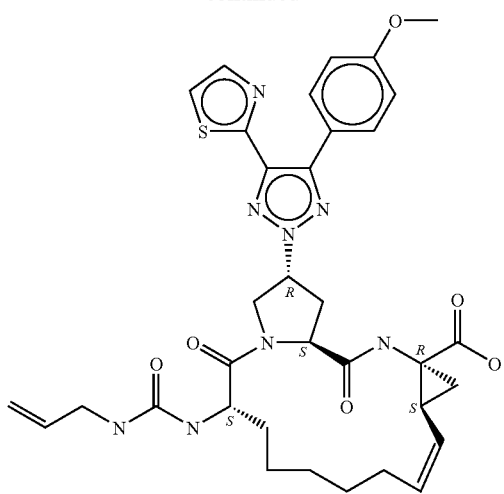
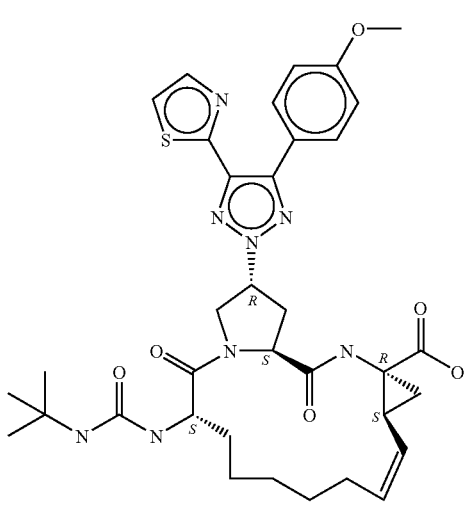
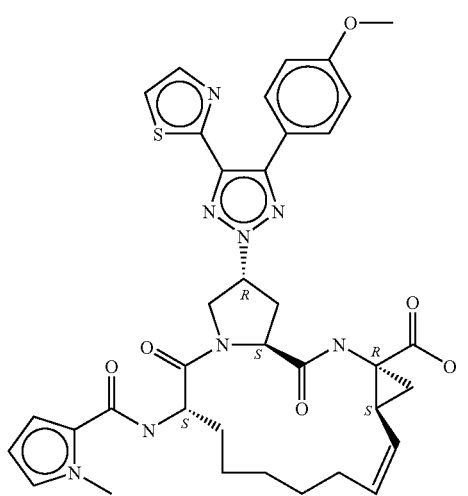
108
-continued
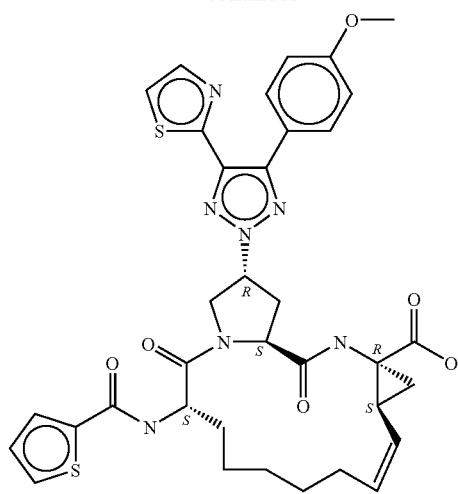
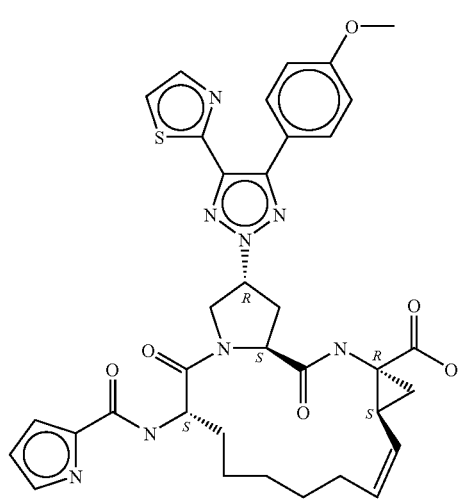
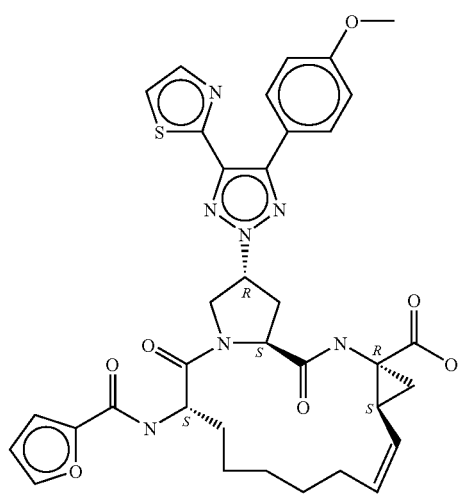

109
-continued
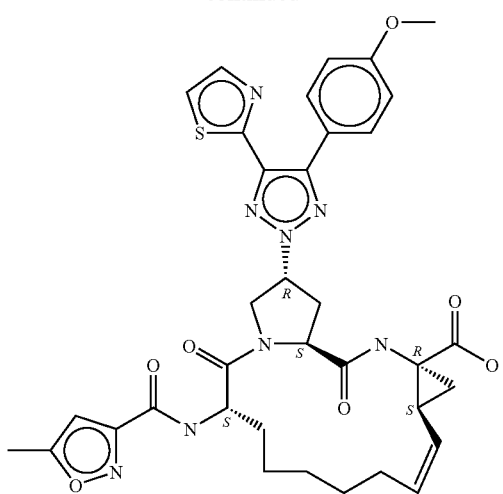
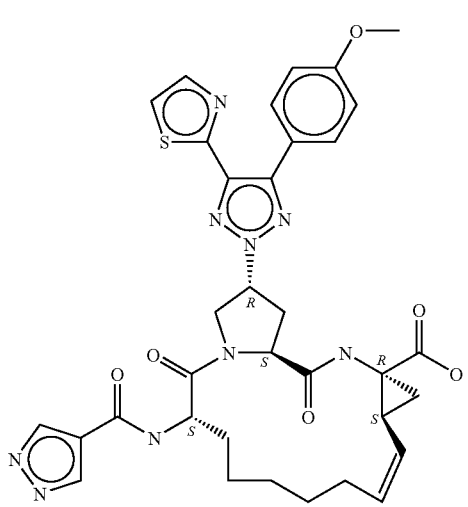
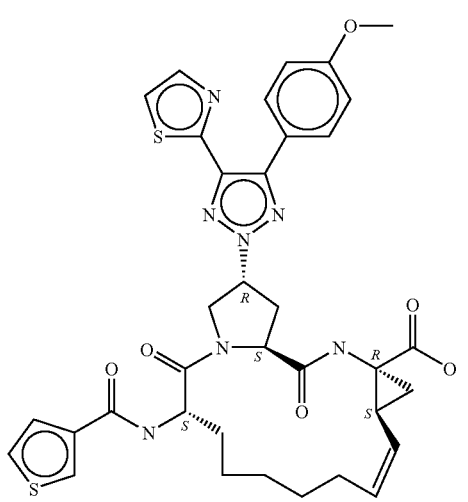
110
-continued
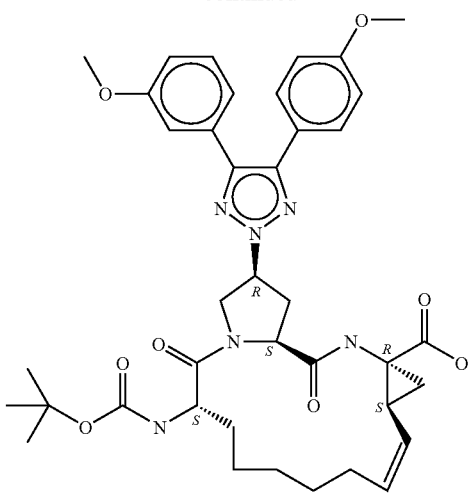
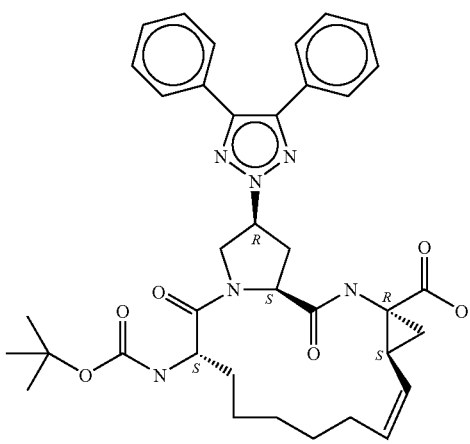
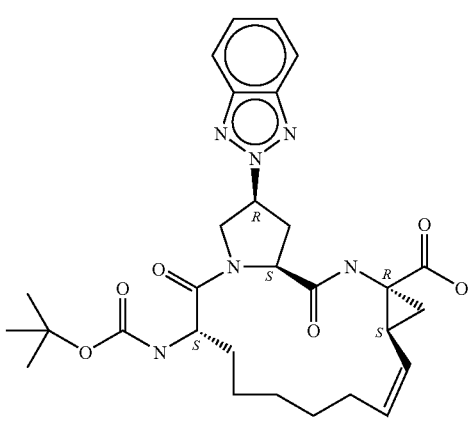

-continued

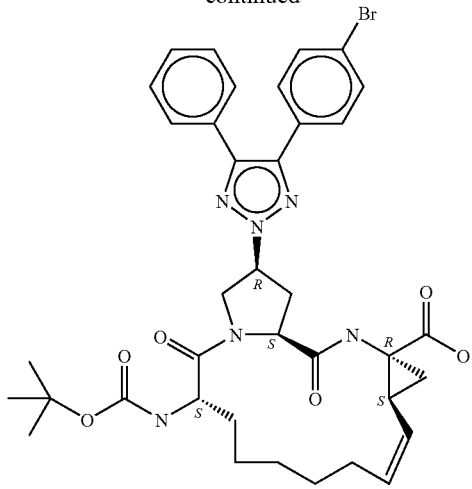

Another embodiment of the invention is a compound, or a pharmaceutically acceptable salt, ester or prodrug thereof, represented by Formula II as described above where W is a pyridazinone or derivative thereof, in combination with a pharmaceutically acceptable carrier or excipient.

Another embodiment of the invention is a compound, or a pharmaceutically acceptable salt, ester or prodrug thereof, represented by Formula III as described above where W is a pyridazinone or derivative thereof, in combination with a pharmaceutically acceptable carrier or excipient.

Exemplary pyridazinone macrocyclic compounds and associated methods of the invention are disclosed in U.S. Provisional Patent application No. 60/608,955 (conversion of U.S. Ser. No. 10/384,120), filed Mar. 7, 2003. Representative subgenera of the invention include, but are not limited to:

A compound of Formula II, wherein A is —(C=O)—O—$R^1$; G is hydroxyl; L is absent; j=3; m=s=1; W=

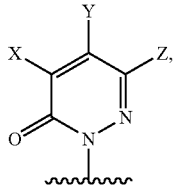

and $R^3$ and $R^4$ are hydrogen;

A compound of Formula II, wherein A is —(C=O)—O-tert-butyl; G is hydroxyl; L is absent; j=3; m=s=1; W=

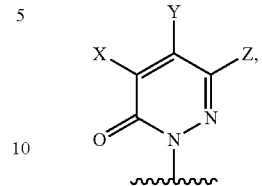

and $R^3$ and $R^4$ are hydrogen;

A compound of Formula III, wherein A is —(C=O)—O—$R^1$; L is absent; j=3; m=s=1; W=

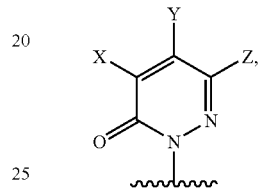

and $R^3$ and $R^4$ are hydrogen; and

A compound of Formula III, wherein A is —(C=O)—O-tert-butyl; G is hydroxyl; L is absent; j=3; m=s=1; W=

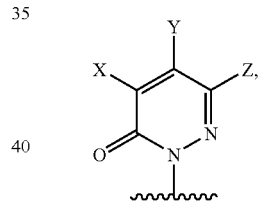

and $R^3$ and $R^4$ are hydrogen.

Representative compounds of the invention include, but are not limited to, the following compounds:

TABLE 3 compounds of formula II where W =

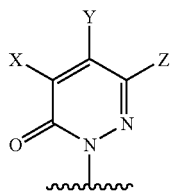

and m = s = 1

| A | G | L | X, Y | Z | j | $R^3$, $R^4$ |
|---|---|---|---|---|---|---|
| TBOC | OEt | absent | X = Y = bromo | Z = hydrogen | 3 | $R^3$ = hydrogen; |
| TBOC | OEt | absent | X = Y = | Z = hydrogen | 3 | $R^3$ = $R^4$ = |

TABLE 3-continued compounds of formula II where W =

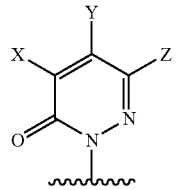

and m = s = 1

| A | G | L | X, Y | Z | j | $R^3, R^4$ |
|---|---|---|---|---|---|---|
| TBOC | OH | absent | X = Y = thiophen-3-yl | Z = hydrogen | 3 | $R^3 = R^4 =$ hydrogen; |
| TBOC | OH | absent | X = Y = phenyl | Z = hydrogen | 3 | $R^3 = R^4 =$ hydrogen; |
| TBOC | OH | absent | X = Y = 4-(N,N-dimethylamino)phenyl | Z = hydrogen | 3 | $R^3 = R^4 =$ hydrogen; |
| TBOC | OH | absent | X = Y = 4-(trifluoromethoxy)phenyl | Z = hydrogen | 3 | $R^3 = R^4 =$ hydrogen; |
| TBOC | OH | absent | X = Y = 4-(methanesulfonyl)phenyl | Z = hydrogen | 3 | $R^3 = R^4 =$ hydrogen; |
| TBOC | OH | absent | X = Y = 4-(cyano)phenyl | Z = hydrogen | 3 | $R^3 = R^4 =$ hydrogen; |
| TBOC | OH | absent | X = Y = 3-pyridyl | Z = hydrogen | 3 | $R^3 = R^4 =$ hydrogen; |
| TBOC | OH | absent | X = Y = 4-(morpholin-4-yl-methanonyl)phenyl | Z = hydrogen | 3 | $R^3 = R^4 =$ hydrogen; |
| TBOC | OH | absent | X = Y = bromo | Z = hydrogen | 3 | $R^3 = R^4 =$ hydrogen; |
| TBOC | OH | absent | X and Y taken together = phenyl | Z = 4-methoxyphenyl | 3 | $R^3 = R^4 =$ hydrogen; |
| TBOC | OH | absent | X and Y taken together = phenyl | Z = 4-chlorophenyl | 3 | $R^3 = R^4 =$ hydrogen; |
| TBOC | OH | absent | X = 4-fluorophenyl Y = hydrogen | Z = phenyl | 3 | $R^3 = R^4 =$ hydrogen; |
| TBOC | OH | absent | X = hydrogen Y = 1-piperidyl | Z = phenyl | 3 | $R^3 = R^4 =$ hydrogen; |
| TBOC | OEt | absent | X = hydrogen Y = bromo | Z = phenyl | 3 | $R^3 = R^4 =$ hydrogen; |
| TBOC | OH | absent | X = hydrogen Y = thiophen-3-yl | Z = phenyl | 3 | $R^3 = R^4 =$ hydrogen; |
| TBOC | OEt | absent | X = bromo Y = pyrrolid-1-yl | Z = hydrogen | 3 | $R^3 = R^4 =$ hydrogen; |
| TBOC | OH | absent | X = thiophen-3-yl Y = pyrrolid-1-yl | Z = hydrogen | 3 | $R^3 = R^4 =$ hydrogen; |
| TBOC | OEt | absent | X = bromo Y = azido | Z = hydrogen | 3 | $R^3 = R^4 =$ hydrogen; |
| TBOC | OEt | absent | X = thiophen-3-yl Y = azido | Z = hydrogen | 3 | $R^3 = R^4 =$ hydrogen; |
| TBOC | OH | absent | X = thiophen-3-yl Y = azido | Z = hydrogen | 3 | $R^3 = R^4 =$ hydrogen; |
| TBOC | OH | absent | X = thiophen-3-yl Y = tetrazol-2-yl | Z = hydrogen | 3 | $R^3 = R^4 =$ hydrogen; |
| TBOC | OH | absent | X = Y = mercapto-2-pyrimidine | Z = hydrogen | 3 | $R^3 = R^4 =$ hydrogen; |
| TBOC | OH | absent | X = bromo Y = | Z = hydrogen | 3 | $R^3 = R^4 =$ hydrogen; |

TABLE 3-continued compounds of formula II where W =

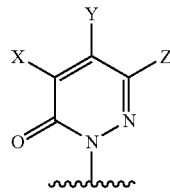

and m = s = 1

| A | G | L | X, Y | Z | j | $R^3$, $R^4$ |
|---|---|---|---|---|---|---|
| | | | mercapto-2-pyrimidine | | | |
| TBOC | OH | absent | X = thiophen-3-yl<br>Y = mercapto-2-pyrimidine | Z = hydrogen | 3 | $R^3 = R^4 =$ hydrogen; |
| TBOC | OH | absent | X = Y = thiazol-2-yl | Z = hydrogen | 3 | $R^3 = R^4 =$ hydrogen; |
| TBOC | OH | absent | X = Y = imidazol-1-yl | Z = hydrogen | 3 | $R^3 = R^4 =$ hydrogen; |
| TBOC | OH | absent | X = 2-(cyclopropylamino)-thiazol-4-yl<br>Y = 4-methoxyphenyl | Z = hydrogen | 3 | $R^3 = R^4 =$ hydrogen; |
| TBOC | OH | absent | X and Y taken together = 6-methoxy-isoquinolinyl | Z = hydrogen | 3 | $R^3 = R^4 =$ hydrogen; |
| —(C═O)—O—$R^1$ Wherein $R^1$ = cyclopentyl | OH | absent | X = Y = thiophen-3-yl | Z = hydrogen | 3 | $R^3 = R^4 =$ hydrogen; |
| —(C═O)—O—$R^1$ wherein $R^1$ = cyclobutyl | OH | absent | X = Y = thiophen-3-yl | Z = hydrogen | 3 | $R^3 = R^4 =$ hydrogen; |
| —(C═O)—O—$R^1$ wherein $R^1$ = cyclohexyl | OH | absent | X = Y = thiophen-3-yl | Z = hydrogen | 3 | $R^3 = R^4 =$ hydrogen; |
| —(C═O)—O—$R^1$ where $R^1$ = (tetrahydrofuran-3-yl, racemic) | OH | absent | X = Y = thiophen-3-yl | Z = hydrogen | 3 | $R^3 = R^4 =$ hydrogen; |
| —(C═O)—O—$R^1$ where $R^1$ = (tetrahydrofuran-3-yl) | OH | absent | X = Y = thiophen-3-yl | Z = hydrogen | 3 | $R^3 = R^4 =$ hydrogen; |
| —(C═O)—O—$R^1$ where $R^1$ = (hexahydrofuro[2,3-b]furan-3-yl) | OH | absent | X = Y = thiophen-3-yl | Z = hydrogen | 3 | $R^3 = R^4 =$ hydrogen; |

TABLE 3-continued compounds of formula II where W =

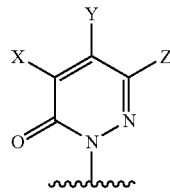

and m = s = 1

| A | G | L | X, Y | Z | j | $R^3$, $R^4$ |
|---|---|---|---|---|---|---|
| TBOC | OH | —(C=O)CH$_2$— | X = Y = thiophen-3-yl | Z = hydrogen | 1 | $R^3$ = $R^4$ = hydrogen; |
| TBOC | OH | —CH(CH$_3$)CH$_2$— | X = Y = thiophen-3-yl | Z = hydrogen | 1 | $R^3$ = methyl $R^4$ = hydrogen |
| TBOC | OH | —O— | X = Y = thiophen-3-yl | Z = hydrogen | 0 | $R^3$ = methyl and $R^4$ = hydrogen |
| TBOC | OH | —S— | X = Y = thiophen-3-yl | Z = hydrogen | 0 | $R^3$ = methyl and $R^4$ = hydrogen |
| TBOC | OH | —S(O)— | X = Y = thiophen-3-yl | Z = hydrogen | 2 | $R^3$ = methyl and $R^4$ = hydrogen |
| TBOC | OH | —S(O)$_2$— | X = Y = thiophen-3-yl | Z = hydrogen | 2 | $R^3$ = methyl and $R^4$ = hydrogen |
| TBOC | OH | —SCH$_2$CH$_2$— | X = Y = thiophen-3-yl | Z = hydrogen | 0 | $R^3$ = $R^4$ = CH$_3$; |
| TBOC | OH | —CF$_2$CH$_2$— | X = Y = thiophen-3-yl | Z = hydrogen | 1 | $R^3$ = $R^4$ = hydrogen; |
| TBOC | OH | —CFHCH$_2$— | X = Y = thiophen-3-yl | Z = hydrogen | 1 | $R^3$ = $R^4$ = hydrogen; |
| —(C=O)—O—$R^1$ $R^1$ = cyclopentyl | —O-phenethyl | absent | X = Y = thiophen-3-yl | Z = hydrogen | 3 | $R^3$ = $R^4$ = hydrogen; |
| —(C=O)—O—$R^1$ $R^1$ = cyclopentyl | —NH-phenethyl | absent | X = Y = thiophen-3-yl | Z = hydrogen | 3 | $R^3$ = $R^4$ = hydrogen; |
| —(C=O)—O—$R^1$ $R^1$ = cyclopentyl | —NHS(O)$_2$-phenethyl | absent | X = Y = thiophen-3-yl | Z = hydrogen | 3 | $R^3$ = $R^4$ = hydrogen; |
| —(C=O)—O—$R^1$ $R^1$ = cyclopentyl | —(C=O)—OH | absent | X = Y = thiophen-3-yl | Z = hydrogen | 3 | $R^3$ = $R^4$ = hydrogen; |
| —(C=O)—O—$R^1$ $R^1$ = cyclopentyl | —(C=O)—O-phenethyl | absent | X = Y = thiophen-3-yl | Z = hydrogen | 3 | $R^3$ = $R^4$ = hydrogen; |
| —(C=O)—O—$R^1$ $R^1$ = cyclopentyl | —(C=O)—NH-phenethyl | absent | X = Y = thiophen-3-yl | Z = hydrogen | 3 | $R^3$ = $R^4$ = hydrogen; |
| —(C=O)—O—$R^1$ $R^1$ = cyclopentyl | —(C=O)—NH—S(O)$_2$-benzyl | absent | X = Y = thiophen-3-yl | Z = hydrogen | 3 | $R^3$ = $R^4$ = hydrogen. |

The following additional pyridazinone macrocyclic molecules of the invention were made by the methods and procedures described herein. While stereochemistry is shown, the invention is not limited to the stereochemistry depicted. Those of ordinary skill in the art will readily appreciate that other isomers of these compounds are also within the scope of the invention.

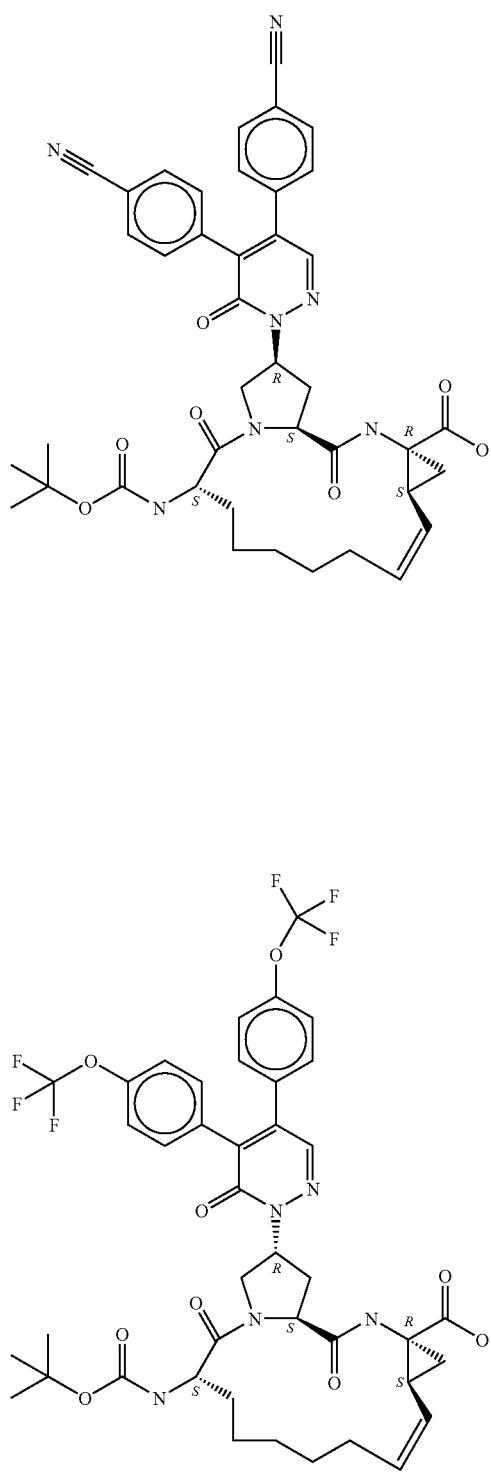

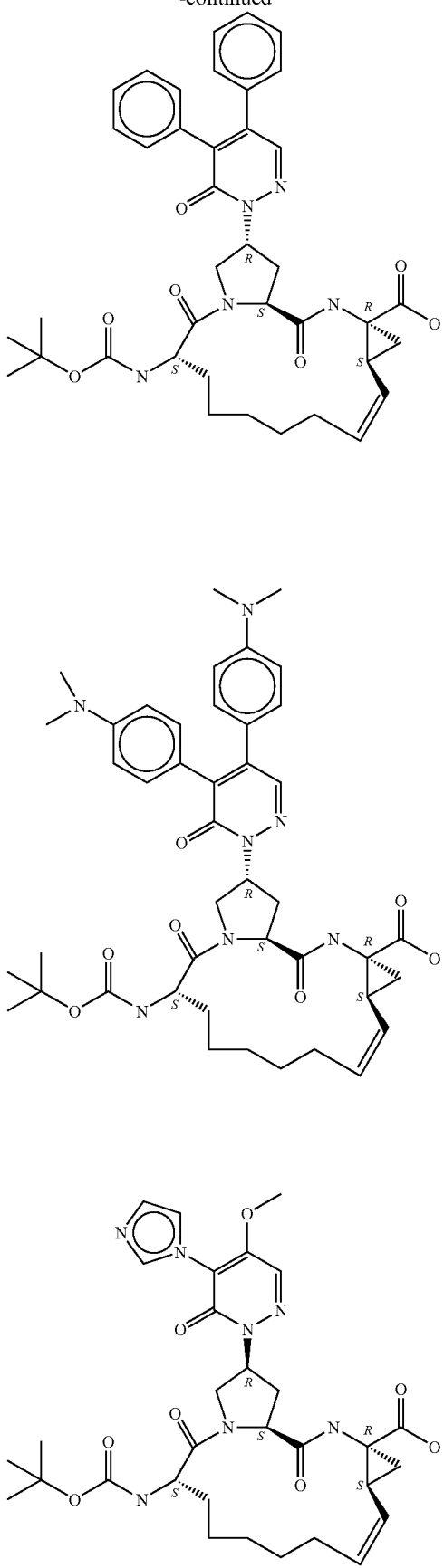

121
-continued
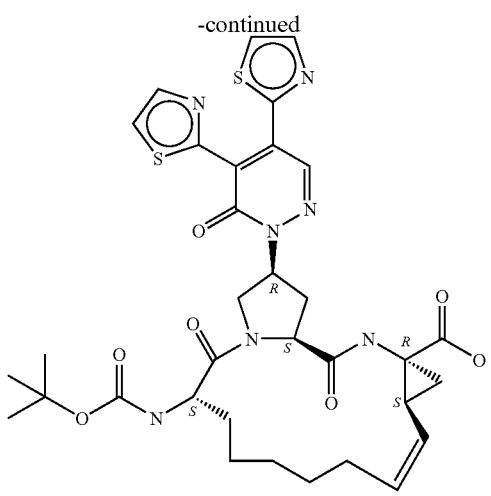
122
-continued
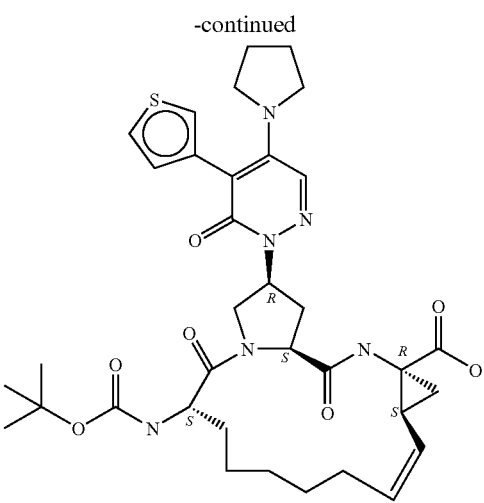
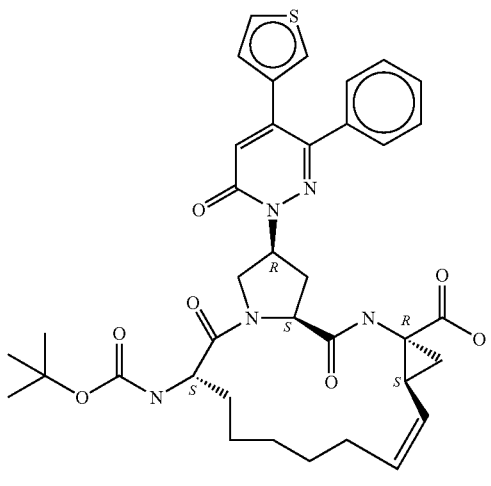
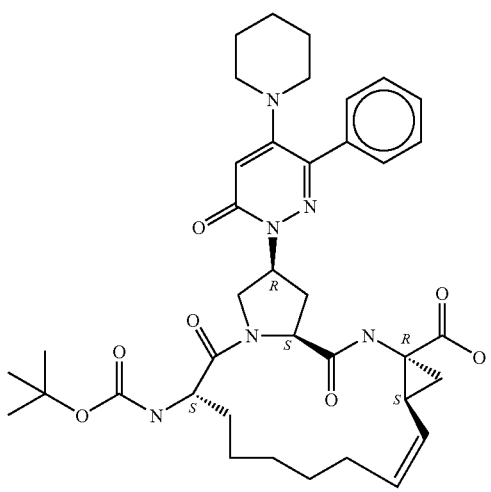
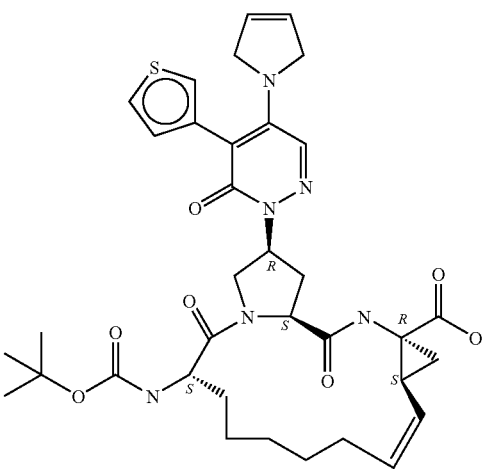

123
-continued
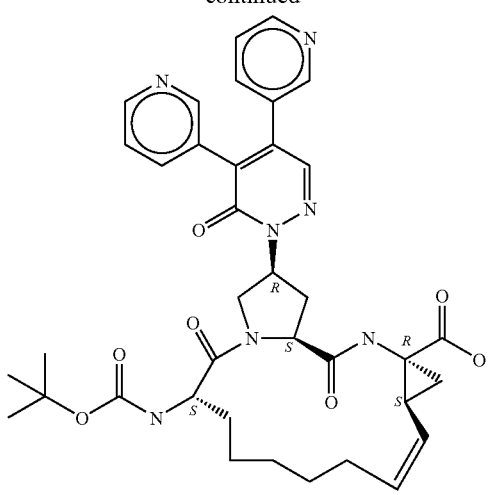
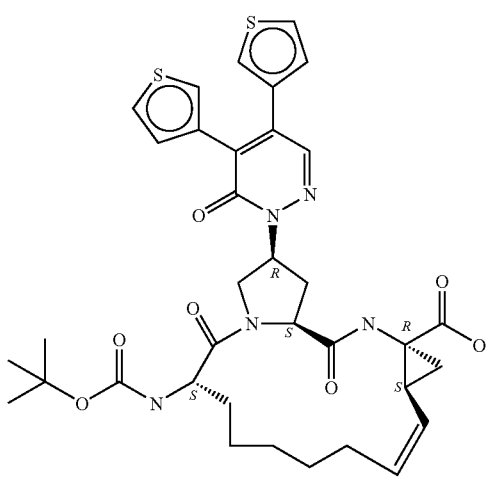
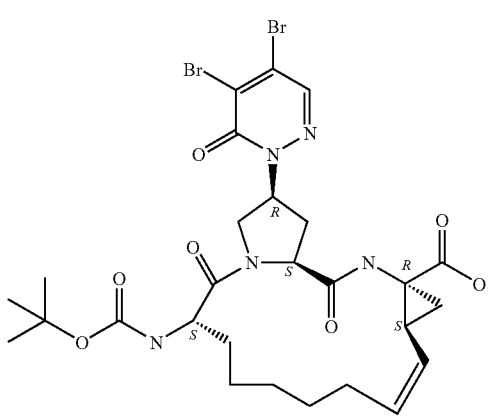
124
-continued
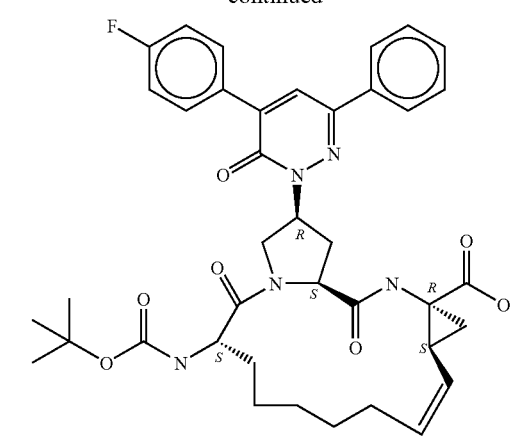
Additional compounds of the invention are those of formula I, II or II, wherein W is a substituted benzimidazolyl, including those wherein the benzimidazolyl is substituted with 1 or 2 heteroaryl groups, each of which may be independently substituted. Examples of such compounds include:
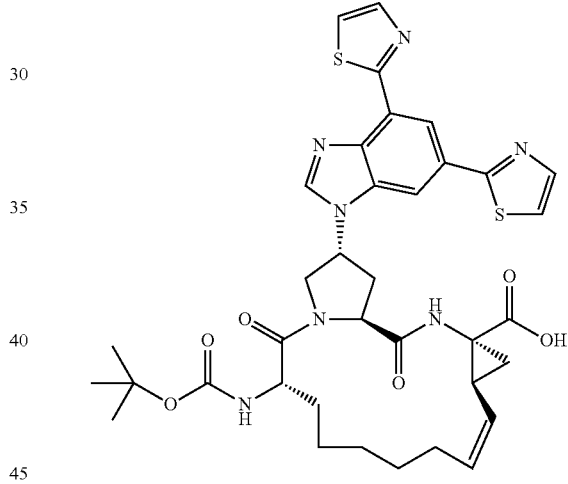
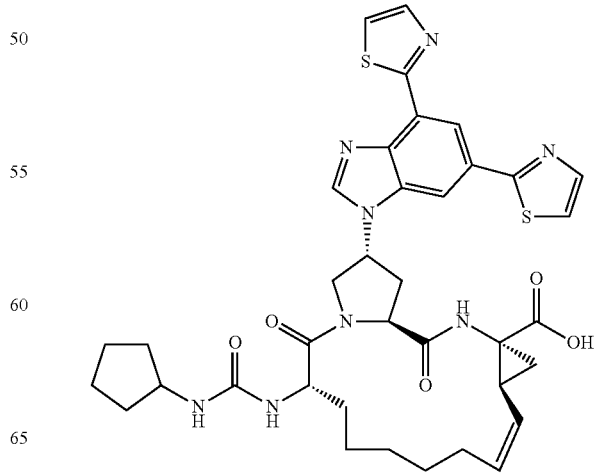

-continued

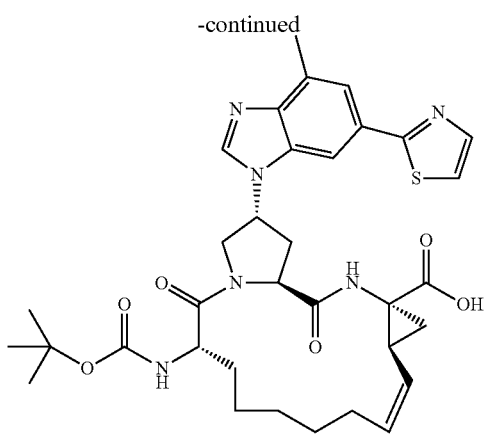

According to an alternate embodiment, the pharmaceutical compositions of the present invention may further contain other anti-HCV agents. Examples of anti-HCV agents include, but are not limited to, α-interferon, β-interferon, ribavirin, and amantadine.

According to an additional alternate embodiment, the pharmaceutical compositions of the present invention may further contain other HCV protease inhibitors.

According to yet another alternate embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to a further embodiment, the present invention includes methods of treating hepatitis C infections in a subject in need of such treatment by administering to said subject an anti-HCV virally effective amount of the pharmaceutical compounds or compositions of the present invention. The methods can further include administration of an additional therapeutic agent, including another antiviral agent or an anti-HCV agent. The additional agent can be co-administered, concurrently administered or sequentially administered with the compound or composition delineated herein. The methods herein can further include the step of identifying that the subject is in need of treatment for hepatitis C infection. The identification can be by subjective (e.g., health care provider determination) or objective (e.g., diagnostic test) means.

All references, including patents, patent publications, articles, texts, etc. disclosed throughout this specification are hereby incorporated by reference in their entirety.

DEFINITIONS

The following definitions of various terms and phrases used to describe the invention are consistent with their normal use in the art and apply to the terms as they are used throughout this specification and claims unless otherwise limited in specific instances, either individually or as part of a larger group.

The term "$C_x$-$C_y$," as used herein, is used in conjunction with the name of a carbon-containing group to indicate that the group contains from x to y carbon atoms where x and y are whole numbers.

The term "halo" and "halogen," as used herein, refer to an atom selected from fluorine, chlorine, bromine and iodine.

The term "alkyl," as used herein, refers to saturated, straight- or branched-chain hydrocarbon radicals. Examples include, but are not limited to methyl, ethyl, propyl, isopropyl, n-butyl, tert-butyl, neopentyl, n-hexyl, octyl, decyl, dodecyl radicals.

The term "substituted alkyl," as used herein, refers to an "alkyl" group substituted by independent replacement of one or more (e.g., 1, 2, or 3) of the hydrogen atoms thereon with F, Cl, Br, I, OH, $NO_2$, CN, $C_1$-$C_6$-alkyl-OH, C(O)—$C_1$-$C_6$-alkyl, $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—($C_1$-$C_6$-alkyl), CONH-aryl, CONH-heteroaryl, OC(O)—($C_1$-$C_6$-alkyl), OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—$C_1$-$C_6$ alkyl, $SO_2$-aryl, $SO_2$-heteroaryl, $SO_2NH_2$, $SO_2NH$—$C_1$-$C_6$-alkyl, $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The term "haloalkyl," as used herein, refers to an acyclic, straight or branched chain alkyl substituent having one or more hydrogen substituted for a halogen selected from bromo, chloro, fluoro, or iodo.

The term "thioalkyl," as used herein, refers to an acyclic, straight or branched chain alkyl substituent containing a thiol group, such as, for example and not limitation, thiopropyl.

The term "alkoxy," as used herein, refers to an alkyl group, as previously defined, attached to the parent molecular moiety through an oxygen atom. Examples of alkoxy include, but are not limited to, methoxy, ethoxy, propoxy, isopropoxy, n-butoxy, tert-butoxy, neopentoxy and n-hexoxy.

The term "alkenyl," as used herein, denotes a monovalent group derived by the removal of a single hydrogen atom from a hydrocarbon moiety having at least one carbon-carbon double bond. Alkenyl groups include, but are not limited to, for example, ethenyl, propenyl, butenyl, 1-methyl-2-buten-1-yl, and the like.

The term "substituted alkenyl," as used herein, refers to an "alkenyl" group substituted by independent replacement of one or more of the hydrogen atoms thereon with F, Cl, Br, I, OH, $NO_2$, CN, $C_1$-$C_6$-alkyl-OH, C(O)—($C_1$-$C_6$-alkyl), $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—($C_1$-$C_6$-alkyl), OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—$C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The term "alkynyl," as used herein, denotes a monovalent group derived by the removal of a single hydrogen atom from a hydrocarbon moiety having at least one carbon-carbon triple bond. Representative alkynyl groups include, but are not limited to, for example, ethynyl, 1-propynyl, 1-butynyl, and the like.

The term "substituted alkynyl," as used herein, refers to an "alkynyl" group substituted by independent replacement of one or more of the hydrogen atoms thereon with F, Cl, Br, I, OH, $NO_2$, CN, $C_1$-$C_6$-alkyl-OH, C(O)—($C_1$-$C_6$-alkyl), $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—($C_1$-$C_6$-alkyl), CONH-aryl, CONH-heteroaryl, OC(O)—($C_1$-$C_6$-alkyl), OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as defined herein, substituted by independent replacement of one or more of the hydrogen atoms thereon with F, Cl, Br, I, OH, $NO_2$, CN, $C_1$-$C_6$-alkyl-OH, C(O)—($C_1$-$C_6$-alkyl), $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—($C_1$-$C_6$-alkyl), CONH-aryl, CONH-heteroaryl, OC(O)—($C_1$-$C_6$-alkyl), OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "substituted arylalkyl," as used herein, refers to an arylalkyl group, as previously defined, substituted by independent replacement of one or more of the hydrogen atoms thereon with F, Cl, Br, I, OH, $NO_2$, CN, $C_1$-$C_6$-alkyl-OH, C(O)—$C_1$-$C_6$-alkyl, $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—($C_1$-$C_6$-alkyl), OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The term "cycloalkyl" denotes a monovalent group derived by the removal of a single hydrogen atom from a monocyclic or bicyclic saturated carbocyclic ring compound. Examples include, but are not limited to, cyclopropyl, cyclobutyl, cyclopentyl, cyclohexyl, bicyclo [2.2.1] heptyl, and bicyclo [2.2.2] octyl.

The term "substituted cycloalkyl," as used herein, refers to a cycloalkyl group as defined herein, substituted by independent replacement of one, two or three of the hydrogen atoms thereon with F, Cl, Br, I, OH, $NO_2$, CN, $C_1$-$C_6$-alkyl-OH, C(O)—($C_1$-$C_6$-alkyl), $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—($C_1$-$C_6$-alkyl), CONH-aryl, CONH-heteroaryl, OC(O)—($C_1$-$C_6$-alkyl), OC(O)-aryl, OC(O)-heteroaryl, $OCO_2$-alkyl, $OCO_2$-aryl, $OCO_2$-heteroaryl, $OCONH_2$, OCONH—$C_1$-$C_6$-alkyl, OCONH-aryl, OCONH-heteroaryl, NHC(O)—($C_1$-$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The terms "heterocyclo" and "heterocyclic" as used herein, refer to a monovalent substituent derived by removal of a hydrogen from a three to seven-membered saturated or unsaturated (including aromatic) cycle having 1 to 4 non-carbon ring atoms selected from the heteroatoms consisting of N, O, and S. Examples of suitable heterocycles include but are not limited to tetrahydrofuran, thiophene, diazepine, isoxazole, piperidine, dioxane, morpholine, and pyrimidine. The term also includes a heterocycle as defined herein fused to one or more other cycles whether hetero or carbocyclic. One example is thiazolo[4,5-b]-pyridine. Although the terms "heterocycloalkyl," "aliphatic heteromonocyclic ring system," "aliphatic heterobicyclic ring system," "aliphatic heterotricyclic ring system," "heteroaryl," "aromatic heteromonocyclic ring system," "aromatic heterobicyclic ring system," "aromatic heterotricyclic ring system," "heteroarylalkyl," are covered generally by the term "heterocycle," their specific meanings are set forth in further detail below.

The term "heterocycloalkyl," as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted heterocycloalkyl," as used herein, refers to a heterocycloalkyl group, as previously defined, substituted by independent replacement of one or more of the hydrogen atoms thereon with F, Cl, Br, I, OH, $NO_2$, CN, $C_1$-$C_6$-alkyl-OH, C(O)—$C_1$-$C_6$-alkyl, $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

As used herein, the term "aliphatic heteromonocyclic ring system" is intended to mean a ring system containing a non-aromatic ring that includes at least one ring hetero (i.e., non-carbon) atom selected from O, N and S. The term "aliphatic heterobicyclic ring system" is intended to mean a ring system containing a two fused rings, at least one of which is a non-aromatic ring that includes at least one ring hetero (i.e., non-carbon) atom selected from O, N and S. The term "aliphatic heterotricyclic ring system" is intended to mean a ring system containing three fused rings, at least one of which is a non-aromatic ring that includes at least one ring hetero (i.e., non-carbon) atom selected from O, N and S. As will be appreciated, the aliphatic heterocyclic ring systems can possess any degree of saturation (i.e., double or triple bonds) provided that none of the heteroatom-containing constituent rings are aromatic. Thus, structures such as indoline, which contains a non-aromatic heterocyclic ring (i.e., a pyrroline ring) fused to an aromatic carbocyclic ring (specifically, a phenyl ring), and phthalimide, are examples of an "aliphatic heterobicyclic ring systems."

As used herein, the term "aromatic heteromonocyclic ring system" is intended to mean an aromatic ring that includes at least one ring hetero (i.e., non-carbon) atom selected from O, N and S. The term "aromatic heterobicyclic ring system" is intended to mean an aromatic ring system containing two fused rings that includes at least one ring hetero (i.e., non-carbon) atom selected from O, N and S. The term "aromatic heterotricyclic ring system" is intended to mean an aromatic ring system containing three fused rings that includes at least one ring hetero (i.e., non-carbon) atom selected from O, N and S. Substituent atoms of the aromatic heterocyclic ring systems can, together with additional atoms, form further fused ring structures that are not aromatic. Thus, 5,6,7,8 tetrahydroisoquinoline is an example of an aromatic heterobicyclic ring system, whereas 1,2,3,4 tetrahydroisoquinoline is an example of an aliphatic heterobicyclic ring system.

The term "heteroaryl," as used herein, refers to a cyclic aromatic radical having from five to ten ring atoms of which at least one ring atom is selected from S, O and N and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "substituted heteroaryl," as used herein, refers to a heteroaryl group as defined herein, substituted by independent replacement of one, two or three of the hydrogen atoms thereon with F, Cl, Br, I, OH, $NO_2$, CN, $C_1$-$C_6$-alkyl-OH, C(O)—$C_1$-$C_6$-alkyl, $OCH_2$—($C_3$-$C_{12}$-cycloalkyl), C(O)-aryl, C(O)-heteroaryl, $CO_2$-alkyl, $CO_2$-aryl, $CO_2$— heteroaryl, $CONH_2$, CONH—($C_1$-$C_6$-alkyl), CONH-aryl, CONH-heteroaryl, OC(O)—($C_1$-$C_6$)-alkyl, OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one or more of the hydrogen atoms thereon with F, Cl, Br, I, OH, $NO_2$, CN, $C_1$-$C_6$-alkyl-OH, C(O)—$C_1$-$C_6$-alkyl, $OCH_2$—($C_3$-$C_{12}$-cycloalkyl), C(O)-aryl, C(O)-heteroaryl, $CO_2$-alkyl, $CO_2$-aryl, $CO_2$-heteroaryl, $CONH_2$, CONH—$C_1$-$C_6$-alkyl, CONH-aryl, CONH-heteroaryl, OC(O)—$C_1$-$C_6$-alkyl, OC(O)-aryl, OC(O)-heteroaryl, $OCO_2$-alkyl, $OCO_2$-aryl, $OCO_2$-heteroaryl, $OCONH_2$, OCONH—($C_1$-$C_6$-alkyl), OCONH-aryl, OCONH-heteroaryl, NHC(O)—($C_1$-$C_6$-alkyl), NHC(O)-aryl, NHC(O)-heteroaryl, $NHCO_2$-alkyl, $NHCO_2$-aryl, $NHCO_2$-heteroaryl, $NHCONH_2$, NHCONH—($C_1$-$C_6$-alkyl), NHCONH-aryl, NHCONH-heteroaryl, $SO_2$—($C_1$-$C_6$-alkyl), $SO_2$-aryl, $SO_2$-heteroaryl, $SO_2NH_2$, $SO_2NH$—($C_1$-$C_6$-alkyl), $SO_2NH$-aryl, $SO_2NH$-heteroaryl, $C_1$-$C_6$-alkyl, $C_3$-$C_6$-cycloalkyl, $CF_3$, $CH_2CF_3$, $CHCl_2$, $CH_2NH_2$, $CH_2SO_2CH_3H$, $C_1$-$C_6$ alkyl, halo alkyl, $C_3$-$C_{12}$ cycloalkyl, substituted $C_3$-$C_{12}$ cycloalkyl, aryl, substituted aryl, arylalkyl, heteroaryl, heteroarylalkyl, heterocycloalkyl, benzyl, benzyloxy, aryloxy, heteroaryloxy, $C_1$-$C_6$-alkoxy, methoxymethoxy, methoxyethoxy, amino, benzylamino, arylamino, heteroarylamino, $C_1$-$C_3$-alkylamino, thio, aryl-thio, heteroarylthio, benzyl-thio, $C_1$-$C_6$-alkyl-thio, or methylthiomethyl.

Substituent groups substituted on any group (e.g., alkyl, alkenyl, alkynyl, cycloalkyl, aryl, heteroaryl, heterocycloalkyl, heterocyclic) delineated herein also include any of F, Cl, Br, I, OH, protected hydroxy, aliphatic ethers, aromatic ethers, oxo, $NO_2$, CN, $C_1$-$C_{12}$-alkyl optionally substituted with halogen (such as perhaloalkyls), $C_2$-$C_{12}$-alkenyl optionally substituted with halogen, $C_2$-$C_{12}$-alkynyl optionally substituted with halogen, $NH_2$, protected amino, NH—$C_1$-$C_{12}$-alkyl, NH—$C_2$-$C_{12}$-alkenyl, NH—$C_2$-$C_{12}$-alkynyl, NH—$C_3$-$C_{12}$-cycloalkyl, NH-aryl, NH-heteroaryl, NH-heterocycloalkyl, dialkylamino, diarylamino, diheteroarylamino, O—$C_1$-$C_{12}$-alkyl, O—$C_2$-$C_{12}$-alkenyl, O—$C_2$-$C_{12}$-alkynyl, O—$C_3$-$C_{12}$-cycloalkyl, O-aryl, O-heteroaryl, O-heterocycloalkyl, C(O)—$C_1$-$C_{12}$-alkyl, C(O)—$C_2$-$C_{12}$-alkenyl, C(O)—$C_2$-$C_{12}$-alkynyl, C(O)—$C_3$-$C_{12}$-cycloalkyl, C(O)-aryl, C(O)-heteroaryl, C(O)-heterocycloalkyl, $CONH_2$, CONH—$C_1$-$C_{12}$-alkyl, CONH—$C_2$-$C_{12}$-alkenyl, CONH—$C_2$-$C_{12}$-alkynyl, CONH—$C_3$-$C_{12}$-cycloalkyl, CONH-aryl, CONH-heteroaryl, CONH-heterocycloalkyl, $CO_2$—$C_1$-$C_{12}$-alkyl, $CO_2$—$C_2$-$C_{12}$-alkenyl, $CO_2$—$C_2$-$C_{12}$-alkynyl, $CO_2$—$C_3$-$C_{12}$-cycloalkyl, $CO_2$-aryl, $CO_2$-heteroaryl, $CO_2$-heterocycloalkyl, $CO_2$—$C_1$-$C_{12}$-alkyl, $OCO_2$—$C_2$-$C_{12}$-alkenyl, $OCO_2$—$C_2$-$C_{12}$-alkynyl, $OCO_2$—$C_3$-$C_{12}$-cycloalkyl, $OCO_2$-aryl, $OCO_2$-heteroaryl, $OCO_2$-heterocycloalkyl, $OCONH_2$, OCONH—$C_1$-$C_{12}$-alkyl, OCONH—$C_2$-$C_{12}$-alkenyl, OCONH—$C_2$-$C_{12}$-alkynyl, OCONH—$C_3$-$C_{12}$-cycloalkyl, OCONH-aryl, OCONH-heteroaryl, OCONH-heterocycloalkyl, NHC(O)—$C_1$-$C_{12}$-alkyl, NHC(O)—$C_2$-$C_{12}$-alkenyl, NHC(O)—$C_2$-$C_{12}$-alkynyl, NHC(O)—$C_3$-$C_{12}$-cycloalkyl, NHC(O)-aryl, NHC(O)-heteroaryl, NHC(O)-heterocycloalkyl, $NHCO_2$—$C_1$-$C_{12}$-alkyl, $NHCO_2$—$C_2$-$C_{12}$-alkenyl, $NHCO_2$—$C_2$-$C_{12}$-alkynyl, $NHCO_2$—$C_3$-$C_{12}$-cycloalkyl, $NHCO_2$-aryl, $NHCO_2$— heteroaryl, $NHCO_2$-heterocycloalkyl, $NHC(O)NH_2$, NHC(O)NH—$C_1$-$C_{12}$-alkyl, NHC(O)NH—$C_2$-$C_{12}$-alkenyl, NHC(O)NH—$C_2$-$C_{12}$-alkynyl, NHC(O)NH—$C_3$-$C_{12}$-cycloalkyl, NHC(O)NH-aryl, NHC(O)NH-heteroaryl, NHC(O)NH-heterocycloalkyl, $NHC(S)NH_2$, NHC(S)NH—$C_1$-$C_{12}$-alkyl, NHC(S)NH—$C_2$-$C_{12}$-alkenyl, NHC(S)NH—$C_2$-$C_{12}$-alkynyl, NHC(S)NH—$C_3$-$C_{12}$-cycloalkyl, NHC(S)NH-aryl, NHC(S)NH-heteroaryl, NHC(S)NH-heterocycloalkyl, $NHC(NH)NH_2$, NHC(NH)NH—$C_1$-$C_{12}$-alkyl, NHC(NH)NH—$C_2$-$C_{12}$-alkenyl, NHC(NH)NH—$C_2$-$C_{12}$-alkynyl,NHC(NH)NH—$C_3$-$C_{12}$-cycloalkyl, NHC(NH)NH-aryl, NHC(NH)NH-heteroaryl, NHC(NH)NH-heterocycloalkyl, NHC(NH)—$C_1$-$C_{12}$-alkyl, NHC(NH)—$C_2$-$C_{12}$-alkenyl, NHC(NH)—$C_2$-$C_{12}$-alkynyl, NHC(NH)—$C_3$-$C_{12}$-cycloalkyl, NHC(NH)-aryl, NHC(NH)-heteroaryl, NHC(NH)-heterocycloalkyl, C(NH)NH—$C_1$-$C_{12}$-alkyl, C(NH)NH—$C_2$-$C_{12}$-alkenyl, C(NH)NH—$C_2$-$C_{12}$-alkynyl, C(NH)NH—$C_3$-$C_{12}$-cycloalkyl, C(NH)NH-aryl, C(NH)NH-heteroaryl, C(NH)NH-heterocycloalkyl, S(O)—$C_1$-$C_{12}$-alkyl, S(O)—$C_2$-$C_{12}$-alkenyl, S(O)—$C_2$-$C_{12}$-alkynyl, S(O)—$C_3$-$C_{12}$-cycloalkyl, S(O)-aryl, S(O)-heteroaryl, S(O)-heterocycloalkyl $SO_2NH_2$, $SO_2NH$—$C_1$-$C_{12}$-alkyl, $SO_2NH$—$C_2$-$C_{12}$-alkenyl, $SO_2NH$—$C_2$-$C_{12}$-alkynyl, $SO_2NH$—$C_3$-$C_{12}$-cycloalkyl, $SO_2NH$-aryl, $SO_2NH$-heteroaryl, $SO_2NH$-heterocycloalkyl, $NHSO_2$—$C_1$-$C_{12}$-alkyl, $NHSO_2$—$C_2$-$C_{12}$-alkenyl, $NHSO_2$—$C_2$-$C_{12}$-alkynyl, $NHSO_2$—$C_3$-$C_{12}$-cycloalkyl, $NHSO_2$-aryl, $NHSO_2$-heteroaryl, $NHSO_2$-heterocycloalkyl, $CH_2NH_2$, $CH_2SO_2CH_3$, aryl, arylalkyl, heteroaryl, heteroarylalkyl, heterocycloalkyl, $C_3$-$C_{12}$-cycloalkyl, polyalkoxyalkyl, polyalkoxy, methoxymethoxy, methoxyethoxy, SH, S—$C_1$-$C_{12}$-alkyl, S—$C_2$-$C_{12}$-alkenyl, S—$C_2$-$C_{12}$-alkynyl, S—$C_3$-$C_{12}$-cycloalkyl, S-aryl, S-heteroaryl, S-heterocycloalkyl, or methylthiomethyl. It is understood that the aryls, heteroaryls, alkyls and the like can be further substituted.

The term "alkylamino," as used herein, refers to a group having the structure —NH($C_1$-$C_{12}$ alkyl) where $C_1$-$C_{12}$ alkyl is as previously defined. The term "dialkylamino" refers to a group having the structure —N($C_1$-$C_{12}$ alkyl)$_2$ where $C_1$-$C_{12}$ alkyl is as previously defined. Examples of dialkylamino are, but not limited to, N,N-dimethylamino, N,N-diethylamino, N,N-methylethylamino, piperidino, and the like.

The term "diarylamino" refers to a group having the structure —N(aryl)$_2$ or —N(substituted aryl)$_2$ where substituted aryl is as previously defined. Examples of diarylamino are, but not limited to, N,N-diphenylamino, N,N-dinapthylamino, N,N-di(toluenyl)amino, and the like.

The term "diheteroarylamino" refers to a group having the structure —N(heteroaryl)$_2$ or —N(substituted heteroaryl)$_2$, where heteroaryl and substituted heteroaryl is as previously defined. Examples of diheteroarylamino are, but not limited to, N,N-difuranylamino, N,N-dithiazolidinylamino, N,N-di (imidazole)amino, and the like.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bn or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "nitrogen (or amino) protecting group," as used herein, refers to a labile chemical moiety which is known in the art to protect a nitrogen group against undesired reactions during synthetic procedures. After said synthetic procedure(s) the nitrogen protecting group as described herein may be selectively removed. Nitrogen protecting groups as known in the are described generally in T. H. Greene and P. G. M. Wuts, *Protective Groups in Organic Synthesis,* 3rd edition, John Wiley & Sons, New York (1999). Examples of nitrogen protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "nucleophilic heterocyclic compound" refers to a heterocyclic group in a nucleophilic form (e.g., metal salt form, protonated form) such that it is capable of reacting with another molecule resulting in a covalent bond between the two molecules (e.g., a nucleophile in a nucleophilic displacement reaction). Examples of such nucleophilic heterocyclic compounds are known in the art and delineated herein.

The term "leaving group: refers to a moiety that can be detached from a molecule during a reaction, especially nucleophilic displacement reactions. Examples of leaving groups include, for example, halides, mesyl groups, tosyl groups, alkoxides, hydroxides, and protonated forms thereof. Examples of such leaving groups are known in the art and delineated herein.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); (1995) and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The term "subject" as used herein refers to a mammal. Preferably the mammal is a human. A subject also refers to, for example, dogs, cats, horses, cows, pigs, guinea pigs and the like.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. The salts can be prepared in situ during the final isolation and purification of the compounds of the invention, or separately by reacting the free base function with a suitable organic acid. Examples of pharmaceutically acceptable, non-toxic acid addition salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_1$-$C_6$ sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, but are not limited to, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems*, Vol. 14 of the A.C.S. Symposium Series and in Edward B. Roche, ed., *Bioreversible Carriers in Drug Design* (American Pharmaceutical Association and Pergamon Press, 1987), both of which are incorporated by reference herein.

The term "effective amount" or "therapeutically effective amount," as used herein, means an amount which is capable of inhibiting the HCV NS3 serine protease, therefore interfering with the production of the viral polyprotein essential for viral replication. The HCV serine protease inhibition contemplated by the present method includes both therapeutic and prophylactic treatment, as appropriate for the subject in need of such treatment. Methods of treatment, dosage levels and requirements may be selected by those of ordinary skill in the art from available methods and techniques. For example, a compound of the present invention may be combined with a pharmaceutically acceptable excipient for administration to a virally-infected patient in a pharmaceutically acceptable manner and in an amount effective to lessen the severity of the viral infection. Alternatively, the compounds of the present invention may be used in vaccines and methods for protecting individuals against HCV viral infection over an extended period of time. The compounds may be employed in a manner consistent with the conventional utilization of protease inhibitors in vaccines. For example, a compound of the present invention may be combined with pharmaceutically acceptable excipients conventionally employed in vaccines and administered in prophylactically effective amounts to protect individuals over an extended period of time against HCV viral infection. As such, the protease inhibitors of the present invention can be administered as agents for treating or preventing HCV viral infection in a subject.

The compounds of this invention may be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds described herein contain two or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers Racemates, and Resolutions (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents, commonly used in the art such as, for example, water or other solvents, solubilizing agents and 30 emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

According to the methods of treatment of the present invention, viral infections are treated or prevented in a subject, such as a human or lower mammal, by administering to the subject an effective amount of a compound of the invention, in such amounts and for such time as is necessary to achieve the desired result. The term "anti-hepatitis C virally effective amount" of a compound of the invention, as used herein, means a sufficient amount of the compound so as to decrease the viral load in a subject, thus decreasing said subject's chronic HCV symptoms. As well understood in the medical arts an anti-hepatitis C virally effective amount of a compound of this invention will be at a reasonable benefit/risk ratio applicable to any medical treatment.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific anti-HCV virally effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the schemes and the examples that follow are:

ACN for acetonitrile;
BME for 2-mercaptoethanol;
BOP for benzotriazol-1-yloxy-tris(dimethylamino)phosphonium hexafluorophosphate;
COD for cyclooctadiene;
DABCYL for 6-(N-4'-carboxy-4-(dimethylamino) azobenzene)-aminohexyl-1-O-(2-cyanoethyl)-(N,N-diisopropyl)-phosphoramidite;
DAST for diethylaminosulfur trifluoride;
DCM for dichloromethane;
DIAD for diisopropyl azodicarboxylate;
DIBAL-H for diisobutylaluminum hydride;
DIEA for diisopropyl ethylamine;
DMAP for N,N-dimethylaminopyridine;
DME for ethylene glycol dimethyl ether;
DMEM for Dulbecco's Modified Eagles Media;
DMF for N,N-dimethyl formamide;
DMSO for dimethylsulfoxide;
DUPHOS for

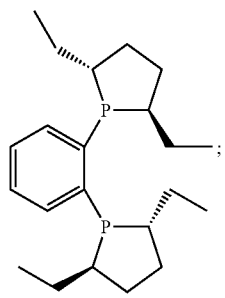

EDANS for 5-(2-Amino-ethylamino)-naphthalene-1-sulfonic acid;
EDCI or EDC for 1-(3-diethylaminopropyl)-3-ethylcarbodiimide hydrochloride;
EtOAc for ethyl acetate;
HATU for 0 (7-Azabenzotriazole-1-yl)-N,N,N',N'-tetramethyluronium hexafluorophosphate;
HMBA is 4-Hydroxymethylbenzoic acid AM resin;
Hoveyda's Cat. for Dichloro(o-isopropoxyphenylmethylene) (tricyclohexylphosphine)ruthenium(II);
KHMDS is potassium bis(trimethylsilyl) amide;
Ms for mesyl;
NMM for N-4-methylmorpholine;
Ph for phenyl;
PuPHOS;
PyBrOP for Bromo-tri-pyrrolidino-phosphonium hexafluorophosphate;
RCM for ring-closing metathesis;
RT for room temperature;
RT-PCR for reverse transcription-polymerase chain reaction;
tBOC or Boc for tert-butyloxy carbonyl;
TEA for triethyl amine;
TFA for trifluoroacetic acid;
THF for tetrahydrofuran;
TLC for thin layer chromatography;
TPP or PPh$_3$ for triphenylphosphine; and
Xantphos for 4,5-Bis-diphenylphosphanyl-9,9-dimethyl-9H-xanthene.

Certain chemical structures herein having —NH or —OH groups appear without those hydrogen atoms attached to oxygen or nitrogen atoms depicted. Thus, where a nitrogen or oxygen atom in such structure appears to lack proper valency, the presence of those hydrogen atoms are implied.

Synthetic Methods

The compounds and processes of the present invention will be better understood in connection with the following synthetic schemes which illustrate the methods by which the compounds of the invention may be prepared.

I. Replacement Method

Compounds of the present invention can be made via a replacement procedure described generally in the following scheme:

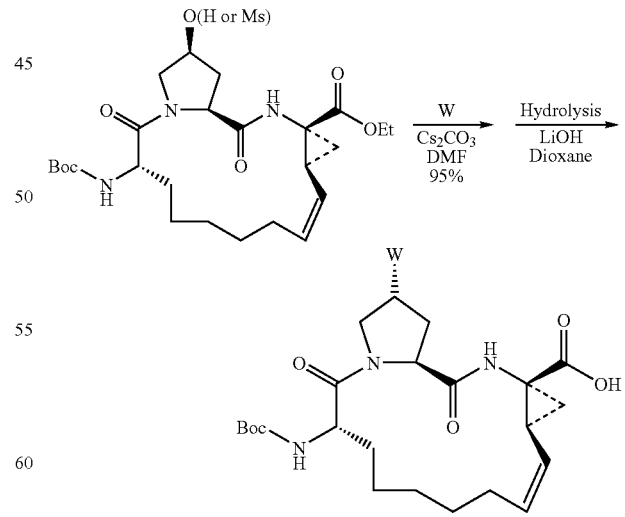

The hydroxyl proline or mesylated proline precursor may be used. This replacement method protocol is suitable for converting any hydroxy (or corresponding mesylate) proline compound or derivative starting compound to a heterocyclic substituted proline derivative. The subsequent synthetic methods set forth the various procedures and intermediate steps that may be used to prepare the compounds disclosed herein.

A. Synthesis of Hydroxyl Proline Cyclic Peptide Precursors

A cyclic peptide precursor may be used to synthesize the compounds of the invention. In some embodiments, a mesylated version of the cyclic precursor may be used.

In some embodiments, commercially available Boc-hydroxyproline A

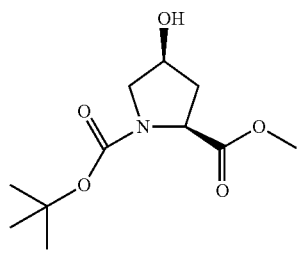

is treated with HCl in dioxane to yield starting material Ib.
Synthesis of Cyclic Peptide Precursor The cyclic peptide precursor Ig was synthesized from Boc-L-2-amino-8-nonenoic acid Ia and cis-L-hydroxyproline methyl ester Ib via steps A-D set forth generally in Scheme 1. For further details of the synthetic methods employed to produce the cyclic peptide precursor Ig, see U.S. Pat. No. 6,608,027, which is herein incorporated by reference in its entirety.

Synthesis of Mesylate of Macrocyclic Peptide Precursor

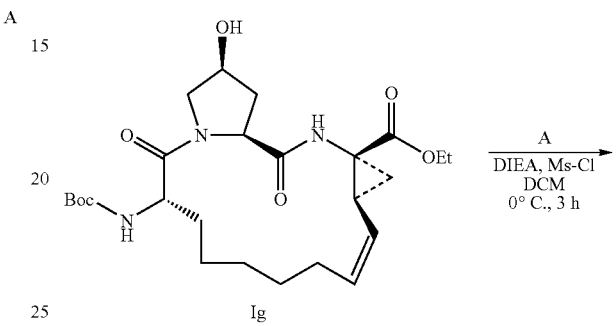

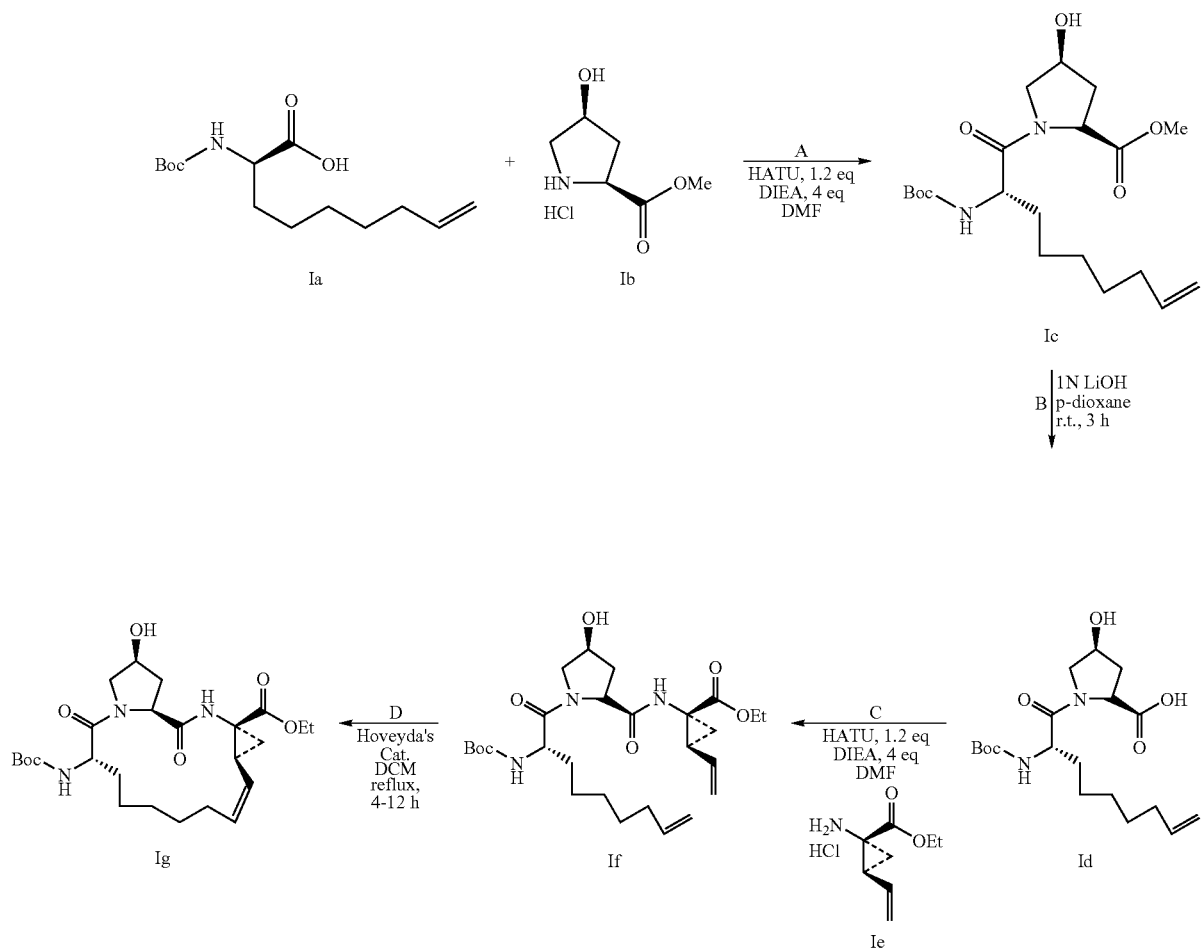

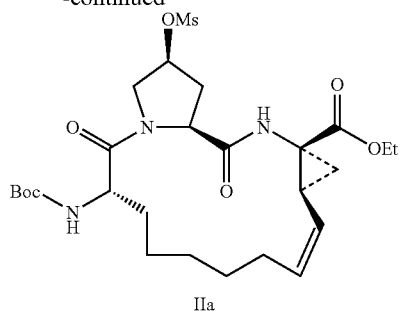

IIa

The cyclic precursor mesylate was synthesized by forming the mesylate upon the hydroxyl of the hydroxyl proline residue of the cyclic peptide precursor via the synthetic route generally described above in Scheme 2.

Scheme 3

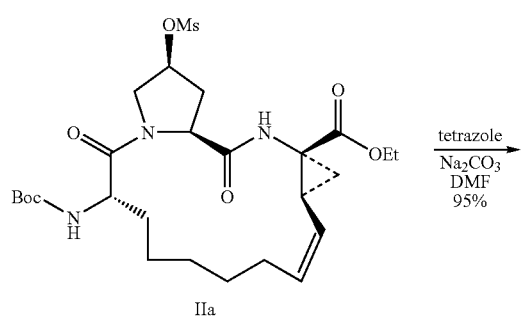

IIa

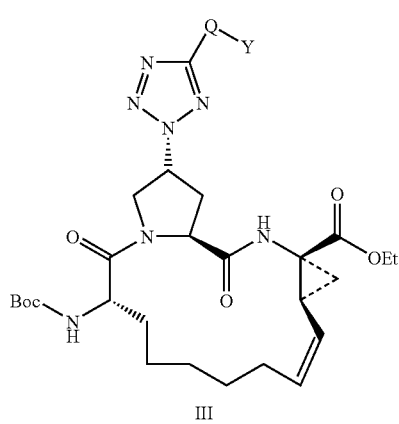

III

The compounds of the present invention are made via the replacement of the mesylate of the macrocyclic peptide mesylate IIa with a 5-substituted-2H-tetrazole, Exemplary syntheses of such tetrazoloes as described in Scheme 5, below, via the synthetic route described generally in Scheme 3.

Scheme 4

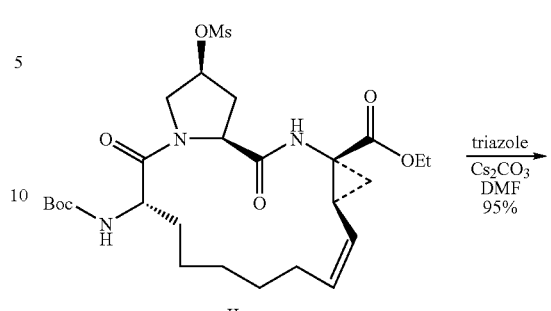

IIa

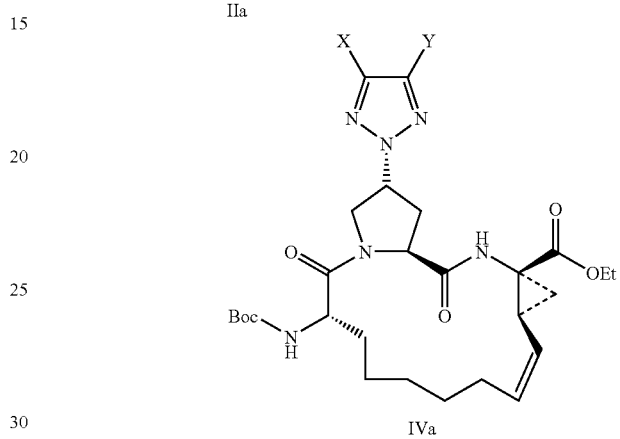

IVa

The compounds of the present invention are made via the replacement of the mesylate of the macrocyclic peptide mesylate IIa with a 4,5-substituted-1H-triazole via the synthetic route described generally in Scheme 4. Exemplary syntheses of such triazoles are described in scheme 6, below.

B. Synthesis of Substitutes for W

W may be any of the substitutents described previously herein. Synthesis of these various substituents is within the skill of those of ordinary skill in the art. Some exemplary syntheses are presented herein by way of example and not of limitation. Other substituents are either commercially available or readily synthesized by those of ordinary skill in the art.

Synthesis of Tetrazoles

Structurally diverse tetrazoles Va-Vq were synthesized from commercially available nitrile compounds as described in Scheme 5 below:

Scheme 5

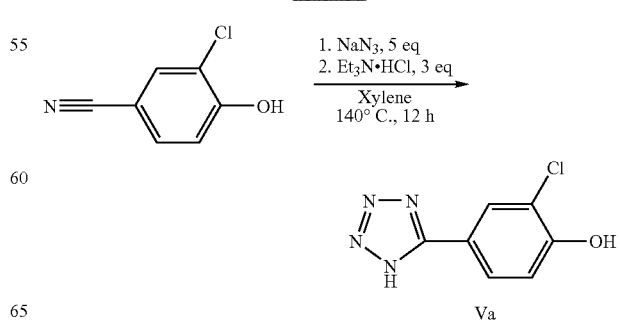

Va

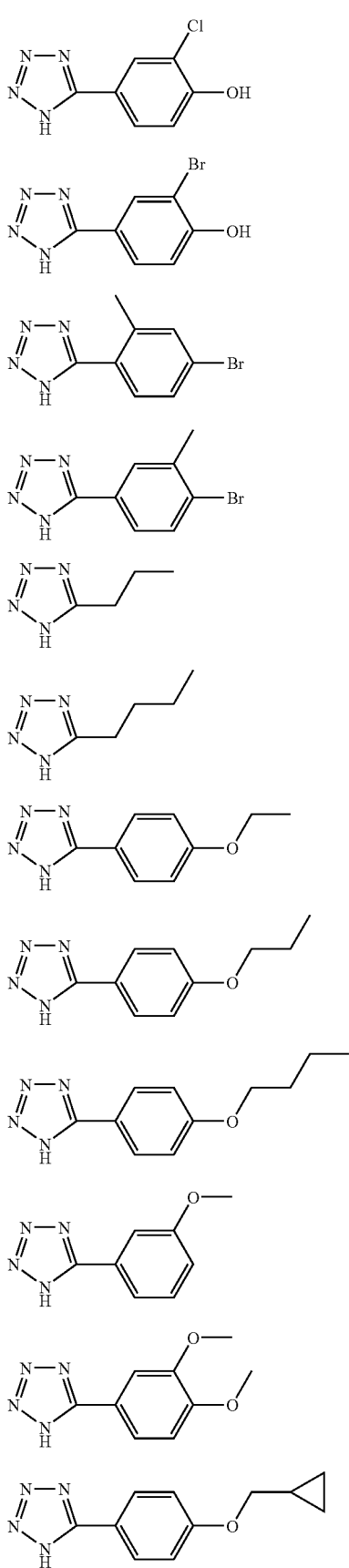

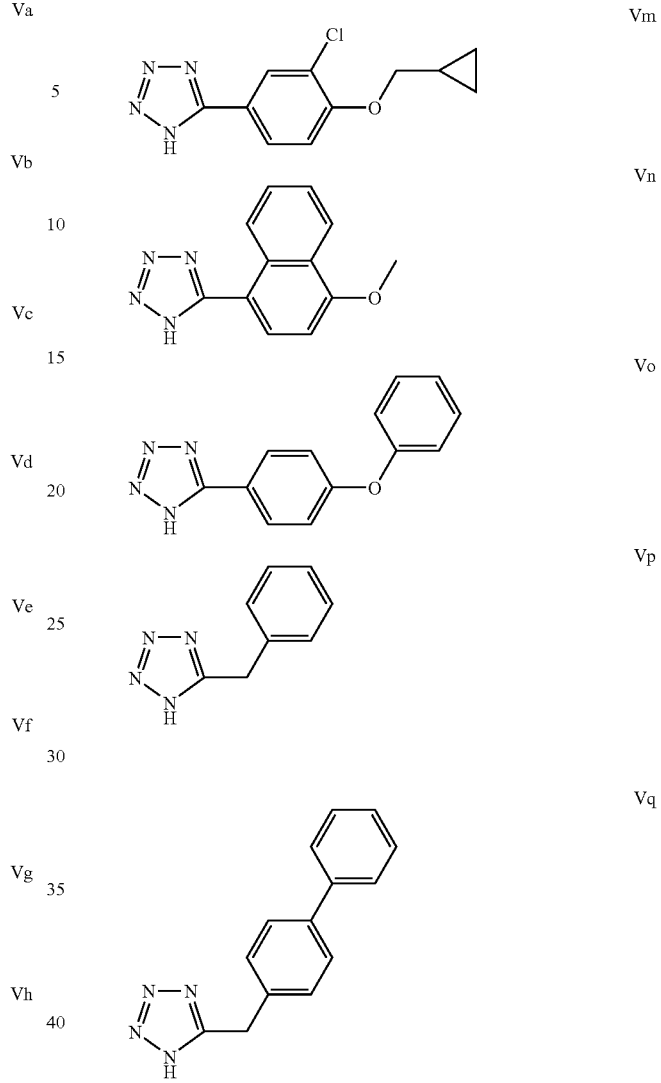

One skilled in the art will recognize that several 5-substituted tetrazole compounds may be produced in this manner with any nitrile-containing compound suitable for the reaction conditions set forth above.

Synthesis of Triazoles

Scheme 6

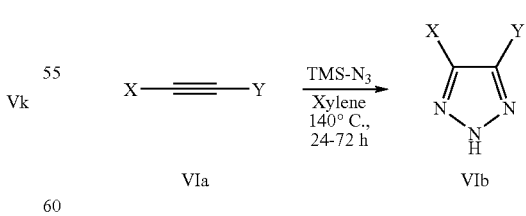

Triazoles of the present invention are prepared by reacting alkyne compound VIa, which is commercially available or made from procedures elucidated infra, and trimethylsilyl azide via the synthetic route described generally in Scheme 6. Commercially available alkynes suitable for triazole formation include, but are not limited to:

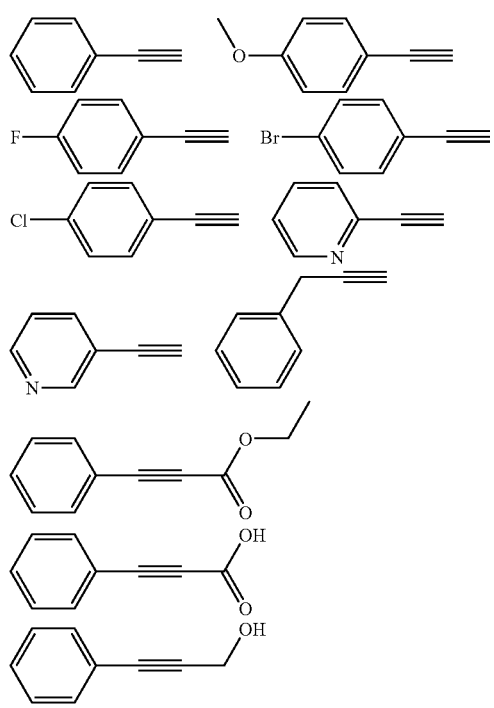

Synthesis of Alkynes

Alkynes useful in the synthesis of triazoles may be made by any appropriate method. Below are some exemplary syntheses.

Sonogashira Reaction

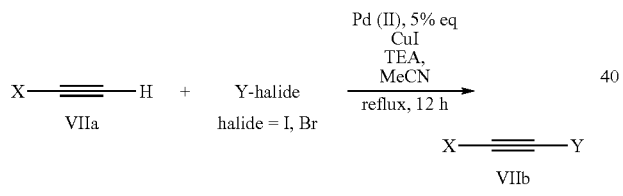

Alkynes used in the present invention can be made by the Sonogashira reaction with primary alkyne compound VIa, an aryl halide (Y-halide), and triethylamine in acetonitrile with $PdCl_2(PPh_3)_2$ and CuI via the synthetic route described generally in Scheme 7.

Commercially-available aryl halides suitable for the Sonogashira reaction include, but are not limited to:

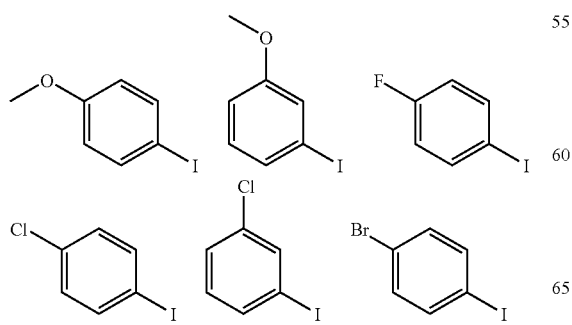

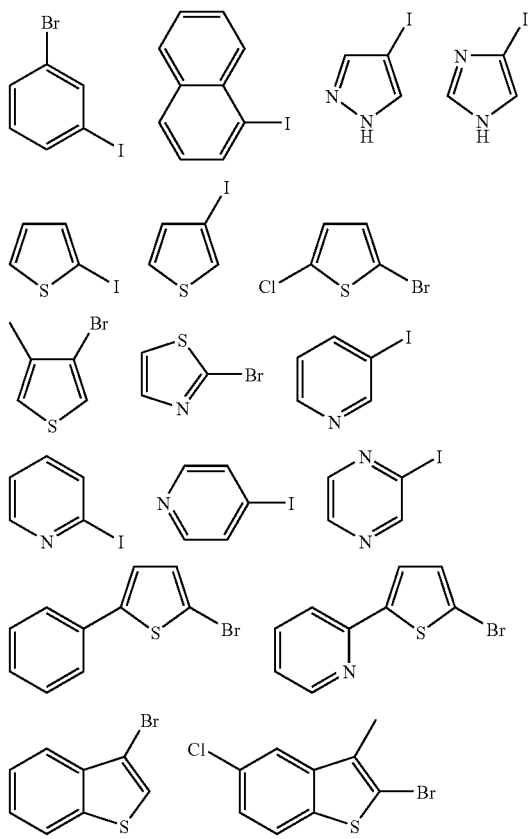

Commercially-available primary alkynes suitable for the Sonogashira reaction include, but are not limited to:

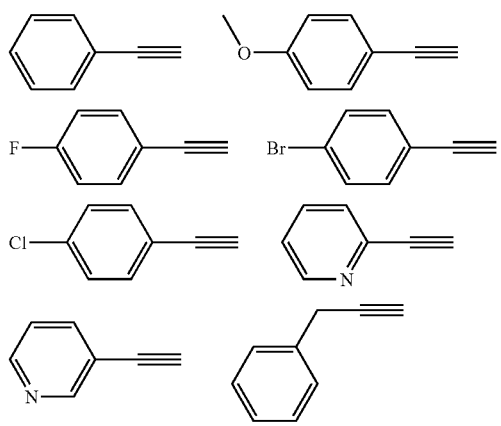

Synthesis of Alkynyl Amides

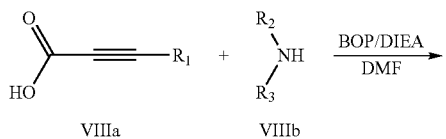

149
-continued

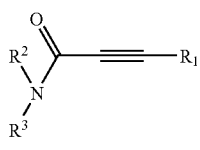

VIIIc

Additional alkynes used in the present invention can be made by reacting alkynyl acid Va, BOP, and DIEA in DMF with amine VIIIb via the synthetic route described generally in Scheme 8.

Post-Replacement Modification

The resultant macrocyclic compound may be modified after W is attached. Some exemplary modifications follow.

1. Synthesis of Phenolic Esters

Scheme 9

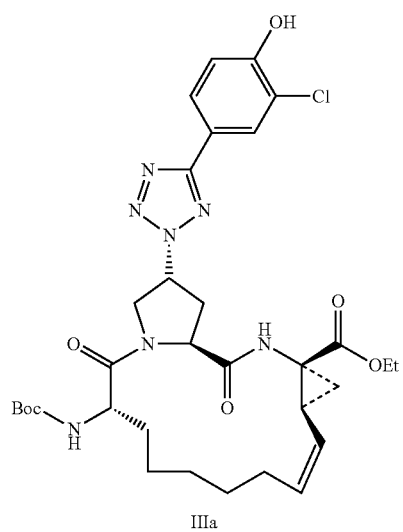

IIIa

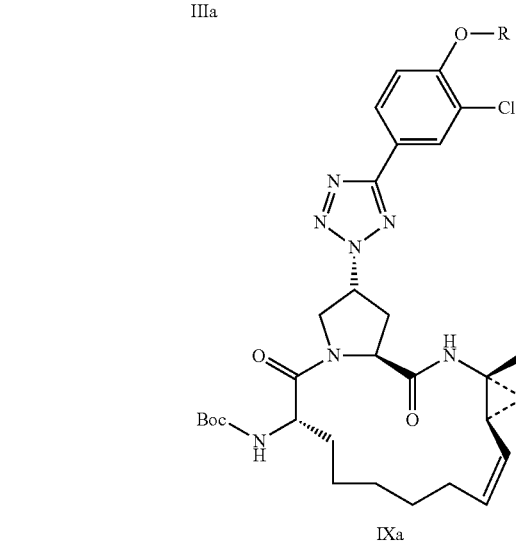

IXa

R=methyl, ethyl, allyl, 2-hydroxyethyl, isopropyl, methiomethyl

The post-replacement modification of macrocyclic compound IIIa to obtain various phenolic esters was performed by the synthetic route described generally in Scheme 9.

150

2. Hydrolysis of Macrocyclic Peptide Ethyl Ester

Scheme 10

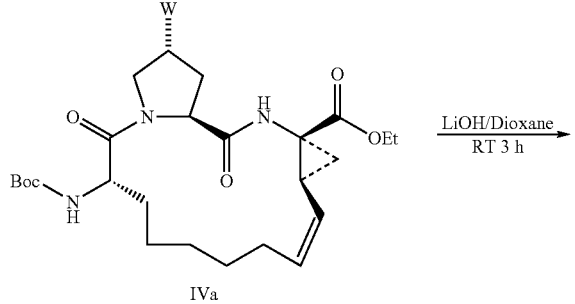

IVa

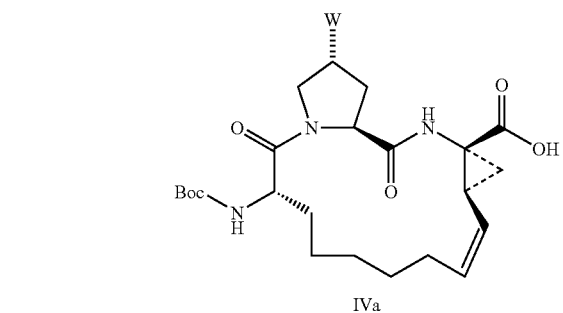

IVa

The hydrolysis of macrocyclic peptide ethyl esters of the present invention is performed by dissolving macrocyclic peptide ethyl ester IV in dioxane and adding 1M LiOH via the synthetic route described generally in Scheme 10.

3. Using Suzuki Coupling to Generate More Bi-aryl Compounds

Scheme 11

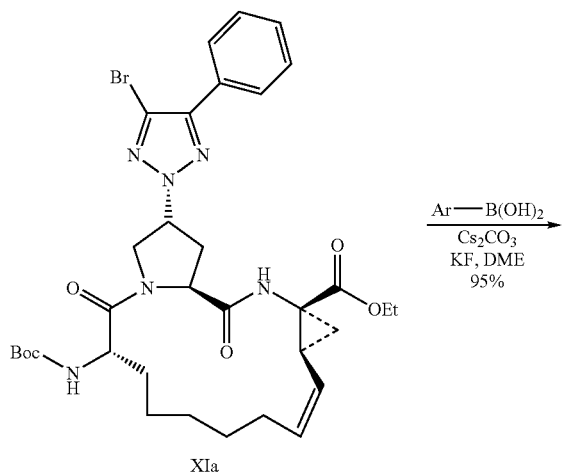

XIa

-continued

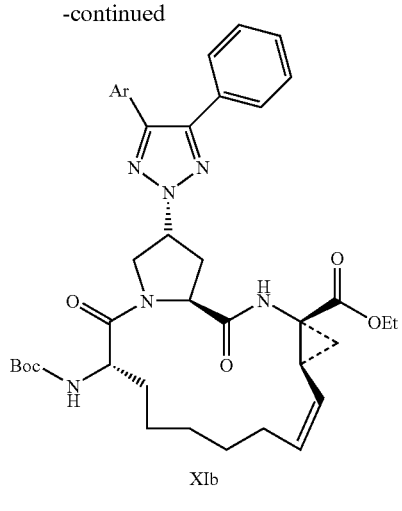

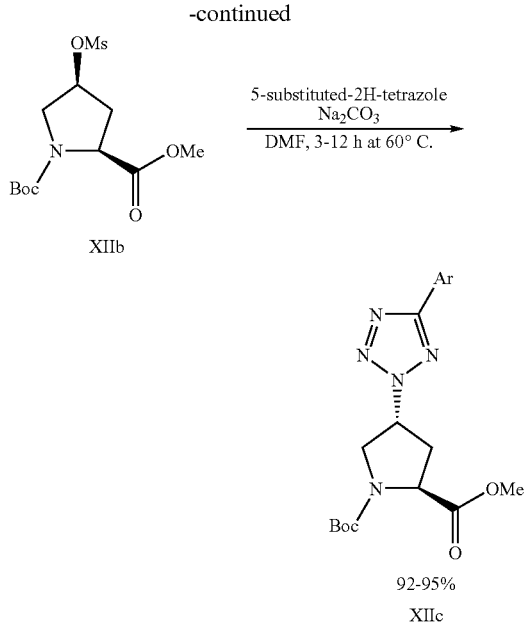

Compounds of the present invention may be further diversified by performing a Suzuki coupling adding to bromo-substituted triazole macrocyclic ethyl ester (see infra Example 26 for preparation) DME an aromatic boric acid, cesium carbonate and KF via the synthetic route described generally in Scheme 11.

II. Stepwise Synthesis

Compounds of the invention may also be prepared though a stepwise synthesis rather than a replacement mechanism. Below is an exemplary synthesis where W is a tetrazole.

A. Synthesis of Proline Derivatives.

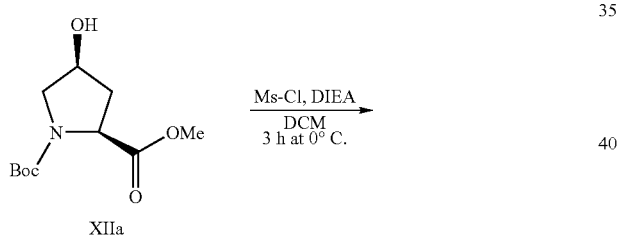

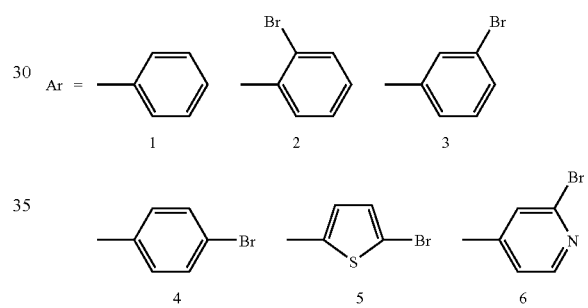

B. Synthesis of Linear Tripeptides.

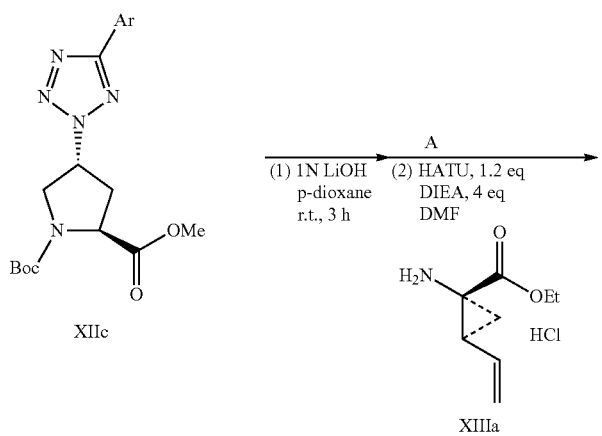

-continued
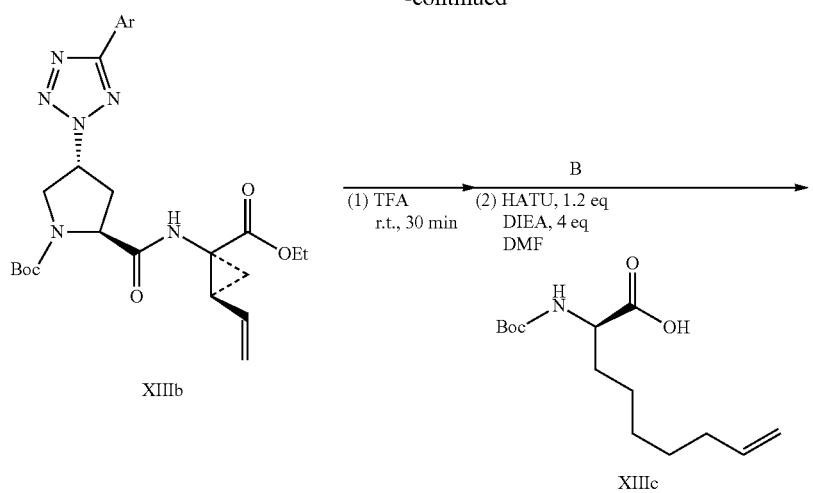
XIIIb
(1) TFA
r.t., 30 min
(2) HATU, 1.2 eq
DIEA, 4 eq
DMF
B
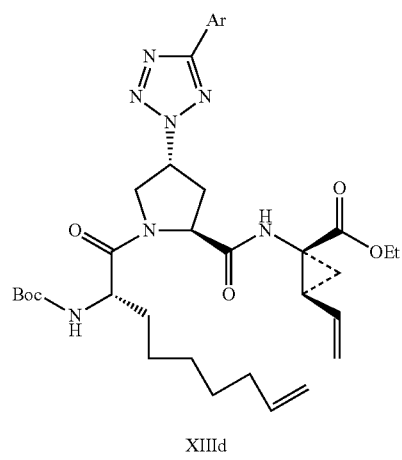
XIIIc
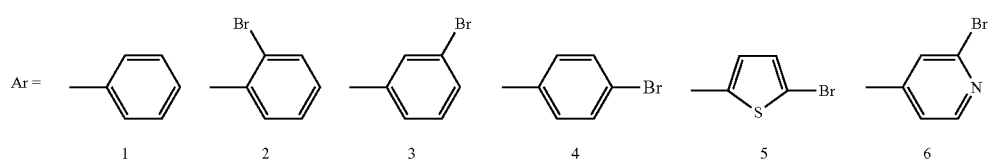

The linear tri-peptide containing tetrazole-substituted proline derivatives XIIc were prepared via the synthetic route described generally in Scheme 12.

C. Synthesis of Cyclic Peptide Via Ring-closing-Metathesis (RCM).

Scheme 14

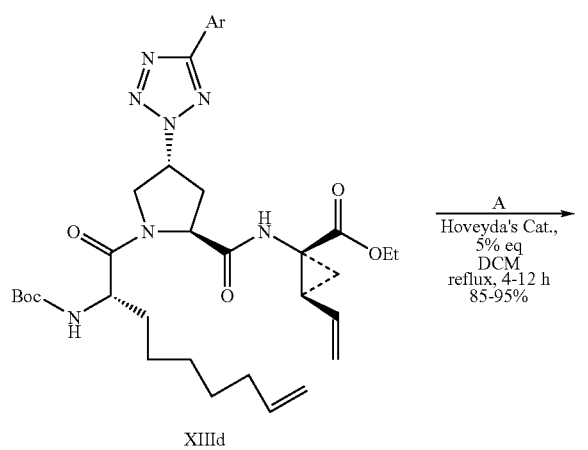

XIIId

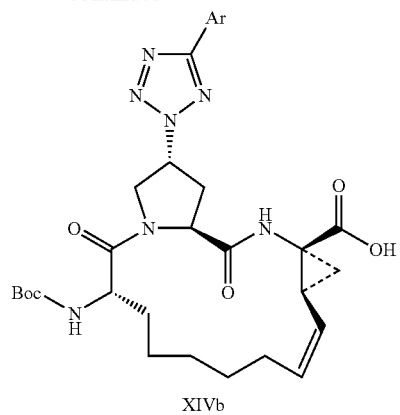

XIVb

-continued

Ar =

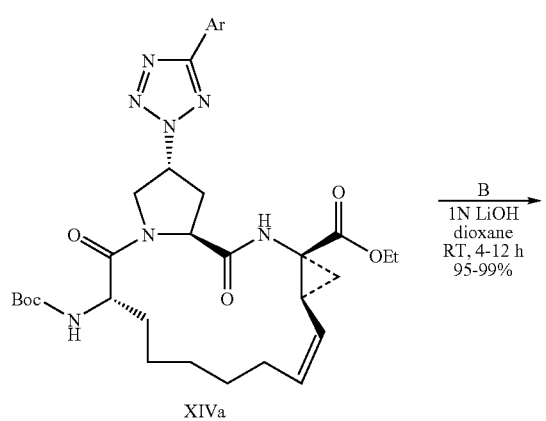

XIVa

Formation of macrocyclic compound Xb was performed using linear tripeptide XIIId via the Ring-Closing Metathesis reaction described generally in Scheme 14.

D. Other Derivatives

1. Tetrazole-substituted proline derivatives of the present invention were synthesized by the synthetic route described generally in Scheme 12.

Scheme 15
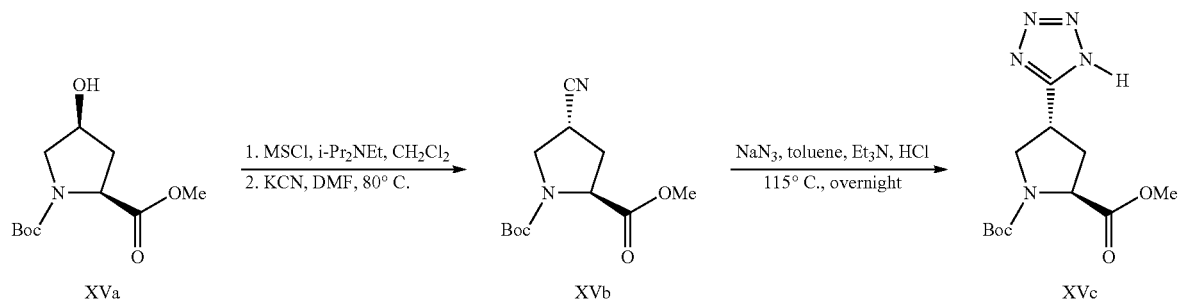
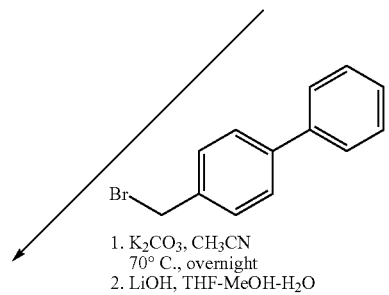
1. $K_2CO_3$, $CH_3CN$
   70° C., overnight
2. LiOH, THF-MeOH-$H_2O$
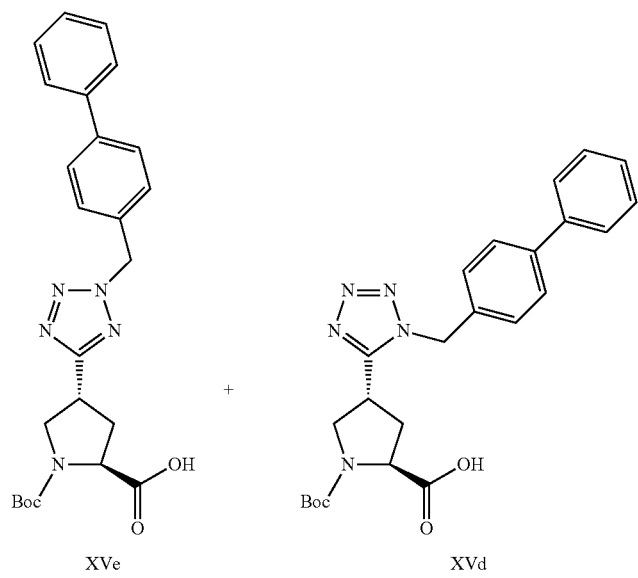

Additional tetrazole-substituted proline derivatives of the present invention were synthesized by the synthetic route described generally in Scheme 15.

2. Suzuki coupling

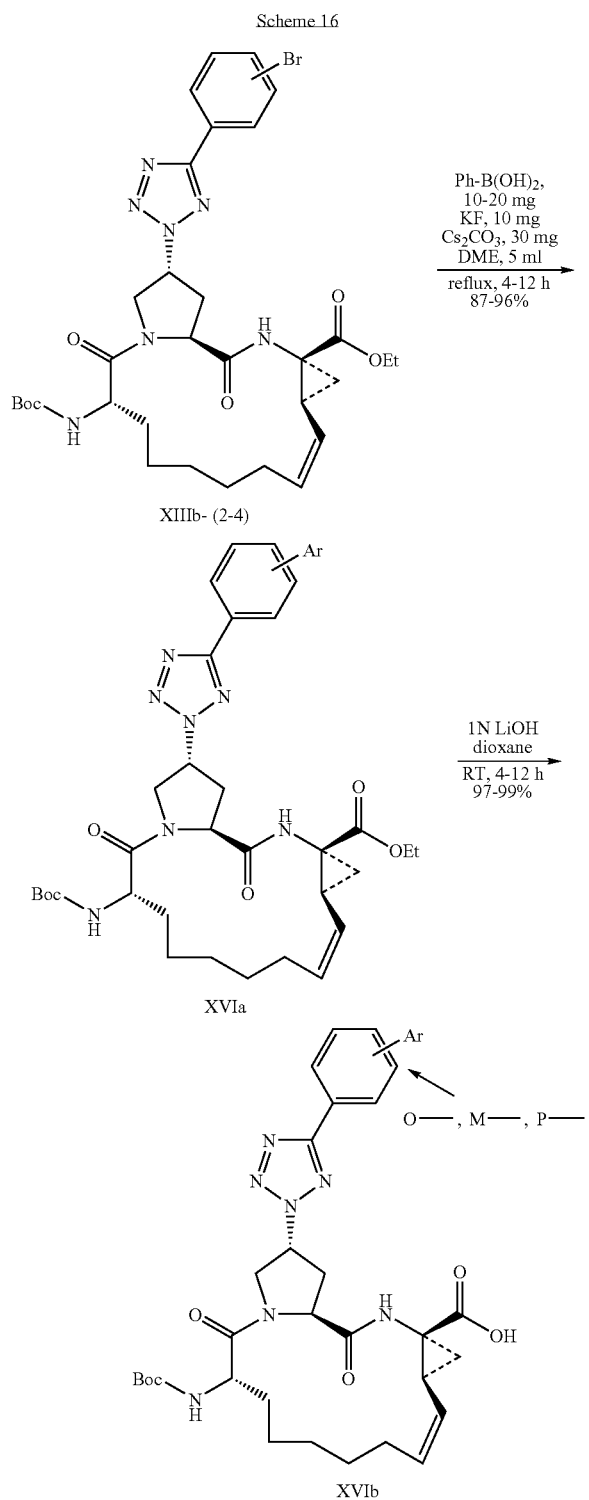

Further derivatives were prepared using the Suzuki Coupling reaction described generally in Scheme 16.

III. Solid Phase Synthesis

Some compounds of the invention are amenable to synthesis by solid phase synthesis. For example, the triazole-substituted proline derivatives (P2) can be synthesized and used in an on-resin assembly of a linear tripeptide chain. The resin-bound tripeptides, containing the triazole-substituted proline derivatives, undergo Ring-Closing-Metathesis (RCM) to furnish a cyclic tripeptide that is cleaved from the resin by hydrolysis affording the final product.

The following synthetic schemes set forth manners in which the triazole-substituted proline derivatives are made and the solid-phase synthesis of the compounds of the present invention.

A. Synthesis of Proline Derivatives

Two methods were employed to synthesize the triazole-substituted proline derivatives which are described generally by the following schemes:

1. Cyclo-addition Method

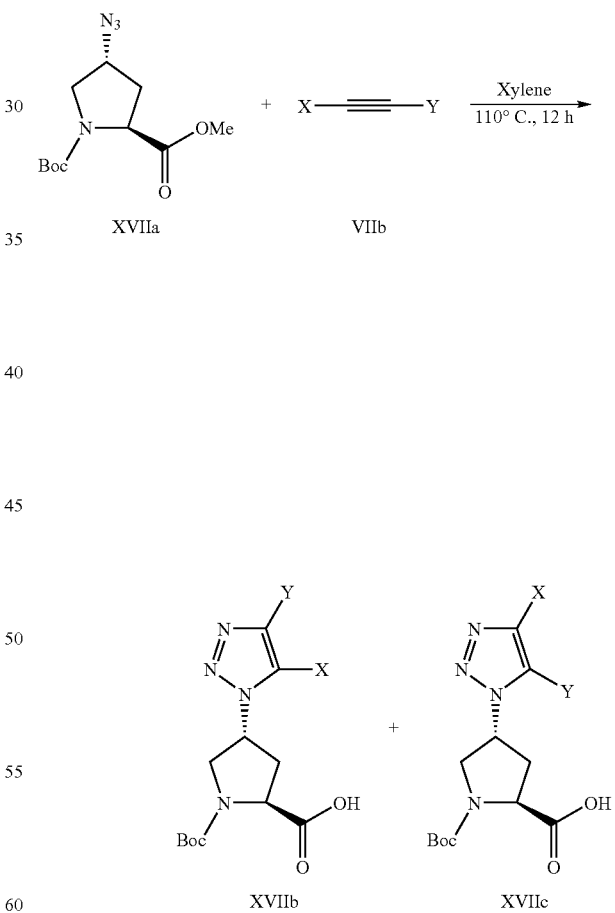

The cyclo-addition method to create triazolyl proline derivatives involves the 3+2 cyclo-addition of azide proline derivative XVIIb and alkyne VIIb via the synthetic route described generally in Scheme 17. Exemplary syntheses of alkynes are described in Scheme 7 above.

2. Mesylate Method
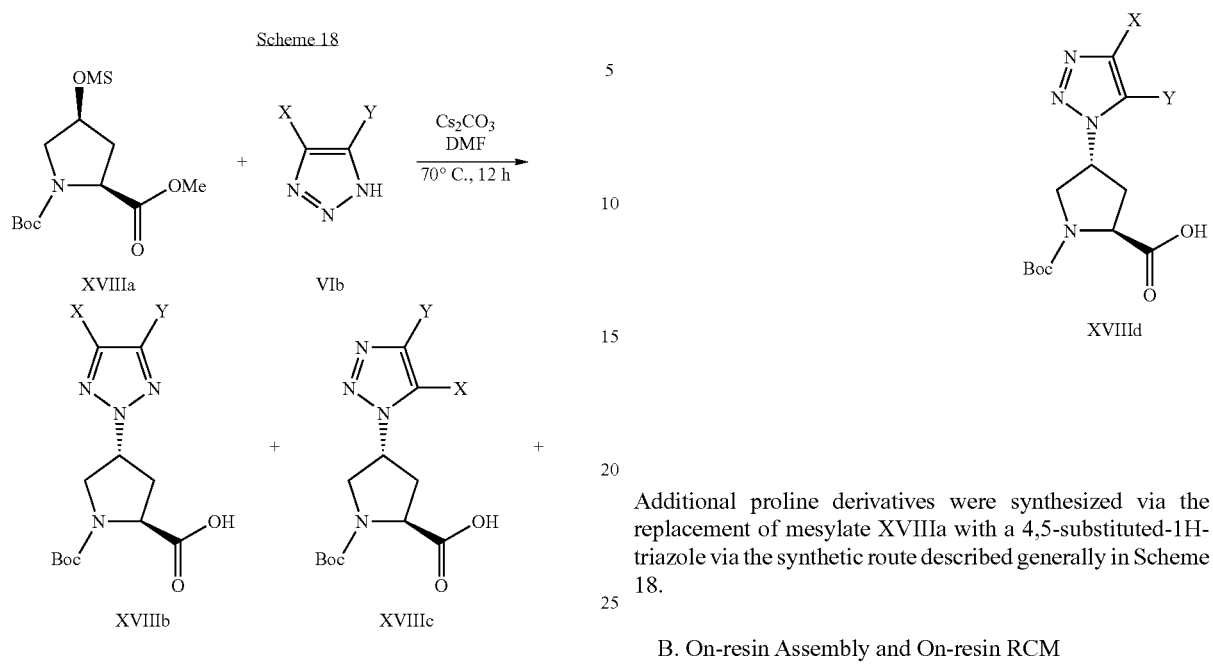
Additional proline derivatives were synthesized via the replacement of mesylate XVIIIa with a 4,5-substituted-1H-triazole via the synthetic route described generally in Scheme 18.
B. On-resin Assembly and On-resin RCM
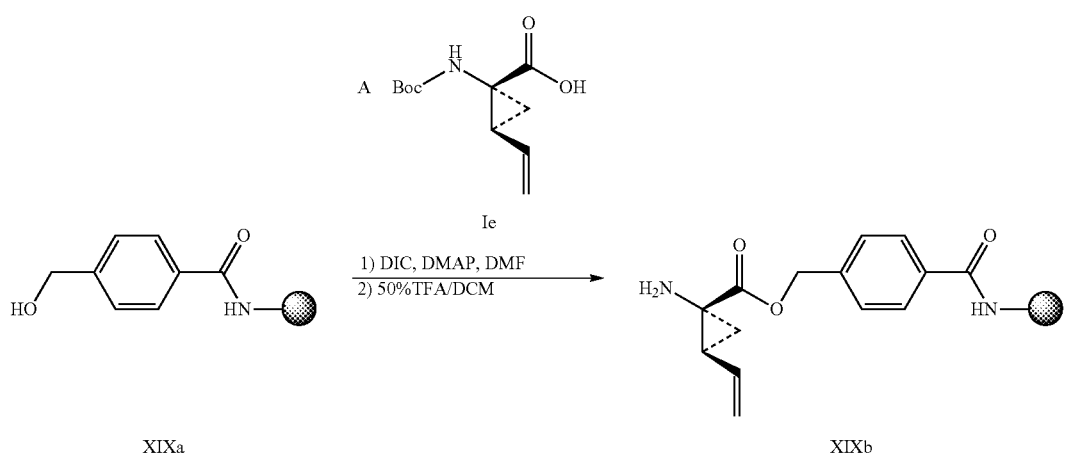
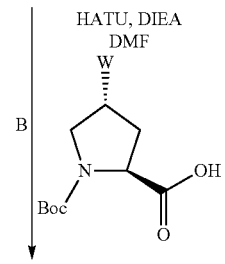

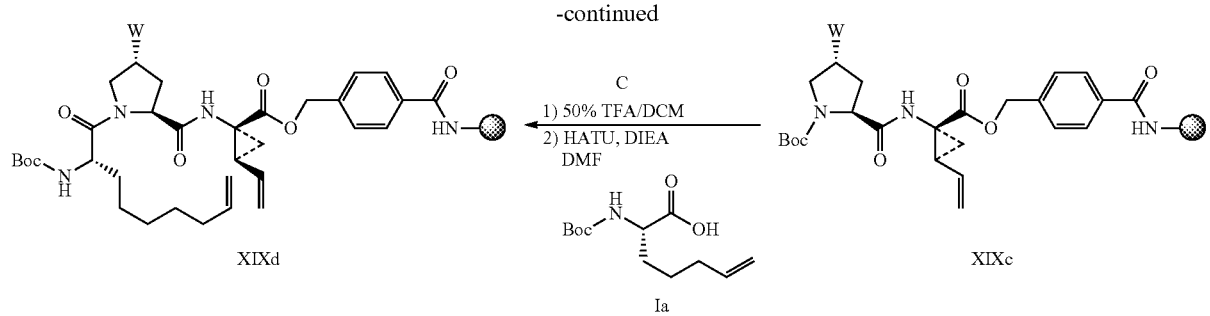

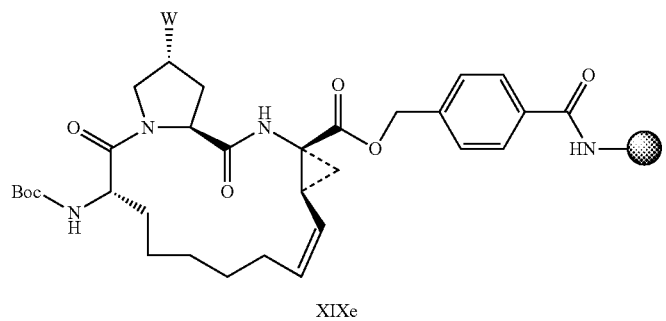

XIXe

W = triazole derivatives as previously defined

On Resin Assembly

The on-resin assembly of linear peptide XIXd followed by the on-resin RCM to obtain resin-bound cyclic peptide precursor XIXe was performed via steps A-D described generally in Scheme 19.

IV. Other Reactions

In some embodiments, the substituent W is well-suited to other types of reactions. For example, and not by limitation, when W is a pyridazinone, the following reaction schemes are used. These methods may be used for other substituents, but are discussed here in the context of pyridazinones.

A. Condensation Reactions

Scheme 20

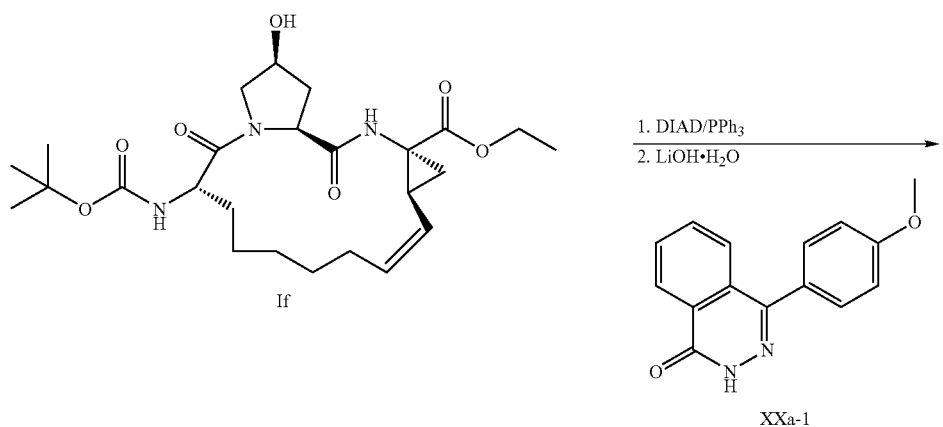

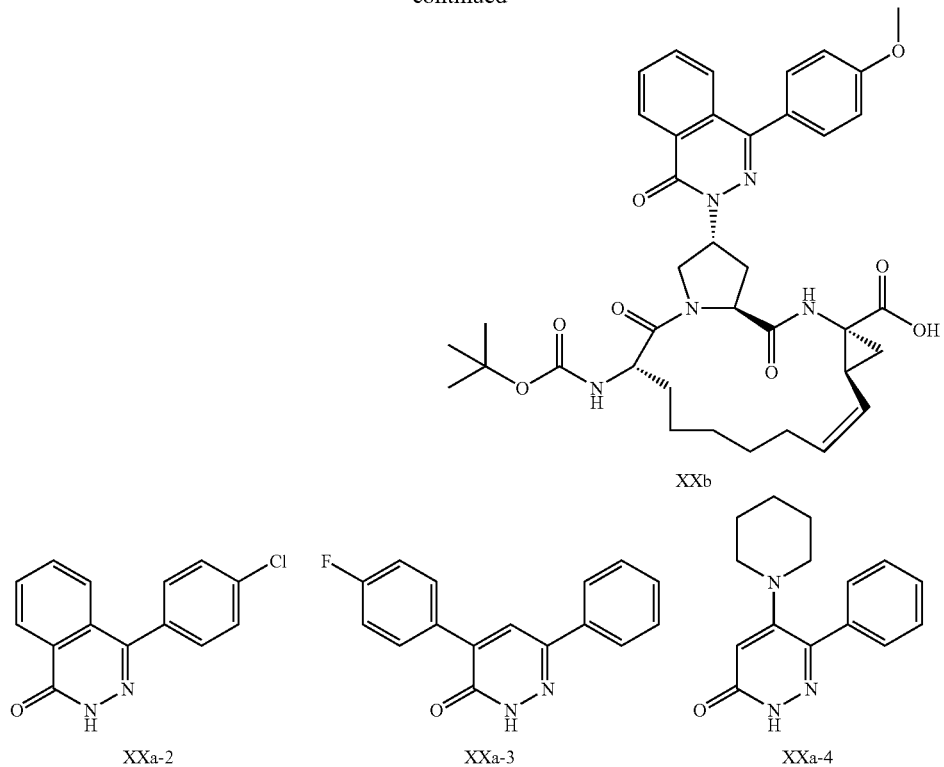

The simplest method, shown in Scheme 20, is to condense commercially available pyridazinones (XXa-1-XXa-4) with key intermediate If by using Mitsunobu conditions followed by hydrolysis with LiOH. For further details on the Mitsunobu reaction see O. Mitsunobu, *Synthesis* 1981, 1-28; D. L. Hughes, *Org. React.* 29, 1-162 (1983); D. L. Hughes, *Organic Preparations and Procedures Int.* 28, 127-164 (1996); and J. A. Dodge, S. A. Jones, *Recent Res. Dev. Org. Chem.* 1, 273-283 (1997).

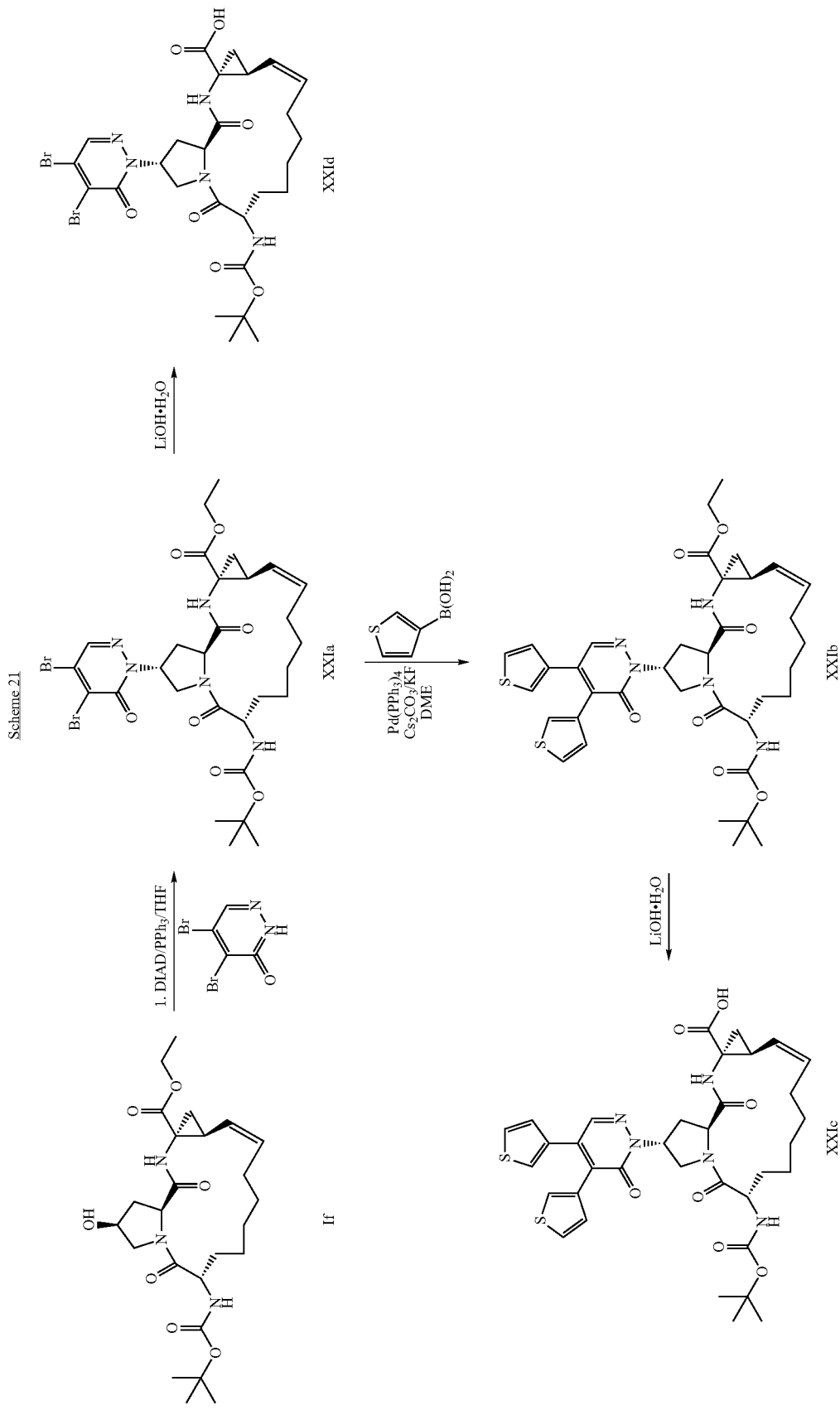

The second method of preparing pyridazinone analogs of the present invention is to further chemically manipulate dibromo intermediate XXIa (Scheme 21). The standard Mitsunobu coupling of the commercially available 4,5-dibromopyridazinone with hydroxyl If afforded the desired macrocycle XXIa. Coupling of XXIa with excess 3-thiophene boronic acid, cesium carbonate and potassium fluoride furnished di-thiophene XXIb. Hydrolysis of compound compounds XXIa and XXIb with LiOH gave the desired analogs XXId and XXIc respectively. Many different boronic acids may be used in a similar manner to yield a plethora of di-substituted pyridazinonyl macrocycles.

B. Bromide Differentiation Reaction

Differentiation between the bromides on macrocyclic XXIa is achieved via Michael addition. As shown in Scheme 22, commercially available pyrrolidine is coupled with dibromide to give compound XXIIa in 87% yield. The bromide moiety to the carbonyl is then under goes a Suzuki coupling reaction with 3-thiophene boronic acid to produce intermediate XXIIb, which is further treated with LiOH to afford analog XXIIc. For further details concerning the Suzuki coupling reaction see A. Suzuki, *Pure Appl. Chem.* 63, 419-422 (1991) and A. R. Martin, Y. Yang, *Acta Chem. Scand.* 47, 221-230 (1993).

C. Sulfur Containing Nucleophiles

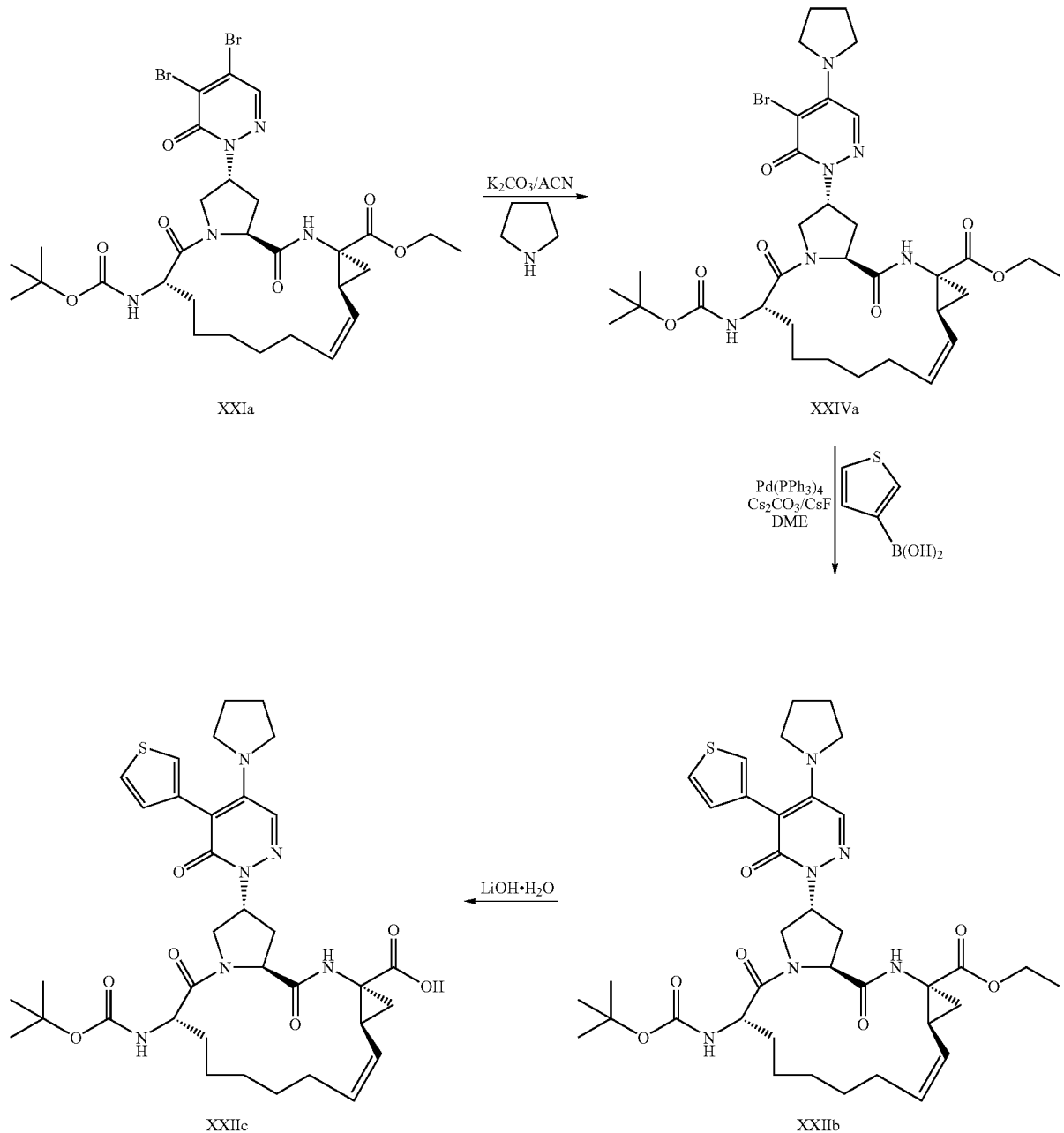

Scheme 22

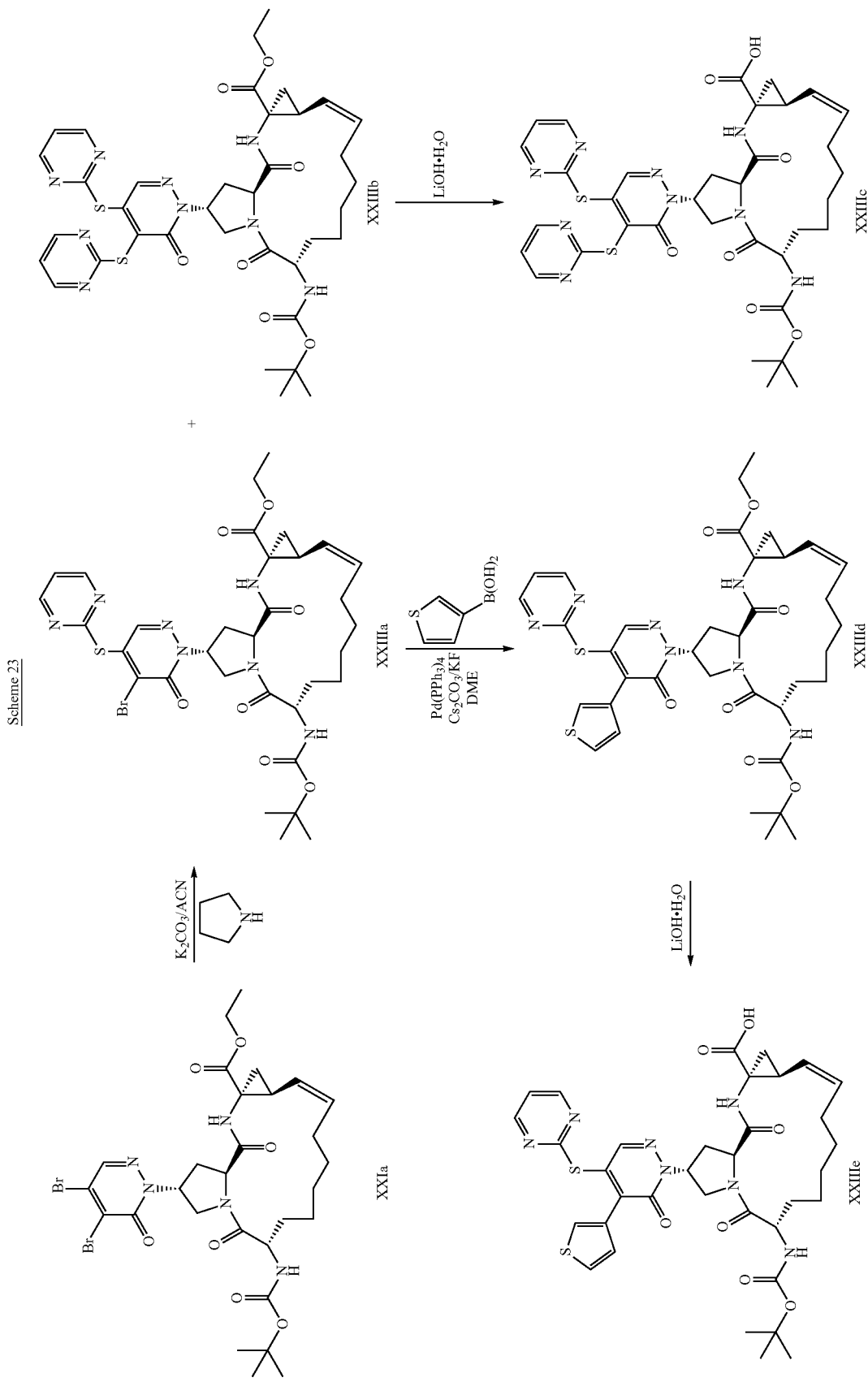

While the secondary amine nucleophile pyrrolidine gave exclusive addition to the 5-bromide position on macrocycle XXIa, sulfur-containing nucleophiles did not exhibit the same selectivity as shown in Scheme 23. With sulfur-containing nucleophiles, addition on both bromines of XXIa is observed together with the mono-coupled product XXIIa with only one equivalent of mercaptopyrimidine. The separability of compounds XXIIIa, XXIIIB and starting material XXIa by flash column chromatography allowed for a further Suzuki coupling of the mono-alkylated XXIIIa with 3-thiophene boronic acid followed by hydrolysis of XXIIId with LiOH to furnish analog XXIIIe. The di-alkylated product XXIIIb is also hydrolyzed with LiOH to produce analog XXIIIc.

D. Suzuki Coupling with Boronic Acid

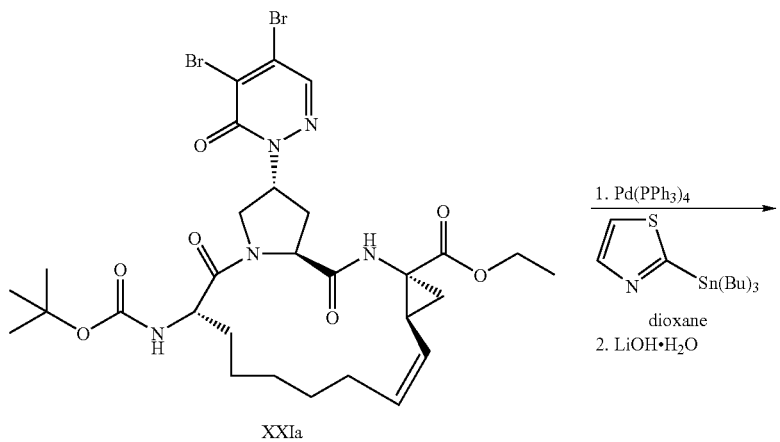

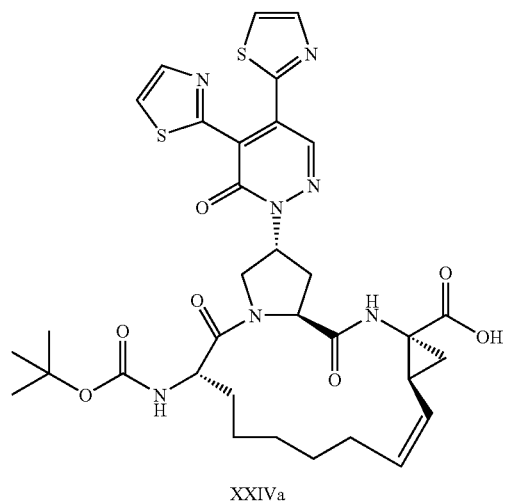

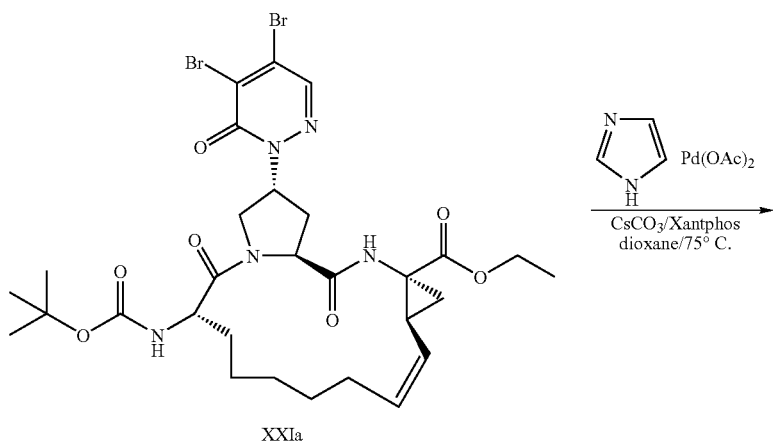

-continued

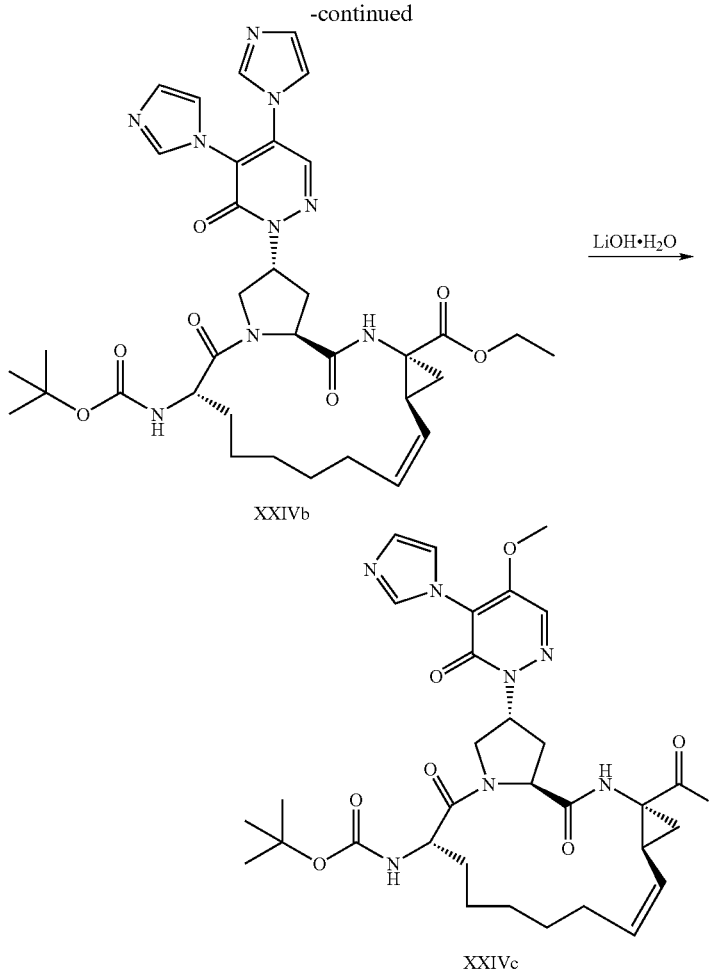

XXIVb

XXIVc

With only a limited number of boronic acids available for Suzuki coupling, other coupling methods such as Stille coupling and N-arylation using Buchwald's chemistry were also explored (Scheme 24). Coupling of intermediate XXIa with 2-stannylthiazole with Stille standard conditions followed by hydrolysis afforded analog XXIVa. As for N-arylation, coupling of imidazole to di-bromide 6 proceeded smoothly. Unfortunately, hydrolysis with LiOH resulted in replacement of the imidazole moiety on position 5 with a methoxy (XX-IVb. For further details concerning Stille coupling reactions see J. K. Stille, *Angew. Chem. Int. Ed.* 25, 508-524 (1986); M. Pereyre et al., *Tin in Organic Synthesis* (Butterworths, Boston, 1987) pp 185-207 passim., and T. N. Mitchell, *Synthesis* 1992, 803-815. For further details of the Buchwald reaction see J. F. Hartwig, *Angew. Chem. Int. Ed.* 37, 2046-2067 (1998).

E. Other Diversified Pyridazinone Analogs

Scheme 25
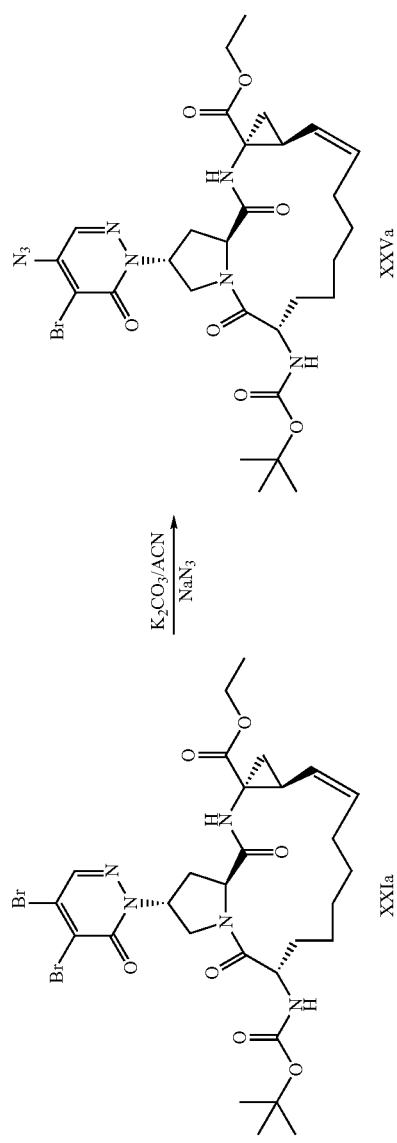
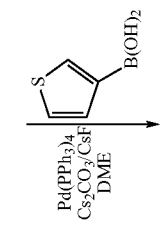
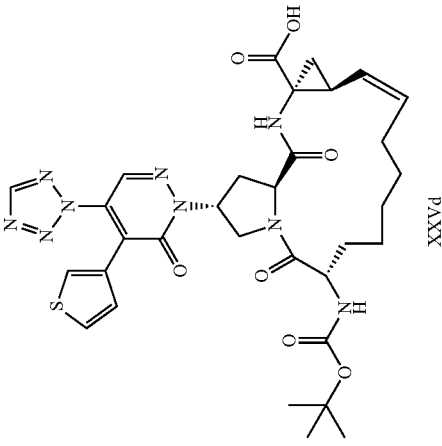
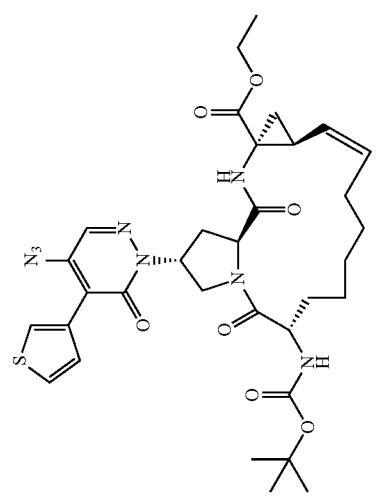
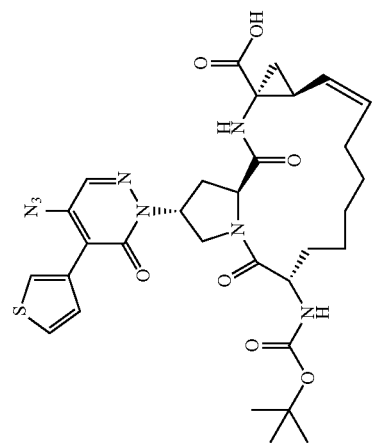

Another method for diversifying pyridazinone analogs is outlined in Scheme 25. Michael addition with sodium azide as the nucleophile to di-bromo XXIa yielded, as in the secondary amine case, only the mono-coupled compound XXVa. Further Suzuki coupling with 3-thiophene boronic acid produced azide XXVb. Compound XXVb is hydrolyzed to give analog XXVc. In addition, the azide moiety of compound XXVb is further converted to tetrazole under standard conditions with sodium cyanide, followed by hydrolysis to provide analog XXVd.

F. Synthesis of 5,6 Pyridazinoyl Macrocycle diate If via Mitsunobu conditions to give compound XXVIa. Product XXVIa is further subjected to Suzuki coupling conditions with 3-thiophene boronic acid, followed by hydrolysis to give the desired analog XXVb.

EXAMPLES

The compounds and processes of the present invention will be better understood in connection with the following examples, which are intended as an illustration only and not to limit the scope of the invention. Various changes and modi-

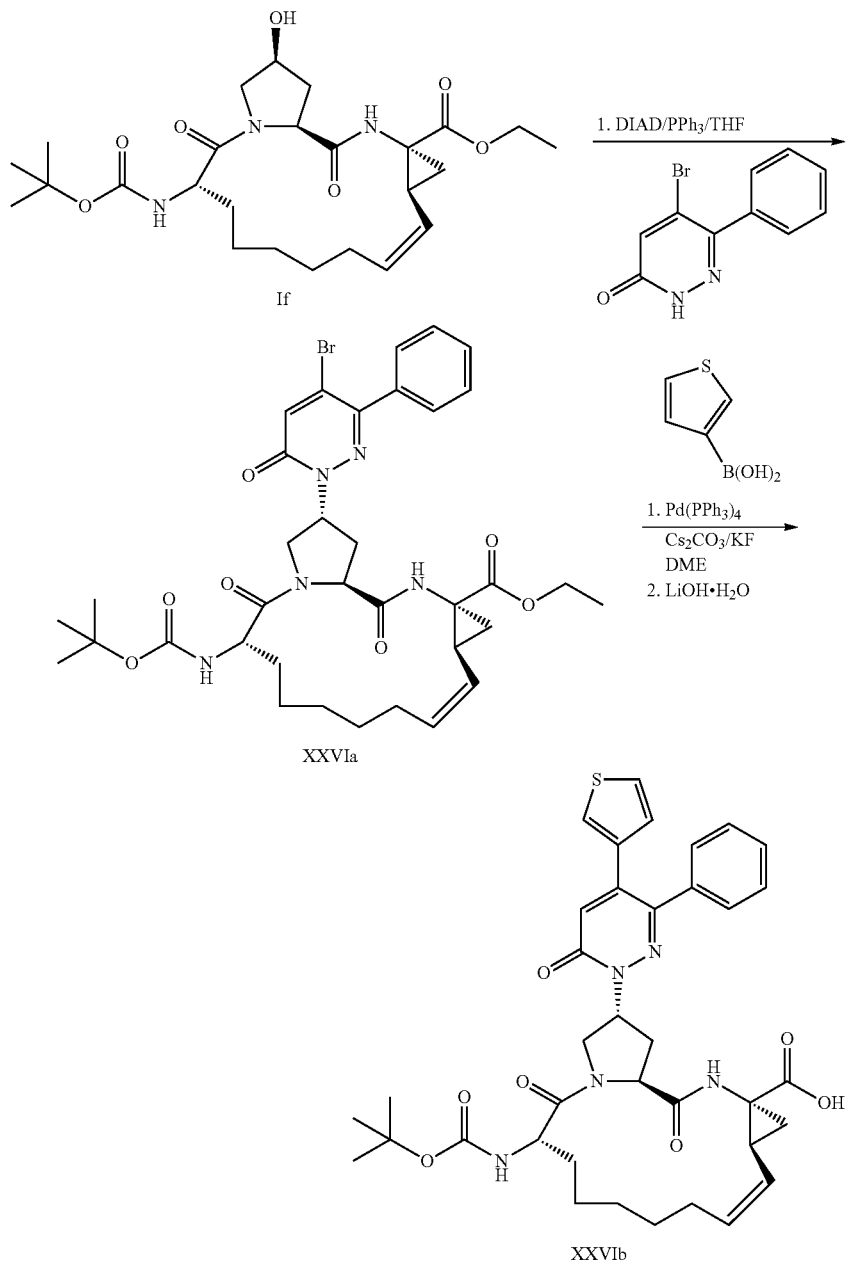

The synthesis of 5,6 pyridazinonyl macrocycle XXVIb is outlined in Scheme 26. Commercially available 5-bromo-6-phenyl-2H-pyridazin-3-one is condensed with key intermefications to the disclosed embodiments will be apparent to those skilled in the art. Such changes and modifications including, without limitation, those relating to the chemical structures, substituents, derivatives, formulations and/or methods of the invention may be made without departing from the spirit of the invention and the scope of the appended claims.

Example 1

Synthesis of the Cyclic Peptide Precursor

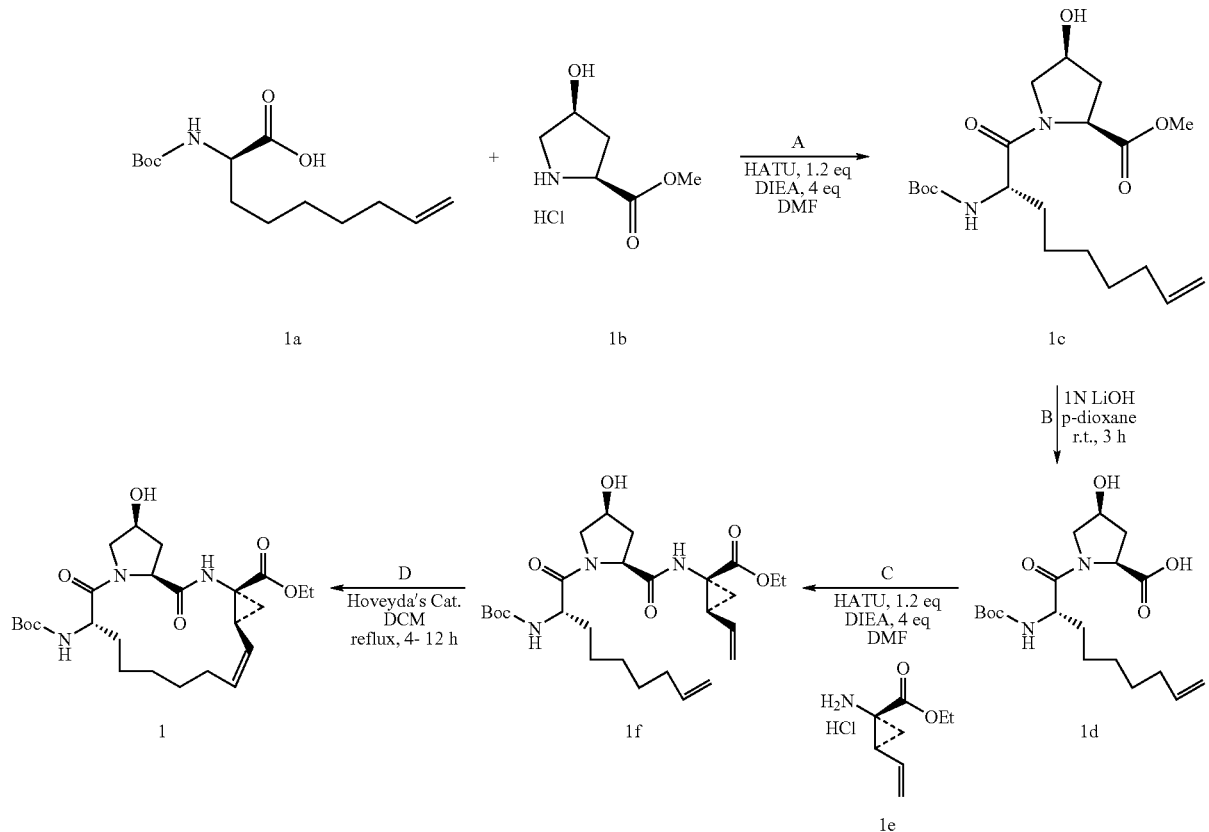

1A. To a solution of Boc-L-2-amino-8-nonenoic acid 1a (1.36 g, 5 mol) and the commercially available cis-L-hydroxyproline methyl ester 1b (1.09 g, 6 mmol) in 15 ml DMF, was added DIEA (4 ml, 4 eq.) and HATU (4 g, 2 eq). The coupling was carried out at 0° C. over a period of 1 hour. The reaction mixture was diluted with 100 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then was evaporated, affording the dipeptide 1c (1.91 g, 95.8%) that was identified by HPLC (Retention time=8.9 min, 30-70%, 90% B), and MS (found 421.37, M+Na$^+$).

1B. The dipeptide 1c (1.91 g) was dissolved in 15 mL of dioxane and 15 mL of 1 N LiOH aqueous solution and the hydrolysis reaction was carried out at RT for 4 hours. The reaction mixture was acidified by 5% citric acid and extracted with 100 mL EtOAc, and followed by washing with water 2×20 ml, 1M NaHCO$_3$ 2×20 ml and brine 2×20 ml, respectively. The organic phase was dried over anhydrous Na$_2$SO$_4$ and then removed in vacuum, yielding the free carboxylic acid compound 1d (1.79 g, 97%), which was used for next step synthesis without need for further purification.

1C. To a solution of the free acid obtained above (1.77, 4.64 mmol) in 5 ml DMF, D-1-vinyl cyclopropane amino acid ethyl ester 1e (0.95 g, 5 mmol), DIEA (4 ml, 4 eq.) and HATU (4 g, 2 eq) were added. The coupling was carried out at 0° C. over a period of 5 hours. The reaction mixture was diluted with 80 mL EtOAc, and followed by washing with 5% citric acid 2×20 ml, water 2×20 ml, 1M NaHCO$_3$ 4×20 ml and brine 2×10 ml, respectively. The organic phase was dried over anhydrous Na$_2$SO$_4$ and then evaporated. The residue was purified by silica gel flash chromatography using different ratios of hexanes:EtOAc as elution phase (5:1→3:1→1:1→1:2→1:5). The linear tripeptide 1f was isolated as an oil after removal of the elution solvents (1.59 g, 65.4%), identified by HPLC (Retention time=11.43 min) and MS (found 544.84, M+Na$^+$).

1D. Ring Closing Metathesis (RCM). A solution of the linear tripeptide 1f (1.51 g, 2.89 mmol) in 200 ml dry DCM was deoxygenated by bubbling N$_2$. Hoveyda's 1$^{st}$ generation catalyst (5 mol % eq.) was then added as solid. The reaction was refluxed under N$_2$ atmosphere 12 hours. The solvent was evaporated and the residue was purified by silica gel flash chromatography using different ratios of hexanes:EtOAc as elution phase (9:1→5:1→3:1→1:1→1:2→1:5). The cyclic peptide precursor 1 was isolated as a white powder after removal of the elution solvents (1.24 g, 87%), identified by HPLC (Retention time=7.84 min, 30-70%, 90% B), and MS (found 516.28, M+Na$^+$). For further details of the synthetic methods employed to produce the cyclic peptide precursor 1, see U.S. Pat. No. 6,608,027, which is herein incorporated by reference in its entirety.

Example 2

Synthesis of the Cyclic Peptide Precursor Mesylate

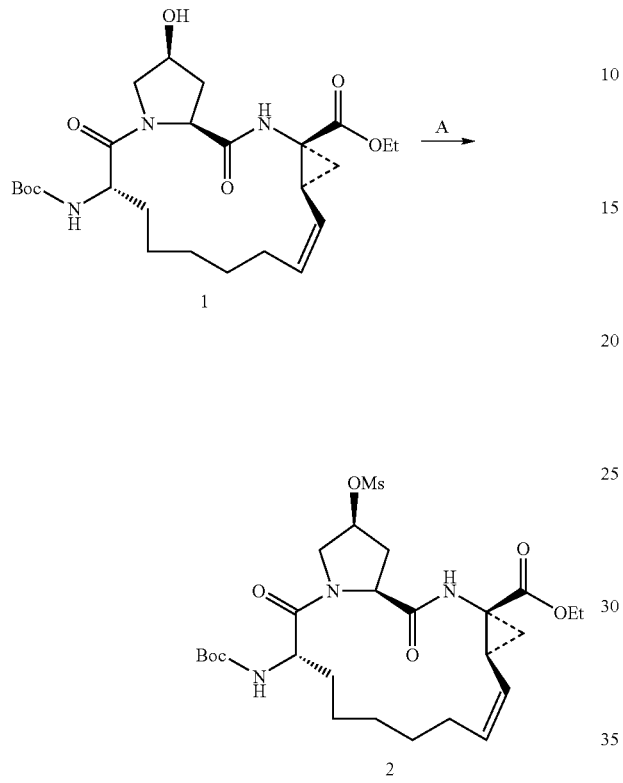

2A. To a solution of the macrocyclic peptide precursor 1 (500 mg, 1.01 mmol) and DIEA (0.4 ml, 2 mmol) in 2.0 ml DCM, mesylate chloride (0.1 ml) was added slowly at 0° C. where the reaction was kept for 3 hours. 30 mL EtOAc was then added and followed by washing with 5% citric acid 2×10 ml, water 2×10 ml, 1M NaHCO₃ 2×10 ml and brine 2×10 ml, respectively. The organic phase was dried over anhydrous Na₂SO₄ and evaporated, yielding the title compound mesylate that was used for next step synthesis without need for further purification.

Example 3

Tetrazole Synthesis

Structurally diverse tetrazoles IIIa-IIIq, for use in preparing tetrazolyl macrocycles of the invention were synthesized from commercially available nitrile compounds as described below:

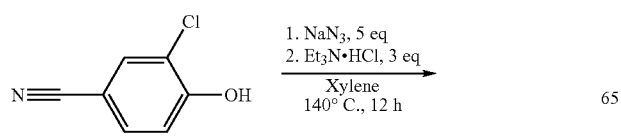

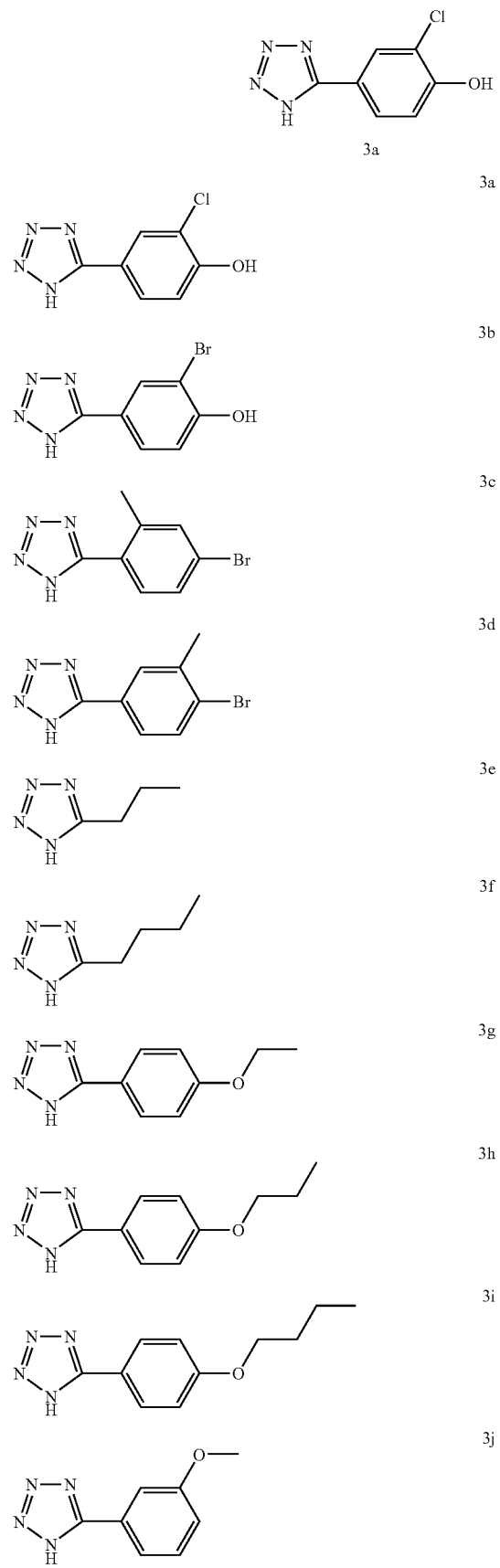

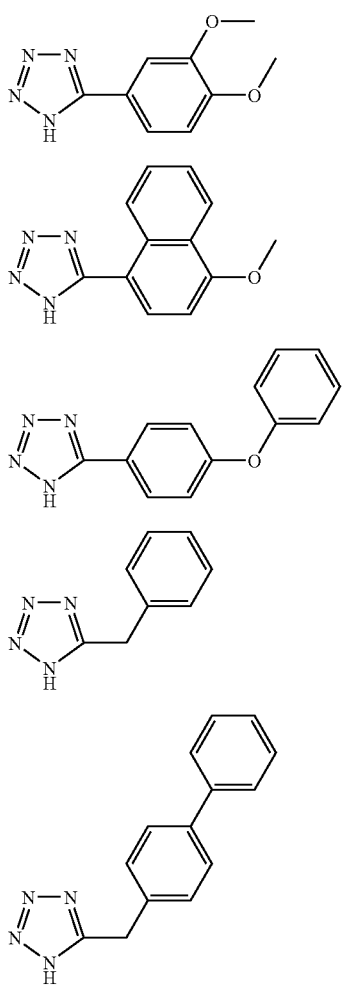

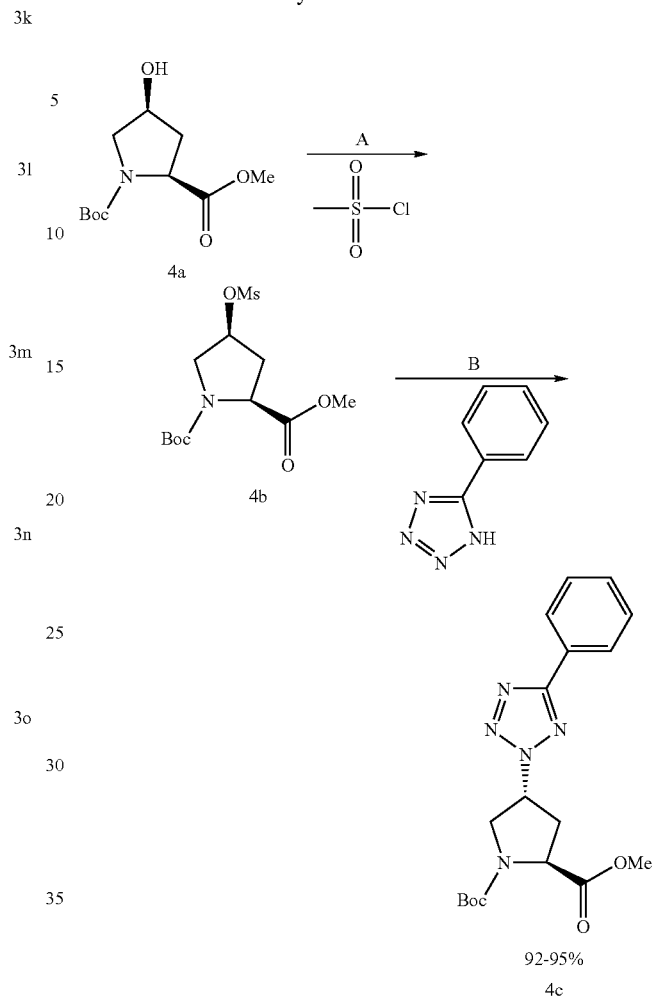

To a sealed tube containing 5 ml xylene, was added 3-Cl-4-hydroxy-benzoacetonitile (0.31 g, 5 mol), NaN$_3$ (0.65 g, 10 mmol) and the triethylamine hydrochloride (0.52 g, 3 mmol). The mixture was stirred vigorously at 140° C. over a period of 20-30 hours. The reaction mixture was then cooled and poured to a mixture of EtOAc (30 ml) and aqueous citric acid solution (20 mL). After washing with water 2×10 ml and brine 2×10 ml, the organic phase was dried over anhydrous Na$_2$SO$_4$ and was evaporated to a yellowish solid. After re-crystallization with EtOAc-hexanes, the tetrazole compound 3a was obtained in good yield (0.4 g, 86%%), high purity (>90%, by HPLC), and identified by NMR and MS (found 197.35 and 199.38, M+H$^+$).

Example 4

Compound of Formula II, wherein A=tBOC, G=OH, L=absent, W is

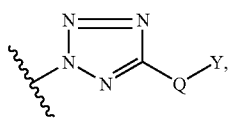

Q=absent, Y=Phenyl, j=3, m=s=1, and R$^3$=R$^4$=H.

Proline Derivative Synthesis

To a solution of N-Boc-cis-hydroxyproline methyl ester 4a (10 g, 40.8 mmol) and N,N-Diisopropylethyl amine (DIEA, 12 mL, 60 mmol) in 110 mL of DCM, was added 3.85 mL of mesylate chloride (50 mmol) in a dropwise manner and the resulting reaction mixture was stirred at 0° C. for 3 hours. TLC (hexanes:ethyl acetate=1:1, v/v) showed that Boc-cis-Hyp-OMe 4a was totally converted to its mesylate 4b. After the reaction was deemed complete by TLC, the reaction mixture was diluted with 100 ml EtOAc, washed with 5% citric acid 2×50 ml and brine 2×30 ml, and dried over anhydrous Na$_2$SO$_4$. Removal of solvents gave 13 g (98% yield) N-Boc-cis-4-mesylate-proline methyl ester 4b, which was used in Step B without need for further purification.

To a solution of the mesylate 4b (0.65 g, 2 mmol) in 5 mL DMF, was added 4 mmol of 5-phenyl-1H-tetrazole and anhydrous sodium carbonate (0.53 g, 5 mmol). The resulting reaction mixture was stirred vigorously at 60° C. for 6-12 hours. TLC (hexanes:ethyl acetate=1:1, v/v) showed the mesylate 4b was completely converted to trans 4-tetrazole-substituted proline derivative 4c. After the reaction was deemed complete by TLC, the reaction mixture was diluted with 30 ml EtOAc and washed with 1 M Na$_2$CO$_3$ (3×10 ml), water (3×10 ml), 5% citric acid (3×10 ml) and brine (3×10 ml), respectively. The organic phase was dried over anhydrous Na$_2$SO$_4$ and concentrated in vacuo, giving the 5-phenyl tetrazole substituted proline derivative 4c in excellent yield (94%) and high purity (>90%). 4c: 94% yield, [M+Na]$^+$=396.39.

Synthesis of Linear Tripeptides

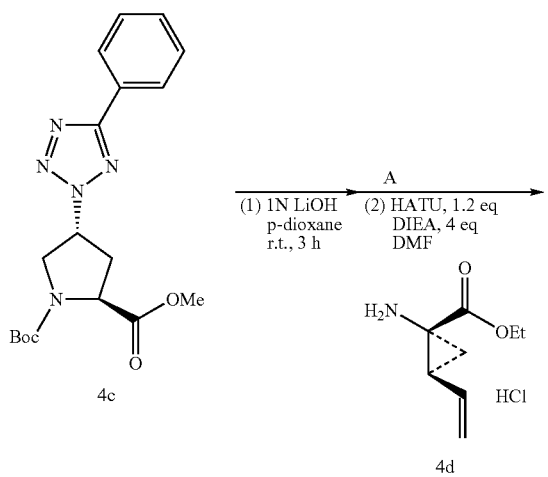

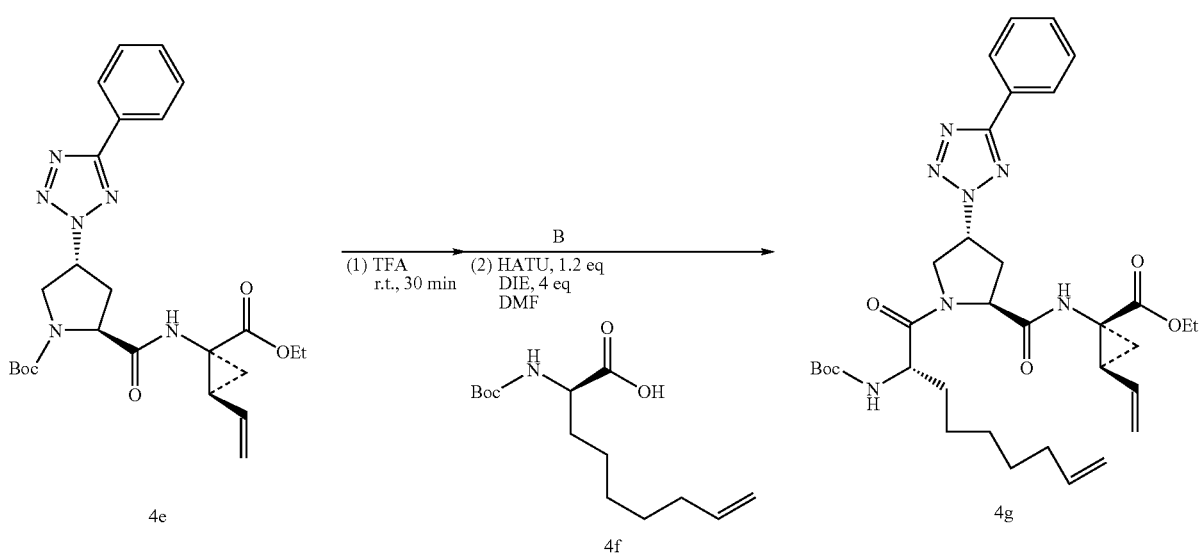

A. (1) The dipeptide 4e was prepared by dissolving 0.22 g (0.6 mmol) of N-Boc-trans-4-(3-phenyl tetrazolyl)-proline methyl ester 4c in 6 mL of dioxane and 2 mL of 1 N LiOH aqueous solution. The resulting reaction mixture was stirred at RT for 3-8 hours to allow the for the hydrolysis of the methyl ester. The reaction mixture was acidified by 5% citric acid, extracted with 40 mL EtOAc, and washed with water 2×20 ml, 1M NaHCO$_3$ 2×20 ml and brine 2×10 ml, respectively. The organic phase was dried over anhydrous Na$_2$SO$_4$ and concentrated in vacuo, yielding the free carboxylic acid compound (0.20 g, 92%), which was used for next step synthesis without need for further purification. (2) To a cooled (0° C.) solution of the free acid obtained above (0.20 g, 0.55 mmol) in 2 ml DMF, was added D-1-vinyl cyclopropane amino acid ethyl ester 4d (0.1 g, 0.52 mmol), DIEA (0.4 ml, 4 eq.) and HATU (0.4 g, 2 eq). The resulting reaction mixture was stirred at 0° C. for 0.5-3 hours. The reaction mixture was diluted with 40 mL EtOAc, and washed with 5% citric acid 2×20 ml, water 2×20 ml, 1M NaHCO$_3$ 4×20 ml, and brine 2×10 ml, respectively. The organic phase was dried over anhydrous Na$_2$SO$_4$ and concentrated in vacuo, affording the dipeptide 4e (0.24 g, 94%), identified by HPLC (Retention time=10.03 min) and MS (found 519.22, M+Na$^+$).

B. (1) Tripeptide 4g was prepared by deprotecting the amine of dipeptide 4e (0.24 g, 0.49 mmol) in 2 mL TFA at 0° C. for 10 min. After removal of TFA in vacuo, the free amine product was subjected to next coupling reaction directly. (2) To a cooled (0° C.) solution of the free amine compound obtained above in 2 ml DMF, was added Boc-2-amino-8-nonenoic acid 4f (0.136 g, 0.50 mmol), DIEA (0.4 ml, 4 eq.) and HATU (0.4 g, 2 eq). The coupling was carried out at 0° C. over a period of 0.5-3 hours. The reaction mixture was diluted with 40 mL EtOAc and washed with 5% citric acid 2×20 ml, water 2×20 ml, 1M NaHCO$_3$ 4×20 ml and brine 2×10 ml, respectively. The organic phase was dried over anhydrous Na$_2$SO$_4$ and concentrated in vacuo, affording tripeptide 4g (0.28 g, 88% for two steps) that was identified by HPLC (Retention time=14.03 min), and MS (found 672.30, M+Na$^+$).

Synthesis of Cyclic Peptide via Ring-closing-Metathesis (RCM).

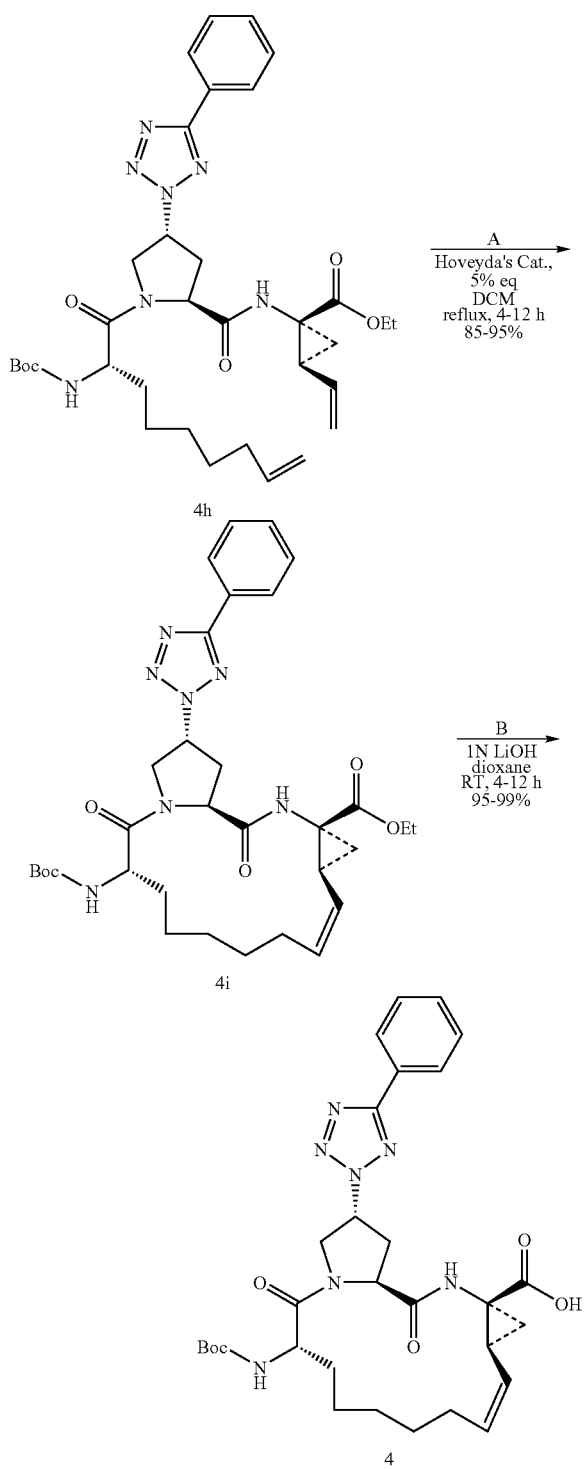

A. A solution of linear tripeptide 4g (71 mg, 0.109 mmol) in 50 ml dry DCM was deoxygenated by bubbling $N_2$. To the resulting degassed solution was added Hoveyda's Cat. (5-10 mol % eq.) was as solid and the resulting reaction mixture was refluxed under $N_2$ over for 5-20 hours. The reaction mixture was then concentrated in vacuo and the residue was purified by silica gel flash chromatography using different ratios of hexanes:EtOAc as elution phase (9:1→5:1→3:1→1:1→1:2). The macrocyclic peptide 4i was isolated as a white powder by evaporation of the elution solvents (58 mg, 85.5%), identified by HPLC (Retention time=11.80 min, 30-80%, 90% B), and MS (found 644.66, M+Na$^+$).

IV. Hydrolysis of the Ethyl Ester

The title compound was prepared by dissolving compound 4i (20 mg) in 2 mL of dioxane and 1 mL of 1 N LiOH aqueous solution. The resulting reaction mixture was stirred at RT for 4-8 hours. The reaction mixture was then acidified with 5% citric acid, extracted with 10 mL EtOAc, and washed with water 2×20 ml. The solvent was evaporated and the residue was purified by HPLC on a YMC AQ12S11-0520WT column with a 30-80% (100% acetonitrile) gradient over a 20 min period. After lyophilization, title compound was obtained as a white amorphous solid.

[M+Na]+=616.72.

Example 5

Compound of Formula II, wherein A=tBOC, G=OH, L=absent, W is

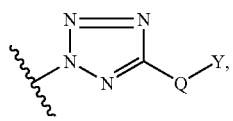

Q=absent, Y=2-bromophenyl, j=3, m=s=1, and $R^3=R^4=H$.

5A. Proline Derivative Synthesis

The proline derivative of the present example was prepared by the procedure set forth in Example 4 (I) with 5-(2-bromophenyl)-1H-tetrazole and N-Boc-cis-hydroxyproline methyl ester 4a.

[M+Na]$^+$=396.39.

5B. Synthesis of Linear Tripeptides

The linear peptide of the present example was prepared via the procedure set forth in Example 4 (II) with the proline derivative prepared in step 5A, D-β-vinyl cyclopropane amino acid ethyl ester, and Boc-2-amino-8-nonenoic acid.

[M+H]$^+$=728.41

5C. Ring Closing Metathesis

The macrocyclic peptide ethyl ester of the present example was prepared with the linear peptide of Step 5B via the procedure set forth in Example 4 (III).

[M+Na]$^+$=722.37.

5D. Hydrolysis of the Ethyl Ester

The title compound was ultimately obtained via hydrolysis described in Example 4 (IV) from the ethyl ester of Step 5C.

[M+H]$^+$=672.49.

Example 6

Compound of Formula II, wherein A=tBOC, G=OH, L=absent, W is

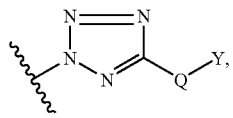

Q=absent, Y=3-bromophenyl, j=3, m=s=1, and $R^3=R^4=H$.

6A. Proline Derivative Synthesis

The proline derivative of the present example was prepared by the procedure set forth in Example 4 (I) with 5-(3-bromophenyl)-1H-tetrazole and N-Boc-cis-hydroxyproline methyl ester 4a.

[M+Na]$^+$=396.39.

6B. Synthesis of Linear Tripeptides

The linear peptide of the present example was prepared via the procedure set forth in Example 4 (II) with the proline derivative prepared in step 6A, D-β-vinyl cyclopropane amino acid ethyl ester, and Boc-2-amino-8-nonenoic acid.

[M+H]$^+$=728.41.

6C. Ring Closing Metathesis

The macrocyclic peptide ethyl ester of the present example was prepared with the linear peptide of Step 6B via the procedure set forth in Example 4 (III).

[M+Na]$^+$=722.37.

6D. Hydrolysis of the Ethyl Ester

The title compound was ultimately obtained via hydrolysis described in Example 4 (IV) from the ethyl ester of Step 6C.

[M+H]$^+$=672.49.

Example 7

Compound of Formula II, wherein A=tBOC, G=OH, L=absent, W is

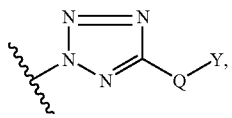

Q=absent, Y=4-bromophenyl, j=3, m=s=1, and R$^3$=R$^4$=H.

7A. Proline Derivative Synthesis

The proline derivative of the present example was prepared by the procedure set forth in Example 4 (I) with 5-(4-bromophenyl)-1H-tetrazole and N-Boc-cis-hydroxyproline methyl ester 4a.

[M+Na]$^+$=396.39.

7B. Synthesis of Linear Tripeptides

The linear peptide of the present example was prepared via the procedure set forth in Example 4 (II) with the proline derivative prepared in step 7A, D-β-vinyl cyclopropane amino acid ethyl ester, and Boc-2-amino-8-nonenoic acid.

[[M+Na]+H]$^+$=728.41.

7C. Ring Closing Metathesis

The macrocyclic peptide ethyl ester of the present example was prepared with the linear peptide of Step 7B via the procedure set forth in Example 4 (III).

[M+Na]$^+$=722.37.

7D. Hydrolysis of the Ethyl Ester

The title compound was ultimately obtained via hydrolysis described in Example 4 (IV) from the ethyl ester of Step 7C.

[M+H]$^+$=672.49.

Example 8

Compound of Formula II, wherein A=tBOC, G=OH, L=absent, W is

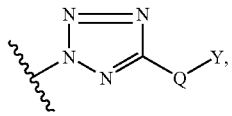

Q=absent, Y=5-Bromo-2-thienyl, j=3, m=s=1, and R$^3$=R$^4$=H.

8A. Proline Derivative Synthesis

The proline derivative of the present example was prepared by the procedure set forth in Example 4 (I) with 5-(5-Bromo-2-thienyl)-1H-tetrazole and N-Boc-cis-hydroxyproline methyl ester 4a.

[M+Na]$^+$=480.23.

8B. Synthesis of Linear Tripeptides

The linear peptide of the present example was prepared via the procedure set forth in Example 4 (II) with the proline derivative prepared in step 8A, D-β-vinyl cyclopropane amino acid ethyl ester, and Boc-2-amino-8-nonenoic acid.

[M-Boc+H]$^+$=634.29.

8C. Ring Closing Metathesis

The macrocyclic peptide ethyl ester of the present example was prepared with the linear peptide of Step 8B via the procedure set forth in Example 4 (III).

[M+Na]$^+$=736.21.

8D. Hydrolysis of the Ethyl Ester

The title compound was ultimately obtained via hydrolysis described in Example 4 (IV) from the ethyl ester of Step 8C.

[M+H]$^+$=678.22.

Example 9

Compound of Formula II, wherein A=tBOC, G=OH, L=absent, W is

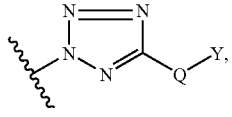

Q=absent, Y=2-bromo-4-pyridyl, j=3, m=s=1, and R$^3$=R$^4$=H.

9A. Proline Derivative Synthesis

The proline derivative of the present example was prepared by the procedure set forth in Example 4 (I) with 5-(2-bromo-4-pyridyl)-1H-tetrazole and N-Boc-cis-hydroxyproline methyl ester 4a.

[M+Na]$^+$=453.23.

9B. Synthesis of Linear Tripeptides

The linear peptide of the present example was prepared via the procedure set forth in Example 4 (II) with the proline derivative prepared in step 9A, D-β-vinyl cyclopropane amino acid ethyl ester, and Boc-2-amino-8-nonenoic acid.

[M-Boc+H]$^+$=629.31.

9C. Ring Closing Metathesis

The macrocyclic peptide ethyl ester of the present example was prepared with the linear peptide of Step 9B via the procedure set forth in Example 4 (III).

[M+Na]$^+$=723.36.

9D. Hydrolysis of the Ethyl Ester

The title compound was ultimately obtained via hydrolysis described in Example 4 (IV) from the ethyl ester of Step 9C.
[M+H]$^+$=673.26.

Example 10

Compound of Formula II, wherein A=tBOC, G=OH, L=absent, W is

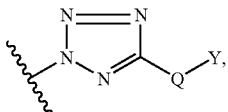

Q=absent, Y=2-biphenyl, j=3, m=s=1, and R$^3$=R$^4$=H.

To a deoxygenated solution of ethyl ester compound from Step 5C obtained above (40 mg), phenylboronic acid (10 mg), KF (100 mg), and Cs$_2$CO$_3$ (80 mg) in 5 ml DME was added Pd(PPh$_3$)$_4$ (5 mg) in its solid form. The resulting reaction mixture was heated in an oil bath to 90° C. and vigorously stirred for 6-12 hours. The solvent was evaporated and the residue was purified by silica gel flash chromatography using different ratios of hexanes:EtOAc as the elution phase (9:1→5:1→3:1→1:1→2:1). The macrocyclic bi-aryl peptide ethyl ester was then isolated as a white powder by evaporation of the elution solvents (31 mg, 78%) that was directly subjected to hydrolysis, as previously described in Example 4 (IV), and purified by HPLC.
[M+Na]$^+$=692.38.

Example 11

Compound of Formula II, wherein A=tBOC, G=OH, L=absent, W is

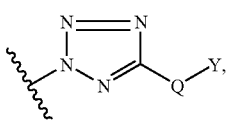

Q=absent, Y=3-biphenyl, j=3, m=s=1, and R$^3$=R$^4$=H.

The title compound was prepared with the ethyl ester compound from Step 6C and phenylboronic acid via the procedure set forth in Example 10, followed by hydrolysis of the ethyl ester according to the procedure of Example 4 (IV).
[M+Na]$^+$=692.38.

Example 12

Compound of Formula II, wherein A=tBOC, G=OH, L=absent, W is

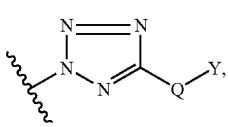

Q=absent, Y=4-biphenyl, j=3, m=s=1, and R$^3$=R$^4$=H.

The title compound was prepared with the ethyl ester compound from Step 7C phenylboronic acid via the procedure set forth in Example 10, followed by hydrolysis of the ethyl ester according to the procedure of Example 4 (IV).
[M+Na]$^+$=692.38.

Example 13

Compound of Formula II, wherein A=tBOC, G=OH, L=absent, W is

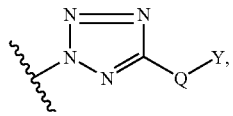

Q=absent, Y=3-(3-thienyl)phenyl, j=3, m=s=1, and R$^3$=R$^4$=H.

The title compound was prepared with the ethyl ester compound from Step 6C and 3-thienylboronic acid via the procedure set forth in Example 10, followed by hydrolysis of the ethyl ester according to the procedure of Example 4 (IV).
[M+Na]$^+$=698.32.

Example 14

Compound of Formula II, wherein A=tBOC, G=OH, L=absent, W is

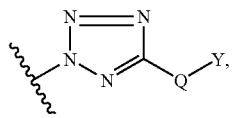

Q=absent, Y=3-(p-trifluoromethoxyphenyl)phenyl, j=3, m=s=1, and R$^3$=R$^4$=H.

The title compound was prepared with the ethyl ester compound from Step 6C and p-trifluoromethoxyphenylboronic acid via the procedure set forth in Example 10, followed by hydrolysis of the ethyl ester according to the procedure of Example 4 (IV).
[M+Na]$^+$=776.35.

Example 15

Compound of Formula II, wherein A=tBOC, G=OH, L=absent, W is

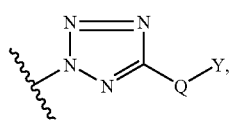

Q=absent, Y=3-(p-cyanophenyl)phenyl, j=3, m=s=1, and R$^3$=R$^4$=H.

The title compound was prepared with the ethyl ester compound from Step 6C and p-cyanophenylboronic acid via the procedure set forth in Example 10, followed by hydrolysis of the ethyl ester according to the procedure of Example 4 (IV).
[M+Na]$^+$=692.38.

Example 16

Compound of Formula II, wherein A=tBOC, G=OH, L=absent, W is

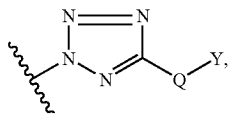

Q=absent, Y=4-(3-thienyl)phenyl, j=3, m=s=1, and $R^3=R^4=H$.

The title compound was prepared with the ethyl ester compound from Step 7C and 3-thienylboronic acid via the procedure set forth in Example 10, followed by hydrolysis of the ethyl ester according to the procedure of Example 4 (IV).

$[M+Na]^+$=698.32.

Example 17

Compound of Formula II, wherein A=tBOC, G=OH, L=absent, W is

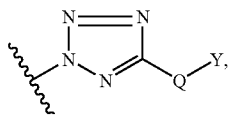

Q=absent, Y=4-(p-trifluoromethoxyphenyl)phenyl, j=3, m=s=1, and $R^3=R^4=H$.

The title compound was prepared with the ethyl ester compound from Step 7C and p-trifluoromethoxyphenylboronic acid via the procedure set forth in Example 10, followed by hydrolysis of the ethyl ester according to the procedure of Example 4 (IV).

$[M+Na]^+$=776.35.

Example 18

Compound of Formula II, wherein A=tBOC, G=OH, L=absent, W is

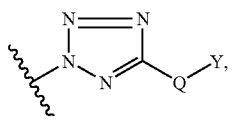

Q=absent, Y=4-(p-cyanophenyl)phenyl, j=3, m=s=1, and $R^3=R^4=H$.

The title compound was prepared with the ethyl ester compound from Step 7C and p-cyanophenylboronic acid via the procedure set forth in Example 10, followed by hydrolysis of the ethyl ester according to the procedure of Example 4 (IV).

$[M+Na]^+$=692.38.

Example 19

Compound of Formula II, wherein A=tBOC, G=OH, L=absent, W is

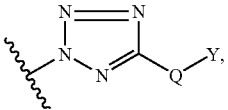

Q=absent, Y=5-phenyl-2-thienyl, j=3, m=s=1, and $R^3=R^4=H$.

The title compound was prepared with the ethyl ester compound from Step 8C and phenylboronic acid via the procedure set forth in Example 10, followed by hydrolysis of the ethyl ester according to the procedure of Example 4 (IV).

$[M+Na]^+$=698.32.

Example 20

Compound of Formula II, wherein A=tBOC, G=OH, L=absent, W is

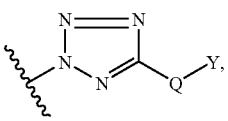

Q=absent, Y=5-phenyl-3-pyridyl, j=3, m=s=1, and $R^3=R^4=H$.

The title compound was prepared with the ethyl ester compound from Step 9C and phenylboronic acid via the procedure set forth in Example 10, followed by hydrolysis of the ethyl ester according to the procedure of Example 4 (IV).

$[M+Na]^+$=708.30.

Example 21

Compound of Formula II, wherein A=tBOC, G=OEt, L=absent, W is

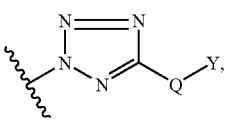

Q=absent, Y=3-chloro-4-hydroxyphenyl, j=3, m=s=1, and $R^3=R^4=H$.

Replacement Method

The title compound was prepared via the replacement of the mesylate 2 and tetrazole 3a. The replacement method is performed by dissolving 0.041 mmol of the macrocyclic peptide precursor mesylate 2 and 0.123 mmol of tetrazole 3a in 3 ml of DMF and adding 0.246 mmol of sodium carbonate (60 mg). The resulting reaction mixture is stirred at 60° C. for 4-10 hours and subsequently cooled and extracted with ethyl acetate. The organic extract was washed with water (2×30 ml), and the organic solution is concentrated in vacuo to be used in crude form for hydrolysis of the ethyl ester.

Example 22

Compound of Formula II, wherein A=tBOC, G=OH, L=absent, W is

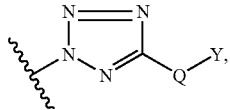

Q=absent, Y=3-chloro-4-hydroxyphenyl, j=3, m=s=1, and $R^3=R^4=H$.

The title compound was prepared by dissolving the title compound of Example 4 (20 mg) in 2 mL of dioxane and 1 mL of 1 N LiOH aqueous solution. The resulting reaction mixture was stirred at RT for 4-8 hours. The reaction mixture was acidified with 5% citric acid, extracted with 10 mL EtOAc, and washed with water 2×20 ml. The solvent was evaporated and the residue was purified by HPLC on a YMC AQ12S11-0520WT column with a 30-80% (100% acetonitrile) gradient over a 20 min period. After lyophilization, title compound was obtained as a white amorphous solid.

$[M+Na]^+=666.24$.

Example 23

Compound of Formula II, wherein A=tBOC, G=OH, L=absent, W is

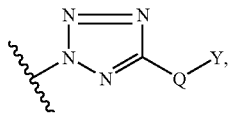

Q=absent, Y=3-bromo-4-hydroxyphenyl, j=3, m=s=1, and $R^3=R^4=H$.

The title compound was prepared via the replacement method described in Example 21 with mesylate 2 and tetrazole 3b from Example 3, followed by hydrolysis of the ethyl ester by the procedure of Example 22.

$[M+Na]^+=712.18$.

Example 24

Compound of Formula II, wherein A=tBOC, G=OH, L=absent, W is

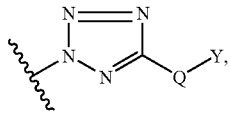

Q=absent, Y=2-methyl-4-bromophenyl, j=3, m=s=1, and $R^3=R^4=H$.

The title compound was prepared via the replacement method described in Example 21 with mesylate 2 and tetrazole 3c from Example 3, followed by hydrolysis of the ethyl ester by the procedure of Example 22.

$[M+Na]^+=708.30$.

Example 25

Compound of Formula II, wherein A=tBOC, G=OH, L=absent, W is

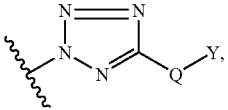

Q=absent, Y=3-methyl-4-bromophenyl, j=3, m=s=1, and $R^3=R^4=H$.

The title compound was prepared via the replacement method described in Example 21 with mesylate 2 and tetrazole 3d from Example 3, followed by hydrolysis of the ethyl ester by the procedure of Example 22.

$[M+Na]^+=708.30$.

Example 26

Compound of Formula II, wherein A=tBOC, G=OH, L=absent, W is

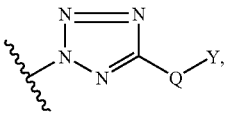

Q=absent, Y=n-propyl, j=3, m=s=1, and $R^3=R^4=H$.

The title compound was prepared via the replacement method described in Example 21 with mesylate 2 and tetrazole 3e from Example 3, followed by hydrolysis of the ethyl ester by the procedure of Example 22.

$[M+Na]^+=582.33$.

Example 27

Compound of Formula II, wherein A=tBOC, G=OH, L=absent, W is

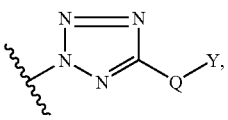

Q=absent, Y=n-butyl, j=3, m=s=1, and $R^3=R^4=H$.

The title compound was prepared via the replacement method described in Example 21 with mesylate 2 and tetrazole 3f from Example 3, followed by hydrolysis of the ethyl ester by the procedure of Example 22.

$[M+Na]^+=596.36$.

Example 28

Compound of Formula II, wherein A=tBOC, G=OH, L=absent, W is

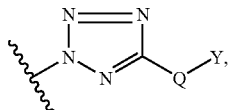

Q=absent, Y=4-ethoxyphenyl, j=3, m=s=1, and $R^3$=$R^4$=H.

The title compound was prepared via the replacement method described in Example 21 with mesylate 2 and tetrazole 3g from Example 3, followed by hydrolysis of the ethyl ester by the procedure of Example 22.

$[M+H]^+$=660.92.

Example 29

Compound of Formula II, wherein A=tBOC, G=OH, L=absent, W is

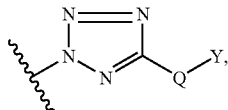

Q=absent, Y=4-propoxyphenyl, j=3, m=s=1, and $R^3$=$R^4$=H.

The title compound was prepared via the replacement method described in Example 21 with mesylate 2 and tetrazole 3h from Example 3, followed by hydrolysis of the ethyl ester by the procedure of Example 22.

$[M+Na]^+$=674.29.

Example 30

Compound of Formula II, wherein A=tBOC, G=OH, L=absent, W is

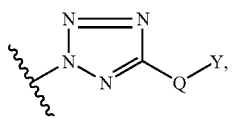

Q=absent, Y=4-butoxyphenyl, j=3, m=s=1, and $R^3$=$R^4$=H.

The title compound was prepared via the replacement method described in Example 21 with mesylate 2 and tetrazole 3l from Example 3, followed by hydrolysis of the ethyl ester by the procedure of Example 22.

$[M+Na]^+$=688.32.

Example 31

Compound of Formula II, wherein A=tBOC, G=OH, L=absent, W is

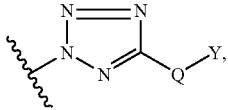

Q=absent, Y=3-methoxyphenyl, j=3, m=s=1, and $R^3$=$R^4$=H.

The title compound was prepared via the replacement method described in Example 21 with mesylate 2 and tetrazole 3j from Example 3, followed by hydrolysis of the ethyl ester by the procedure of Example 22.

$[M+Na]^+$=646.92.

Example 32

Compound of Formula II, wherein A=tBOC, G=OH, L=absent, W is

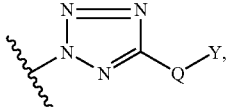

Q=absent, Y=3,4-dimethoxyphenyl, j=3, m=s=1, and $R^3$=$R^4$=H.

The title compound was prepared via the replacement method described in Example 21 with mesylate 2 and tetrazole 3k from Example 3, followed by hydrolysis of the ethyl ester by the procedure of Example 22.

$[M+Na]^+$=676.38.

Example 33

Compound of Formula II, wherein A=tBOC, G=OH, L=absent, W is

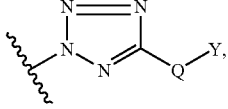

Q=absent, Y=4-methoxy-1-naphthyl, j=3, m=s=1, and $R^3$=$R^4$=H.

The title compound was prepared via the replacement method described in Example 21 with mesylate 2 and tetrazole 3l from Example 3, followed by hydrolysis of the ethyl ester by the procedure of Example 22.

$[M+Na]^+$=697.00.

Example 34

Compound of Formula II, wherein A=tBOC, G=OH, L=absent, W is

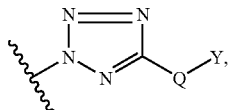

Q=absent, Y=4-phenoxyphenyl, j=3, m=s=1, and $R^3=R^4=H$.

The title compound was prepared via the replacement method described in Example 21 with mesylate 2 and tetrazole 3m from Example 3, followed by hydrolysis of the ethyl ester by the procedure of Example 22.

$[M+Na]^+$=708.51.

Example 35

Compound of Formula II, wherein A=tBOC, G=OH, L=absent, W is

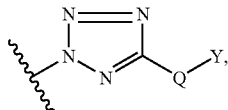

Q=absent, Y=benzyl, j=3, m=s=1, and $R^3=R^4=H$.

The title compound was prepared via the replacement method described in Example 21 with mesylate 2 and tetrazole 3n from Example 3, followed by hydrolysis of the ethyl ester by the procedure of Example 22.

$[M+Na]^+$=630.35.

Example 36

Compound of Formula II, wherein A=tBOC, G=OH, L=absent, W is

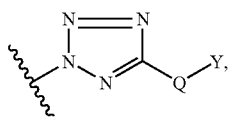

Q=absent, Y=p-phenylbenzyl, j=3, m=s=1, and $R^3=R^4=H$.

The title compound was prepared via the replacement method described in Example 21 with mesylate 2 and tetrazole 3o from Example 3, followed by hydrolysis of the ethyl ester by the procedure of Example 22.

$[M+Na]^+$=706.38.

Example 37

Compound of Formula II, wherein A=tBOC, G=OH, L=absent, W is

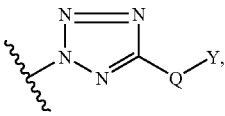

Q=absent, Y=3-chlorophenyl, j=3, m=s=1, and $R^3=R^4=H$.

The title compound was prepared via the replacement method described in Example 21 with mesylate 2 and 5-(3-chlorophenyl)-1H-tetrazole, followed by hydrolysis of the ethyl ester by the procedure of Example 22.

$[M+Na]^+$=650.33.

Example 38

Compound of Formula II, wherein A=tBOC, G=OH, L=absent, W is

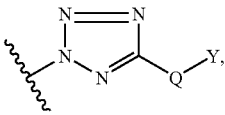

Q=absent, Y=3-fluorophenyl, j=3, m=s=1, and $R^3=R^4=H$.

The title compound was prepared via the replacement method described in Example 21 with mesylate 2 and 5-(3-fluorophenyl)-1H-tetrazole, followed by hydrolysis of the ethyl ester by the procedure of Example 22.

$[M+Na]^+$=634.37.

Example 39

Compound of Formula II, wherein A=tBOC, G=OH, L=absent, W is

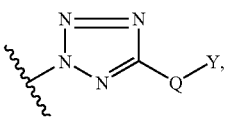

Q=absent, Y=3-methoxyphenyl, j=3, m=s=1, and $R^3=R^4=H$.

The title compound was prepared via the replacement method described in Example 21 with mesylate 2 and 5-(3-methoxyphenyl)-1H-tetrazole, followed by hydrolysis of the ethyl ester by the procedure of Example 22.

$[M+Na]^+$=646.92.

Example 40

Compound of Formula II, wherein A=tBOC, G=OH, L=absent, W is

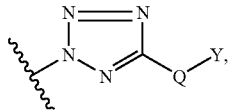

Q=absent, Y=3-phenoxyphenyl, j=3, m=s=1, and $R^3=R^4=H$.

The title compound was prepared via the replacement method described in Example 21 with mesylate 2 and 5-(3-phenoxyphenyl)-1H-tetrazole, followed by hydrolysis of the ethyl ester by the procedure of Example 22.

$[M+Na]^+=708.51$.

Example 41

Compound of Formula II, wherein A=tBOC, G=OH, L=absent, W is

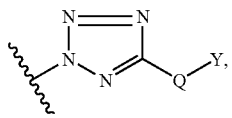

Q=absent, Y=3-benzyloxyphenyl, j=3, m=s=1, and $R^3=R^4=H$.

The title compound was prepared via the replacement method described in Example 21 with mesylate 2 and 5-(3-benzyloxyphenyl)-1H-tetrazole, followed by hydrolysis of the ethyl ester by the procedure of Example 22.

$[M+Na]^+=722.32$.

Example 42

Compound of Formula II, wherein A=tBOC, G=OH, L=absent, W is

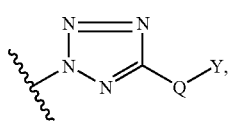

Q=absent, Y=3-trifluormethylphenyl, j=3, m=s=1, and $R^3=R^4=H$.

The title compound was prepared via the replacement method described in Example 21 with mesylate 2 and 5-(3-trifluormethylphenyl)-1H-tetrazole, followed by hydrolysis of the ethyl ester by the procedure of Example 22.

$[M+Na]^+=684.32$.

Example 43

Compound of Formula II, wherein A=tBOC, G=OH, L=absent, W is

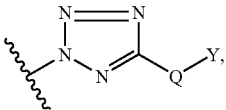

Q=absent, Y=4-bromophenyl, j=3, m=s=1, and $R^3=R^4=H$.

The title compound was prepared via the replacement method described in Example 21 with mesylate 2 and 5-(4-bromophenyl)-1H-tetrazole, followed by hydrolysis of the ethyl ester by the procedure of Example 22.

$[M+Na]^+=696.28$.

Example 44

Compound of Formula II, wherein A=tBOC, G=OH, L=absent, W is

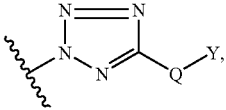

Q=absent, Y=4-fluorophenyl, j=3, m=s=1, and $R^3=R^4=H$.

The title compound was prepared via the replacement method described in Example 21 with mesylate 2 and 5-(4-fluorophenyl)-1H-tetrazole, followed by hydrolysis of the ethyl ester by the procedure of Example 22.

$[M+Na]^+=634.36$.

Example 45

Compound of Formula II, wherein A=tBOC, G=OH, L=absent, W is

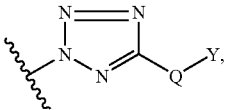

Q=absent, Y=4-methoxyphenyl, j=3, m=s=1, and $R^3=R^4=H$.

The title compound was prepared via the replacement method described in Example 21 with mesylate 2 and 5-(4-methoxyphenyl)-1H-tetrazole, followed by hydrolysis of the ethyl ester by the procedure of Example 22.

$[M+Na]^+=646.36$.

Example 46

Compound of Formula II, wherein A=tBOC, G=OH, L=absent, W is

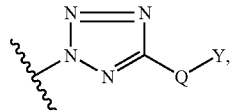

Q=absent, Y=4-ethoxyphenyl, j=3, m=s=1, and $R^3=R^4=H$.

The title compound was prepared via the replacement method described in Example 21 with mesylate 2 and 5-(4-ethoxyphenyl)-1H-tetrazole, followed by hydrolysis of the ethyl ester by the procedure of Example 22.

$[M+H]^+=660.92$.

Example 47

Compound of Formula II, wherein A=tBOC, G=OH, L=absent, W is

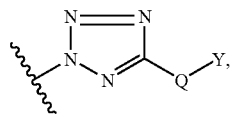

Q=absent, Y=4-trifluoromethylphenyl, j=3, m=s=1, and $R^3=R^4=H$.

The title compound was prepared via the replacement method described in Example 21 with mesylate 2 and 5-(4-trifluoromethylphenyl)-1H-tetrazole, followed by hydrolysis of the ethyl ester by the procedure of Example 22.

$[M+Na]^+=684.32$.

Example 48

Compound of Formula II, wherein A=tBOC, G=OH, L=absent, W is

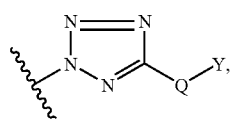

Q=absent, Y=3,5-di(trifluoromethyl)phenyl, j=3, m=s=1, and $R^3=R^4=H$.

The title compound was prepared via the replacement method described in Example 21 with mesylate 2 and 5-(3,5-di(trifluoromethyl)phenyl)-1H-tetrazole, followed by hydrolysis of the ethyl ester by the procedure of Example 22.

$[M+Na]^+=766.32$.

Example 49

Compound of Formula II, wherein A=tBOC, G=OH, L=absent, W is

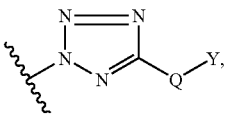

Q=absent, Y=4-(N,N-dimethylamino)-3,5-di(trifluoromethyl)phenyl, j=3, m=s=1, and $R^3=R^4=H$.

The title compound was prepared via the replacement method described in Example 21 with mesylate 2 and 5-(4-(N,N-dimethylamino)-3,5-di(trifluoromethyl)phenyl)-1H-tetrazole, followed by hydrolysis of the ethyl ester by the procedure of Example 22.

$[M+Na]^+=695.39$.

Example 50

Compound of Formula II, wherein A=tBOC, G=OH, L=absent, W is

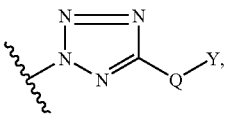

Q=absent, Y=2,4-dichlorophenyl, j=3, m=s=1, and $R^3=R^4=H$.

The title compound was prepared via the replacement method described in Example 21 with mesylate 2 and 5-(2,4-dichlorophenyl)-1H-tetrazole, followed by hydrolysis of the ethyl ester by the procedure of Example 22.

$[M+Na]^+=684.27$.

Example 51

Compound of Formula II, wherein A=tBOC, G=OH, L=absent, W is

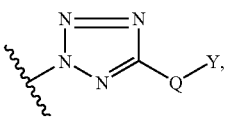

Q=absent, Y=3,5-dichlorophenyl, j=3, m=s=1, and $R^3=R^4=H$.

The title compound was prepared via the replacement method described in Example 21 with mesylate 2 and 5-(3,5-dichlorophenyl)-1H-tetrazole, followed by hydrolysis of the ethyl ester by the procedure of Example 22.

$[M+Na]^+=684.27$.

Example 52

Compound of Formula II, wherein A=tBOC, G=OH, L=absent, W is

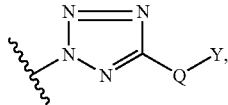

Q=absent, Y=3,4-dichlorophenyl, j=3, m=s=1, and $R^3=R^4=H$.

The title compound was prepared via the replacement method described in Example 21 with mesylate 2 and 5-(3,4-dichlorophenyl)-1H-tetrazole, followed by hydrolysis of the ethyl ester by the procedure of Example 22.

$[M+Na]^+=684.27$.

Example 53

Compound of Formula II, wherein A=tBOC, G=OH, L=absent, W is

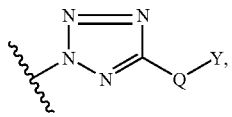

Q=absent, Y=2-pyridyl, j=3, m=s=1, and $R^3=R^4=H$.

The title compound was prepared via the replacement method described in Example 21 with mesylate 2 and 5-(2-pyridyl)-1H-tetrazole, followed by hydrolysis of the ethyl ester by the procedure of Example 22.

$[M+Na]^+=617.60$.

Example 54

Compound of Formula II, wherein A=tBOC, G=OH, L=absent, W is

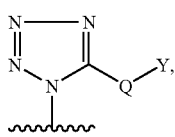

Q=absent, Y=2-pyridyl, j=3, m=s=1, and $R^3=R^4=H$.

The title compound was prepared via the replacement method described in Example 21 with mesylate 2 and 5-(2-pyridyl)-1H-tetrazole, followed by hydrolysis of the ethyl ester by the procedure of Example 22.

$[M+Na]^+=617.60$.

Example 55

Compound of Formula II, wherein A=tBOC, G=OH, L=absent, W is

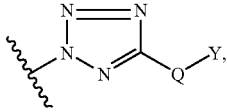

Q=absent, Y=3-pyridyl, j=3, m=s=1, and $R^3=R^4=H$.

The title compound was prepared via the replacement method described in Example 21 with mesylate 2 and 5-(3-pyridyl)-1H-tetrazole, followed by hydrolysis of the ethyl ester by the procedure of Example 22.

$[M+Na]^+=645.24$.

Example 56

Compound of Formula II, wherein A=tBOC, G=OH, L=absent, W is

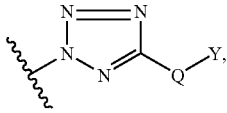

Q=absent, Y=4-pyridyl, j=3, m=s=1, and $R^3=R^4=H$.

The title compound was prepared via the replacement method described in Example 21 with mesylate 2 and 5-(4-pyridyl)-1H-tetrazole, followed by hydrolysis of the ethyl ester by the procedure of Example 22.

$[M+H]^+=595.50$.

Example 57

Compound of Formula II, wherein A=tBOC, G=OH, L=absent, W is

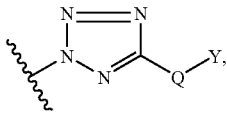

Q=absent, Y=4-methoxy-3-bromophenyl, j=3, m=s=1, and $R^3=R^4=H$.

57A. Tetrazole Formation

The tetrazole of the present example was prepared by dissolving 4-hydroxy-3-bromo-4-hydroxy-benzonitrile in DMF and adding methyl iodide and stirring at RT for 3-12 hours. The resulting reaction mixture was diluted with EtOAc and washed with water and brine. The resulting organic phase was then dried over $Na_2SO_4$ and concentrated in vacuo to yield the 3-bromo-4-methoxy-benzonitrile. This compound then was used to form the corresponding tetrazole via the method described in Example 3.

The title compound was prepared via the replacement method described in Example 21 with mesylate 2 and 5-(3-bromo-4-methoxy-phenyl)-1H-tetrazole from 57A, followed by hydrolysis of the ethyl ester by the procedure of Example 22.

$[M+Na]^+=724.91$.

Example 58

Compound of Formula II, wherein A=tBOC, G=OH, L=absent, W is

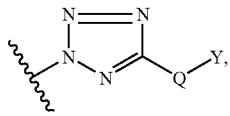

Q=absent, Y=4-(methylcyclopropane)phenyl, j=3, m=s=1, and $R^3=R^4=H$.

58A. Tetrazole Formation

The tetrazole of the present example was prepared by dissolving 4-cyano-phenol in DMF and adding (bromomethyl)cyclopropane and stirring at RT for 3-12 hours. The resulting reaction mixture was diluted with EtOAc and washed with water and brine. The resulting organic phase was then dried over $Na_2SO_4$ and concentrated in vacuo to yield the 4-(methylcyclopropane)benzonitrile. This compound then was used to form the corresponding tetrazole via the method described in Example 3.

The title compound was prepared via the replacement method described in Example 21 with mesylate 2 and 5-(4-(methylcyclopropane)-phenyl)-1H-tetrazole from 58A, followed by hydrolysis of the ethyl ester by the procedure of Example 22.

$[M+Na]^+=686.29$.

Example 59

Compound of Formula II, wherein A=tBOC, G=OH, L=absent, W is

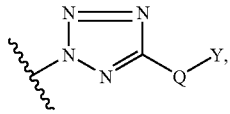

Q=absent, Y=3-chloro-4-(methylcyclopropane)phenyl, j=3, m=s=1, and $R^3=R^4=H$.

The title compound was prepared by using ethyl ester title compound from Example 21 without workup, adding (bromomethyl)cyclopropane, and stirring at 60° C. for 3-12 hours. The resulting reaction mixture was cooled to RT, poured into a mixture of 50:50 EtOAc:water, washed with water, and concentrated in vacuo. The resulting crude ethyl ester compound is then hydrolyzed to the free acid by the procedure set forth in Example 22.

$[M+Na]^+=720.24$.

Example 60

Compound of Formula II, wherein A=tBOC, G=OH, L=absent, W is

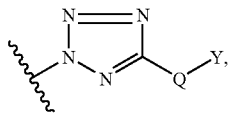

Q=absent, Y=3-chloro-4-methoxyphenyl, j=3, m=s=1, and $R^3=R^4=H$.

The title compound was prepared with the title compound of Example 21 and methyl iodide according to the procedure set forth in Example 59.

$[M+Na]^+=680.23$.

Example 61

Compound of Formula II, wherein A=tBOC, G=OH, L=absent, W is

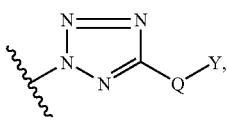

Q=absent, Y=3-chloro-4-ethoxyphenyl, j=3, m=s=1, and $R^3=R^4=Hp$

The title compound was prepared with the title compound of Example 21 and ethyl iodide according to the procedure set forth in Example 59.

$[M+Na]^+=694.28$.

Example 62

Compound of Formula II, wherein A=tBOC, G=OH, L=absent, W is

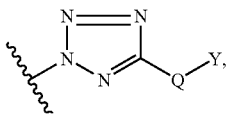

Q=absent, Y=3-bromo-4-ethoxyphenyl, j=3, m=s=1, and $R^3=R^4=H$.

The title compound was prepared with the ethyl ester precursor to the title compound of Example 23 and ethyl iodide according to the procedure set forth in Example 59.

$[M+Na]^+=740.17$.

Example 63

Compound of Formula II, wherein A=tBOC, G=OH, L=absent, W is

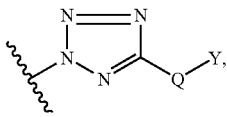

Q=absent, Y=3-chloro-4-(2-hydroxyethoxy)phenyl, j=3, m=s=1, and $R^3=R^4=H$.

The title compound is prepared with the title compound from Example 21 and 2-iodoethanol according to the procedure set forth in Example 59.

Example 64

Compound of Formula II, wherein A=tBOC, G=OH, L=absent, W is

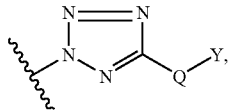

Q=absent, Y=3-bromo-4-(2-hydroxyethoxy)phenyl, j=3, m=s=1, and $R^3=R^4=H$.

The title compound was prepared with the ethyl ester precursor to the title compound of Example 23 and 2-iodoethanol according to the procedure set forth in Example 59.

$[M+Na]^+=754.27$.

Example 65

Compound of Formula II, wherein A=tBOC, G=OH, L=absent, W is

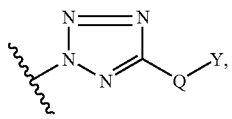

Q=absent, Y=3-chloro-4-(O-allyl)phenyl, j=3, m=s=1, and $R^3=R^4=H$.

The title compound was prepared with the title compound from Example 21 and 3-iodopropene according to the procedure set forth in Example 59.

$[M+Na]^+=706.24$.

Example 66

Compound of Formula II, wherein A=tBOC, G=OH, L=absent, W is

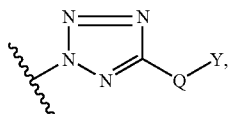

Q=absent, Y=3-bromo-4-(O-allyl)phenyl, j=3, m=s=1, and $R^3=R^4=H$.

The title compound was prepared with the ethyl ester precursor to the title compound of Example 23 and 3-iodopropene according to the procedure set forth in Example 59.

$[M+Na]^+=752.15$.

Example 67

Compound of Formula II, wherein A=tBOC, G=OH, L=absent, W is

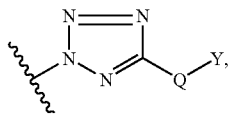

Q=absent, Y=3-chloro-4-(O—$CH_2SCH_3$)phenyl, j=3, m=s=1, and $R^3=R^4=H$.

The title compound is prepared with the title compound from Example 21 and Cl—$CH_2SCH_3$ according to the procedure set forth in Example 59.

Example 68

Compound of Formula II, wherein A=tBOC, G=OH, L=absent, W is

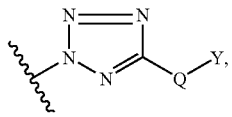

Q=absent, Y=3-chloro-4-(O—$CH_2SCH_3$)phenyl, j=3, m=s=1, and $R^3=R^4=H$.

The title compound was prepared with the ethyl ester precursor to the title compound of Example 23 and Cl—$CH_2SCH_3$ according to the procedure set forth in Example 59.

$[M+Na]^+=752.15$.

Example 69

Compound of Formula II, wherein A=tBOC, G=OH, L=absent, W is

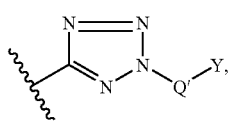

wherein Q'=—$CH_2$—, Y=

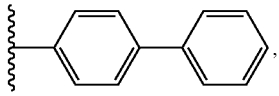

j=3, m=s=1, and $R^3=R^4=H$.

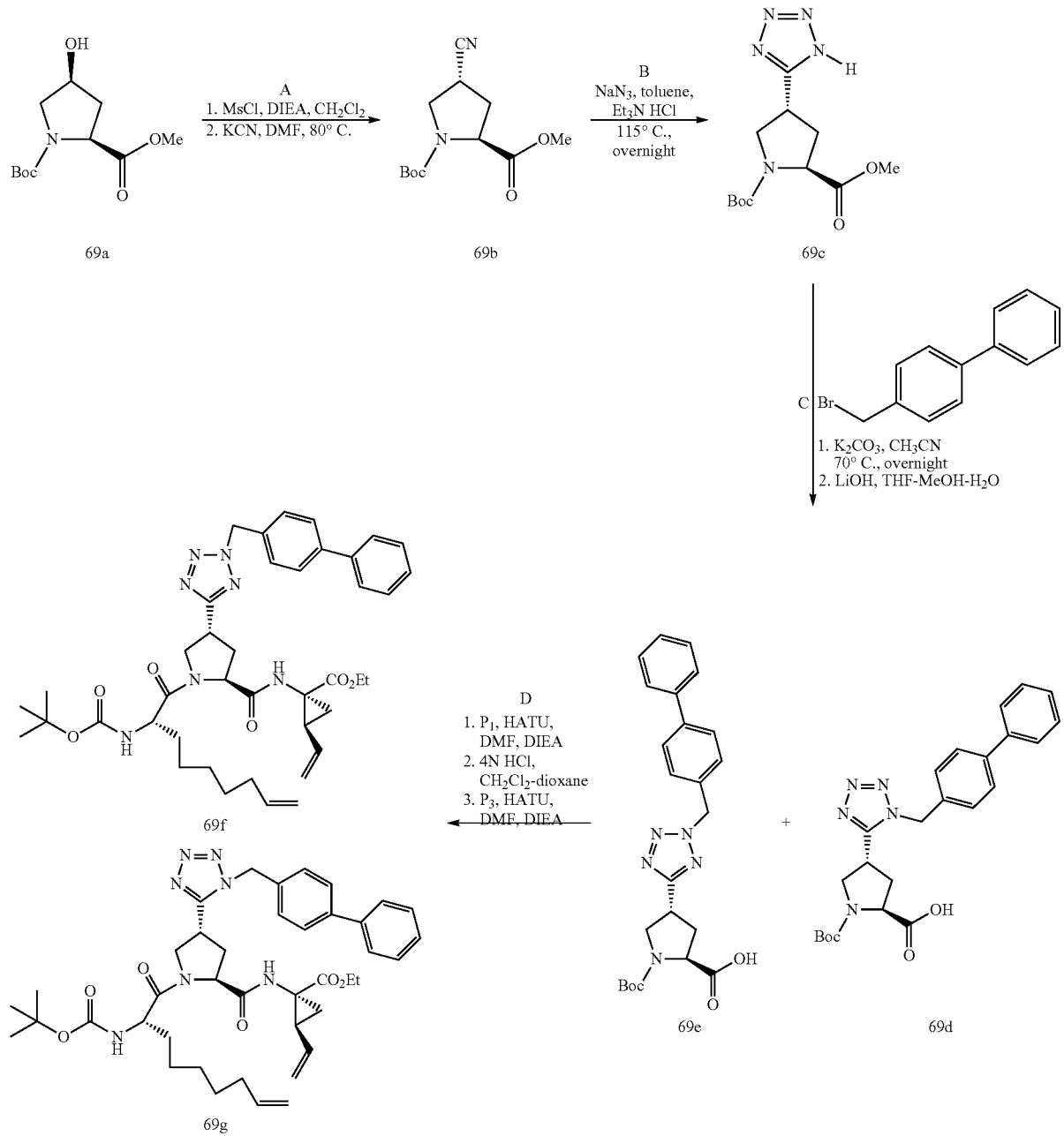

69A. Preparation of Cyano Proline Derivative (69b)

To a solution of cis-4-hydroxy-pyrrolidine-1,2-dicarboxylic acid 1-tert-butyl ester 2-methyl ester (69a) (3.94 g, 16.06 mmol) in $CH_2Cl_2$ (40 ml) at 0° C. was DIEA (4.3 ml) and methanesulfonyl chloride (1.40 ml) dropwise. After addition, the mixture was stirred for 1.5 hours. The reaction was complete as determined by TLC analysis (50% EtOAc-hexane was used to develop the TLC). The mixture was diluted with EtOAc, washed with sat. $NaHCO_3$, brine and dried ($Na_2SO_4$). After evaporation of the solvents, the oil residue was used for next step without further purification. $[M+H]^+=324$.

The crude product from the previous step was dissolved in DMF (35 ml) and grounded KCN (2.5 g) was added. The mixture was heated at 90° C. overnight. After cooled to room temperature, the mixture was diluted with EtOAc, washed with $H_2O$ and brine, and dried over $Na_2SO_4$. The crude product was purified by silica gel chromatography (20% EtOAc/hexane).

$[M+H]^+=255$.

69B. Preparation of Tetrazolyl Proline Derivative (69c)

To a solution of nitrile 69b (669 mg, 2.63 mmol) in toluene (8 ml) was added $NaN_3$ (684 mg, 10.53 mmol) and $Et_3N.HCl$ (1.45 g, 10.53 mmol). The mixture was heated at 115° C. for 18 hrs. The mixture was diluted with $CH_2Cl_2$, washed with 5% citric acid aqueous solution and dried over $Na_2SO_4$. Evaporation of solvent afforded the crude product 69c.$Et_3N$ additive (660 mg).

$[M+H]^+=298$.

69C. Preparation of the 5-Biphenylmethyl-tetrazolyl Proline (69e)

To a solution of 69c (92.8 mg, 0.31 mmol) in THF (2 ml) was added 4-phenylbenzyl bromide (90.4 mg, 0.37 mmol) and $K_2CO_3$ (140 mg, 1.01 mmol). The mixture was heated at 65° C. overnight and then diluted with EtOAc, washed with brine, dried over $Na_2SO_4$. After evaporation of the solvent, the crude products was dissolved in THF-MeOH—$H_2O$ (2 ml: 1 ml: 1 ml) and LiOH (130 mg) was added. The mixture was stirred at room temperature overnight. THF and MeOH were evaporated under reduced pressure. The residue was dissolved in EtOAc, washed with 5% citric acid and dried with $Na_2SO_4$. Evaporation of solvent afforded the crude product 69d and 69e.

$[M+Boc+H]^+=350$.

1.5 hr. solvent was evaporated. The residue was dissolved in EtOAc, neutralized with sat. $NaHCO_3$, washed with brine and dried with $Na_2SO_4$. After evaporation of solvent, the residue was dissolved in DMF (2 ml), to which P3 (120 mg), DIEA and HATU were added sequentially. The resulting mixture was stirred and monitored by TLC analysis. After the reaction was complete, the mixture was diluted with EtOAc, washed with brine, 5% citric acid, sat. $NaHCO_3$, and brine again. The organic solution was dried with $Na_2SO_4$, and evaporated under vacuum to give the crude product mixture which was purified by silica gel chromatography (30% to 50% EtOAc-Hexane).

$[M+H]^+=740$.

69E. Ring-Closing Metathesis (69k).

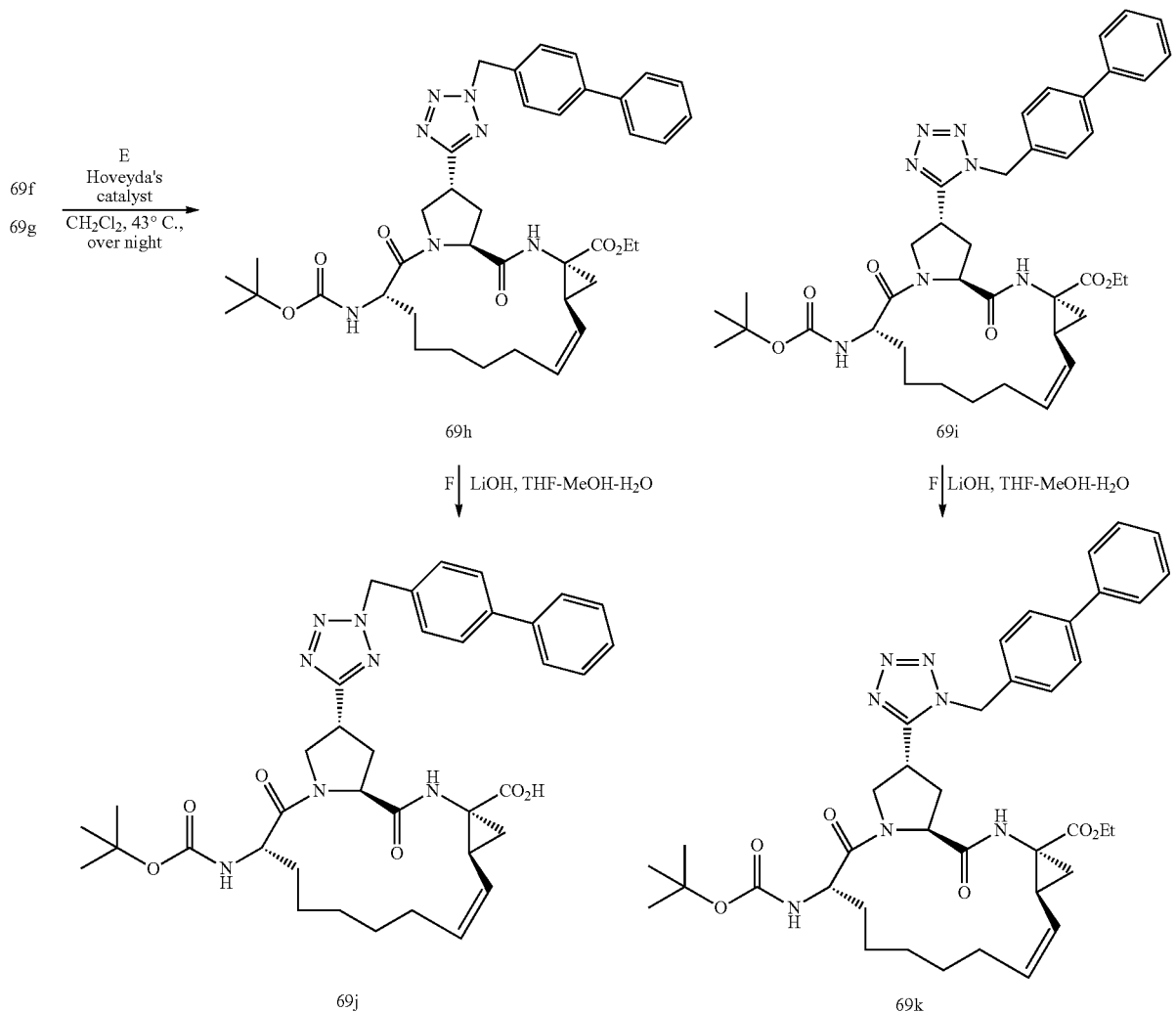

69D. Preparation of the Tripeptide (69g)

To a solution of 69d and 69e (about 0.31 mmol) in DMF (2.0 ml) was added D-β-vinyl cyclopropane amino acid ethyl ester.HCl (66 mg), DIEA (0.25 ml) and HATU (164 mg), sequentially. The mixture was stirred for 1 hr and then was diluted with EtOAc, washed with brine, 5% citric acid and dried with $Na_2SO_4$. After evaporation of solvent, the residue was dissolved in 2 ml of $CH_2Cl_2$, 2 ml of 4 N HCl in dioxane was added. The mixture was stirred at room temperature for The mixture of 69f and 69g (60 mg) was dissolved in dry $CH_2Cl_2$ to make the concentration about 0.01 molar. The solution was carefully degassed with $N_2$ stream for 15 min. 5% mol of Hoveyda's catalyst was added under $N_2$. The mixture was refluxed overnight. Solvent was evaporated. The residue was loaded on silica gel column and eluted with 10% EtOAc to remove the catalyst. The two regioisomers were separated by elution with 30-40% EtOAc-hexane to give a less polar product 69j (37.9 mg) and more polar product 69k (14.8 mg). The regiochemistry of 69j and 69k were determined by NMR analysis.

[M+H]⁺=712.

69F. Ethyl Ester Hydrolysis (69)

The ester 69h (37.9 mg) was dissolved in THF-MeOH—H₂O (2 ml:1 ml:1 ml) and LiOH (21 mg) was added. The mixture was stirred at room temperature overnight. THF and MeOH were evaporated under reduced pressure. The residue was dissolved in EtOAc, washed with 5% citric acid and dried with Na₂SO₄. Evaporation of solvent afforded the crude product. The crude product was purified by silica gel chromatography (5% MeOH in CH₂Cl₂) to give the title compound 69k.

[M+H]⁺=684.

Example 70

Compound of Formula II, wherein A=tBOC, G=OH, L=absent, W is

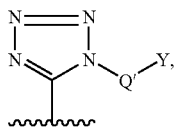

wherein Q'=—CH₂—, Y=

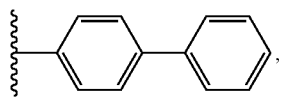

j=3, m=s=1, and R³=R⁴=H.

The ester 69i (14.8 mg) was dissolved in THF-MeOH—H₂O (2 ml:1 ml:1 ml) and LiOH (21 mg) was added. The mixture was stirred at room temperature overnight. THF and MeOH were evaporated under reduced pressure. The residue was dissolved in EtOAc, washed with 5% citric acid and dried with Na₂SO₄. Evaporation of solvent afforded the crude product. The crude product was purified by silica gel chromatography (5% MeOH in CH₂Cl₂) to give title compound 70.

[M+H]⁺=684.

Example 71

Compound of Formula II, wherein A=—(C=O)—O—R¹, wherein R¹=cyclopentyl, G=OH, L=absent, W is

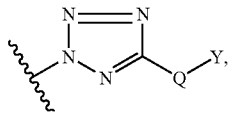

Q=absent, Y=phenyl, j=3, m=s=1, and R³=R⁴=H.

71a—Amine Deprotection.

0.041 mmol of the title compound of Example 21 is dissolved in 4 ml of a 4M solution of HCl in dioxane and stirred for 1 hour. The reaction residue 69a is concentrated in vacuo.

71b—Chloroformate Reagent

The chloroformate reagent 71b is prepared by dissolving 0.045 mmol of cyclopentanol in THF (3 ml) and adding 0.09 mmol of phosgene in toluene (20%). The resulting reaction mixture is stirred at room temperature for 2 hours and the solvent is removed in vacuo. To the residue is added DCM and subsequently concentrated to dryness twice in vacuo yielding chloroformate reagent 71b.

71c—Carbamate Formation

The title carbamate is prepared by dissolving residue 71a in 1 ml of THF, adding 0.045 mmol of TEA, and cooling the resulting reaction mixture to 0° C. To this 0° C. reaction mixture is added chloroformate reagent 71b in 3 ml of THF. The resulting reaction mixture is reacted for 2 hours at 0° C., extracted with EtOAc, washed by 1M sodium bicarbonate, water and brine, dried over MgSO₄, and concentrated in vacuo to dryness. The crude compound is purified by silica column and the ethyl ester is subsequently hydrolyzed by procedure set forth in Example 22.

Example 72

Compound of Formula II, wherein A=—(C=O)—O—R¹, wherein R¹=cyclobutyl, G=OH, L=absent, W is

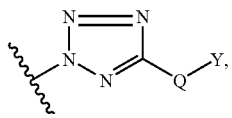

Q=absent, Y=phenyl, j=3, m=s=1, and R³=R⁴=H.

The title compound is prepared by the method described in Example 71 with the title compound of Example 21 and cyclobutanol, followed by ethyl ester hydrolysis by the procedure set forth in Example 22.

Example 73

Compound of Formula II, wherein A=—(C=O)—O—R¹, wherein R¹=cyclohexyl, G=OH, L=absent, W is

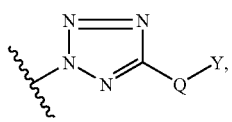

Q=absent, Y=phenyl, j=3, m=s=1, and R³=R⁴=H.

The title compound is prepared by the method described in Example 71 with the title compound of Example 21 and cyclohexanol, followed by ethyl ester hydrolysis by the procedure set forth in Example 22.

Example 74

Compound of Formula II, wherein A=—(C=O)—O—R¹, wherein R¹=

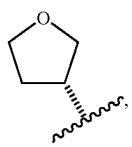

G=OH, L=absent, W is

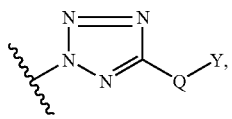

Q=absent, Y=phenyl, j=3, m=s=1, and $R^3=R^4=H$.

The title compound is prepared by the method described in Example 71 with the title compound of Example 21 and (R)-3-hydroxytetrahydrofuran, followed by ethyl ester hydrolysis by the procedure set forth in Example 22.

Example 75

Compound of Formula II, wherein A=—(C=O)—O—$R^1$, wherein $R^1$=

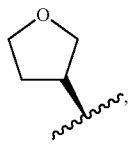

G=OH, L=absent, W is

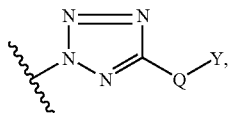

Q=absent, Y=phenyl, j=3, m=s=1, and $R^3=R^4=H$.

The title compound is prepared by the method described in Example 71 with the title compound of Example 21 and (S)-3-hydroxytetrahydrofuran, followed by ethyl ester hydrolysis by the procedure set forth in Example 22.

Example 76

Compound of Formula II, wherein A=—(C=O)—O—$R^1$, wherein $R^1$=

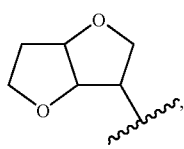

G=OH, L=absent, W is

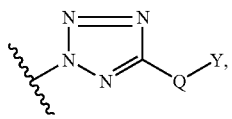

Q=absent, Y=phenyl, j=3, m=s=1, and $R^3=R^4=H$.

The title compound is prepared by the method described in Example 71 with the title compound of Example 21 and

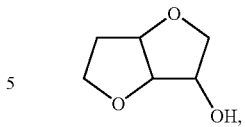

followed by ethyl ester hydrolysis by the procedure set forth in Example 22.

Example 77

Compound of Formula II, wherein A=—(C=O)—$R^1$, wherein $R^1$=cyclopentyl, G=OH, L=absent, W is

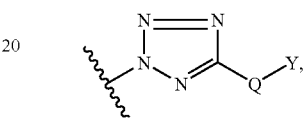

Q=absent, Y=phenyl, j=3, m=s=1, and $R^3=R^4=H$.

The title compound is prepared by dissolving 0.041 mmol of the title compound from Example 21 in 4 ml of a 4M solution of HCl in dioxane and stirring the reaction mixture for 1 hour. The reaction residue is concentrated in vacuo. To this residue, 4 ml of THF and 0.045 mmol of TEA is added, the mixture is cooled to 0° C., to which is added 0.045 mmol of the cyclopental acid chloride. The resulting reaction mixture is stirred for 2 hours at 0° C. The reaction mixture is then extracted with EtOAc, washed with 1M sodium bicarbonate, water and brine, dried over $MgSO_4$ and concentrated to dryness in vacuo. The crude compound is purified by silica column and the ethyl ester is subsequently hydrolyzed by the procedure set forth in Example 22.

Example 78

Compound of Formula II, wherein A=—(C=O)—NH—$R^1$, wherein $R^1$=cyclopentyl, G=OH, L=absent, W is

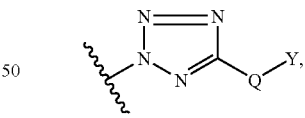

Q=absent, Y=phenyl, j=3, m=s=1, and $R^3=R^4=H$.

The title compound is prepared by dissolving 0.041 mmol of the title compound from Example 21 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isocyanate and the resulting reaction mixture is stirred at RT for 4 hours. The solution is then extracted with EtOAc, washed with 1% HCl, water and brine, dried over $MgSO_4$, and concentrated in vacuo to dryness. The crude compound is purified by silica column and the ethyl ester is subsequently hydrolyzed by the procedure set forth in Example 22.

Example 79

Compound of Formula II, wherein A=—(C=S)—NH—R¹, wherein R¹=cyclopentyl, G=OH, L=absent, W is

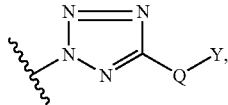

Q=absent, Y=phenyl, j=3, m=s=1, and R³=R⁴=H.

The title compound is prepared by dissolving 0.041 mmol of the title compound from Example 21 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isothiocyanate and the resulting reaction mixture is stirred at RT for 4 hours. The solution is then extracted with EtOAc, washed with 1% HCl, water and brine, dried over MgSO₄, and concentrated in vacuo to dryness. The crude compound is purified by silica column and the ethyl ester is subsequently hydrolyzed by the procedure set forth in Example 22.

Example 80

Compound of Formula II, wherein A=—S(O)₂—R¹, wherein R¹=cyclopentyl, G=OH, L=absent, W is

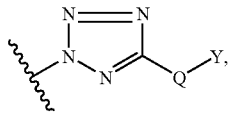

Q=absent, Y=phenyl, j=3, m=s=1, and R³=R⁴=H.

The title compound is prepared by dissolving 0.041 mmol of the title compound from Example 21 in 4 ml of a 4M solution of HCl in dioxane and stirring for 1 hour. To the resulting concentrated reaction residue, which has been dissolved in 4 ml THF, is added 0.045 mmol of TEA, and cooled to 0° C. To the 0° C. solution is added 0.045 mmol of cyclopentyl solfonyl chloride and the resulting reaction mixture is stirred at 0° C. for 2 hours. The solution is then extracted with EtOAc, washed with 1M sodium bicarbonate, water and brine, dried over MgSO₄, and concentrated in vacuo to dryness. The crude compound is purified by silica column and the ethyl ester is subsequently hydrolyzed by the procedure set forth in Example 22.

Example 81

Compound of Formula II, wherein A=—(C=O)—O—R¹, R¹=cyclopentyl, G=—O-phenethyl, L=absent, W is

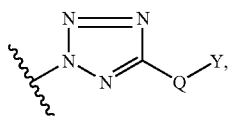

Q=absent, Y=phenyl, j=3, m=s=1, and R3=R4=H.

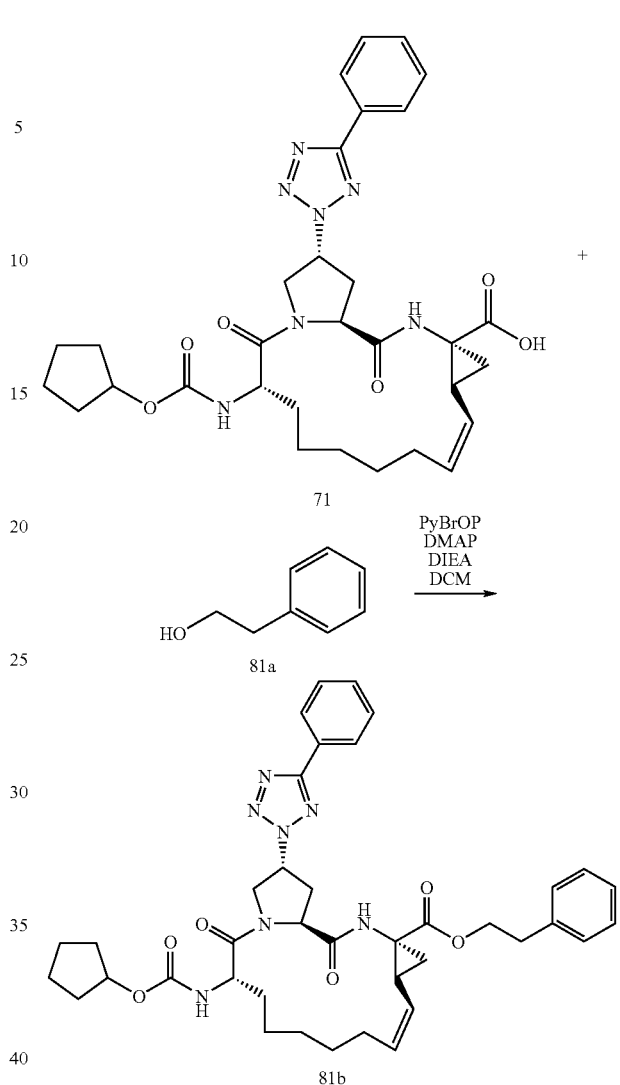

The title compound is prepared by adding to a solution of the title compound of Example 71 and phenethyl alcohol 81a in 0.5 ml DCM, is added 1.2 eq. PyBrOP, 4 eq. DIEA, and catalytic amount of DMAP at 0° C. The resulting reaction mixture is stirred for 1 hour at 0° C. and then warmed to RT over a period of 4-12 hours. The reaction mixture is purified by silica gel flash chromatography using different ratios of hexanes:EtOAc as elution phase (9:1→5:1→3:1→1:1) to afford the title compound isolated phenethyl ester 81b.

Other esters can be made using the same procedure.

Example 82

Compound of Formula II, wherein A=—(C=O)—O—R¹, R¹=cyclopentyl, G=—NH-phenethyl, L=absent, W is

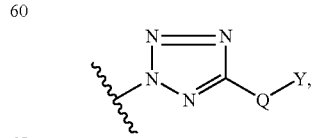

Q=absent, Y=phenyl, j=3, m=s=1, and R3=R4=H.

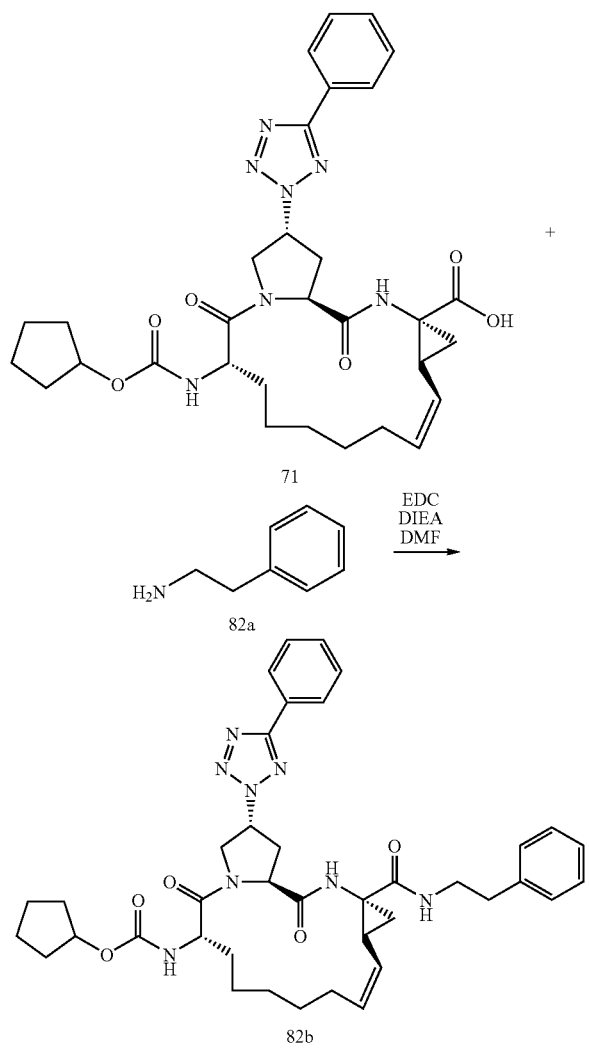

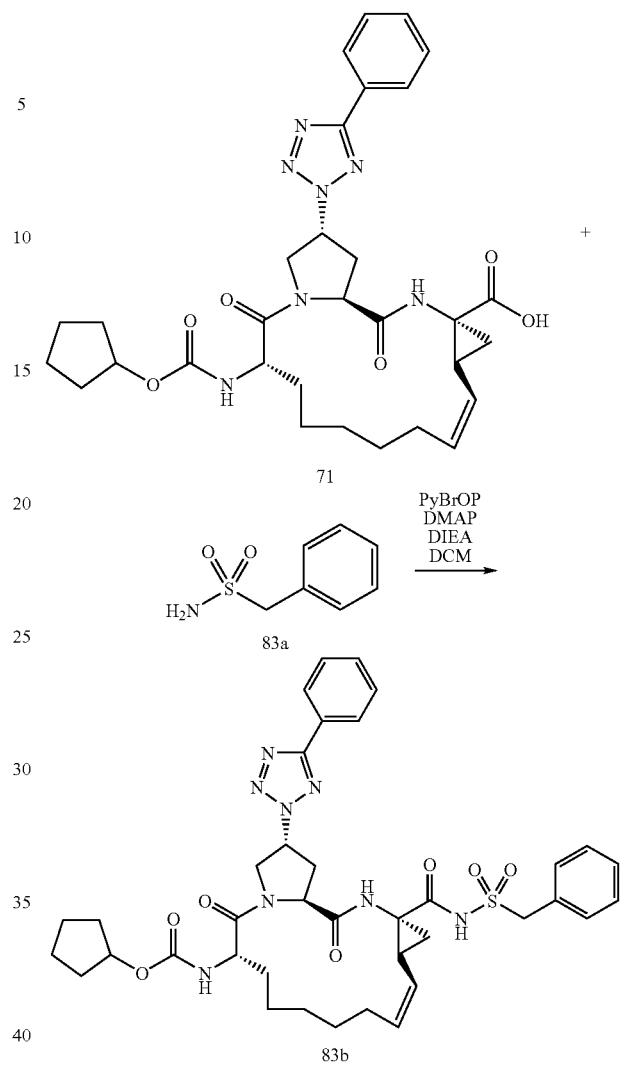

The title compound is prepared by adding to a solution of the title compound of Example 71 and phenethylamine 82a (0.05 ml) in 0.5 ml DMF, EDC (1.2 eq.) and DIEA (4 eq.) at 0° C. The resulting reaction mixture is stirred at 1 hour. Subsequently, the reaction is warmed to RT over a period of 4-12 hours. The reaction mixture is purified by silica gel flash chromatography using different ratios of hexanes:EtOAc as elution phase (9:1→5:1→3:1→1:1) to afford title compound phenethyl amide 82b. Other amides can be made using the same procedure.

Example 83

Compound of Formula II, wherein A=—(C=O)—O—R$^1$, R$^1$=cyclopentyl, G=—NHS(O)$_2$-phenethyl, L=absent, W is

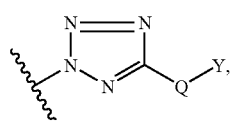

Q=absent, Y=phenyl, j=3, m=s=1, and R3=R4=H.

The title compound is prepared by adding to a solution of the title compound of Example 71 and α-toluenesulfonamide 83a (10 mg) in 0.5 ml DCM, is added 1.2 eq. PyBrOP, 4 eq. DIEA, and catalytic amount of DMAP at 0° C. The resulting reaction mixture is stirred for 1 hour and then allowed to warm to RT over a period of 4-12 hours. The reaction mixture is purified by silica gel flash chromatography using different ratios of hexanes:EtOAc as elution phase (9:1→5:1→3:1→1: 1) to afford the title compound sulfonamide 83c.

Other sulfonamides can be made using the same procedure.

Example 84

Compound of Formula II, wherein A=—(C=O)—O—R$^1$, R$^1$=cyclopentyl, G=—(C=O)—OH, L=absent, W is

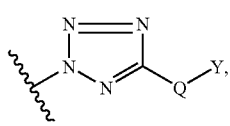

Q=absent, Y=phenyl, j=3, m=s=1, and R$^3$=R$^4$=H.

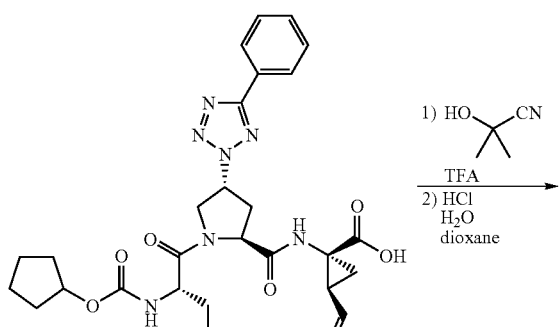

71

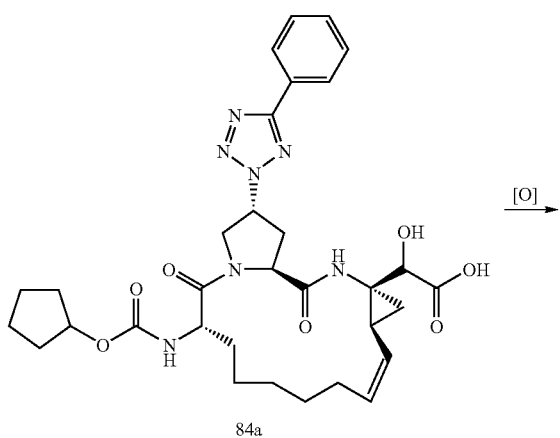

84a

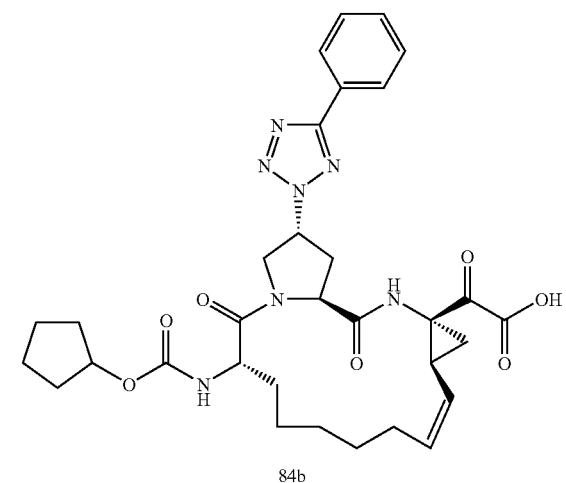

84b

The title compound is prepared by adding to a solution of the title compound of Example 71 in 0.5 ml THF, is added α-hydroxy-α-methyl-propionitrile (0.1 ml) and catalytic amount TFA at 0° C. The resulting reaction mixture is warmed from 0° C. to RT over a period of 4-12 h followed by hydrolysis with concentrated hydrochloric acid in dioxane. The reaction is then extracted with EtOAc, and washed with water and brine to yield α-hydroxy compound 83a in its crude form. The crude compound 84a undergoes a Dess-Martin oxidation in THF (0.5 ml), providing the α-carbonyl compound 84b in crude form. The crude 84b is purified by silica gel flash chromatography using different ratios of hexanes:EtOAc as elution phase (9:1→5:1→3:1→1:1) to afford the title compound isolated keto acid 84b.

Example 85

Compound of Formula II, wherein A=—(C=O)—O—$R^1$, $R^1$=cyclopentyl, G=—(C=O)—O-phenethyl, L=absent, W is

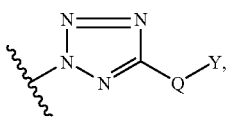

Q=absent, Y=phenyl, j=3, m=s=1 and $R^3=R^4$=H.

The title compound is prepared with the title compound keto acid of Example 84 and phenethanol according to the procedure set forth in Example 81.

Example 86

Compound of Formula II, wherein A=—(C=O)—O—$R^1$, $R^1$=cyclopentyl, G=—(C=O)—NH-phenethyl, L=absent, W is

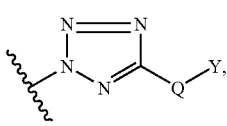

Q=absent, Y=phenyl, j=3, m=s=1, and $R^3=R^4$=H.

The title compound is prepared with the title compound keto acid of Example 84 and phenethyl amine according to the procedure set forth in Example 82.

Example 87

Compound of Formula II, wherein A=—(C=O)—O—$R^1$, $R^1$=cyclopentyl, G=—(C=O)—NH—S(O)$_2$-benzyl, L=absent, W is

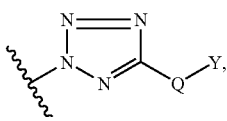

Q=absent, Y=phenyl, j=3, m=s=1, and $R^3=R^4$=H.

The title compound is prepared with the title compound keto acid of Example 84 and α-toluenesulfonamide according to the procedure set forth in Example 83.

Example 88

Compound of Formula II, wherein A=tBOC, G=OH, L=—(C=O)CH$_2$—, W is

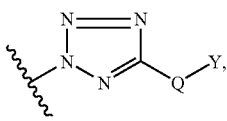

Q=absent, Y=phenyl, j=1, m=s=1, and $R^3=R^4$=H.

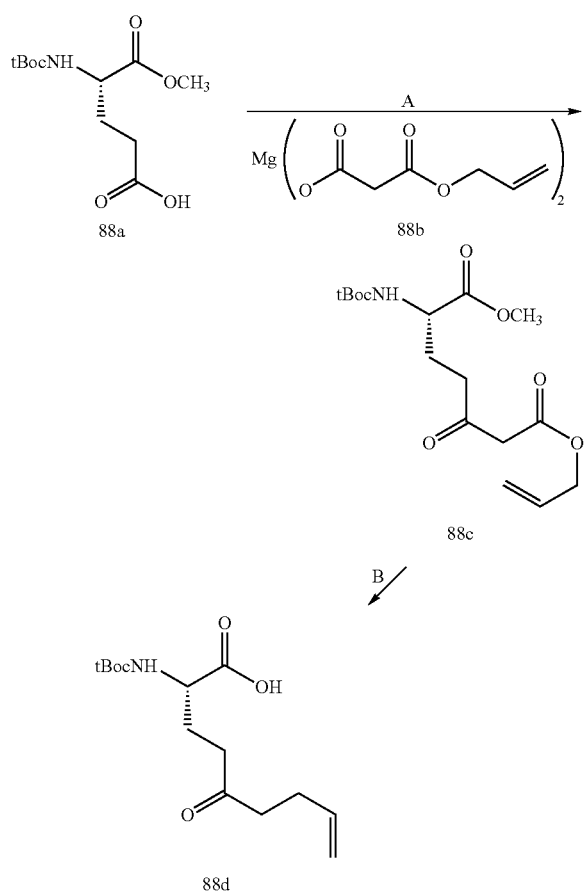

Synthesis of (2S)-N-Boc-amino-5-oxo-non-8-enoic acid

88A. The aforementioned amino acid is prepared by adding to a solution of monoallyl ester of malonic acid in dry THF under $N_2$ at −78° C., n-Bu$_2$Mg dropwise over a period of 5 min. The resulting suspension is then stirred at RT for 1 hour and evaporated to dryness. Solid Mg salt 88b, is dried under vacuum.

Glutamic acid derivative 88a is first mixed with 1,1'-carbonyldiimidazole in anhydrous THF and the mixture is stirred at RT for 1 h to activate the free acid moiety. Subsequently, the activated glutamic acid derivative is cannulated into a solution of Mg salt 88b and the reaction mixture obtained is stirred at RT for 16 h. The mixture then is diluted with ethyl acetate and the organic solution is washed with 0.5 N HCl (at 0° C.) and brine, dried and evaporated. The residue obtained is resolved via silica chromatography with a 35-40% ethyl acetate in hexanes eluent system to yield diester 88c.

88B. To a stirred solution of tetrakis (triphenylphosphine) PD (0) in dry DMF is added the diester in DMF. The mixture is stirred at RT for 3.5 hours. The DMF is evaporated under reduced pressure and the residue diluted with EtOAc. The EtOAc solution is washed with 0.5N 0° C. HCl, brine, dried and evaporated. The residue is chromatographed on silica gel using 15% to 20% EtOAc in hexane as eluent to afford the methyl ester intermediate.

The methyl ester intermediate is then diluted with THF and water, LiOH.H$_2$O is added and the resulting mixture is stirred at RT for 25 hours, wherein the completion of the hydrolysis is monitored by TLC. The reaction mixture is concentrated under vacuum to remove a majority of the THF and further diluted with methylene chloride. The resulting solution is washed with 1 N HCl, dried with anhydrous Na$_2$SO$_4$ and concentrated under vacuum. To remove minor impurities and excess Boc$_2$O, the crude product is purified via flash chromatography using a solvent gradient from 100% hexane→100% EtOAc as the eluent. (2S)-N-Boc-amino-5-oxo-non-8-enoic acid 88d is obtained. For further details of the preceding amino acid synthesis may be found in T. Tsuda et al., *J. Am. Chem. Soc.*, 1980, 102, 6381-6384 and WO 00/59929, which are herein incorporated by reference in their entirety.

88C. Synthesis of Modified Cyclic Peptide Precursor Mesylate

The modified cyclic peptide precursor mesylate is prepared using the synthetic route detailed in Example 1 using (2S)-N-Boc-amino-5-oxo-non-8-enoic acid 88d in place of Boc-L-2-amino-8-nonenoic acid 1a followed by conversion to the corresponding mesylate via the method described in Example 2.

The title compound is prepared with the modified cyclic peptide precursor mesylate formed in 88C and 5-phenyl-1H-tetrazole by the replacement method elucidated in Example 21 followed by hydrolysis of the ethyl ester via the method set forth in Example 22.

Example 89

Compound of Formula II, wherein A=tBOC, G=OH, L=—CH(CH$_3$)CH$_2$—, W is

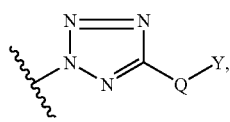

Q=absent, Y=phenyl, j=1, m=s=1, R$^3$=methyl, and R$^4$=H.

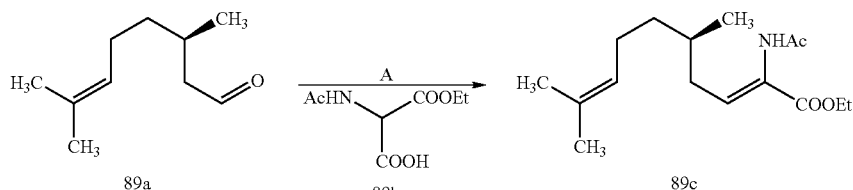

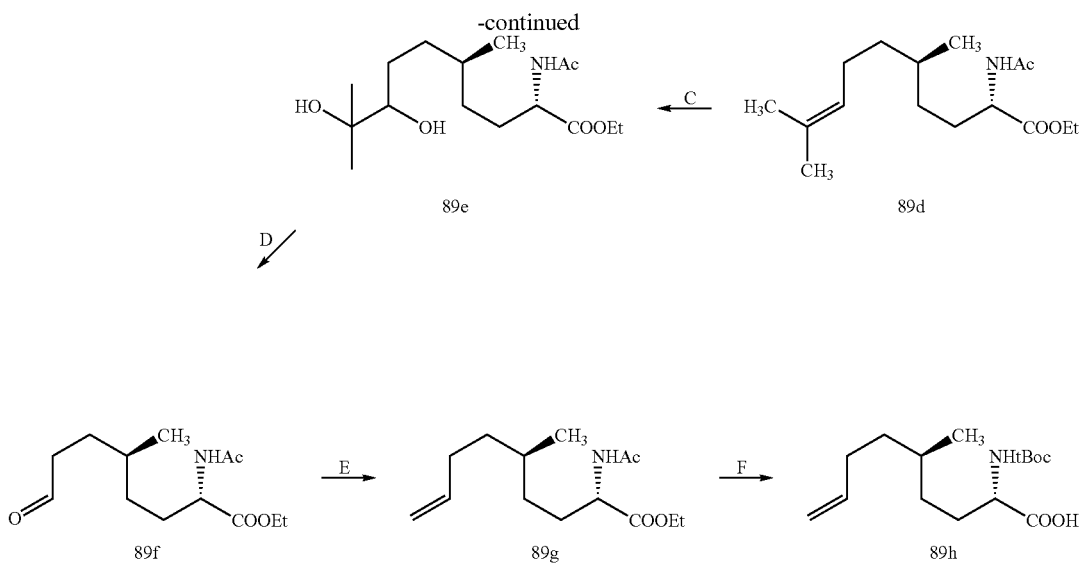

Synthesis of (2S,5R)-N-Boc-2-amino-5-methyl-non-8-enoic acid (89h)

89A. To solid ethyl 2-acetamidomalonate 89b is added (R)-(+)-citronellal 89a in a solution of pyridine over 1 min. The resulting solution is cooled in a 10° C. bath and acetic anhydride is added over 4 min. The resulting solution is stirred for 3 h at RT and another portion of ethyl 2-acetamidomalonate 89a is added. The resulting mixture is stirred at RT for an additional 11 hours. Ice is then added and the solution is stirred for 1.5 hours, then the mixture is diluted with 250 ml water and extracted with two portions of ether. The organic phase is washed with 1N HCl, sat. NaHCO$_3$, dried Na$_2$SO$_4$, concentrated and purified by flash chromatography (40% EtOAc/hexane) to afford compound 89c.

89B. To a degassed solution of 89c in dry ethanol is added (S,S)-Et-PUPHOS Rh(COD)OTf. The mixture is subjected to 30 psi of hydrogen and stirred on a Parr shaker for 2 hours. The resulting mixture is evaporated to dryness to obtain the crude compound 50d, which is used in the subsequent step without purification.

89C. Compound 89d is dissolved in a mixture of tBuOH/acetone/H$_2$O (1:1:1) and placed in an ice bath (0° C.). NMMO and OsO$_4$ is consecutively added and the reaction mixture is stirred at RT for 4 hours. A majority of the acetone is removed by evaporation under vacuum and then the mixture is extracted with ethyl acetate. The organic layer is further washed with water and brine, dried over anhydrous MgSO$_4$ and evaporated to dryness. The diol 50e is obtained in high purity after flash column chromatography using 1% ethanol in ethyl acetate as the eluent.

89D. To a solution of diol 89e in THF/H$_2$O (1:1) at 0° C., NaIO$_4$ is added and the reaction mixture is stirred at RT for 3.5 hours. A majority of the THF solvent is subsequently removed by evaporation under vacuum and the remaining mixture is extracted with EtOAc. The combined organic layers is further washed with 5% aqueous citric acid solution, 5% aq. NaHCO$_3$ and brine, then the organic phase is dried over MgSO$_4$ and evaporated to dryness under vacuum. Aldehyde intermediate 89f is used in the following step in its crude form.

89E. To a solution of Ph$_3$PCH$_3$Br in anhydrous toluene, KHMDS is added forming a suspension which is stirred at RT for 30 min. under N$_2$. After stirring, the suspension is cooled to 0° C., a solution of aldehyde intermediate 89f in THF is added, the mixture is warmed to RT, and stirred for 1 hour. A majority of the THF is evaporated under vacuum, EtOAc is added to the mixture and the organic phase is washed with water, 5% aq. NaHCO$_3$ and brine. The organic phase is then dried over MgSO$_4$ and evaporated to dryness under vacuum. Pure compound 89g is isolated after purification via flash chromatography on silica gel, using hexane:EtOAc (3:2) as the eluent.

89F. To a solution of crude 89g in THF, Boc$_2$O, and DMAP is added and the reaction mixture is heated to reflux for 2.5 hours. Subsequently, a majority of the THF is evaporated, the crude mixture is diluted with methylene chloride and washed with 1 N HCl to remove DMAP. The organic layer is further extracted with saturated aq. NaHCO$_3$, dried with anhydrous Na$_2$SO$_4$ and concentrated under vacuum. The crude product is then diluted with THF and water, LiOH.H$_2$O is added and the resulting mixture is stirred at RT for 25 hours, wherein the completion of the hydrolysis is monitored by TLC. The reaction mixture is concentrated under vacuum to remove a majority of the THF and further diluted with methylene chloride. The resulting solution is washed with 1 N HCl, dried with anhydrous Na$_2$SO$_4$ and concentrated under vacuum. To remove minor impurities and excess Boc$_2$O, the crude product is purified via flash chromatography using a solvent gradient from 100% hexane→100% EtOAc as the eluent. (2S, 5R)-N-Boc-2-amino-5-methyl-non-8-enoic acid 89h is obtained. For further details of the preceding amino acid synthesis see WO 00/59929, which is herein incorporated by reference in its entirety.

89G. Synthesis of Modified Cyclic Peptide Precursor Mesylate

The modified cyclic peptide precursor mesylate is prepared using the synthetic route detailed in Example 1 using ((2S, 5R)-N-Boc-2-amino-5-methyl-non-8-enoic acid 89h in place of Boc-L-2-amino-8-nonenoic acid 1a followed by conversion to the corresponding mesylate via the method described in Example 2.

The title compound is prepared with the modified cyclic peptide precursor mesylate formed in 89G and 5-phenyl-1H-tetrazole by the replacement method elucidated in Example 21 followed by hydrolysis of the ethyl ester via the method set forth in Example 22.

Example 90

Compound of Formula II, wherein A=tBOC, G=OH, L=—O—, W is

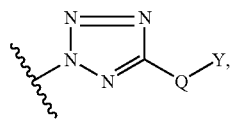

Q=absent, Y=phenyl, j=0, m=s=1, R³=methyl, and R⁴=hydrogen.

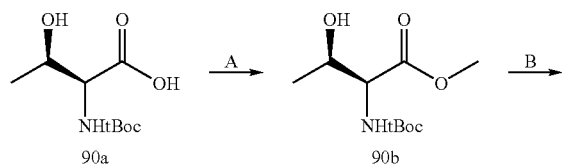

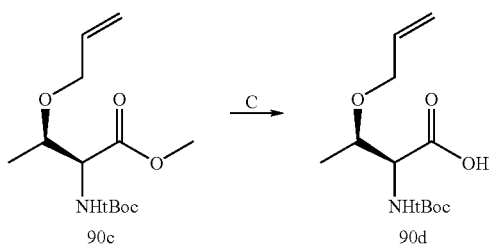

Synthesis of N-Boc-O-allyl-(L)-threonine (90d)

90A. Boc-(L)-threonine 90a is partially dissolved in methylene chloride/methanol at 0° C. A solution of diazomethane in diethyl ether is added until yellow, indicating the presence of diazomethane. Upon evaporation of the solvents, crude methyl ester 90b is obtained.

90B. Intermediate 90b is dissolved in anhydrous diethyl ether, Ag₂O is added and freshly activated 4 Å molecular sieves. Finally, allyl iodide is added to the reaction mixture and is stirred at reflux. Two additional portions of allyl iodide are added to the reaction mixture after a period of 20 hours and 30 hours and stirring is continued for a total of 36 hours. The mixture is then filtered through celite and purified by flash chromatography on silica gel, using EtOAc/hexane (1:4) as the eluent, to afford compound 90c.

90C. Compound 90c is dissolved in a mixture of THF/MeOH/H₂O (2:1:1) and LiOH.H₂O is added. The solution is stirred at RT for 2 h, and the is acidified with 1 N HCl to pH~3 before the solvents are removed under vacuum. The resulting crude compound 90d is obtained. For further details of the preceding amino acid synthesis see WO 00/59929, which is herein incorporated by reference in its entirety.

90D. Synthesis of Modified Cyclic Peptide Precursor Mesylate

The modified cyclic peptide precursor mesylate is prepared using the synthetic route detailed in Example 1 using N-Boc-O-allyl-(L)-threonine 90d in place of Boc-L-2-amino-8-nonenoic acid 1a followed by conversion to the corresponding mesylate via the method described in Example 2.

The title compound is prepared with the modified cyclic peptide precursor mesylate formed in 90D and 5-phenyl-1H-tetrazole by the replacement method elucidated in Example 21 followed by hydrolysis of the ethyl ester via the method set forth in Example 22.

Example 91

Compound of Formula II, wherein A=tBOC, G=OH, L=—S—, W is

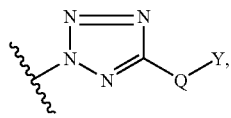

Q=absent, Y=phenyl, j=0, m=s=1, R³ methyl, and R⁴=hydrogen.

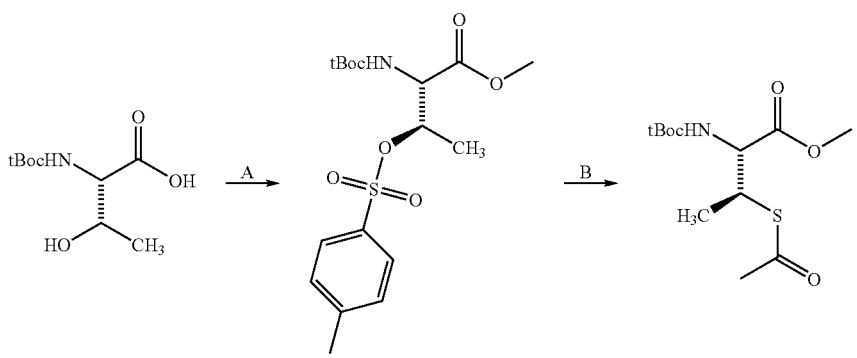

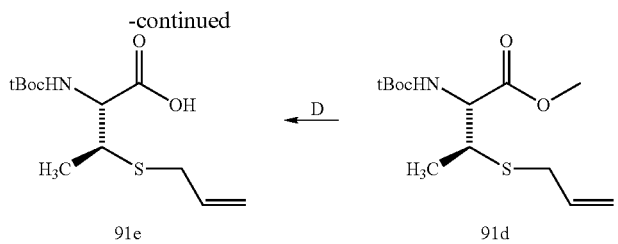

Synthesis of (2S,3S)-N-Boc-2 amino-3 (mercaptoallyl)butanoic acid (91e)

91A. Compound 91a is dissolved in pyridine and the solution is cooled to 0° C. in an ice bath, tosyl chloride is added in small portions and the reaction mixture is partitioned between diethyl ether and $H_2O$. The ether layer is further washed with 0.2 N HCl and brine, dried over anhydrous $MgSO_4$, filtered and concentrated to dryness under vacuum. Purification of the crude material by flash chromatography on silica gel, using hexane/EtOAc (gradient from 8:2 to 7:3 ratio) as the eluent, led to isolation of tosyl derivative 91b.

91B. To a solution of tosyl derivative 91b in anhydrous DMF, potassium thioacetate is added and the reaction mixture is stirred at RT for 24 hours. A majority of the DMF is then evaporated under vacuum and the remaining mixture is partitioned between EtOAc and $H_2O$.

The aqueous layer is re-extracted with EtOAc, the combined organic layers are washed with brine, dried over anhydrous $MgSO_4$ and evaporated to dryness. Purification of the crude material by flash chromatography on silica gel using hexane/EtOAc (4:1 ratio) as the eluent, affords thioester 91c.

91C. To a solution of thioester 91c is $H_2O$/EtOH (3:5 ratio) and aqueous solution of 0.2M NaOH is added and the mixture is stirred at RT for 1.5 hours. Allyl iodide is then added and stirring is continued at RT for an additional 30 min. The reaction mixture is concentrated to half of its original volume and then extracted with EtOAc. The aqueous layer is acidified to pH~3 with cold, aqueous 0.5N HCl and re-extracted with EtOAc. The combined organic layers are washed with brine, dried over anhydrous $MgSO_4$ and evaporated to dryness under vacuum. The crude reaction mixture contains at least four products; all of the products are isolated after flash chromatography on silica gel, using hexane/EtOAc (gradient from 9:1 to 3:1). The desired product 91d is the least polar compound.

91D. A solution of compound 91d in MeOH/$H_2O$ (3:1) is mixed with aqueous NaOH (0.3 N) for 24 hours at RT and for 1 hour at 40° C. The reaction mixture is acidified with cold aqueous 0.5 N HCl, the MeOH is removed under vacuum and the remaining aqueous mixture is extracted with EtOAc. The organic phase is dried over $MgSO_4$ and evaporated to dryness in order to obtain compound 91e. For further details of the preceding amino acid synthesis see WO 00/59929, which is herein incorporated by reference in its entirety.

91E. Synthesis of Modified Cyclic Peptide Precursor Mesylate

The modified cyclic peptide precursor mesylate is prepared using the synthetic route detailed in Example 1 using (2S,3S)-N-Boc-2 amino-3(mercaptoallyl)butanoic acid 52e in place of Boc-L-2-amino-8-nonenoic acid 1a followed by conversion to the corresponding mesylate via the method described in Example 2.

The title compound is prepared with the modified cyclic peptide precursor mesylate formed in 91E and 5-phenyl-1H-tetrazole by the replacement method elucidated in Example 21 followed by hydrolysis of the ethyl ester via the method set forth in Example 22.

Example 92

Compound of Formula II, wherein A=tBOC, G=OH, L=—S(O)—, W is

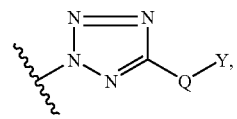

Q=absent, Y=phenyl, j=2, m=s=1, $R^3$=methyl, and $R^4$=hydrogen.

Formation of Modified Amino Acid (92a)

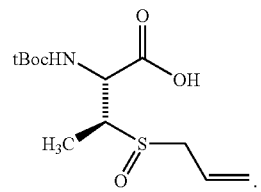

92A. The modified amino acid is prepared by dissolving sodium metaperiodate (1.1 eq.) in water and cooled to 0° C. in an ice bath followed by adding dropwise a solution of compound 91d in dioxane. The resulting reaction mixture is stirred for one hour at 0° C. and 4 hours at 40° C. The reaction mixture is concentrated, water is added, and the mixture is extracted with methylene chloride twice. The combined organic layers are washed with water, brine, dried with anhydrous $MgSO_4$ and concentrated in vacuo. The methyl ester is then reduced via the method set forth in Example 91D to arrive upon the modified amino acid 92a. For further details of the preceding amino acid synthesis may be found in T. Tsuda et al., *J. Am. Chem. Soc.*, 1980, 102, 6381-6384 and WO 00/59929, which are herein incorporated by reference in their entirety.

92B. Synthesis of Modified Cyclic Peptide Precursor Mesylate

The modified cyclic peptide precursor mesylate is prepared using the synthetic route detailed in Example 1 using the modified amino acid 92a in place of Boc-L-2-amino-8-nonenoic acid 1a followed by conversion to the corresponding mesylate via the method described in Example 2.

The title compound is prepared with the modified cyclic peptide precursor mesylate formed in 92B and 5-phenyl-1H- tetrazole by the replacement method elucidated in Example 21 followed by hydrolysis of the ethyl ester via the method set forth in Example 22.

Example 93

Compound of Formula II, wherein A=tBOC, G=OH, L=—S(O)₂—, W is

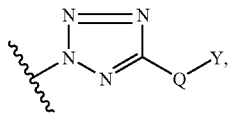

Q=absent, Y=phenyl, j=2, m=s=1, R³=methyl, and R⁴=H.

Formation of Modified Amino Acid

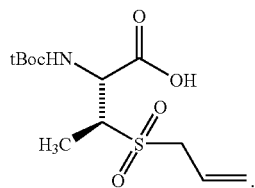

(93a)

93A. The modified amino acid is prepared by dissolving sodium metaperiodate (1.1 eq.) in water and cooled to 0° C. in an ice bath followed by adding dropwise a solution of compound 92d in dioxane. The resulting reaction mixture is stirred for one hour at 0° C. and 4 hours at 40° C. The reaction mixture is concentrated, water is added, and the mixture is extracted with methylene chloride twice. The combined organic layers are washed with water, brine, dried with anhydrous MgSO₄ and concentrated in vacuo. The methyl ester is then reduced via the method set forth in Example 91D to arrive upon the modified amino acid 92a. For further details of the preceding amino acid synthesis may be found in T. Tsuda et al., *J. Am. Chem. Soc.*, 1980, 102, 6381-6384 and WO 00/59929, which are herein incorporated by reference in their entirety.

93B. Synthesis of Modified Cyclic Peptide Precursor Mesylate

The modified cyclic peptide precursor mesylate is prepared using the synthetic route detailed in Example 1 using the modified amino acid 93a in place of Boc-L-2-amino-8-nonenoic acid 1a followed by conversion to the corresponding mesylate via the method described in Example 2.

The title compound is prepared with the modified cyclic peptide precursor mesylate formed in 93B and 5-phenyl-1H-tetrazole by the replacement method elucidated in Example 21 followed by hydrolysis of the ethyl ester via the method set forth in Example 22.

Example 94

Compound of Formula II, wherein A=tBOC, G=OH, L=—SCH₂CH₂—, W is

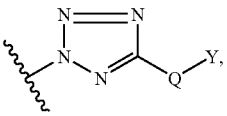

Q=absent, Y=phenyl, j=0, m=s=1, and R³=R⁴=CH₃

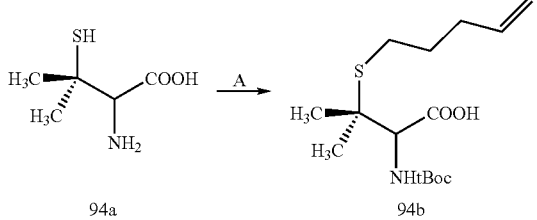

94a          94b

94A. Synthesis of (S)-N-Boc-2-amino-3-methyl-3(1-mercapto-4-butenyl)butanoic acid (94b)

L-Penicillamine 94a is dissolved in DMF/DMSO (5:1), subsequently, 4-bromopentene and CsOH.H₂O are added to the mixture and stirring is continued for an additional 12 hours. The DMF is subsequently removed in vacuo, the remaining mixture is diluted with 0.5 N HCl (at 0° C.) to adjust the pH to 4-5 and then extracted with 2 portions of EtOAc. The organic phase is washed with brine (2×), dried over MgSO₄ and evaporated to dryness to afford the crude carboxylic acid 94a. For further details of the preceding amino acid synthesis see WO 00/59929, which is herein incorporated by reference in its entirety.

94B. Synthesis of Modified Cyclic Peptide Precursor Mesylate

The modified cyclic peptide precursor mesylate is prepared using the synthetic route detailed in Example 1 using the modified amino acid 94a in place of Boc-L-2-amino-8-nonenoic acid 1a followed by conversion to the corresponding mesylate via the method described in Example 2.

The title compound is prepared with the modified cyclic peptide precursor mesylate formed in 94B and 5-phenyl-1H-tetrazole by the replacement method elucidated in Example 21 followed by hydrolysis of the ethyl ester via the method set forth in Example 22.

Example 95

Compound of Formula II, wherein A=tBOC, G=OH, L=—CF₂CH₂—, W is

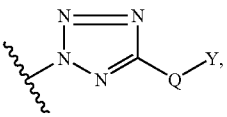

Q=absent, Y=phenyl, j=1, m=s=1, and R³=R⁴=H.

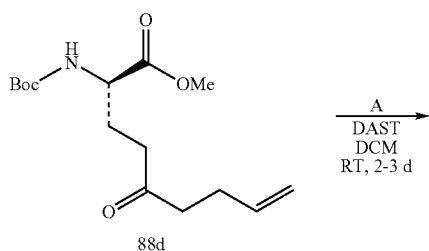

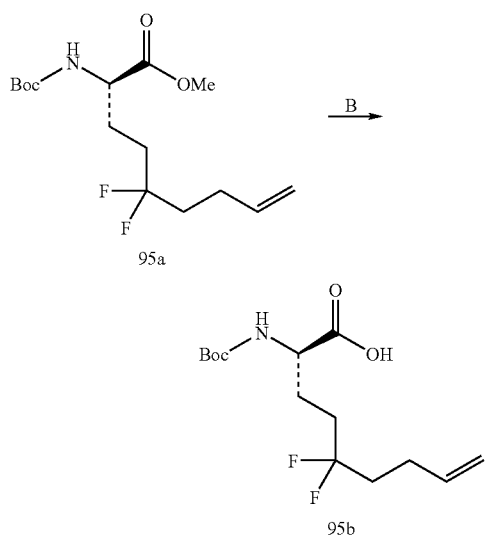

Synthesis of (2S)-N-Boc-amino-5-difluoro-non-8-enoic acid (95b)

95A. To a solution of the ketone compound 88d (0.30 g, 1 mmol) in 5 ml DCM, DAST (Diethylaminosulfurtrifluoride, 0.2 g, 1.2 eq) is added. The reaction is kept at RT over a period of 2-3 days. The solvent is evaporated and the residue is purified by silica gel flash chromatography using different ratios of hexanes:EtOAc as eluent (9:1→5:1→3:1→1:1), providing the isolated methyl ester 95a. For further details concerning the preceding synthesis, see Tius, Marcus A et al., Tetrahedron, 1993, 49, 16; 3291-3304, which is herein incorporated by reference in its entirety.

95B. Methyl ester 95a is dissolved in THF/MeOH/H$_2$O (2:1:1) and LiOH.H$_2$O is added.

The solution is stirred at RT for 2 hours, and is then acidifies with 1N HCl to pH~3 before the solvents are removed in vacuo to afford the crude (2S)-N-Boc-amino-5-difluoro-non-8-enoic acid 95b.

95C. Synthesis of Modified Cyclic Peptide Precursor Mesylate

The modified cyclic peptide precursor mesylate is prepared using the synthetic route detailed in Example 1 using crude (2S)-N-Boc-amino-5-difluoro-non-8-enoic acid 95b in place of Boc-L-2-amino-8-nonenoic acid 1a followed by conversion to the corresponding mesylate via the method described in Example 2.

The title compound is prepared with the modified cyclic peptide precursor mesylate formed in 95C and 5-phenyl-1H-tetrazole by the replacement method elucidated in Example 21 followed by hydrolysis of the ethyl ester via the method set forth in Example 22.

Example 96

Compound of Formula II, wherein A=tBOC, G=OH, L=—CFHCH$_2$—, W is

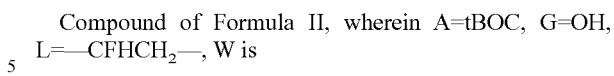

Q=absent, Y=phenyl, j=1, m=s=1, and R$^3$=R$^4$=H.

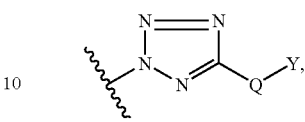

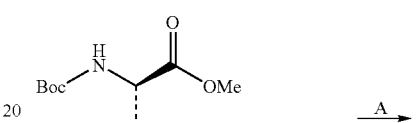

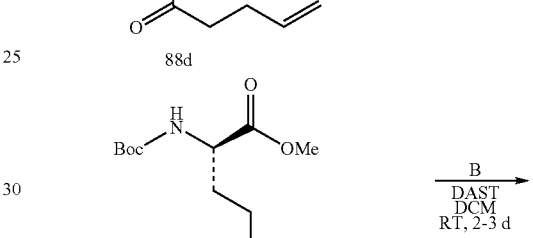

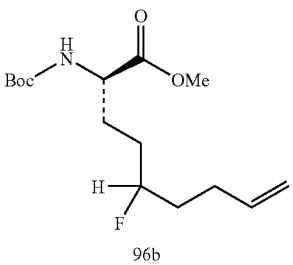

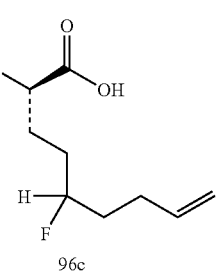

Synthesis of (2S)-N-Boc-amino-5-fluoro-non-8-enoic acid (96c)

96A. To a solution of the ketone compound 88d in 5 ml methanol, NaBH$_4$ (2.2 eq) is added. The reaction mixture is stirred at RT over a period of 2-6 hours, and then quenched by 1M ammonium chloride and extracted with EtOAc (30 ml). The solvent is evaporated and the crude hydroxy compound 96a is obtained.

96B. The hydroxy compound 96a is dissolved in 5 ml DCM to which DAST (0.2 g, 1.2 eq) is added and stirred at −45° C. for 1 hour. The reaction mixture is then warmed to RT and stirred over a period of 2-3 days. The solvent is evaporated and the residue is purified by silica gel flash chromatography using different ratios of hexanes:EtOAc as eluent (9:1→5:1→3:1→1:1), providing the isolated monofluoro compound methyl ester 95b. For further details concerning this synthesis see Buist, Peter H et al., *Tetrahedron Lett.*, 1987, 28, 3891-3894, which is herein incorporated by reference in its entirety.

96M. Methyl ester 96b is dissolved in THF/MeOH/H$_2$O (2:1:1) and LiOH.OH$_2$O is added. The solution is stirred at RT for 2 hours, and is then acidifies with 1N HCl to pH 3 before the solvents are removed in vacuo to afford the crude (2S)-N-Boc-amino-5-difluoro-non-8-enoic acid 96c.

96C. Synthesis of Modified Cyclic Peptide Precursor Mesylate

The modified cyclic peptide precursor mesylate is prepared using the synthetic route detailed in Example 1 using crude (2S)-N-Boc-amino-5-monofluoro-non-8-enoic acid 96M in place of Boc-L-2-amino-8-nonenoic acid 1a followed by conversion to the corresponding mesylate via the method described in Example 2.

The title compound is prepared with the modified cyclic peptide precursor mesylate formed in 96C and 5-phenyl-1H-tetrazole by the replacement method elucidated in Example 21 followed by hydrolysis of the ethyl ester via the method set forth in Example 22.

Example 97

Compound of Formula III, wherein A=tBOC, G=OH, L=absent, W is

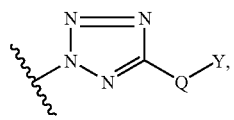

Q=absent, Y=phenyl, j=3, m=s=1, and R$^3$=R$^4$=H.

97A. The saturated cyclic peptide precursor mesylate is prepared by catalytic reduction of the mesylate cyclic peptide precursor 2 with Pd/C in MeOH in the presence of H$_2$.

The title compound is prepared with the saturated cyclic peptide precursor mesylate formed in 97A and 5-phenyl-1H-tetrazole by the replacement method elucidated in Example 21 followed by hydrolysis of the ethyl ester via the method set forth in Example 22.

The compounds of the present invention exhibit potent inhibitory properties against the HCV NS3 protease. The following examples elucidate assays in which the compounds of the present invention were tested for anti-HCV effects.

Example 98

Triazole Synthesis

Exemplary triazole derivatives for use in preparing compounds of the invention may be prepared as set forth in the examples below:

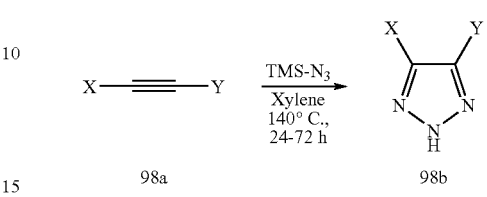

Triazoles of the present invention may be prepared by reacting 4 mmol of alkyne compound 98a, which is commercially available or made from procedures elucidated infra, and 8 mmol of trimethylsilyl azide in 2 ml of xylenes in a pressure tube for 24-72 hours at 140° C. The resulting reaction mixture was directly separated by silica column, yielding triazole 98b in 30-90% yield.

Example 99

Alykyne Synthesis
99A. Sonogashira Reaction

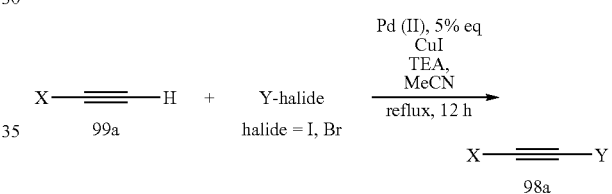

Alkynes used in the present invention can be made by the Sonogashira reaction by reaction of a degassed solution of 4 mmol of primary alkyne compound 99a, 4 mmol of an aryl halide (Y-halide), and 1 ml of triethylamine and 10 ml of acetonitrile with 140 mg (0.2 mmol) of PdCl$_2$(PPh$_3$)$_2$ and 19 mg (0.1 mmol) of CuI. The resulting reaction mixture is degassed and stirred for 5 minutes at RT. The reaction is then heated to 90° C. and stirred for 12 hours. Subsequently, the reaction mixture is concentrated in vacuo and purified by silica column to afford the substituted alkyne 98a in a 60-90% yield.

99B. Synthesis of Alkynyl Amides

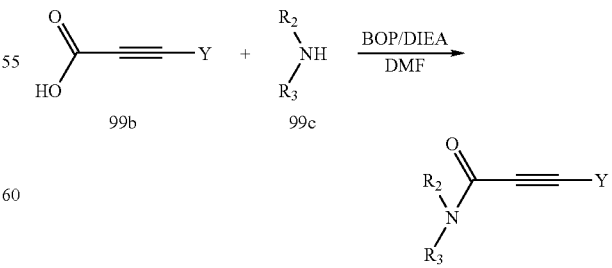

Additional alkynes used in the present invention can be made by reacting 10 mmol of alkynyl acid 99b, 11 mmol of BOP, and 22 mmol of DIEA in 15 ml of DMF with 11 mmol of amine 99b and stirring at room temperature for 3 hours. The reaction mixture is then extracted by ethyl acetate (2×50 ml); washed with 1M NaHCO3 (2×30 ml), water (2×30 ml), 5% citric acid (2×50 ml) and brine (2×30 ml); dried over anhydrous sodium sulfate; and concentrated in vacuo to afford alkyne 99d in a 90% yield.

Example 100

Compound of Formula II, wherein A=tBOC, G=OH, L=absent, W is

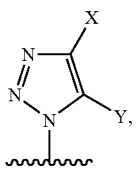

X=H, Y=4-t-butylphenyl, j=3, m=s=1, and $R^3=R^4=H$.

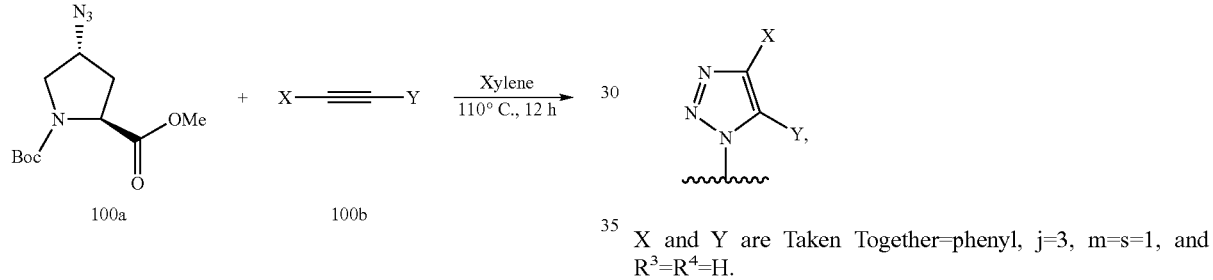

The title compound was prepared by the following method: 2 mmol (0.54 g) of Boc methyl ester azidoproline 100a and 2.5 mmol of 4-tert-Butylphenylacetylene 100b were dissolved in 2 ml of xylenes and stirred at 110° C. for 12 hours. The resulting reaction mixture was directly separated by silica column to resolve isomers 100c and 100d, with a yield of 90%.

The title compound was then formed via the RCM procedure described in Example 1 using 100b in the place of hydroxyl proline, followed by hydrolysis of the ethyl ester via the procedure described in Example 106.

$[M+Na]^+=671.72$.

Example 101

Compound of Formula II, wherein A=tBOC, G=OH, L=absent, W is

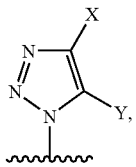

X=4-t-butylphenyl, Y=H, j=3, m=s=1, and $R^3=R^4=H$.

The title compound was prepared via RCM procedure described in Example 1 using 100c in the place of hydroxyl proline, followed by hydrolysis of the ethyl ester via the procedure described in Example 106.

$[M+H]^+=649.44$.

Example 102

Compound of Formula II, wherein A=tBOC, G=OH, L=absent, W is

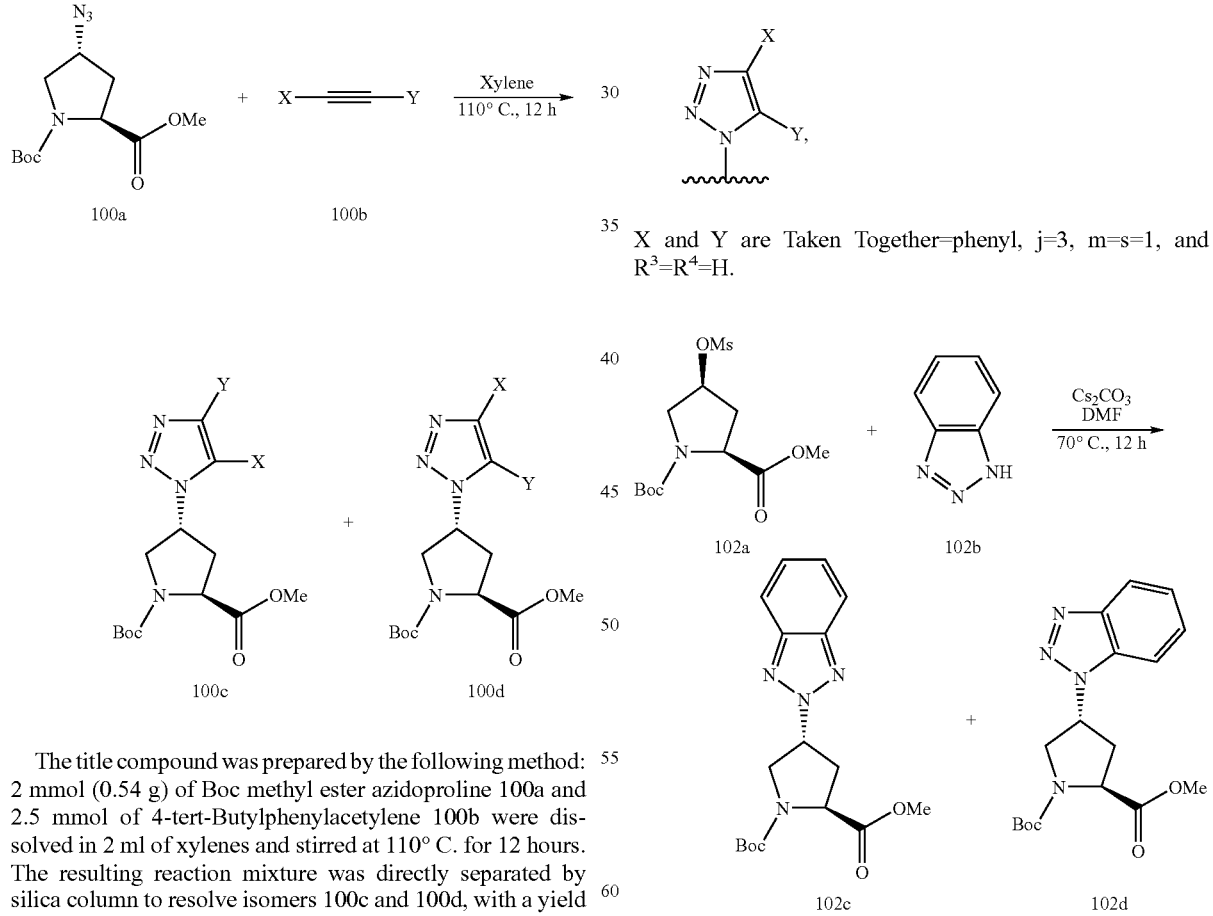

X and Y are Taken Together=phenyl, j=3, m=s=1, and $R^3=R^4=H$.

The triazole-substituted proline corresponding to the title compound was prepared by dissolving 1.5 mmol (0.5 g) of hydroxyproline mesylate 102a and 4.5 mmol of benzotriazole 102b in 5 ml of DMF, adding 9 mmol (2.9 g) of cesium carbonate and stirring the resulting reaction mixture at 70° C.

for 12 hours. The reaction mixture was extracted with EtOAc, washed with 1M sodium bicarbonate and brine. The organic layer was dried over MgSO₄ and concentrated in vacuo. Expected isomers 102c and 102d were resolved via silica column chromatography.

The title compound was then formed via the RCM procedure described in Example 1 using 102d in the place of hydroxyl proline, followed by hydrolysis of the ethyl ester via the procedure described in Example 106.

[M+Na]⁺=588.46.

Example 103

Compound of Formula II, wherein A=tBOC, G=OH, L=absent, W is

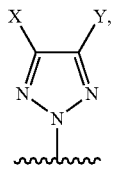

X and Y Taken Together=phenyl, j=3, m=s=1, and R³=R⁴=H.

The title compound was formed via the RCM procedure described in Example 1 using 102c in the place of hydroxyl proline, followed by hydrolysis of the ethyl ester via the procedure described in Example 106.

[M+Na]⁺=588.50.

Example 104

Compound of Formula II, wherein A=tBOC, G=OH, L=absent, W is

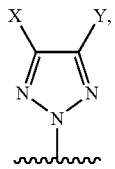

X=Y=phenyl, j=3, m=s=1, and R³=R⁴=H.

The triazole-substituted proline corresponding to the title compound was prepared by dissolving 1.5 mmol (0.5 g) of hydroxyproline mesylate 102a and 4.5 mmol of benzotriazole 102b in 5 ml of DMF, adding 9 mmol (2.9 g) of cesium carbonate and stirring the resulting reaction mixture at 70° C. for 12 hours. The reaction mixture was extracted with EtOAc, washed with 1M sodium bicarbonate and brine. The organic layer was dried over MgSO₄ and concentrated in vacuo.

The title compound was then formed via the RCM procedure described in Example 1 using the triazole-substituted proline of the present example in the place of hydroxyl proline, followed by hydrolysis of the ethyl ester via the procedure described in Example 106.

[M+Na]⁺=690.42.

Example 105

Compound of Formula II, wherein A=tBOC, G=OEt, L=absent, W is

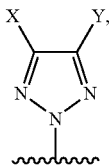

X=Y=phenyl, j=3, m=s=1, and R³=R⁴=H.

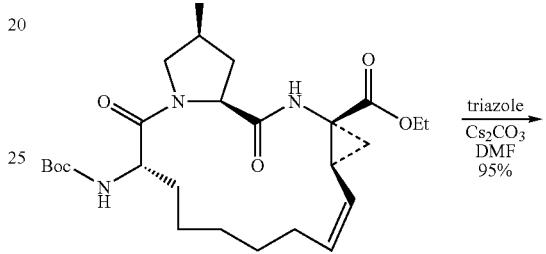

2

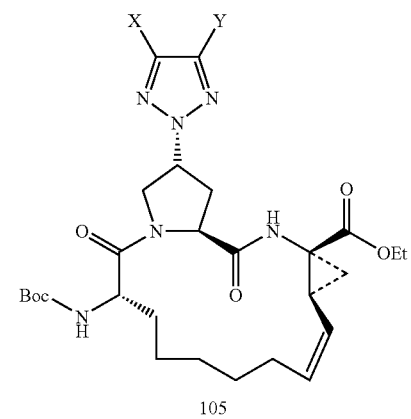

105

The title compound was prepared by dissolving 0.041 mmol of the title compound of Example 2 and 0.123 mmol of 4,5-diphenyltriazole in 3 ml of DMF, adding 0.246 mmol of cesium carbonate (80 mg), and reacting at 70° C. for 12 hours. The reaction mixture was then extracted with EtOAc and washed with 1M sodium bicarbonate (2×30 ml) and water (2×30 ml). The resulting organic solution was concentrated in vacuo to dryness.

Example 106

Compound of Formula II, wherein A=tBOC, G=OH, L=absent, W is

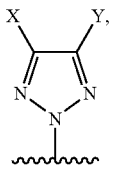

X=Y=phenyl, j=3, m=s=1, and R³=R⁴=H.

The title compound was prepared by dissolving 0.041 mmol of the title compound of Example 105 in 3 ml of dioxane, adding 2 ml of 1M LiOH, and reacting at RT for 8 hours. Subsequently, the pH of reaction mixture was adjusted to 3 with citric acid, extracted with EtOAc, followed by washing with brine and water. The organic solution was concentrated in vacuo for purification by HPLC.

[M+Na]⁺=690.42.

Example 107

Compound of Formula II, wherein A=tBOC, G=OH, L=absent, W is

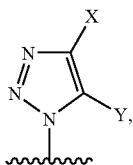

X=Y=phenyl, j=3, m=s=1, and R³=R⁴=H.

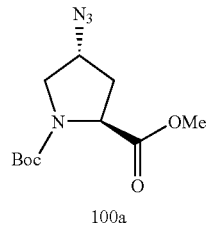

100a

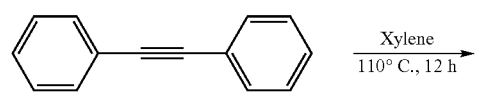

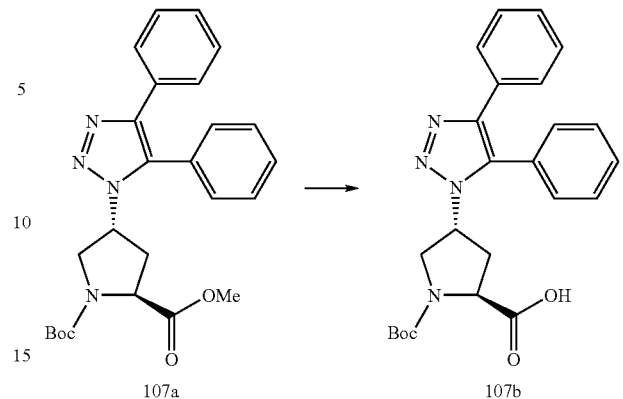

107a → 107b

The triazole-substituted proline precursor of the title compound was prepared by dissolving 0.93 mmol (0.25 g) of azidoproline 100a and 1 mmol of diphenyl acetylene in 2 ml of xylenes, heated to 110° C., and stirred for 12 hours. The reaction mixture was directly separated by silica column to afford 0.27 g of 107a (90%). [M+H]+: 449.05. 0.26 g of 107b was obtained by the hydrolysis procedure elucidated in Example 105 (99%).

The title compound was then formed via the RCM procedure described in Example 1 using 107b in the place of hydroxyl proline.

[M+Na]⁺=691.99.

Example 108

Compound of Formula II, wherein A=tBOC, G=OH, L=absent, W is

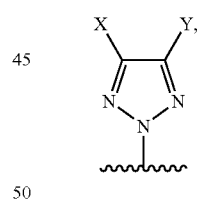

X=n-propyl, Y=phenyl, j=3, m=s=1, and R³=R⁴=H.

108a Triazole Formation

The 4-(n-propyl)-5-phenyltriazole was prepared via the procedure of Example 98 using n-propyl phenylacetylene and sodium azide.

The title compound was prepared with the title compound of Example 2 and 4-(n-propyl)-5-phenyltriazole 108a according to the procedure set forth in Example 105 and subsequent hydrolysis of the ethyl ester via the procedure of Example 106.

[M+Na]⁺=657.99.

Example 109

Compound of Formula II, wherein A=tBOC, G=OH, L=absent, W is

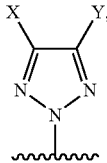

X=m-methoxyphenyl Y=p-methoxyphenyl, j=3, m=s=1, and $R^3=R^4=H$.

109a Alkyne Formation

The 2-(m-methoxyphenyl)-4-methoxyphenylacetylene was prepared via the procedure of Example 99A from 4-methoxyphenylacetylene and 3-bromoanisole.

109b Triazole Formation

The 4-(m-methoxyphenyl)-5-(p-methoxyphenyl)triazole was prepared via the procedure of Example 3 using alkyne 109a and sodium azide.

The title compound was prepared with the title compound of Example 2 and the 4-(m-methoxyphenyl)-5-(p-methoxyphenyl)triazole 109a according to the procedure set forth in Example 105 and subsequent hydrolysis of the ethyl ester via the procedure of Example 106.

$[M+Na]^+=752.08$.

Example 110

Compound of Formula II, wherein A=tBOC, G=OH, L=absent, W is

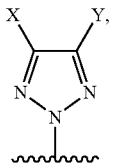

X=m-bromophenyl Y=p-methoxyphenyl, j=3, m=s=1, and $R^3=R^4=H$.

110a Alkyne Formation

The 2-(m-bromophenyl)-4-methoxyphenylacetylene was prepared via the procedure of Example 99A from 4-methoxyphenylacetylene and 3-iodo-5-bromobenzene.

110b Triazole Formation

The 4-(m-bromophenyl)-5-(p-methoxyphenyl)triazole was prepared via the procedure of Example 3 using alkyne 110a and sodium azide.

The title compound was prepared with the title compound of Example 2 and the 4-(m-bromophenyl)-5-(p-methoxyphenyl)triazole 110a according to the procedure set forth in Example 105 and subsequent hydrolysis of the ethyl ester via the procedure of Example 106.

$[M+Na]^+=800.05$.

Example 111

Compound of Formula II, wherein A=tBOC, G=OH, L=absent, W is

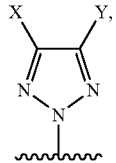

X=1-napthyl, Y=p-methoxyphenyl, j=3, m=s=1, and $R^3=R^4=H$.

111a Alkyne Formation

The 2-(1-napthyl)-4-methoxyphenylacetylene was prepared via the procedure of Example 99A from 1-iodonapthelene and 4-methoxyphenylacetylene.

111b Triazole Formation

The 4-(m-bromophenyl)-5-(p-methoxyphenyl)triazole was prepared via the procedure of Example 3 using 2-(1-napthyl)-4-methoxyphenylacetylene 113a and sodium azide.

The title compound was prepared with the title compound of Example 2 and the 4-(1-napthyl)-5-(p-methoxyphenyl)triazole 113a according to the procedure set forth in Example 105 and subsequent hydrolysis of the ethyl ester via the procedure of Example 106.

$[M+Na]^+=772.11$.

Example 112

Compound of Formula II, wherein A=tBOC, G=OH, L=absent, W is

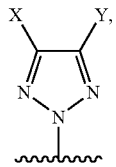

X=2-thienyl, Y=p-methoxyphenyl, j=3, m=s=1, and $R^3=R^4=H$.

112a Alkyne Formation

The 2-(2-thienyl)-4-methoxyphenylacetylene was prepared via the procedure of Example 99A from 2-iodothiophene and 4-methoxyphenylacetylene.

112b Triazole Formation

The 4-(2-thienyl)-5-(p-methoxyphenyl)triazole was prepared via the procedure of Example 3 using 2-(2-thienyl)-4-methoxyphenylacetylene 112a and sodium azide.

The title compound was prepared with the title compound of Example 2 and the 4-(2-thienyl)-5-(p-methoxyphenyl)triazole 112a according to the procedure set forth in Example 105 and subsequent hydrolysis of the ethyl ester via the procedure of Example 106.

$[M+H]^+=705.31$.

Example 113

Compound of Formula II, wherein A=tBOC, G=OH, L=absent, W is

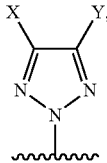

X=3-thienyl, Y=p-methoxyphenyl, j=3, m=s=1, and $R^3=R^4=H$.

113a Alkyne Formation

The 2-(3-thienyl)-4-methoxyphenylacetylene was prepared via the procedure of Example 99a from 2-iodothiophene and 4-methoxyphenylacetylene.

113b Triazole Formation

The 4-(3-thienyl)-5-(p-methoxyphenyl)triazole was prepared via the procedure of Example 3 using 2-(3-thienyl)-4-methoxyphenylacetylene 113a and sodium azide.

The title compound was prepared with the title compound of Example 2 and the 4-(3-thienyl)-5-(p-methoxyphenyl)triazole 113a according to the procedure set forth in Example 105 and subsequent hydrolysis of the ethyl ester via the procedure of Example 106.

$[M+Na]^+=727.21$.

Example 114

Compound of Formula II, wherein A=tBOC, G=OH, L=absent, W is

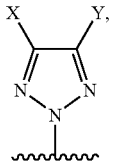

X=4-pyrazolyl, Y=p-methoxyphenyl, j=3, m=s=1, and $R^3=R^4=H$.

114a Alkyne Formation

The 2-(4-pyrazolyl)-4-methoxyphenylacetylene was prepared via the procedure of Example 99A from 4-iodopyrazole and 4-methoxyphenylacetylene.

114b Triazole Formation

The 4-(4-pyrazolyl)-5-(p-methoxyphenyl)triazole was prepared via the procedure of Example 3 using 2-(4-pyrazolyl)-4-methoxyphenylacetylene 114a and sodium azide.

The title compound was prepared with the title compound of Example 2 and the 4-(4-pyrazolyl)-5-(p-methoxyphenyl) triazole 114a according to the procedure set forth in Example 105 and subsequent hydrolysis of the ethyl ester via the procedure of Example 106.

$[M+H]^+=700.82$.

Example 115

Compound of Formula II, wherein A=tBOC, G=OH, L=absent, W is

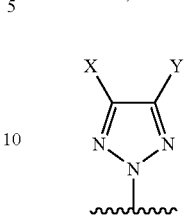

X=3-pyridyl, Y=p-methoxyphenyl, j=3, m=s=1, and $R^3=R^4=H$.

115a Alkyne Formation

The 2-(3-pyridyl)-4-methoxyphenylacetylene was prepared via the procedure of Example 99A from 3-iodopyridine and 4-methoxyphenylacetylene.

115b Triazole Formation

The 4-(3-pyridyl)-5-(p-methoxyphenyl)triazole was prepared via the procedure of Example 3 using 2-(3-pyridyl)-4-methoxyphenylacetylene 115a and sodium azide.

The title compound was prepared with the title compound of Example 2 and the 4-(3-pyridyl)-5-(p-methoxyphenyl) triazole 115a according to the procedure set forth in Example 105 and subsequent hydrolysis of the ethyl ester via the procedure of Example 106.

$[M+H]^+=700.36$.

Example 116

Compound of Formula II, wherein A=tBOC, G=OH, L=absent, W is

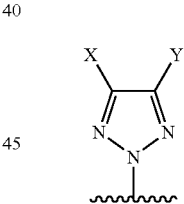

X=2-pyridyl, Y=p-methoxyphenyl, j=3, m=s=1, and $R^3=R^4=H$.

116a Alkyne Formation

The 2-(2-pyridyl)-4-methoxyphenylacetylene was prepared via the procedure of Example 99A from 2-iodopyridine and 4-methoxyphenylacetylene.

116b Triazole Formation

The 4-(2-pyridyl)-5-(p-methoxyphenyl)triazole was prepared via the procedure of Example 3 using 2-(2-pyridyl)-4-methoxyphenylacetylene 116a and sodium azide.

The title compound was prepared with the title compound of Example 2 and the 4-(2-pyridyl)-5-(p-methoxyphenyl) triazole 116a according to the procedure set forth in Example 105 and subsequent hydrolysis of the ethyl ester via the procedure of Example 106.

$[M+H]^+=700.82$.

Example 117

Compound of Formula II, wherein A=tBOC, G=OH, L=absent, W is

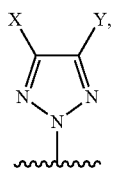

X=2-thiazolyl, Y=p-methoxyphenyl, j=3, m=s=1, and $R^3=R^4=H$.

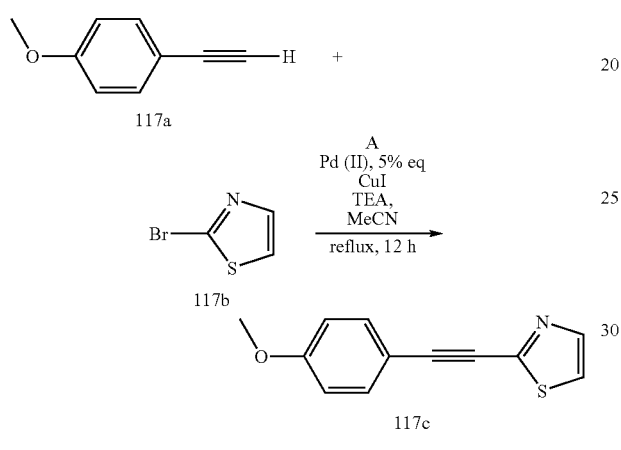

117A. Alkyne Formation

The alkyne of the current example, 2-(2-thiazolyl)-4-methoxyphenylacetylene was prepared by adding to a degassed solution of 4 mmol of 4-ethynylanisole, 4 mmol of 2-bromothiazole, and 1 ml of triethylamine in 10 ml of acetonitrile, 140 mg (0.2 mmol) of $PdCl_2(PPh_3)_2$ and 19 mg (0.1 mmol) of CuI. The mixture was degassed and stirred for 5 minutes at RT and heated to 90° C. for 12 hours. The reaction mixture was concentrated in vacuo and purified by silica column to afford 0.61 g of brown liquid in a 70% yield.

[M+H]+: 216.17, 1HNMR (CDCl$_3$, 500 MHz) δ7.765 (d, J=3 Hz, 1H), 7.4727.455 (m, 2H), 7.277 (d, J=3.5 Hz, 1H), 6.837-6.820 (m, 2H), 3.768 (s, 3H).

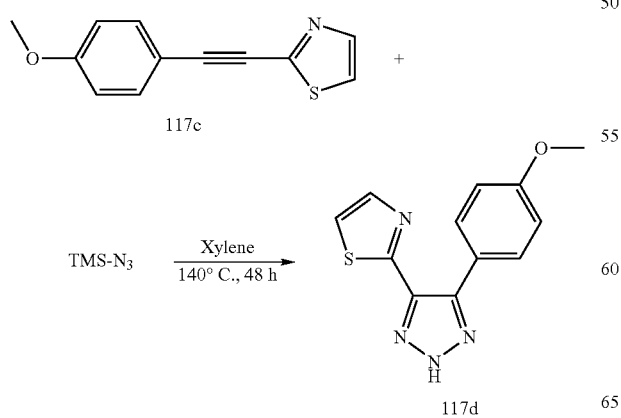

117B. Triazole Formation

The 4-(2-thiazolyl)-5-(p-methoxyphenyl) triazole 117d was prepared by adding to a pressure tube 0.3 g of 117c, 0.74 ml of trimethylsilyl azide, and 4 ml of xylenes and heating the mixture to 140° C. for 48 hours. The reaction mixture was directly separated by silica column to afford a brown liquid (117d) after purification (0.18 g, 50%).

[M+H]+: 259.27, 1HNMR (DMSO-d$_6$), 500 MHz) δ 8.016 (d, J=8.5 Hz, 2H), 7.929 (d, J=3 Hz, 1H), 7.817 (d, J=3 Hz, 1H), 7.066 (d, J=8.5 Hz, 2H), 3.824 (s, 3H).

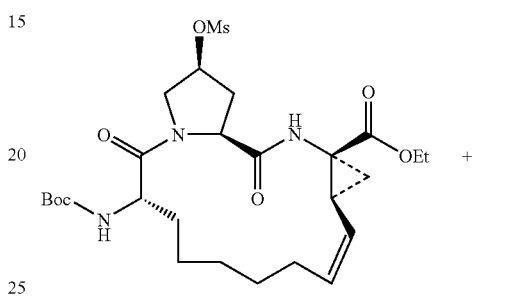

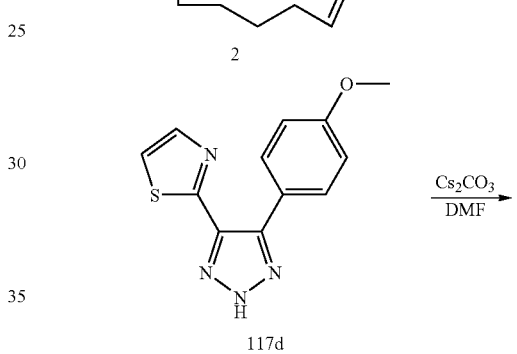

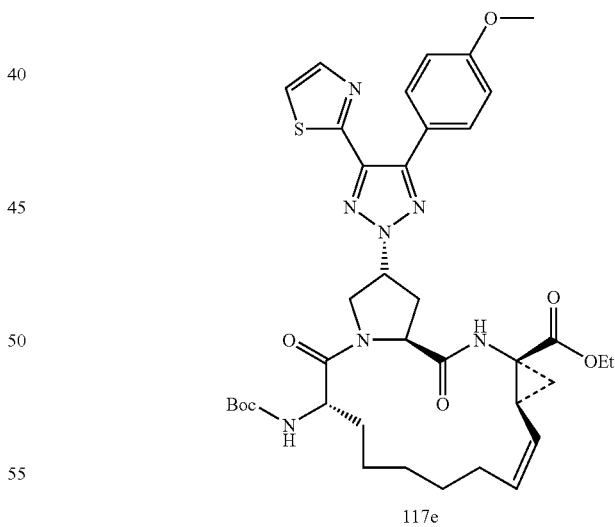

117c. Ethyl Ester 117e was prepared by dissolving 0.041 mmol of mesylate of macrocyclic precursor 117d and 0.123 mmol of 117d in 3 ml of DMF, adding 0.246 mmol cesium carbonate, and reacting at 70° C. for 12 hours. The reaction mixture was extracted with EtOAc, washed with 1M sodium bicarbonate (2×30 ml) and water (2×30 ml), and concentrated in vacuo to obtain ethyl ester 117e.

[M+H]+: 734.34

Preparation of Title Compound

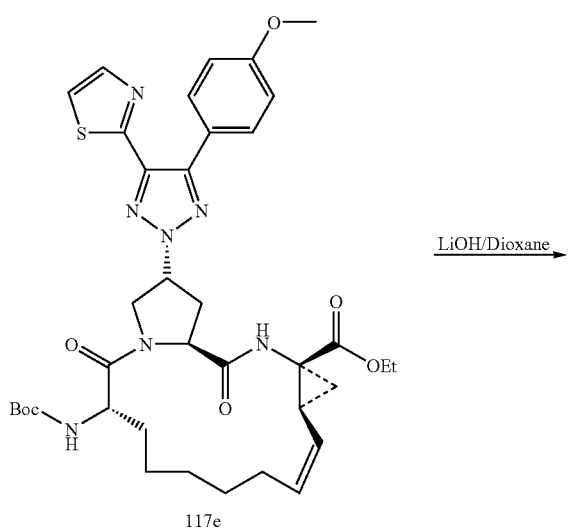

117e

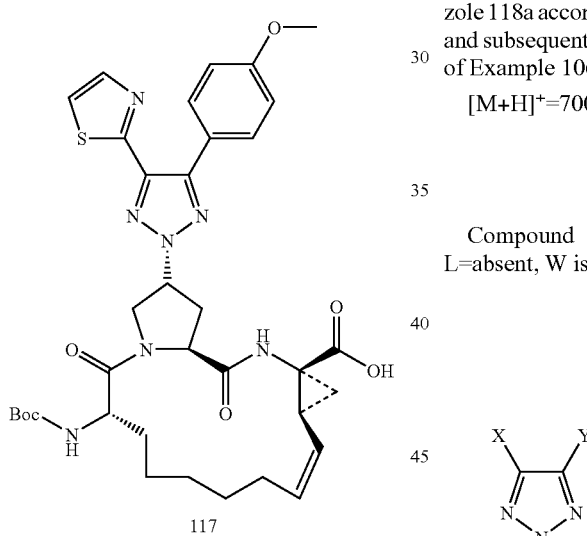

117

Hydrolysis of ethyl ester 117c was achieved by dissolving 117e in 3 ml of dioxane, adding 2 ml of 1M LiOH, and stirring the resulting reaction mixture at RT for 8 hours. The pH of the reaction mixture was adjusted to 3 with citric acid; then the reaction mixture was extracted with EtOAc, and washed with brine and water. The organic solution was concentrated in vacuo for purification by HPLC which afforded a yellow powder after lyophilization (10 mg, yield 34%).

[M+H]+: 706.33, 1HNMR (DMSO-$d_6$, 500 MHz) δ 12.283 (s, broad, 1H), 8.750 (s, broad, 1H), 8.014 (d, J=9 Hz, 2H), 7.938 (d, J=3.5 Hz, 1H), 7.852 (d, J=3.5 Hz, 1H), 6.997 (d, J=8 Hz, 2H), 6.927 (d, J=7, 1H), 5.555 (s, broad, 1H), 5.499 (m, 1H), 5.298 (t, J=18 Hz and 9 Hz, 1H), 4.643 (t, J=16 Hz and 8 Hz, 1H), 4.558 (d, J=11.5 Hz, 1H), 4.125~4.093 (m, 2H), 3.802 (s, 3H), 2.890~2.847 (m, 1H), 2.542~2.497 (m, 2H), 2.123~2.106 (m, 1H), 1.806 (s, broad, 1H), 1.701~1.663 (m, 1H), 1.519 (s, broad, 1H), 1.460~1.435 (m, 1H), 1.314~1.074 (m, 16H).

Example 118

Compound of Formula II, wherein A=tBOC, G=OH, L=absent, W is

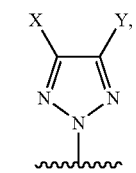

X=benzyl, Y=phenyl, j=3, m=s=1, and $R^3=R^4=H$.

118a Alkyne Formation

The 2-(benzyl)-4-methoxyphenylacetylene was prepared via the procedure of Example 117A from 4-iodobenzene and 3-phenyl-propyne.

118b Triazole Formation

The 4-(benzyl)-5-(p-methoxyphenyl)triazole was prepared via the procedure of Example 3 using 2-(benzyl)-4-methoxyphenylacetylene 118a and sodium azide.

The title compound was prepared with the title compound of Example 2 and the 4-(2-benzyl)-5-(p-methoxyphenyl)triazole 118a according to the procedure set forth in Example 105 and subsequent hydrolysis of the ethyl ester via the procedure of Example 106.

[M+H]+=700.82.

Example 119

Compound of Formula II, wherein A=tBOC, G=OH, L=absent, W is

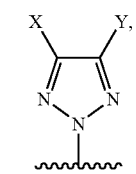

X=n-butyl, Y=phenyl, j=3, m=s=1, and $R^3=R^4=H$.

119a Triazole Formation

The 4-(n-butyl)-5-phenyl triazole was prepared via the procedure of Example 3 using n-butyl-1-phenylacetylene and sodium azide.

The title compound was prepared with the title compound of Example 2 and the 4-(n-butyl)-5-phenyl triazole 119a according to the procedure set forth in Example 105 and subsequent hydrolysis of the ethyl ester via the procedure of Example 106.

[M+H]+=649.44.

Example 120

Compound of Formula II, wherein A=tBOC, G=OH, L=absent, W is

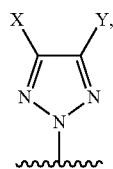

X=n-propyl, Y=n-propyl, j=3, m=s=1, and $R^3=R^4=H$.

120a Triazole Formation

The 4,5-(n-propyl)triazole was prepared via the procedure of Example 3 using 4-octyne and sodium azide.

The title compound was prepared with the title compound of Example 2 and the 4,5-(n-propyl)triazole 120a according to the procedure set forth in Example 105 and subsequent hydrolysis of the ethyl ester via the procedure of Example 106 $[M+H]^+=601.46$.

Example 121

Compound of Formula II, wherein A=tBOC, G=OH, L=absent, W is

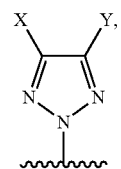

X=4-(N,N-dimethylamino)phenyl, Y=phenyl, j=3, m=s=1, and $R^3=R^4=H$.

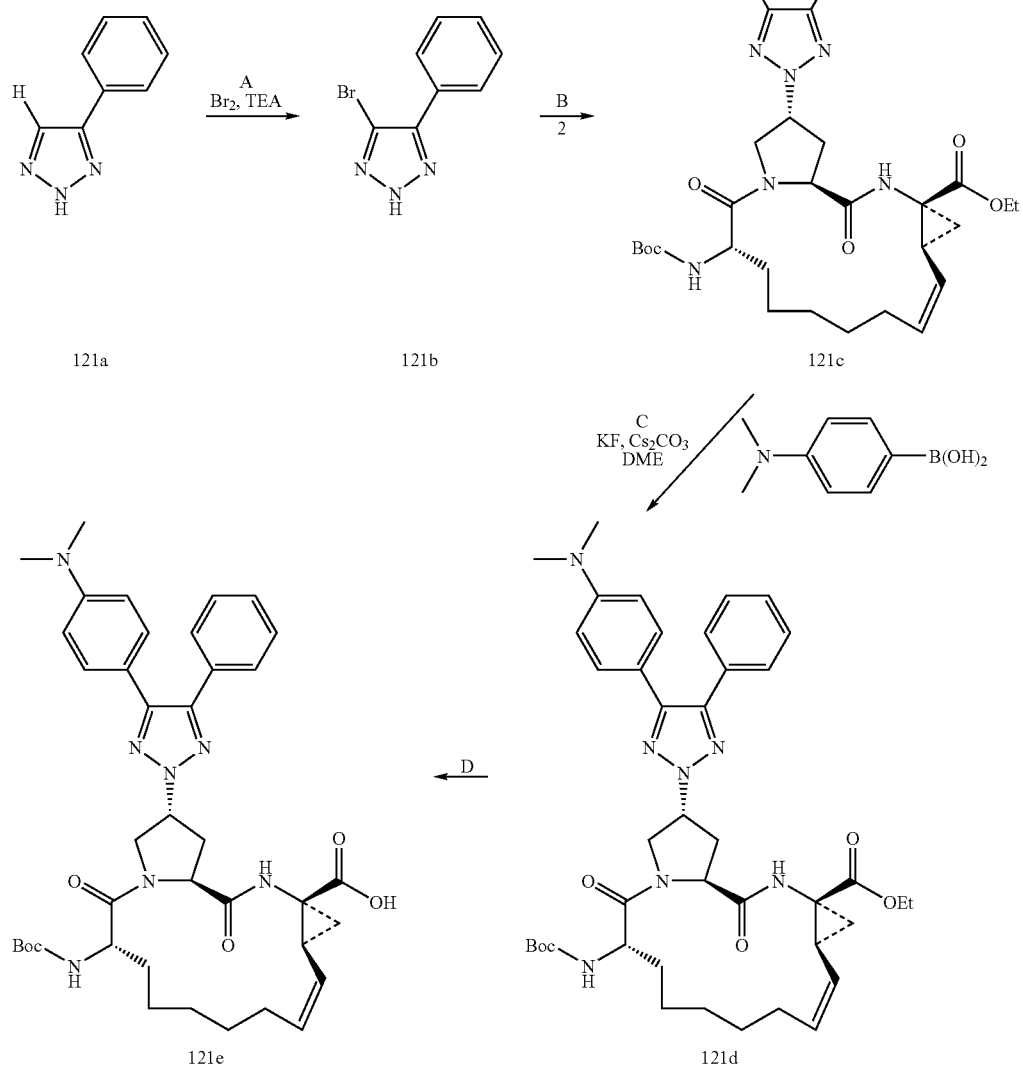

121A. Bromination. Bromo-substituted phenyl triazole 121b was prepared by dissolving 1 mmol of 121a (Triazole 121a was prepared by the method set forth in Example 2 using commercial phenyl acetylene and sodium azide) in 16 ml 1:15 MeOH/CHCl$_3$, adding 0.28 ml of TEA, and in a dropwise manner adding 0.128 ml of bromine. The resulting reaction mixture was stirred for 2 hours. To the reaction mixture was added cold 10% Na$_2$S$_2$O$_5$ until the mixture turned colorless. The mixture was extracted with EtOAc, washed with brine and water, dried over Na$_2$SO$_4$, and concentrated in vacuo to afford 0.216 g of 121b after purification by silica column (97%). [M+H]+: 224.19.

121B. Mesylate replacement. 0.2 g of 121c was prepared via the procedure elucidated in Example 3 from purified 121b and the title compound from Example 2. [M+Na]+: 721.00.

121C. Suzuki Coupling. Ethyl ester 121d was prepared by dissolving 0.07 mmol (50 mg) of 121c in 3 ml of DME and adding to this solution 0.21 mmol (35 mg) of 4-dimethylaminophenyl boric acid, 137 mg of cesium carbonate, and 100 mg of KF. To the subsequently degassed reaction mixture was added 5 mg of Pd(PPh$_3$)$_4$. The resulting reaction mixture was heated to 90° C. and stirred for 12 hours. The reaction mixture then was extracted with EtOAc, washed with brine and water, dried over Na$_2$SO$_4$, concentrated in vacuo, and purified by silica column to afford 40 mg (78% yield) of 121d.

121D. Ethyl Ester Hydrolysis. 12 mg of 121e was made via the procedure set forth in 106 from 121d after purification by HPLC (30%). [M+H]+: 712.33.

Example 122

Compound of Formula II, wherein A=tBOC, G=OH, L=absent, W is

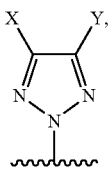

X=(N,N-diethylamino)methyl, Y=phenyl, j=3, m=s=1, and R$^3$=R$^4$=H.

122a Triazole Formation

The 4-(N,N-diethylaminomethyl)-5-phenyltriazole was prepared via the procedure of Example 3 using 3-diethylamino-1-phenylpropyne and sodium azide.

The title compound was prepared with the title compound of Example 2 and the 4-(N,N-diethylaminomethyl)-5-phenyltriazole 122a according to the procedure set forth in Example 105 and subsequent hydrolysis of the ethyl ester via the procedure of Example 106.

[M+H]+=678.44.

Example 123

Compound of Formula II, wherein A=tBOC, G=OH, L=absent, W is

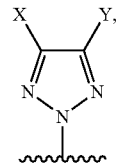

X=N,N-diethylaminocarbonyl, Y=phenyl, j=3, m=s=1, and R$^3$=R$^4$=H.

123A. Alkyne Formation

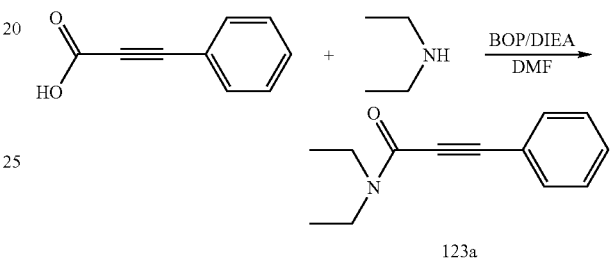

123a

Alkyne 123a was prepared by dissolving 10 mmol of phenylpropynoic acid, 11 mmol of BOP, and 22 mmol of DIEA in 15 ml of DMF and to which was added 11 mmol of diethylamine. The resulting reaction mixture was then stirred at RT for 3 hours. The reaction mixture was extracted with EtOAc (2×50 ml), washed with 1M NaHCO$_3$ (2×30 ml), water (2×30 ml), 5% citric acid (2×50 ml), and brine (2×30 ml). The organic extract was dried over anhydrous Na$_2$SO$_4$ and concentrated in vacuo to afford 1.8 g (90%) of 123a [M+H]+: 202.09.

123B. Triazole Formation

The 4-(N,N-diethylaminocarbonyl)-5-phenyltriazole 123b was prepared via the procedure of Example 3 using 123a and sodium azide.

The title compound was prepared with the title compound of Example 2 and the 4-(N,N-diethylaminocarbonyl)-5-phenyltriazole 123b according to the procedure set forth in Example 105 and subsequent hydrolysis of the ethyl ester via the procedure of Example 106.

[M+H]+: 692.47.

Example 124

Compound of Formula II, wherein A=tBOC, G=OH, L=absent, W is

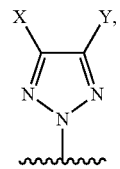

X=m-chlorophenyl, Y=4-ethoxyphenyl, j=3, m=s=1, and R$^3$=R$^4$=H.

124a Alkyne Formation

The 2-(m-chlorophenyl)-4-methoxyphenylacetylene was prepared via the procedure of Example 99 from 3-chlorobromobenzene and 4-methoxyphenylacetylene.

124b Triazole Formation

The 4-(m-chlorophenyl)-5-(p-methoxyphenyl)triazole was prepared via the procedure of Example 3 using 2-(m-chlorophenyl)-4-methoxyphenylacetylene 124a and sodium azide.

The title compound was prepared with the title compound of Example 2 and the 4-(m-chlorophenyl)-5-(p-methoxyphenyl)triazole 124a according to the procedure set forth in Example 105 and subsequent hydrolysis of the ethyl ester via the procedure of Example 106.

[M+H]$^+$=747.37.

Example 125

Compound of Formula II, wherein A=tBOC, G=OH, L=absent, W is

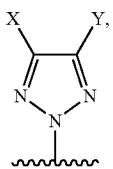

X=2-phenylethenyl, Y=phenyl, j=3, m=s=1, and R$^3$=R$^4$=H.

The title compound was prepared with by the Suzuki reaction described in Example 121 from 121c and phenylethenylboronic acid and subsequent hydrolysis by the procedure described in Example 106.

[M+H]$^+$=695.30.

Example 126

Compound of Formula II, wherein A=tBOC, G=OH, L=absent, W is 5,6-methylbenzotriazole, j=3, m=s=1, and R$^3$=R$^4$=H.

The title compound was prepared with the title compound of Example 2 and the 5,6-methylbenzotriazole according to the procedure set forth in Example 105 and subsequent hydrolysis of the ethyl ester via the procedure of Example 106.

[M+H]$^+$=595.42.

Example 127

Compound of Formula II, wherein A=tBOC, G=OH, L=absent, W is

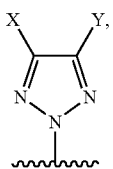

X=N-ethylaminocarbonyl, Y=phenyl, j=3, m=s=1, and R$^3$=R$^4$=H.

127a. Alkyne Formation

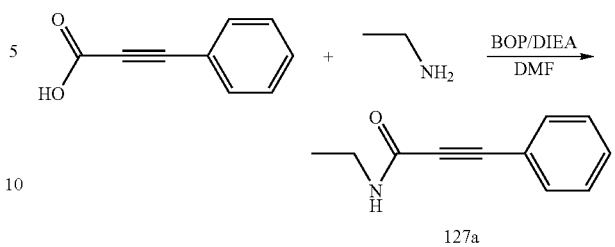

Alkyne 127a was prepared by dissolving 10 mmol of phenylpropynoic acid, 11 mmol of BOP, and 22 mmol of DIEA in 15 ml of DMF and to which was added 11 mmol of ethylamine. The resulting reaction mixture was then stirred at RT for 3 hours. The reaction mixture was extracted with EtOAc (2×50 ml), washed with 1M NaHCO$_3$ (2×30 ml), water (2×30 ml), 5% citric acid (2×50 ml), and brine (2×30 ml). The organic extract was dried over anhydrous Na$_2$SO$_4$ and concentrated in vacuo to afford 1.8 g (90%) of 127a. [M+H]+: 177.09.

127b Triazole Formation

The 4-(N-ethylaminocarbonyl)-5-phenyltriazole was prepared via the procedure of Example 3 using 127a and sodium azide.

The title compound was prepared with the title compound of Example 2 and the 4-(N-ethylaminocarbonyl)-5-phenyltriazole 127b according to the procedure set forth in Example 105 and subsequent hydrolysis of the ethyl ester via the procedure of Example 106.

Example 128

Compound of Formula II, wherein A=—(C=O)—O—R$^1$, wherein R$^1$=cyclopentyl G=OH, L=absent, W is

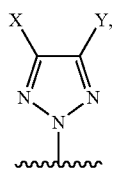

X=phenyl, Y=phenyl, j=3, m=s=1, and R$^3$=R$^4$=H.

128a—Amine Deprotection.

0.041 mmol of the title compound of Example 105 is dissolved in 4 ml of a 4M solution of HCl in dioxane and stirred for 1 hour. The reaction residue 128a is concentrated in vacuo.

128b—Chloroformate Reagent

The chloroformate reagent 128b is prepared by dissolving 0.045 mmol of cyclopentanol in THF (3 ml) and adding 0.09 mmol of phosgene in toluene (20%). The resulting reaction mixture is stirred at room temperature for 2 hours and the solvent is removed in vacuo. To the residue is added DCM and subsequently concentrated to dryness twice in vacuo yielding chloroformate reagent 128b.

128c—Carbamate Formation

The title carbamate is prepared by dissolving residue 128a in 1 ml of THF, adding 0.045 mmol of TEA, and cooling the resulting reaction mixture to 0° C. To this 0° C. reaction mixture is added chloroformate reagent 128b in 3 ml of THF. The resulting reaction mixture is reacted for 2 hours at 0° C., extracted with EtOAc, washed by 1M sodium bicarbonate, water and brine, dried over MgSO$_4$, and concentrated in vacuo to dryness. The crude compound is purified by silica column and the ethyl ester is subsequently hydrolyzed by the procedure set forth in Example 106.

Example 129

Compound of Formula II, wherein A=—(C=O)—O—R$^1$, wherein R$^1$=cyclobutyl, G=OH, L=absent, W is

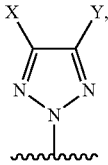

X=phenyl, Y=phenyl, j=3, m=s=1, and R$^3$=R$^4$=H.

The title compound is prepared by the method described in Example 33 with the title compound of Example 105 and cyclobutanol, followed by ethyl ester hydrolysis by the procedure set forth in Example 106.

Example 130

Compound of Formula II, wherein A=—(C=O)—O—R$^1$, wherein R$^1$=cyclohexyl, G=OH, L=absent, W is

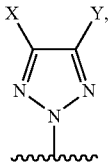

X=phenyl, Y=phenyl, j=3, m=s=1, and R$^3$=R$^4$=H.

The title compound is prepared by the method in Example 33 with the title compound of Example 105 and cyclohexanol, followed by ethyl ester hydrolysis by the procedure set forth in Example 106.

Example 131

Compound of Formula II, wherein A=—(C=O)—O—R$^1$, wherein R$^1$=

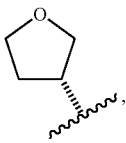

G=OH, L=absent, W is

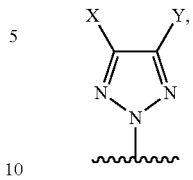

X=phenyl, Y=phenyl, j=3, m=s=1, and R$^3$=R$^4$=H.

The title compound is prepared by the method described in Example 33 with the title compound of Example 105 and (R)-3-hydroxytetrahydrofuran, followed by ethyl ester hydrolysis by the procedure set forth in Example 106.

Example 132

Compound of Formula II, wherein A=—(C=O)—O—R$^1$, wherein R$^1$=

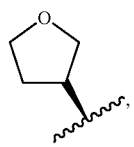

G=OH, L=absent, W is

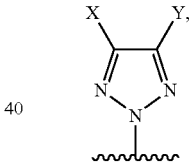

X=phenyl, Y=phenyl, j=3, m=s=1, and R$^3$=R$^4$=H.

The title compound is prepared by the method in Example 33 with the title compound of Example 105 and (S)-3-hydroxytetrahydrofuran, followed by ethyl ester hydrolysis by the procedure set forth in Example 106.

Example 133

Compound of Formula II, wherein A=—(C=O)—O—R$^1$, wherein R$^1$=

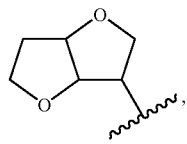

G=OH, L=absent, W is

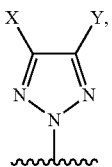

X=phenyl, Y=phenyl, j=3, m=s=1, and $R^3=R^4=H$.

The title compound is prepared by the method in Example 33 with the title compound of Example 105 and

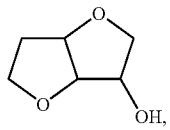

followed by ethyl ester hydrolysis by the procedure set forth in Example 106.

Example 134

Compound of Formula II, wherein A=—(C=O)—$R^1$, wherein $R^1$=cyclopentyl, G=OH, L=absent, W is

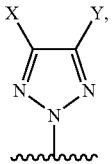

X=phenyl, Y=phenyl, j=3, m=s=1, and $R^3=R^4=H$.

The title compound is prepared by dissolving 0.041 mmol of the title compound from Example 105 in 4 ml of a 4M solution of HCl in dioxane and stirring the reaction mixture for 1 hour. The reaction residue is concentrated in vacuo. To this residue, 4 ml of THF and 0.045 mmol of TEA is added, the mixture is cooled to 0° C., to which is added 0.045 mmol of the cyclopental acid chloride. The resulting reaction mixture is stirred for 2 hours at 0° C. The reaction mixture is then extracted with EtOAc, washed with 1M sodium bicarbonate, water and brine, dried over $MgSO_4$ and concentrated to dryness in vacuo. The crude compound is purified by silica column and the ethyl ester is subsequently hydrolyzed by the procedure set forth in Example 106.

Example 135

Compound of Formula II, wherein A=—(C=O)—NH—$R^1$, wherein $R^1$=cyclopentyl, G=OH, L=absent, W is

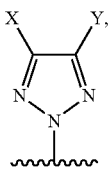

X=phenyl, Y=phenyl, j=3, m=s=1, and $R^3=R^4=H$.

The title compound is prepared by dissolving 0.041 mmol of the title compound from Example 105 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isocyanate and the resulting reaction mixture is stirred at RT for 4 hours. The solution is then extracted with EtOAc, washed with 1% HCl, water and brine, dried over $MgSO_4$, and concentrated in vacuo to dryness. The crude compound is purified by silica column and the ethyl ester is subsequently hydrolyzed by the procedure set forth in Example 106.

Example 136

Compound of Formula II, wherein A=—(C=S)—NH—$R^1$, wherein $R^1$=cyclopentyl, G=OH, L=absent, W is

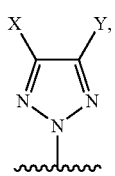

X=phenyl, Y=phenyl, j=3, m=s=1, and $R^3=R^4=H$.

The title compound is prepared by dissolving 0.041 mmol of the title compound from Example 105 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isothiocyanate and the resulting reaction mixture is stirred at RT for 4 hours. The solution is then extracted with EtOAc, washed with 1% HCl, water and brine, dried over $MgSO_4$, and concentrated in vacuo to dryness. The crude compound is purified by silica column and the ethyl ester is subsequently hydrolyzed by the procedure set forth in Example 106.

Example 137

Compound of Formula II, wherein A=—$S(O)_2$—$R^1$, wherein $R^1$=cyclopentyl, G=OH, L=absent, W is

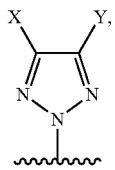

X=phenyl, Y=phenyl, j=3, m=s=1, and $R^3=R^4=H$.

The title compound is prepared by dissolving 0.041 mmol of the title compound from Example 105 in 4 ml of a 4M solution of HCl in dioxane and stirring for 1 hour. To the resulting concentrated reaction residue, which has been dissolved in 4 ml THF, is added 0.045 mmol of TEA, and cooled to 0° C. To the 0° C. solution is added 0.045 mmol of cyclopentyl solfonyl chloride and the resulting reaction mixture is stirred at 0° C. for 2 hours. The solution is then extracted with EtOAc, washed with 1M sodium bicarbonate, water and brine, dried over $MgSO_4$, and concentrated in vacuo to dryness. The crude compound is purified by silica column and the ethyl ester is subsequently hydrolyzed by the procedure set forth in Example 106.

Example 138

Compound of Formula II, wherein A=—(C=O)—O—R¹, R¹=cyclopentyl, G=—O-phenethyl, L=absent, W is

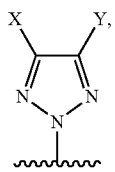

X=phenyl, Y=phenyl, j=3, m=s=1, and R3=R4=H.

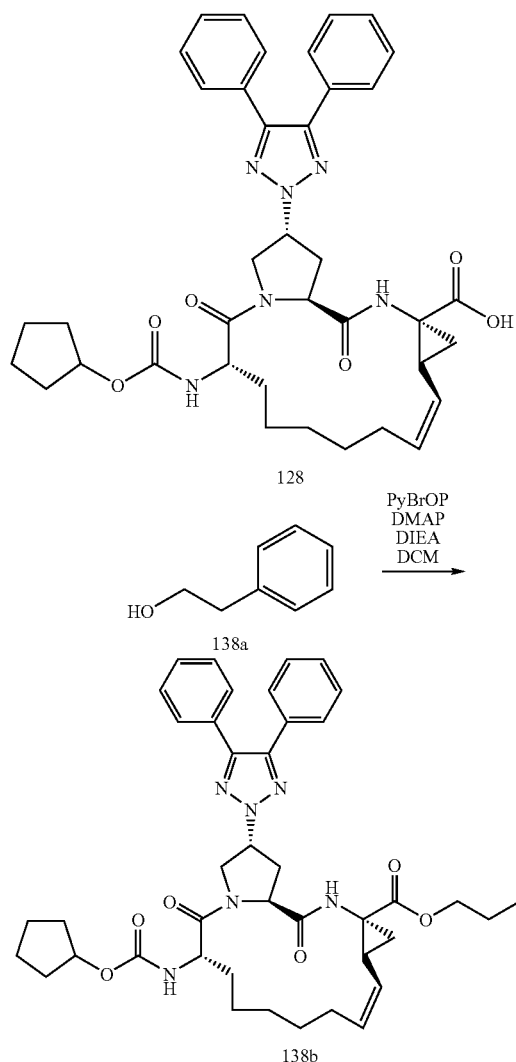

The title compound is prepared by adding to a solution of the title compound of Example 128 and phenethyl alcohol 138a in 0.5 ml DCM, is added 1.2 eq. PyBrOP, 4 eq. DIEA, and catalytic amount of DMAP at 0° C. The resulting reaction mixture is stirred for 1 hour at 0° C. and then warmed to RT over a period of 4-12 hours. The reaction mixture is purified by silica gel flash chromatography using different ratios of hexanes:EtOAc as elution phase (9:1→5:1→3:1→1:1) to afford the title compound isolated phenethyl ester 138b. Other esters can be made using the same procedures.

Example 139

Compound of Formula II, wherein A=—(C=O)—O—R¹, R¹=cyclopentyl, G=—NH-phenethyl, L=absent, W is

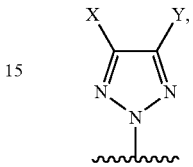

X=phenyl, Y=phenyl, j=3, m=s=1, and R3=R4=H.

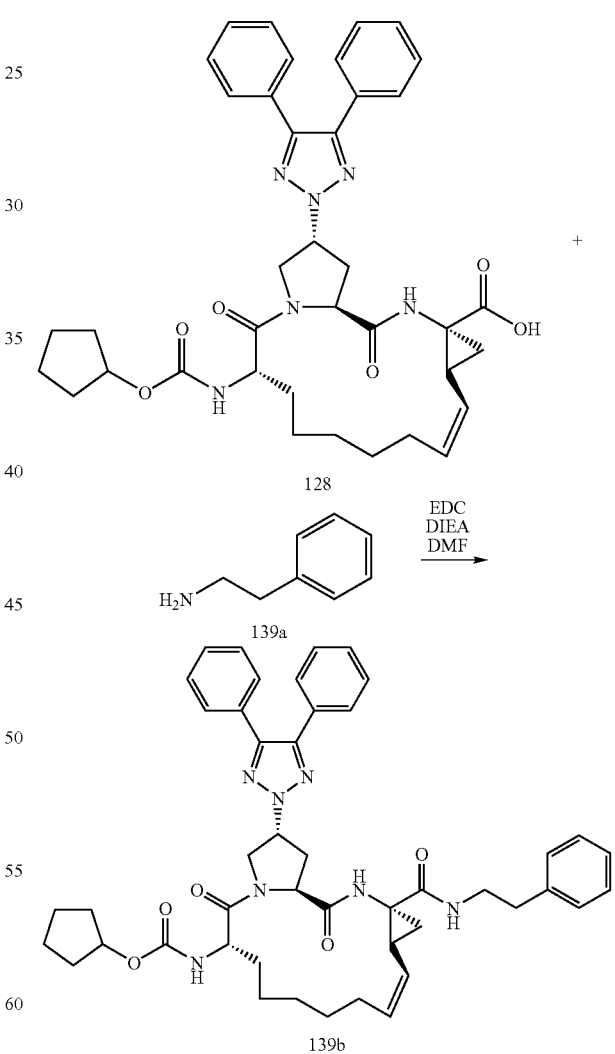

The title compound is prepared by adding to a solution of the title compound of Example 128 and phenethylamine 139a (0.05 ml) in 0.5 ml DMF, EDC (1.2 eq.) and DIEA (4 eq.) at 0° C. The resulting reaction mixture is stirred at 1 hour.

Subsequently, the reaction is warmed to RT over a period of 4-12 hours. The reaction mixture is purified by silica gel flash chromatography using different ratios of hexanes:EtOAc as elution phase (9:1→5:1→3:1→1:1) to afford title compound phenethyl amide 139b. Other amides can be made using the same procedures.

Example 140

Compound of Formula II, wherein A=—(C=O)—O—$R^1$, $R^1$=cyclopentyl, G=—NHS(O)$_2$-phenethyl, L=absent, W is

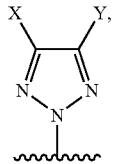

X=phenyl, Y=phenyl, j=3, m=s=1, and

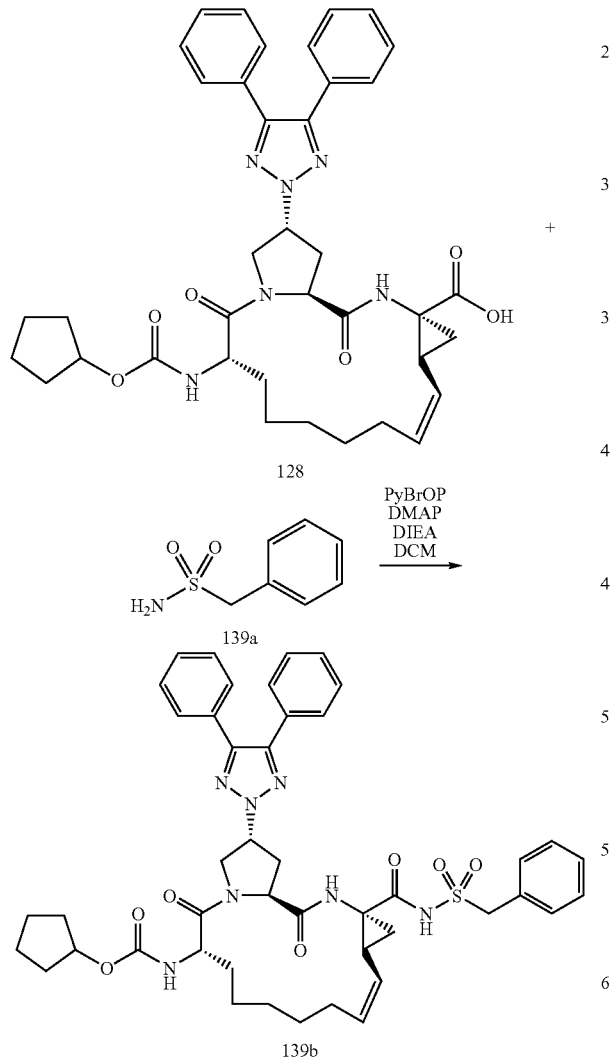

R3=R4=H.

The title compound is prepared by adding to a solution of the title compound of Example 128 and α-toluenesulfona- mide 140a (10 mg) in 0.5 ml DCM, is added 1.2 eq. PyBrOP, 4 eq. DIEA, and catalytic amount of DMAP at 0° C. The resulting reaction mixture is stirred for 1 hour and then allowed to warm to RT over a period of 4-12 hours. The reaction mixture is purified by silica gel flash chromatography using different ratios of hexanes:EtOAc as elution phase (9:1→5:1→3:1→1:1) to afford the title compound sulfonamide 140b.

Other sulfonamides can be made using the same procedure.

Example 141

Compound of Formula II, wherein A=—(C=O)—O—$R^1$, $R^1$=cyclopentyl, G=—(C=O)—OH, L=absent, W is

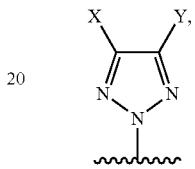

X=phenyl, Y=phenyl, j=3, m=s=1, and $R^3$=$R^4$=H.

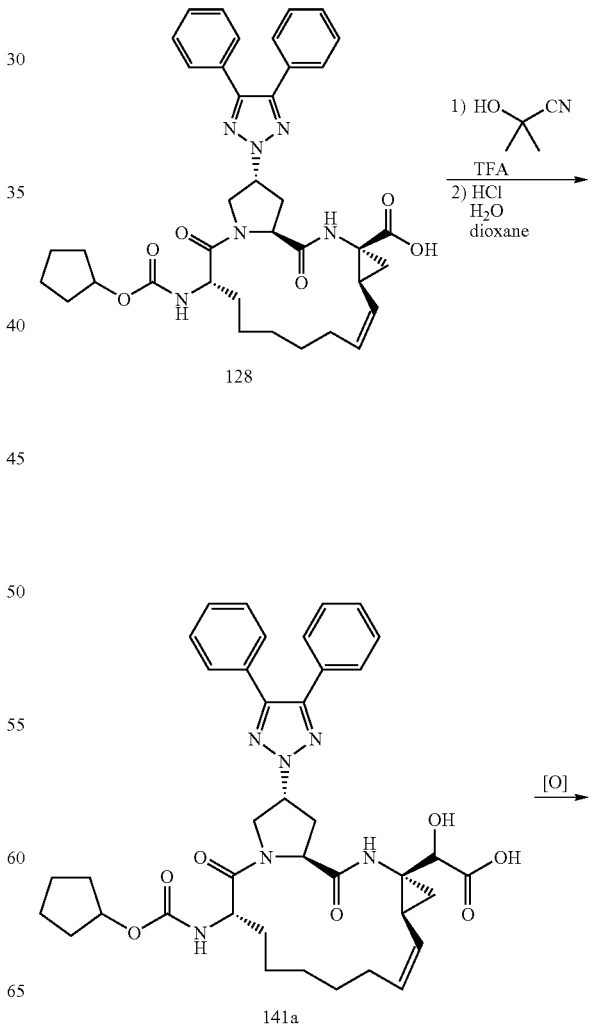

269
-continued

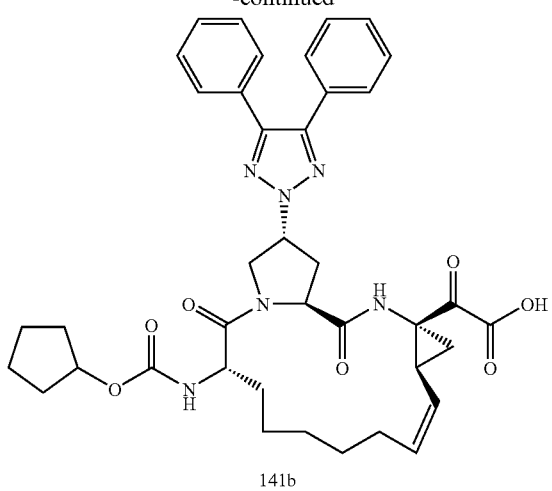

141b

The title compound is prepared by adding to a solution of the title compound of Example 128 in 0.5 ml THF, is added α-hydroxy-α-methyl-propionitrile (0.1 ml) and catalytic amount TFA at 0° C. The resulting reaction mixture is warmed from 0° C. to RT over a period of 4-12 h followed by hydrolysis with concentrated hydrochloric acid in dioxane. The reaction is then extracted with EtOAc, and washed with water and brine to yield α-hydroxy compound 141a in its crude form. The crude compound 46b undergoes a Dess-Martin oxidation in THF (0.5 ml), providing the α-carbonyl compound 46b in crude form. The crude 141b is purified by silica gel flash chromatography using different ratios of hexanes:EtOAc as elution phase (9:1→5:1→3:1→1:1) to afford the title compound isolated keto acid 141c.

Example 142

Compound of Formula II, wherein A=—(C=O)—O—$R^1$, $R^1$=cyclopentyl, G=—(C=O)—O-phenethyl, L=absent, W is

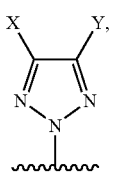

X=phenyl, Y=phenyl, j=3, m=s=1, and $R^3$=$R^4$=H.

The title compound is prepared with the title compound keto acid of Example 141 and phenethanol according to the procedure set forth in Example 138.

270

Example 143

Compound of Formula II, wherein A=—(C=O)—O—$R^1$, $R^1$=cyclopentyl, G=—(C=O)—NH-phenethyl, L=absent, W is

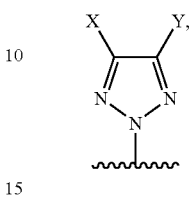

X=phenyl, Y=phenyl, j=3, m=s=1, and and $R^3$=$R^4$=H.

The title compound is prepared with the title compound keto acid of Example 141 and phenethyl amine according to the procedure set forth in Example 139.

Example 144

Compound of Formula II, wherein A=—(C=O)—O—$R^1$, $R^1$=cyclopentyl, G=—(C=O)—NH—S(O)$_2$-benzyl, L=absent, W is

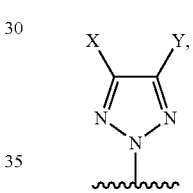

X=phenyl, Y=phenyl, j=3, m=s=1, and $R^3$=$R^4$=H.

The title compound is prepared with the title compound keto acid of Example 141 and α-toluenesulfonamide according to the procedure set forth in Example 140.

Example 145

Compound of Formula II, wherein A=tBOC, G=OH, L=—(C=O)CH$_2$—, W is

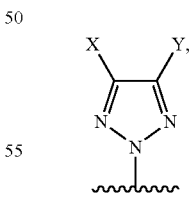

X=phenyl, Y=phenyl, j=1, m=s=1, and $R^3$=$R^4$=H.

The title compound is prepared with the modified cyclic peptide precursor mesylate formed in Example 88C and 4,5-diphenyltriazole by the replacement method elucidated in Example 105 followed by hydrolysis of the ethyl ester via the method set forth in Example 106.

Example 146

Compound of Formula II, wherein A=tBOC, G=OH, L=—CH(CH$_3$)CH$_2$—, W is

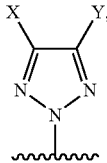

X=phenyl, Y=phenyl, j=1, m=s=1, R$^3$=methyl, and R$^4$=H.

The title compound is prepared with the modified cyclic peptide precursor mesylate formed in Example 89G and 4,5-diphenyltriazole by the replacement method elucidated in Example 105 followed by hydrolysis of the ethyl ester via the method set forth in Example 106.

Example 147

Compound of Formula II, wherein A=tBOC, G=OH, L=—O—, W is

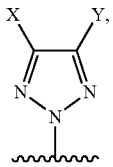

X=phenyl, Y=phenyl, j=0, m=s=1, R$^3$=methyl, and R$^4$=hydrogen.

The title compound is prepared with the modified cyclic peptide precursor mesylate formed in Example 90D and 4,5-diphenyltriazole by the replacement method elucidated in Example 105 followed by hydrolysis of the ethyl ester via the method set forth in Example 106.

Example 148

Compound of Formula II, wherein A=tBOC, G=OH, L=—S—, W is

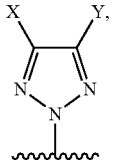

X=phenyl, Y=phenyl, j=0, m=s=1, R$^3$=methyl, and R$^4$=hydrogen.

The title compound is prepared with the modified cyclic peptide precursor mesylate formed in Example 91E and 4,5-diphenyltriazole by the replacement method elucidated in Example 105 followed by hydrolysis of the ethyl ester via the method set forth in Example 106.

Example 149

Compound of Formula II, wherein A=tBOC, G=OH, L=—S(O)—, W is

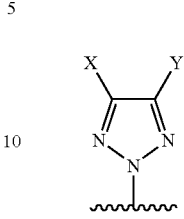

X=phenyl, Y=phenyl, j=2, m=s=1, R$^3$=methyl, and R$^4$=hydrogen.

The title compound is prepared with the modified cyclic peptide precursor mesylate formed in Example 92B and 4,5-diphenyltriazole by the replacement method elucidated in Example 105 followed by hydrolysis of the ethyl ester via the method set forth in Example 106.

Example 150

Compound of Formula II, wherein A=tBOC, G=OH, L=—S(O)$_2$—, W is

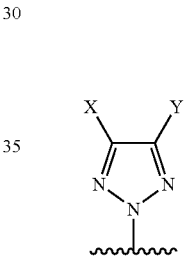

X=phenyl, Y=phenyl, j=2, m=s=1, R$^3$=methyl, and R$^4$=H.

The title compound is prepared with the modified cyclic peptide precursor mesylate formed in Example 93B and 4,5-diphenyltriazole by the replacement method elucidated in Example 105 followed by hydrolysis of the ethyl ester via the method set forth in Example 106.

Example 151

Compound of Formula II, wherein A=tBOC, G=OH, L=—SCH$_2$CH$_2$—, W is

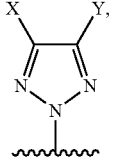

X=phenyl, Y=phenyl, j=0, m=s=1, and R$^3$=R$^4$=CH$_3$

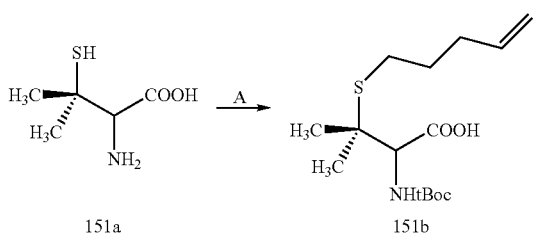

151A. Synthesis of (S)-N-Boc-2-amino-3-methyl-3(1-mercapto-4-butenyl)butanoic acid (151b)

L-Penicillamine 151a is dissolved in DMF/DMSO (5:1), subsequently, 4-bromopentene and CsOH.H$_2$O are added to the mixture and stirring is continued for an additional 12 hours. The DMF is subsequently removed in vacuo, the remaining mixture is diluted with 0.5 N HCl (at 0° C.) to adjust the pH to 4-5 and then extracted with 2 portions of EtOAc. The organic phase is washed with brine (2×), dried over MgSO$_4$ and evaporated to dryness to afford the crude carboxylic acid 151a.

151B. Synthesis of Modified Cyclic Peptide Precursor Mesylate

The modified cyclic peptide precursor mesylate is prepared using the synthetic route detailed in Example 1 using the modified amino acid 151a in place of Boc-L-2-amino-8-nonenoic acid 1a followed by conversion to the corresponding mesylate via the method described in Example 2. The title compound is prepared with the modified cyclic peptide precursor mesylate formed in 151B and 4,5-diphenyltriazole by the replacement method elucidated in Example 105 followed by hydrolysis of the ethyl ester via the method set forth in Example 106.

Example 152

Compound of Formula II, wherein A=tBOC, G=OH, L=CF$_2$CH$_2$, W is

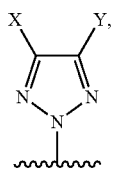

X=phenyl, Y=phenyl, j=1, m=s=1, and R$^3$=R$^4$=H.

The title compound is prepared with the modified cyclic peptide precursor mesylate formed in Example 95C and 4,5-diphenyltriazole by the replacement method elucidated in Example 105 followed by hydrolysis of the ethyl ester via the method set forth in Example 106.

Example 153

Compound of Formula II, wherein A=tBOC, G=OH, L=—CHFCH$_2$—, W is

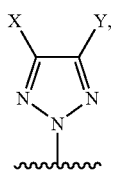

X=phenyl, Y=phenyl, j=1, m=s=1, and R$^3$=R$^4$=H.

The title compound is prepared with the modified cyclic peptide precursor mesylate formed in Example 96C and 4,5-diphenyltriazole by the replacement method elucidated in Example 105 followed by hydrolysis of the ethyl ester via the method set forth in Example 106.

Example 154

Compound of Formula II, wherein A=tBOC, G=OH, L=absent, W is

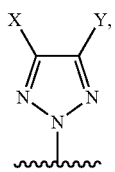

X=phenyl, Y=phenyl, j=3, m=s=1, and R$^3$=R$^4$=H.

154A. The saturated cyclic peptide precursor mesylate is prepared by catalytic reduction of the mesylate cyclic peptide precursor 2 with Pd/C in MeOH in the presence of H$_2$.

The title compound is prepared with the saturated cyclic peptide precursor mesylate formed in 154A and 4,5-diphenyltriazole by the replacement method elucidated in Example 105 followed by hydrolysis of the ethyl ester via the method set forth in Example 106.

Example 155

Compound of Formula II, wherein A=tBOC, G=OH, L=absent, W is

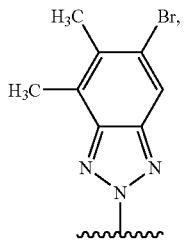

j=3, m=s=1, and R$^3$=R$^4$=H.

155A. Substituted Benzotriazole Formation

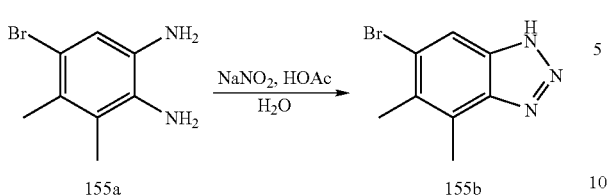

The bromo-substituted benzotriazole 155b of the present Example is prepared by combining 2.15 g (10 mmol) of 5-bromo-3,4-dimethylbenzene-1,2-diamine, 1.15 ml (20 mmol) of glacial acetic acid, and 10 ml of water and heating the resulting mixture to obtain a clear solution. The clear solution is then cooled to 5° C., a cold solution of 0.83 g (12 mmol) of sodium nitrite in 5 ml of water is added, and the reaction mixture is heated to 7080° C. for 2 hours. The reaction mixture is then extracted with EtOAc, washed by brine and water, dried over $Na_2SO_4$, and concentrated in vacuo. The crude product is purified by silica column.

155B. Replacement

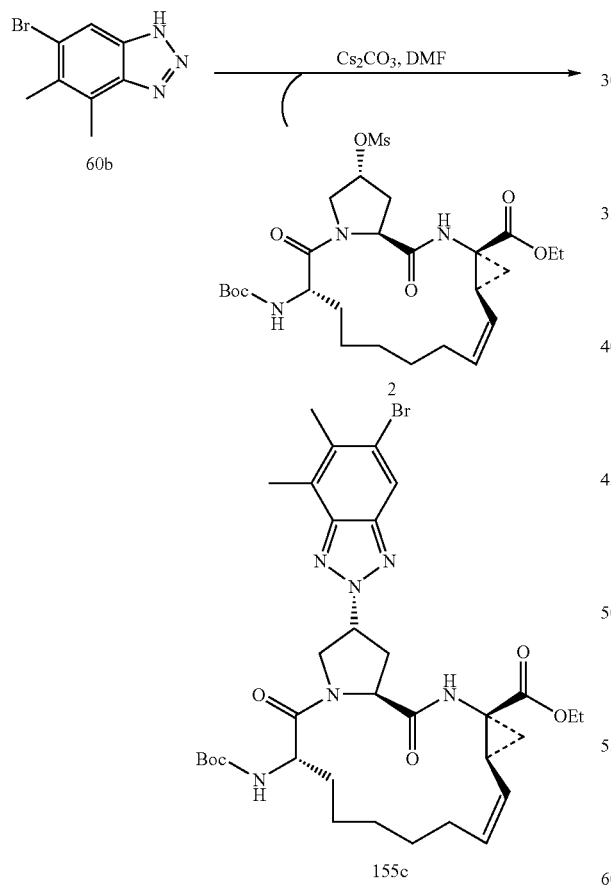

The ethyl ester 155c is prepared by the replacement method described in Example 105 with the title compound of Example 2 and bromo-substituted benzotriazole 155b.

The title compound is ultimately prepared with ethyl ester 155c by the hydrolysis procedure set forth in Example 106.

Example 156

Compound of Formula II, wherein A=tBOC, G=OH, L=absent, W is

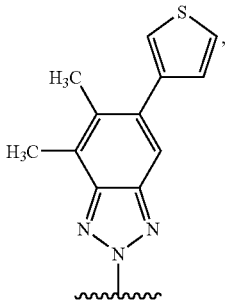

$j=3$, $m=s=1$, and $R^3=R^4=H$.

156A. Suzuki Reaction

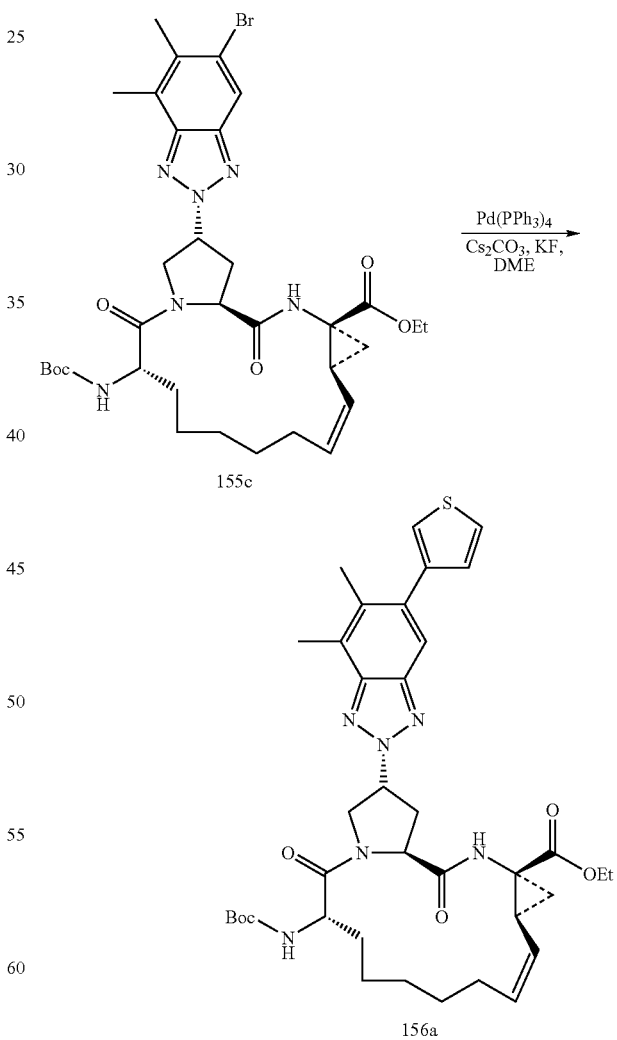

Compound 156a of the present Example is prepared via a Suzuki coupling reaction with 155c and 3-thienyl boronic acid as described in Example 26C.

156B. Hydrolysis

The title compound is prepared with ethyl ester 156a by the hydrolysis procedure set forth in Example 106.

Example 157

Compound of Formula II, wherein A=tBOC, G=OH, L=absent, W is

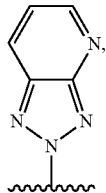

j=3, m=s=1, and $R^3=R^4$=H.

157a. Bicyclic Compound Formation

The bicyclic compound of the present invention is prepared with 2,3-diaminopyridine by the procedure set forth in Example 157A.

The title compound is prepared with the bicyclic compound prepared in 157a and the title compound of Example 2 by the replacement method described in Example 105, followed by hydrolysis of the ethyl ester via the procedure set forth in Example 106.

Example 158

Compound of Formula II, wherein A=tBOC, G=OEt, L=absent, X=Y=bromo, Z=hydrogen, j=3, m=s=1, and $R^3=R^4$=hydrogen.

To a mixture of macrocyclic compound 1 (185 mg, 0.38 mmol), 4,5-dibromo-2H-pyridazin-3-one (95 mg, 0.38 mmol) and triphenylphosphine (197 mg, 0.75 mmol) in THF (5 mL) is added DIAD (148 µL, 0.75 mmol) dropwise at 0° C. After stirring at 0° C. for 15 min., the solution is warmed to room temperature and is further stirred for 16 hours. The mixture is then concentrated in vacuo and the residue is purified by column chromatography eluting with 40% ethyl acetate-hexane to give 235 mg (86%) of the title compound.

$^1$H-NMR (500 MHz, CDCl$_3$) δ (ppm): 7.8 (s, 1H), 7.1 (brs, 1H), 5.5 (m, 2H), 5.2 (m, 2H), 5.0 (m, 1H), 4.4 (brt, 1H), 4.0-4.2 (m, 4H), 2.9 (m, 1H), 2.6 (m, 1H), 1.8-2.3 (m, 5H), 1.4 (s, 9H), 1.2 (t, 3H). [M+H]$^+$=730.6.

Example 159

Compound of Formula II, wherein A=tBOC, G=OEt, L=absent, X=Y=thiophen-3-yl, Z=hydrogen, j=3, m=s=1, and $R^3=R^4$=hydrogen.

A mixture of the title compound of Example 162 (40 mg, 0.055 mmol), 3-thiophene boronic acid (35 mg, 0.28 mmol), cesium carbonate (71 mg, 0.22 mmol), potassium fluoride monohydrate (41 mg, 0.44 mmol) is placed in a round bottom flask and is flushed twice with nitrogen. To this mixture is added DME and the resulting solution is flushed again with nitrogen before palladium tetrakis(triphenylphopshine) (7 mg, 10 mol %) is added. After flushing two more times with nitrogen, the mixture is heated to reflux for 20 hours. The mixture is then cooled and then diluted with water and extracted three times with EtOAc. The combined EtOAc layers are washed once with brine, dried (MgSO$_4$), filtered and concentrated in vacuo. The residue is purified by column chromatography eluting with 20-40% EtOAc-hexane to give the title compound as a clear film (24 mg, 60%).

$^1$H-NMR (500 MHz, CDCl$_3$) δ (ppm): 7.9 (s, 1H), 7.6 (s, 1H), 7.3 (s, 1H), 7.3 (m, 1H), 7.0 (s, 1H), 6.9 (d, 1H), 6.8 (d, 1H), 5.7 (m, 1H), 5.5 (m, 1H), 5.4 (brd, 1H), 5.2 (t, 1H), 5.0 (m, 1H), 4.6 (brt, 1H), 4.0-4.2 (m, 4H), 2.9 (m, 1H), 2.6 (m, 1H), 2.0-2.3 (m, 5H), 1.4 (s, 9H), 1.2 (t, 3H). [M+Na]$^+$=758.63.

Example 160

Compound of Formula II, wherein A=tBOC, G=OH, L=absent, X=Y=thiophen-3-yl, Z=hydrogen, j=3, m=s=1, and $R^3=R^4$=hydrogen.

To a solution of the title compound in Example 2 (24 mg, 0.033 mmol) in THF/MeOH/H$_2$O (2/1/0.5 mL) is added lithium hydroxide (14 mg, 0.33 mmol). After stirring for 16 hours at room temperature, the mixture is acidified to pH 4 with citric acid and extracted three times with EtOAc. The combined organic extracts are washed once with brine, dried (MgSO$_4$), filtered and concentrated in vacuo. The residue is purified by column chromatography eluting with 5-10% methanol-chloroform to give the title compound (13 mg, 56%).

[M+H]$^+$=708.3.

Example 161

Compound of Formula II, wherein A=tBOC, G=OH, L=absent, X=Y=phenyl, Z=hydrogen, j=3, m=s=1, and $R^3=R^4$=hydrogen.

The title compound is prepared by a double Suzuki coupling with phenylboronic acid and the title compound of Example 158 according to the procedure set forth in Example 159, followed by hydrolysis of the ethyl ester via the method described in Example 160.

[M+H]$^+$=696.40

Example 162

Compound of Formula II, wherein A=tBOC, G=OH, L=absent, X=Y=4-(N,N-dimethylamino)phenyl, Z=hydrogen, j=3, m=s=1, and $R^3=R^4$=hydrogen.

The title compound is prepared by a double Suzuki coupling with 4-(N,N-dimethylamino)phenyl boronic acid and the title compound of Example 158 according to the procedure set forth in Example 159, followed by hydrolysis of the ethyl ester via the method described in Example 160.

[M+H]$^+$=782.30

Example 163

Compound of Formula II, wherein A=tBOC, G=OH, L=absent, X=Y=4-(trifluoromethoxy)phenyl, Z=hydrogen, j=3, m=s=1, and $R^3=R^4$=hydrogen.

The title compound is prepared by a double Suzuki coupling with 4-(trifluoromethoxy)phenyl boronic acid and the title compound of Example 158 according to the procedure set forth in Example 159, followed by hydrolysis of the ethyl ester via the method described in Example 160.

[M+H]$^+$=864.09

Example 164

Compound of Formula II, wherein A=tBOC, G=OH, L=absent, X=Y=4-(methanesulfonyl)phenyl, Z=hydrogen, j=3, m=s=1, and $R^3=R^4$=hydrogen.

The title compound is prepared by a double Suzuki coupling with 4-(methanesulfonyl)phenyl boronic acid and the title compound of Example 158 according to the procedure set forth in Example 159, followed by hydrolysis of the ethyl ester via the method described in Example 160.

Example 165

Compound of Formula II, wherein A=tBOC, G=OH, L=absent, X=Y=4-(cyano)phenyl, Z=hydrogen, j=3, m=s=1, and $R^3=R^4$=hydrogen.
The title compound is prepared by a double Suzuki coupling using 4-cyanophenyl boronic acid and the title compound of Example 158 according to the procedure set forth in Example 159, followed by hydrolysis of the ethyl ester via the method described in Example 160.
$[M+H]^+$=746.14

Example 166

Compound of Formula II, wherein A=tBOC, G=OH, L=absent, X=Y=pyrid-3-yl, Z=hydrogen, j=3, m=s=1, and $R^3=R^4$=hydrogen.
The title compound is prepared by a double Suzuki coupling using 3-pyridyl boronic acid and the title compound of Example 158 according to the procedure set forth in Example 159, followed by hydrolysis of the ethyl ester via the method described in Example 160.
$[M+H]^+$=698.3.

Example 167

Compound of Formula II, wherein A=tBOC, G=OH, L=absent, X=Y=4-(morpholin-4-yl-methanonyl)phenyl, Z=hydrogen, j=3, m=s=1, and $R^3=R^4$=hydrogen.
The title compound is prepared by a double Suzuki coupling using 4-carboxyphenyl boronic acid and the title compound of Example 158 according to the procedure set forth in Example 159, followed by amide formation with morpholine, under standard amide bond formation conditions, e.g. PyBrOP, DIEA, and DMAP in DMF. The ethyl ester of the resulting compound is then hydrolyzed via the hydrolysis procedure of Example 160.

Example 168

Compound of Formula II, wherein A=tBOC, G=OH, L=absent, X=bromo, Y=methoxy, Z=hydrogen, j=3, m=s=1, and $R^3=R^4$=hydrogen.
The title compound is prepared from the title compound in Example 158 via hydrolysis of the ethyl ester according to the procedure described in Example 160, however addition of methoxy to the 5 position is observed in addition to hydrolysis of the ethyl ester.
$[M+H]^+$=652.2, 654.2.

Example 169

Compound of Formula II, wherein A=tBOC, G=OH, L=absent, X and Y Taken Together=phenyl, Z=4-methoxyphenyl, j=3, m=s=1, and $R^3=R^4$=hydrogen.
The title compound is prepared according to the Mitsunobu conditions set forth in Scheme 20 with commercially available 4-(4-methoxy-phenyl)-2H-phthalazin-1-one, and subsequent hydrolysis of the ethyl ester via the procedure of Example 160.
$[M+H]^+$=700.1.

Example 170

Compound of Formula II, wherein A=tBOC, G=OH, L=absent, X and Y Taken Together=phenyl Z=4-chlorophenyl, j=3, m=s=1, and $R^3=R^4$=hydrogen.
The title compound is prepared according to the Mitsunobu conditions set forth in Scheme 20 with commercially available 4-(4-chloro-phenyl)-2H-phthalazin-1-one, and subsequent hydrolysis of the ethyl ester via the procedure of Example 160.
$[M+H]^+$=704.2.

Example 171

Compound of Formula II, wherein A=tBOC, G=OH, L=absent, X=4-fluorophenyl, Y=hydrogen, Z=phenyl, j=3, m=s=1, and $R^3=R^4$=hydrogen.
The title compound is prepared according to the Mitsunobu conditions set forth in Scheme 20 with commercially available 4-(4-fluoro-phenyl)-6-phenyl-2H-pyridazin-3-one, and subsequent hydrolysis of the ethyl ester via the procedure of Example 160.
$[M+H]^+$=704.2.

Example 172

Compound of Formula II, wherein A=tBOC, G=OH, L=absent, X=hydrogen, Y=1-piperidyl, Z=phenyl, j=3, m=s=1, and $R^3=R^4$=hydrogen.
The title compound is prepared according to the Mitsunobu conditions set forth in Scheme 20 with commercially available 6-phenyl-5-piperidin-1-yl-2H-pyridazin-3-one, and subsequent hydrolysis of the ethyl ester via the procedure of Example 160.
$[M+H]^+$=702.3.

Example 173

Compound of Formula II, wherein A=tBOC, G=OEt, L=absent, X=hydrogen, Y=bromo, Z=phenyl, j=3, m=s=1, and $R^3=R^4$=hydrogen.
The title compound is prepared according to the Mitsunobu conditions set forth in Scheme 20 with commercially available 5-Bromo-6-phenyl-2H-pyridazin-3-one.
$[M+H]^+$=726.3, 728.3.

Example 174

Compound of Formula II, wherein A=tBOC, G=OH, L=absent, X=hydrogen, Y=thiophen-3-yl, Z=phenyl, j=3, m=s=1, and $R^3=R^4$=hydrogen.
The title compound is prepared with the title compound of Example 173 and thiophen-3-yl boronic acid according to the Suzuki coupling conditions described in Example 159, followed by the hydrolysis of the ethyl ester via the method described in Example 160.
$[M+H]^+$=730.3

Example 175

Compound of Formula II, wherein A=tBOC, G=OEt, L=absent, X=bromo, Y=1-pyrrolidyl, Z=hydrogen, j=3, m=s=1, and $R^3=R^4$=hydrogen.
A mixture of the title compound in Example 158 (45 mg, 0.062 mmol), pyrrolidine (21 mL, 0.25 mmol), and potassium carbonate (34 mg, 0.25 mmol) in 2 mL of acetonitrile is heated to reflux for 3 hours. After cooling to room temperature, the mixture is filtered through a sinter glass funnel and the filtrate is concentrated in vacuo. The residue is re-dissolved in ethyl acetate and then washed once with saturated sodium carbonate, once with brine, dried (MgSO$_4$), filtered, and concentrated under vacuum to give a yellow residue which is chromatographed over silica gel eluting with 3% methanol-chloroform to give 37 mg (83%) of the title compound.

[M+H]$^+$=719.2, 721.2.

Example 176

Compound of Formula II, wherein A=tBOC, G=OH, L=absent, X=thiophen-3-yl, Y=1-pyrrolidyl, Z=hydrogen, j=3, m=s=1, and R$^3$=R$^4$=hydrogen.

The title compound is prepared with the title compound in Example 175 and thiephen-3-yl boronic acid using the Suzuki conditions described in Example 159, followed by hydrolysis of the ethyl ester according to the method set forth in Example 160.

[M+H]$^+$=694.3.

Example 177

Compound of Formula II, wherein A=tBOC, G=OEt, L=absent, X=bromo, Y=azido, Z=hydrogen, j=3, m=s=1, and R$^3$=R$^4$=hydrogen.

A mixture of the title compound in Example 158 (45 mg, 0.062 mmol), sodium azide (16 mg, 0.25 mmol), and potassium carbonate (34 mg, 0.25 mmol) in 2 mL of acetonitrile is heated to reflux for 3 hours. After cooling to room temperature, the mixture is filtered through a sinter glass funnel and the filtrate is concentrated in vacuo. The residue is re-dissolved in ethyl acetate and then washed once with saturated sodium carbonate, once with brine, dried (MgSO$_4$), filtered, and concentrated under vacuum to give a yellow residue which is chromatographed over silica gel eluting with 3% methanol-chloroform to give 37 mg (83%) of the title compound.

Example 178

Compound of Formula II, wherein A=tBOC, G=OEt, L=absent, X=thiophen-3-yl, Y=azido, Z=hydrogen, j=3, m=s=1, and R$^3$=R$^4$=hydrogen.

The title compound is prepared with the title compound in Example 177 and thiophen-3-yl boronic acid using the Suzuki conditions described in Example 159.

Example 179

Compound of Formula II, wherein A=tBOC, G=OH, L=absent, X=thiophen-3-yl, Y=azido, Z=hydrogen, j=3, m=s=1, and R$^3$=R$^4$=hydrogen.

The title compound is prepared by hydrolysis of the ethyl ester of the title compound of Example 178 via the hydrolysis procedure of Example 160.

Example 180

Compound of Formula II, wherein A=tBOC, G=OH, L=absent, X=thiophen-3-yl, Y=tetrazol-2-yl, Z=hydrogen, j=3, m=s=1, and R$^3$=R$^4$=hydrogen.

To a solution of the title compound of Example 178 (2.63 mmol) in toluene (8 ml) is added KCN (10.53 mmol) and Et$_3$N.HCl (10.53 mmol). The mixture is heated at 115° C. for 18 hrs, diluted with DCM, washed with 5% citric acid (aq), dried over anhydrous Na$_2$SO$_4$, and concentrated in vacuo to afford the ethyl ester of the title compound in crude form. Hydrolysis of the ethyl ester via the method described in Example 160 yields the title compound.

Example 181

Compound of Formula II, wherein A=tBOC, G=OH, L=absent, X=Y=mercapto-2-pyrimidine, Z=hydrogen, j=3, m=s=1, and R$^3$=R$^4$=hydrogen.

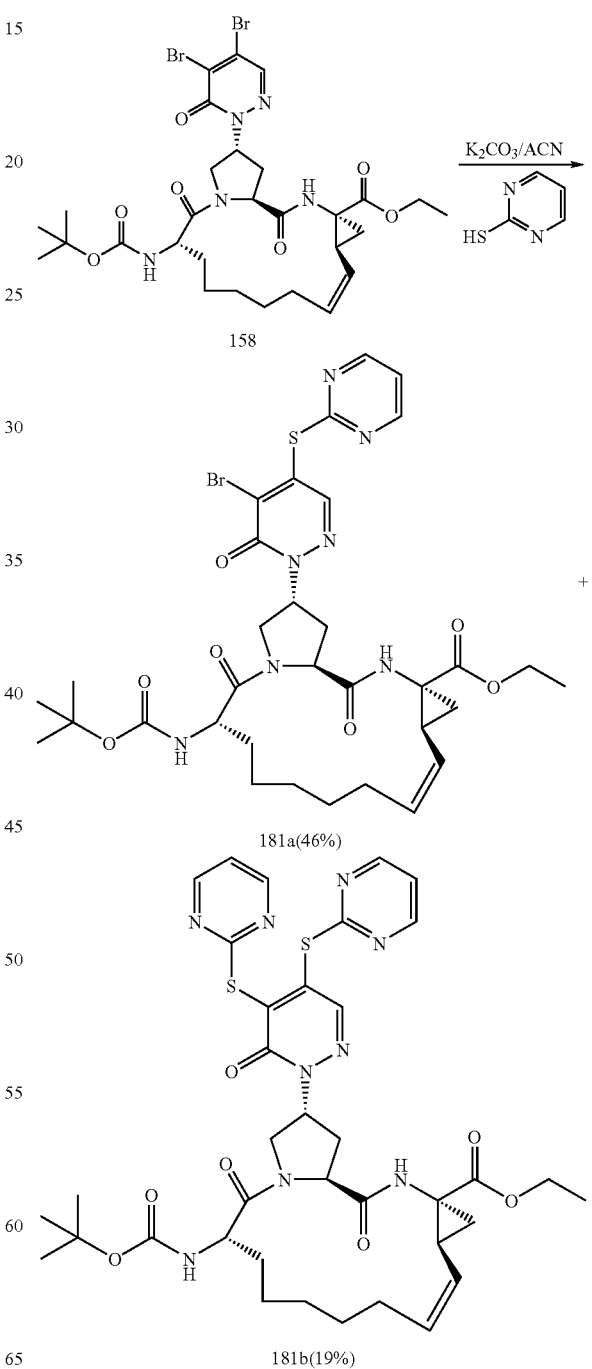

A mixture of the title compound in Example 158 (45 mg, 0.062 mmol), pyrimidine-2-thiol (0.25 mmol), and potassium carbonate (34 mg, 0.25 mmol) in 2 mL of acetonitrile is heated to reflux for 3 hours. After cooling to room temperature, the mixture is filtered through a sinter glass funnel and the filtrate is concentrated in vacuo. The residue is re-dissolved in ethyl acetate and then washed once with saturated sodium carbonate, once with brine, dried (MgSO$_4$), filtered, and concentrated under vacuum to give a yellow residue which is chromatographed over silica gel eluting with 3% methanol-chloroform to afford 181b in a 19% yield. The ethyl ester of compound 181b is then hydrolyzed via the method described in Example 160 to give the title compound.

[M+H]$^+$=764.3.

Example 182

Compound of Formula II, wherein A=tBOC, G=OH, L=absent, X=bromo, Y=mercapto-2-pyrimidine, Z=hydrogen, j=3, m=s=1, and R$^3$=R$^4$=hydrogen.

The title compound is prepared by hydrolysis of the ethyl ester of compound 181a, formed in Example 181, via the method set forth in Example 160.

[M+H]$^+$=732.2, 734.2.

Example 183

Compound of Formula II, wherein A=tBOC, G=OH, L=absent, X=thiophen-3-yl, Y=mercapto-2-pyrimidine, Z=hydrogen, j=3, m=s=1, and R$^3$=R$^4$=hydrogen.

The title compound is prepared with compound 181a from Example 181 and thiophen-3-yl boronic acid according to the Suzuki coupling conditions set forth in Example 159, followed by hydrolysis of the ethyl ester via the method described in Example 160.

Example 184

Compound of Formula II, wherein A=tBOC, G=OEt, L=absent, X=Y=thiazol-2-yl, Z=hydrogen, j=3, m=s=1, and R$^3$=R$^4$=hydrogen.

To a degassed solution of the title compound of Example 158 (1 mmol) and thiazol-2-yl stannane (2 mmol) is added Pd(PPh$_3$)$_4$ (10 mol %). The mixture is degassed with nitrogen 2 more times and is heated to 100° C. for 3 hour. The cooled mixture is concentrated under vacuum and the residue is purified by column chromatography eluting with 30% EtOAc/Hexane followed by the hydrolysis of the ethyl ester via the method of Example 160 to give the title compound.

[M+H]$^+$=710.3.

Example 185

Compound of Formula II, wherein A=tBOC, G=OH, L=absent, X=Y=imidazol-1-yl, Z=hydrogen j=3, m=s=1, and R$^3$=R$^4$=hydrogen.

The title compound is prepared by adding to a dry mixture of the title compound from Example 158 (0.068 mmol), imidazole (2 eq.), Cs$_2$CO$_3$ (3 eq.), Xantphos (30 mol %), and Pd(OAc)$_2$ under nitrogen dioxane. The reaction mixture is then degassed and stirred at 75° C. for 18 hours. Upon completion of the reaction, monitored via TLC, the reaction mixture is diluted with DCM, filtered, and concentrated in vacuo. The reaction mixture is then purified via silica column chromatography with 5% MeOH/CHCl$_3$ to afford the ethyl ester of the title compound. The ethyl ester is then hydrolyzed by the conditions set forth in Example 160 to afford the title compound.

Example 186

Compound of Formula II, wherein A=tBOC, G=OH, L=absent, X=2-(cyclopropylamino)-thiazol-4-yl, Y=4-methoxyphenyl, Z=hydrogen, j=3, m=s=1, and R$^3$=R$^4$=hydrogen.

Formation of 4-(2-Cyclopropylamino-thiazol-4-yl)-5-(4-methoxy-phenyl)-2H-pyridazin-3-one (186h)

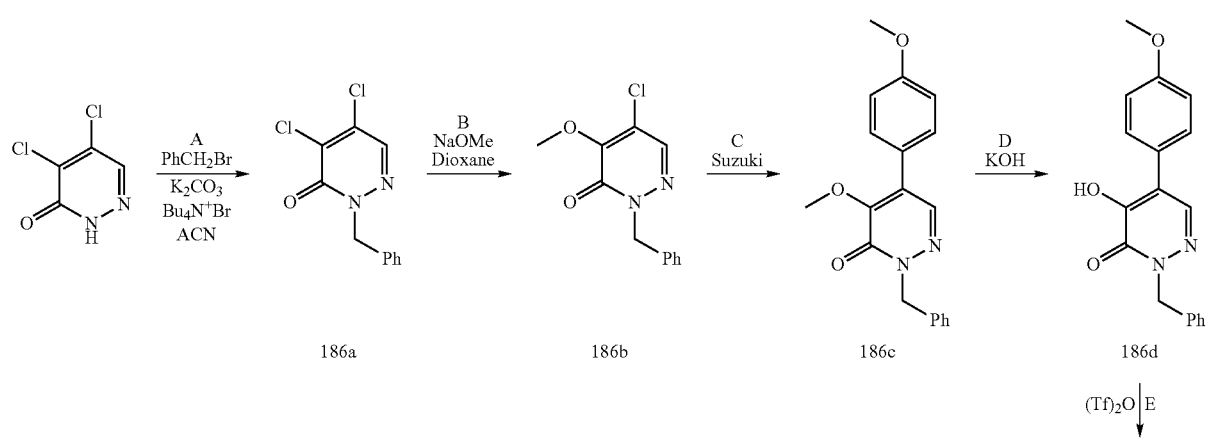

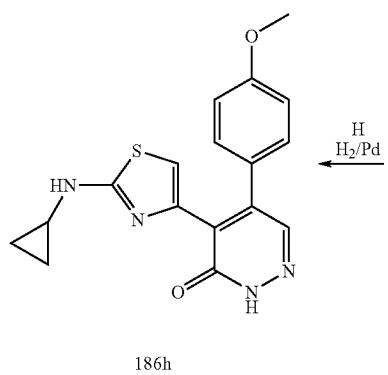

186h

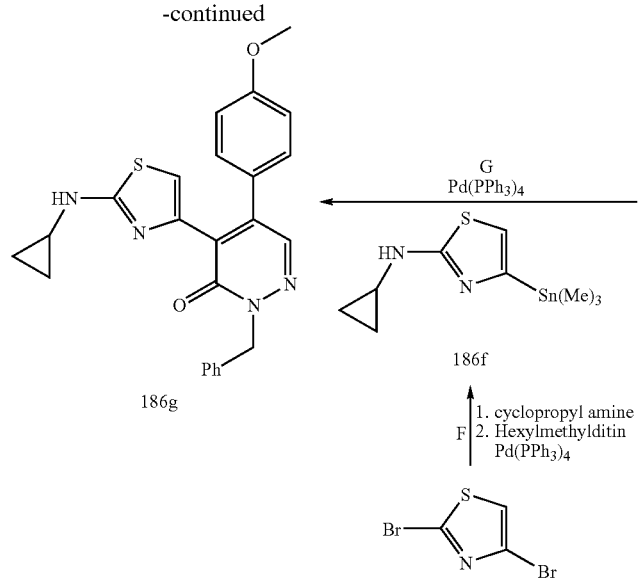

186g

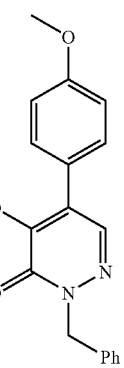

186e

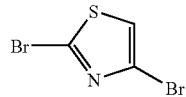

186A. A mixture of commercially available 4,5-dichloro-pyridazin3(2H)-one (18 mmol), benzyl bromide (19 mmol), potassium carbonate (45 mmol), tetrabutylammonium bromide (1 mmol) and acetonitrile (45 mL) is stirred and heated under reflux for 1 h. After cooling, the solvent is evaporated under reduced pressure. The residue is purified by filtration on a small silica gel column eluting with 10% EtOAc/Hexane to give compound 186a as a white powder (81%). [M+H]$^+$= 256.3.

186B. To a magnetically stirred solution of 186a (4.5 mmol) in dry dioxane (20 mL) is added 1.0 mL of 21 wt % solution of sodium methoxide at room temperature. After 1 hour, the mixture is poured into water/ethyl acetate and the organic layer is dried over MgSO$_4$ and concentrated to an oil. The oil residue is purified by column chromatography eluting with 10% EtOAc/Hex to give 85% of 186b. [M+H]$^+$=251.7.

Alternate substitution of pyridazinone 186b can be achieved via this step using MeOH rather than dioxane as a solvent, wherein the methoxy occupies the 5 position on the pyridazinone ring and the chloro resides at the 4 position.

186C. Pyridazinone 186b (1 mmol) is dissolved in DME. To this mixture is added Pd(PPh$_3$)$_4$ (10 mol %) and the mixture is stirred at room temperature for 10 min before 4 methoxybenzeneboronic acid (2 mmol) and aqueous 1 mL of Na$_2$CO$_3$ (10 wt %) are added.

Subsequently, the reaction mixture is heated to reflux for 18 hours. The cooled reaction mixture is diluted with water and extracted 3 times with ethyl acetate. The combined organic layers are dried (MgSO$_4$), filtered and concentrated under vacuum. The residue is purified by column chromatography on silica gel eluting with 15% EtOAc/Hexane to give compound 186c. [M+H]$^+$=323.3.

186D. To a solution of 186c (3 mmol) in DME is added 2N KOH and the resulting mixture is heated to reflux for 1 hour. The cooled mixture is diluted with water and acidified with solid citric acid to pH~5 and extracted 3 times with CH$_2$Cl$_2$. The organic layers are washed once with brine, dried (MgSO$_4$), filtered and concentrated under vacuum to give compound 186d. [M+H]$^+$=309.3.

186E. To a cooled solution of compound 186d (2 mmol), triethylamine (0.4 mL) in dichloromethane (10 mL) (ice-acetone bath) is added trifluoromethanesulfonic anhydride (0.4 mL) dropwise. The resulting solution is stirred for 30 min at −5° C. The reaction mixture is then poured into dilute HCl (0.5 M) and extracted with CH$_2$Cl$_2$. The combined organic layers are washed with a 1% NaHCO$_3$, brine and dried (MgSO$_4$), filtered and concentrated under vacuum to give a brown oil. Compound 186e is used immediately without further purification. [M+H]$^+$=441.4.

186F. Commercially available 2,4-dibromothiazole (2 mmol) is dissolved in cyclopropylamine (3 mL) and the reaction mixture is heated to 50° C. for 8 hour. The cooled mixture is then poured into water and extracted 2 times with ether. After drying the combined organic fractions (MgSO$_4$), evaporation of solvents, and purification by flash column chromatography (silica gel, 15% EtOAc/Hexane) furnished 2-cyclopropylamine-4-bromothiazole which is further converted to the corresponding stannane 186f. A solution of 2-cyclopropylamine-4-bromothiazole in degassed DME is treated with hexamethylditin and Pd(PPh$_3$)$_4$ and heated at 80° C. for 18 hour. The cooled mixture is concentrated under vacuum and the residue is purified by column chromatography eluting with 20% EtOAc/Hexane/2% Et$_3$N to give Stannane 186f. [M+H]$^+$=304.1.

186G. To a degassed solution of compound 186e (1 mmol) and stannane 186f (2 mmol) is added Pd(PPh$_3$)$_4$ (10 mol %). The mixture is degassed two additional times with nitrogen and subsequently heated to 100° C. for 3 hour. The cooled mixture is concentrated under vacuum and the residue is purified by column chromatography eluting with 30% EtOAc/Hexane to give compound 186g. [M+H]$^+$=431.6.

186H. A solution of compound 186g and 10% Pd/C (wet) in MeOH is subjected to a hydrogen balloon for 2 hours. The mixture is filtered through a pad of celite and the filtrate is concentrated under vacuum to give compound 186h. [M+H]$^+$= 341.4.

The title compound is prepared from pyridazinone 186h and the cyclic peptide precursor 1 of Example 1 via the Mitsunobu conditions set forth in Example 158, followed by the hydrolysis of the ethyl ester via the hydrolysis conditions described in Example 159.

Example 187

Compound of Formula II, wherein A=tBOC, G=OH, L=absent, X and Y Taken Together=6-methoxy-isoquinolin-(3,4)-yl, Z=hydrogen, j=3, m=s=1, and R$^3$=R$^4$=hydrogen

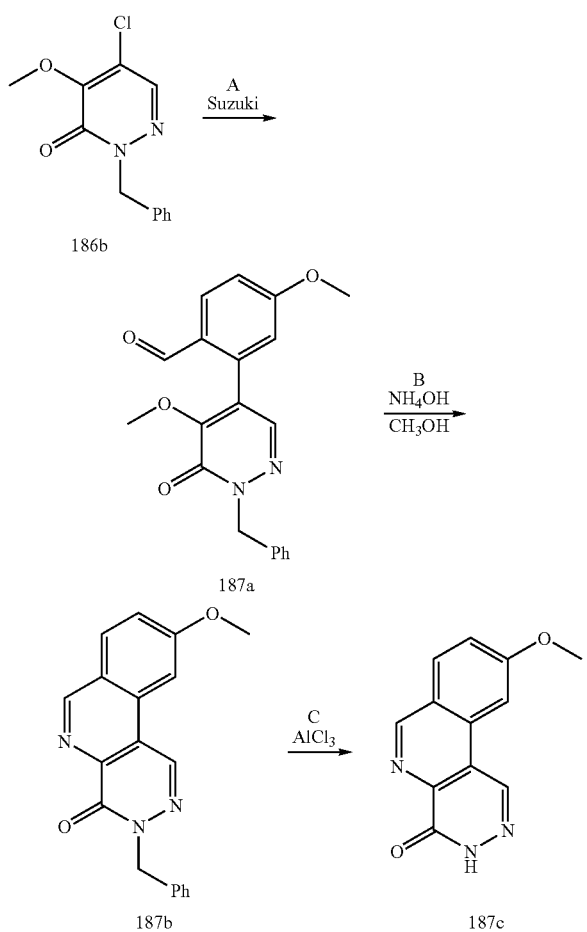

187A. Pyridazinone 186b (2 mmol) is dissolved in DME. To this mixture is added Pd(PPh$_3$)$_4$ and the mixture is stirred at room temperature for 10 min before 2-formyl-4-methoxy-benzeneboronic acid and aqueous Na$_2$CO$_3$ (10 wt %) are added. Subsequently, the reaction mixture is heated to reflux for 18 hours. The cooled reaction mixture is diluted with water and extracted 3 times with ethyl acetate. The combined organic layers are dried (MgSO$_4$), filtered and concentrated under vacuum. The residue is purified by column chromatography on silica gel eluting with 20% EtOAc/Hexane to give compound 187a. [M+H]$^+$=351.4.

187B. A mixture of pyridazinone 187a (1 mmol), MeOH (20 mL) and NH$_4$OH (10 mL, 28-30 wt %) is heated at 60° C. for 30 min. After cooling, the precipitate, compound 187b, is filtered and rinsed with MeOH (15 mL). [M+H]$^+$=317.4.

187C. A mixture of pyridazinoisoquinolinone 187b (0.5 mmol), AlCl$_3$ and toluene is stirred and heated at 70° C. for 1 hour. After cooling, water is added and the mixture is filtered and rinsed with water. The residue is purified by column chromatography on silica gel eluting with 50% EtOAc/Hex to give compound 187c. [M+H]$^+$=227.3.

The title compound is prepared from pyridazinoisoquinolinone 187c and the cyclic peptide precursor 1 of Example 1 via the Mitsunobu conditions set forth in Example 162, followed by the hydrolysis of the ethyl ester via the hydrolysis conditions described in Example 159.

Example 188

Compound of Formula II, wherein A=—(C=O)—O—R$^1$, wherein R$^1$=cyclopentyl, G=OH, L=absent, X=Y=thiophen-3-yl, Z=hydrogen, j=3, m=s=1, and R$^3$=R$^4$=hydrogen 188a—Amine Deprotection.

0.041 mmol of the title compound of Example 159 is dissolved in 4 ml of a 4M solution of HCl in dioxane and stirred for 1 hour. The reaction residue 188a is concentrated in vacuo.

188b—Chloroformate Reagent

The chloroformate reagent 188b is prepared by dissolving 0.045 mmol of cyclopentanol in THF (3 ml) and adding 0.09 mmol of phosgene in toluene (20%). The resulting reaction mixture is stirred at room temperature for 2 hours and the solvent is removed in vacuo. To the residue is added DCM and subsequently concentrated to dryness twice in vacuo yielding chloroformate reagent 188b.

188c—Carbamate Formation

The title carbamate is prepared by dissolving residue 188a in 1 ml of THF, adding 0.045 mmol of TEA, and cooling the resulting reaction mixture to 0° C. To this 0° C. reaction mixture is added chloroformate reagent 188b in 3 ml of THF. The resulting reaction mixture is reacted for 2 hours at 0° C., extracted with EtOAc, washed by 1M sodium bicarbonate, water and brine, dried over MgSO$_4$, and concentrated in vacuo to dryness. The crude compound is purified by silica column and the ethyl ester is subsequently hydrolyzed by the procedure set forth in Example 160.

Example 189

Compound of Formula II, wherein A=—(C=O)—O—R$^1$, wherein R$^1$=cyclobutyl, G=OH, L=absent, X=Y=thiophen-3-yl, Z=hydrogen, j=3, m=s=1, and R$^3$=R$^4$=hydrogen.

The title compound is prepared by the method described in Example 188 with the title compound of Example 159 and cyclobutanol.

Example 190

Compound of Formula II, wherein A=—(C=O)—O—R$^1$, wherein R$^1$=cyclohexyl, G=OH, L=absent, X=Y=thiophen-3-yl, Z=hydrogen, j=3, m=s=1, and R$^3$=R$^4$=Hydrogen.

The title compound is prepared by the method described in Example 188 with the title compound of Example 159 and cyclohexanol.

Example 191

Compound of Formula II, wherein A=—(C=O)—O—R$^1$, wherein R$^1$=

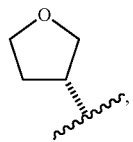

G=OH, L=absent, X=Y=thiophen-3-yl, Z=hydrogen, j=3, m=s=1, and R$^3$=R$^4$=hydrogen.

The title compound is prepared by the method described in Example 188 with the title compound of Example 159 and (R)-3-hydroxytetrahydrofuran.

Example 192

Compound of Formula II, wherein A=—(C=O)—O—R¹, wherein R¹=

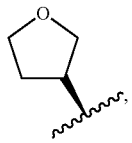

G=OH, L=absent, X=Y=thiophen-3-yl, Z=hydrogen, j=3, m=s=1, and R³=R⁴=hydrogen.

The title compound is prepared by the method described in Example 188 with the title compound of Example 159 and (S)-3-hydroxytetrahydrofuran.

Example 193

Compound of Formula II, wherein A=—(C=O)—O—R¹, wherein R¹=

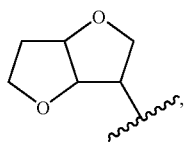

G=OH, L=absent, X=Y=thiophen-3-yl, Z=hydrogen, j=3, m=s=1, and R³=R⁴=hydrogen

The title compound is prepared by the method described in Example 188 with the title compound of Example 159 and

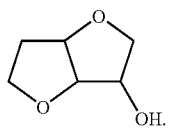

Example 194

Compound of Formula II, wherein A=—(C=O)—R¹, wherein R¹=cyclopentyl, G=OH, L=absent, X=Y=thiophen-3-yl, Z=hydrogen, j=3, m=s=1, and R³=R⁴=hydrogen The title compound is prepared with the title compound from Example 159 in 4 ml of a 4M solution of HCl in dioxane and stirring the reaction mixture for 1 hour. The reaction residue is concentrated in vacuo. To this residue, 4 ml of THF and 0.045 mmol of TEA is added, the mixture is cooled to 0° C., to which is added 0.045 mmol of the cyclopentyl acid chloride. The resulting reaction mixture is stirred for 2 hours at 0° C. The reaction mixture is then extracted with EtOAc, washed with 1M sodium bicarbonate, water and brine, dried over MgSO₄ and concentrated to dryness in vacuo. The crude compound is purified by silica column and the ethyl ester is subsequently hydrolyzed by the procedure set forth in Example 160.

Example 195

Compound of Formula II, wherein A=—(C=O)—NH—R¹, wherein R¹=cyclopentyl, G=OH, L=absent, X=Y=thiophen-3-yl, Z=hydrogen, j=3, m=s=1, and R³=R⁴=hydrogen.

The title compound is prepared with the title compound from Example 159 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isocyanate and the resulting reaction mixture is stirred at RT for 4 hours. The solution is then extracted with EtOAc, washed with 1% HCl, water and brine, dried over MgSO₄, and concentrated in vacuo to dryness. The crude compound is purified by silica column and the ethyl ester is subsequently hydrolyzed by the procedure set forth in Example 160.

Example 196

Compound of Formula II, wherein A=—(C=S)—NH—R¹, wherein R¹=cyclopentyl, G=OH, L=absent, X=Y=thiophen-3-yl, Z=hydrogen, j=3, m=s=1, and R³=R⁴=hydrogen.

The title compound is prepared with the title compound from Example 159 in 4 ml of a 4M solution of HCl in dioxane and stirring for 1 hour. The resulting reaction residue is concentrated in vacuo, dissolved in 4 ml THF, and cooled to 0° C. To the 0° C. solution is added 0.045 mmol of cyclopentyl isothiocyanate and the resulting reaction mixture is stirred at RT for 4 hours. The solution is then extracted with EtOAc, washed with 1% HCl, water and brine, dried over MgSO₄, and concentrated in vacuo to dryness. The crude compound is purified by silica column and the ethyl ester is subsequently hydrolyzed by the procedure set forth in Example 160.

Example 197

Compound of Formula II, wherein A=—S(O)₂—R¹, wherein R¹=cyclopentyl, G=OH, L=absent, X=Y=thiophen-3-yl, Z=hydrogen, j=3, m=s=1, and R³=R⁴=hydrogen.

The title compound is prepared with the title compound from Example 159 in 4 ml of a 4M solution of HCl in dioxane and stirring for 1 hour. To the resulting concentrated reaction residue, which has been dissolved in 4 ml THF, is added 0.045 mmol of TEA, and cooled to 0° C. To the 0° C. solution is added 0.045 mmol of cyclopentyl sulfonyl chloride and the resulting reaction mixture is stirred at 0° C. for 2 hours. The solution is then extracted with EtOAc, washed with 1M sodium bicarbonate, water and brine, dried over MgSO₄, and concentrated in vacuo to dryness. The crude compound is purified by silica column and the ethyl ester is subsequently hydrolyzed by the procedure set forth in Example 160.

Example 198

Compound of Formula II, wherein A=—(C=O)—O—R¹, R¹=cyclopentyl, G=—O-phenethyl, L=absent, X=Y=thiophen-3-yl, Z=hydrogen, j=3, m=s=1, and R³=R⁴=hydrogen.

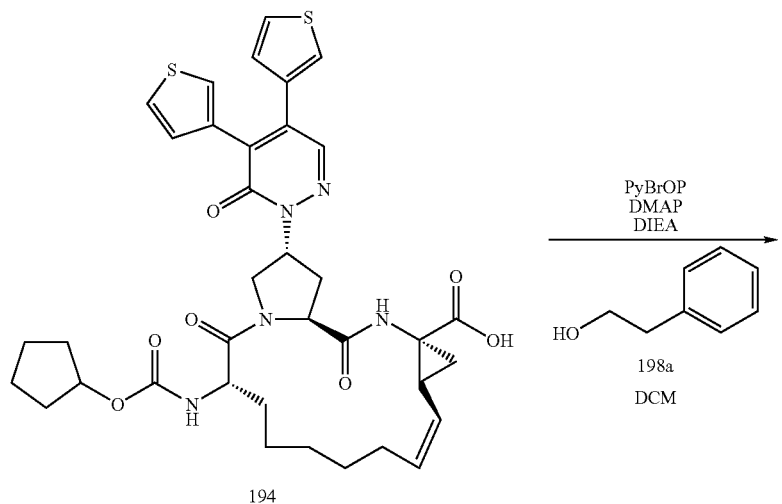

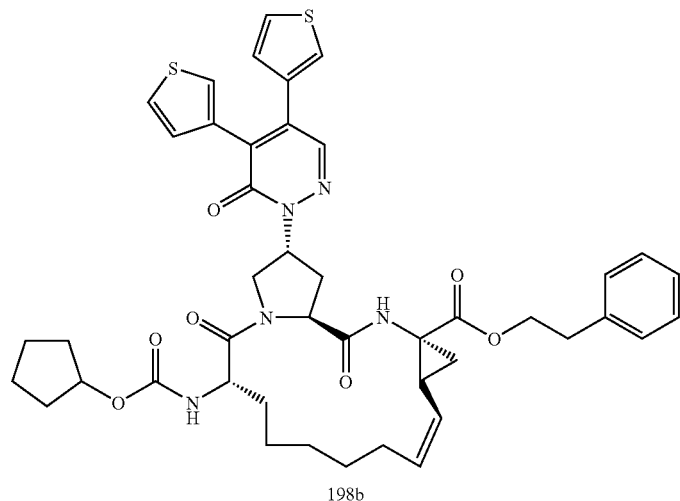

The title compound is prepared by adding to a solution of the title compound of Example 194 and phenethyl alcohol 198a in 0.5 ml DCM, is added 1.2 eq. PyBrOP, 4 eq. DIEA, and catalytic amount of DMAP at 0° C. The resulting reaction mixture is stirred for 1 hour at 0° C. and then warmed to RT over a period of 4-12 hours. The reaction mixture is purified by silica gel flash chromatography using different ratios of hexanes:EtOAc as elution phase (9:1→5:1→3:1→1:1) to afford the title compound isolated phenethyl ester 198b.

Other esters can be made using the same procedures.

Example 199

Compound of Formula II, wherein A=—(C=O)—O—R$^1$, R$^1$=cyclopentyl, G=—NH-phenethyl, L=absent, X=Y=thiophen-3-yl, Z=hydrogen, j=3, m=s=1, and R$^3$=R$^4$=hydrogen.

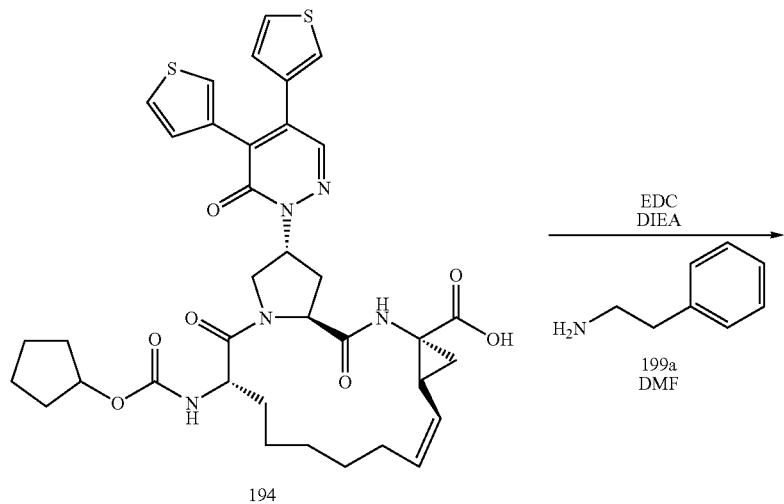

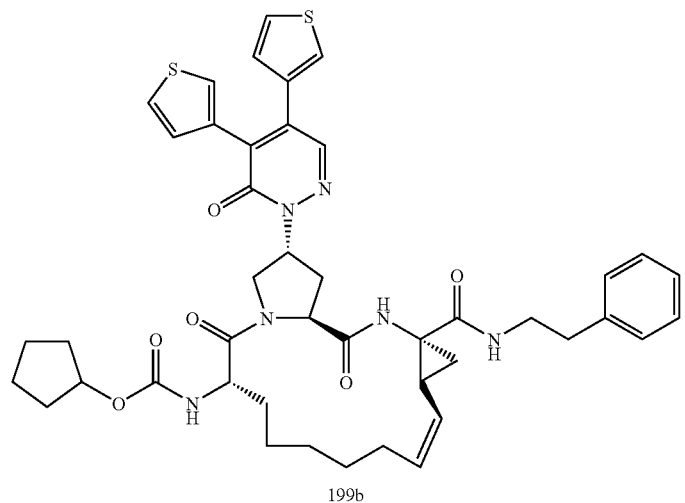

The title compound is prepared by adding to a solution of the title compound of Example 194 and phenethylamine 199a (0.05 ml) in 0.5 ml DMF, EDC (1.2 eq.) and DIEA (4 eq.) at 0° C. The resulting reaction mixture is stirred at 1 hour. Subsequently, the reaction is warmed to RT over a period of 4-12 hours. The reaction mixture is purified by silica gel flash chromatography using different ratios of hexanes:EtOAc as elution phase (9:1→5:1→3:1→1:1) to afford title compound phenethyl amide 199b.

Other amides can be made via the same procedure.

Example 200

Compound of Formula II, wherein A=—(C=O)—O—R$^1$, R$^1$=cyclopentyl, G=—NHS(O)$_2$-phenethyl, L=absent, X=Y=thiophen-3-yl, Z=hydrogen, j=3, m=s=1, and R$^3$=R$^4$=hydrogen.

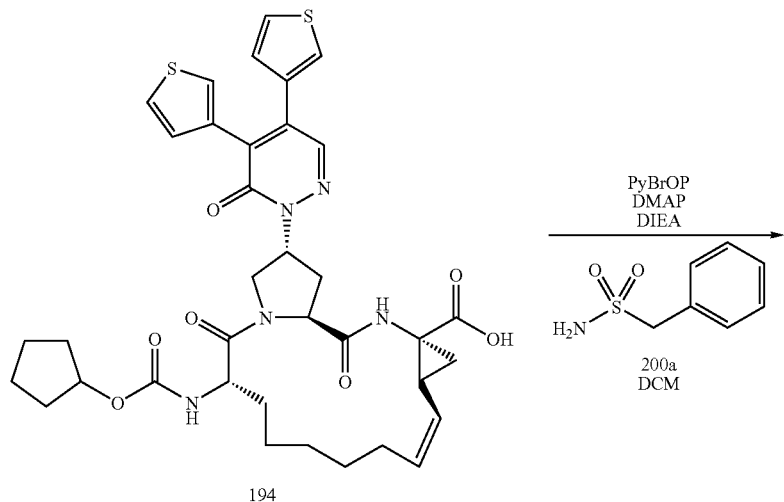

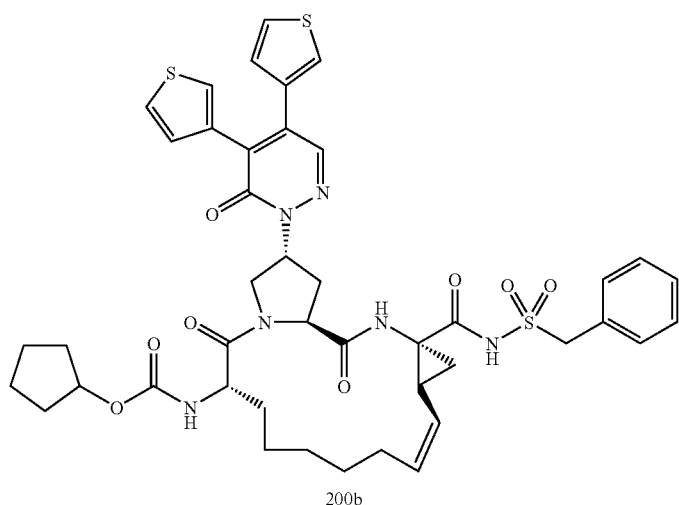

The title compound is prepared by adding to a solution of the title compound of Example 194 and α-toluenesulfonamide 200a (10 mg) in 0.5 ml DCM, is added 1.2 eq. PyBrOP, 4 eq. DIEA, and catalytic amount of DMAP at 0° C. The resulting reaction mixture is stirred for 1 hour and then allowed to warm to RT over a period of 4-12 hours. The reaction mixture is purified by silica gel flash chromatography using different ratios of hexanes:EtOAc as elution phase (9:1→5:1→3:1→1:1) to afford the title compound sulfonamide 200b.

Other sulfonamides can be made via the same procedure.

Example 201

Compound of Formula II, wherein A=—(C=O)—O—R$^1$, R$^1$=cyclopentyl, G=—(C=O)—OH, L=absent, X=Y=thiophen-3-yl, Z=hydrogen, j=3, m=s=1, and R$^3$=R$^4$=hydrogen.

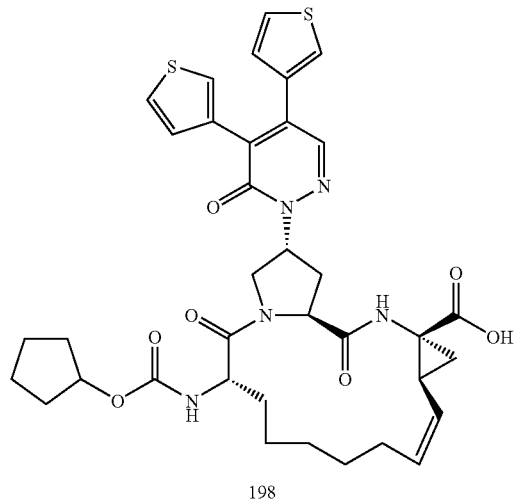

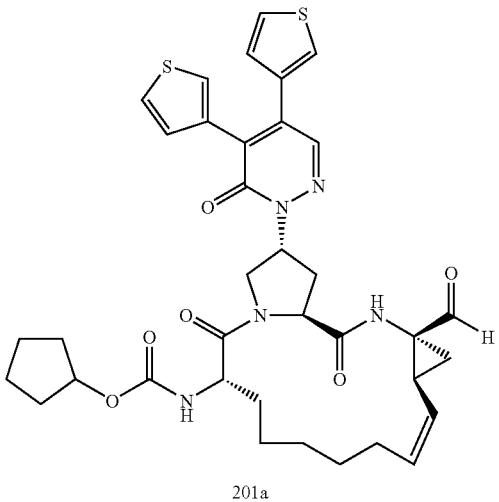

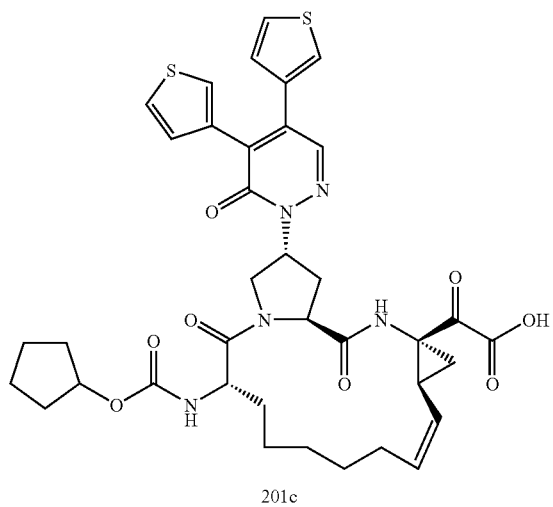

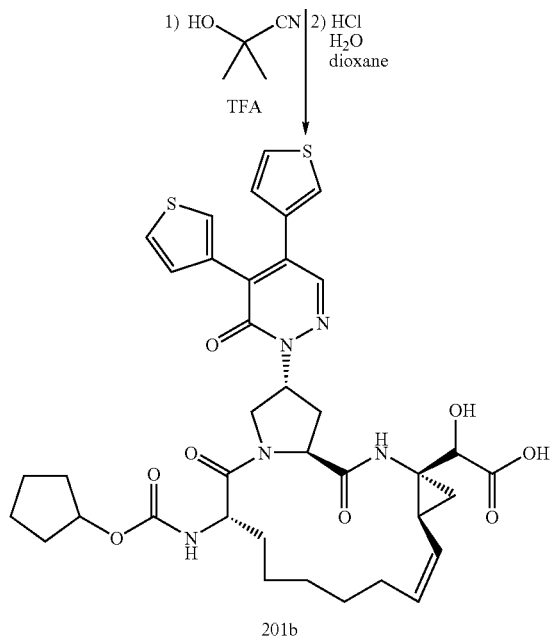

The title compound is prepared by adding to a solution of the title compound of Example 194 in 0.5 ml DMF, EDC (1.2 eq.) and DIEA (4 eq.) at 0° C. The resulting reaction mixture is stirred at 1 hour. Subsequently, the reaction is warmed to RT over a period of 4-12 hours. The reaction mixture is purified by silica gel flash chromatography to afford hydroxyamide. The hydroxyamide is then treated with DIBAL-H at −78° C. in THF for 2 hours. The reaction mixture is then diluted with 8 ml EtOAc, washed with water and brine, dried over Na$_2$SO$_4$, and concentrated in vacuo to yield aldehyde 201a. To a solution of aldehyde 39a in 0.5 ml THF, is added α-hydroxy-α-methyl-propionitrile (0.1 ml) and catalytic amount TFA at 0° C. The resulting reaction mixture is warmed from 0° C. to RT over a period of 4-12 hours followed by hydrolysis with concentrated hydrochloric acid in dioxane. The reaction is then extracted with EtOAc, and washed with water and brine to yield α-hydroxy compound 201b in its crude form. The crude compound 201b undergoes a Dess-Martin oxidation in THF (0.5 ml), providing the α-carbonyl compound 201c in crude form. The crude 201c is purified by silica gel flash chromatography using different ratios of hexanes:EtOAc as elution phase (9:1→5:1→3:1→1:1) to afford the title compound isolated keto acid 201c.

Example 202

Compound of Formula II, wherein A=—(C=O)—O—R$^1$, R$^1$=cyclopentyl, G=—(C=O)—O-phenethyl, L=absent, X=Y=thiophen-3-yl, Z=hydrogen, j=3, m=s=1, and R$^3$=R$^4$=hydrogen.

The title compound is prepared with the title compound keto acid of Example 201 and phenethanol according to the procedure set forth Example 198.

Example 203

Compound of Formula II, wherein A=—(C=O)—O—R$^1$, R$^1$=cyclopentyl, G=—(C=O)—NH-phenethyl, L=absent, X=Y=thiophen-3-yl, Z=hydrogen, j=3, m=s=1, and R$^3$=R$^4$=hydrogen.

The title compound is prepared with the title compound keto acid of Example 201 and phenethyl amine according to the procedure set forth in Example 199.

Example 204

Compound of Formula II, wherein A=—(C=O)—O—R$^1$, R$^1$=cyclopentyl, G=—(C=O)—NH—S(O)$_2$-benzyl L=absent, X=Y=thiophen-3-yl, Z=hydrogen, j=3, m=s=1, and R$^3$=R$^4$=hydrogen.

The title compound is prepared with the title compound keto acid of Example 201 and α-toluenesulfonamide according to the procedure set forth in Example 200.

Example 205

Compound of Formula II, wherein A=tBOC, G=OH, L=—(C=O)CH$_2$—, X=Y=thiophen-3-yl, Z=hydrogen, j=1, m=s=1, and R$^3$=R$^4$=hydrogen.

The title compound is prepared with the modified cyclic peptide precursor mesylate formed in 88C and 4,5-di(thiophen-3-yl)-2H-pyridazin-3-one by the Mitsunobu conditions elucidated in Example 158 followed by hydrolysis of the ethyl ester via the method set forth in Example 160.

Example 206

Compound of Formula II, wherein A=tBOC, G=OH, L=—CH(CH$_3$)CH$_2$—, X=Y=thiophen-3-yl, Z=hydrogen, j=1, m=s=1, R$^3$=methyl, and R$^4$=hydrogen.

The title compound is prepared with the modified cyclic peptide precursor mesylate formed in 89G and 4,5-di(thiophen-3-yl)-2H-pyridazin-3-one by the Mitsunobu conditions elucidated in Example 158 followed by hydrolysis of the ethyl ester via the method set forth in Example 160.

Example 207

Compound of Formula II, wherein A=tBOC, G=OH, L=—O—, X=Y=thiophen-3-yl, Z=hydrogen, j=0, m=s=1, R$^3$=methyl, and R$^4$=hydrogen.

The title compound is prepared with the modified cyclic peptide precursor mesylate formed in 90D and 4,5-di(thiophen-3-yl)-2H-pyridazin-3-one by the Mitsunobu conditions elucidated in Example 158 followed by hydrolysis of the ethyl ester via the method set forth in Example 160.

Example 208

Compound of Formula II, wherein A=tBOC, G=OH, L=—S—, X=Y=thiophen-3-yl, Z=hydrogen, j=0, m=s=1, R$^3$=methyl, and R$^4$=hydrogen.

The title compound is prepared with the modified cyclic peptide precursor mesylate formed in 91E and 4,5-di(thiophen-3-yl)-2H-pyridazin-3-one by the Mitsunobu conditions elucidated in Example 158 followed by hydrolysis of the ethyl ester via the method set forth in Example 160.

Example 209

Compound of Formula II, wherein A=tBOC, G=OH, L=—S(O)—, X=Y=thiophen-3-yl, Z=hydrogen, j=2, m=s=1, R$^3$=methyl, and R$^4$=hydrogen.

The title compound is prepared with the modified cyclic peptide precursor mesylate formed in 92B and 4,5-di(thiophen-3-yl)-2H-pyridazin-3-one by the Mitsunobu conditions elucidated in Example 158 followed by hydrolysis of the ethyl ester via the method set forth in Example 160.

Example 210

Compound of Formula II, wherein A=tBOC, G=OH, L=—S(O)$_2$, X=Y=thiophen-3-yl, Z=hydrogen, j=2, m=s=1, R$^3$=methyl, and R$^4$=hydrogen.

The title compound is prepared with the modified cyclic peptide precursor mesylate formed in 93B and 4,5-di(thiophen-3-yl)-2H-pyridazin-3-one by the Mitsunobu conditions elucidated in Example 158 followed by hydrolysis of the ethyl ester via the method set forth in Example 160.

Example 211

Compound of Formula II, wherein A=tBOC, G=OH, L=—SCH$_2$CH$_2$—, X=Y=thiophen-3-yl, Z=hydrogen, j=0, m=s=1, and R$^3$=R$^4$=CH$_3$ The title compound is prepared with the modified cyclic peptide precursor mesylate formed in 94B and 4,5-di(thiophen-3-yl)-2H-pyridazin-3-one by the Mitsunobu conditions elucidated in Example 158 followed by hydrolysis of the ethyl ester via the method set forth in Example 160.

Example 212

Compound of Formula II, wherein A=tBOC, G=OH, L=CF$_2$CH$_2$, X=Y=thiophen-3-yl, Z=hydrogen, j=1, m=s=1, and R$^3$=R$^4$=hydrogen.

The title compound is prepared with the modified cyclic peptide precursor mesylate formed in 95C and 4,5-di(thiophen-3-yl)-2H-pyridazin-3-one by the Mitsunobu conditions elucidated in Example 158 followed by hydrolysis of the ethyl ester via the method set forth in Example 160.

Example 213

Compound of Formula II, wherein A=tBOC, G=OH, L=—CHFCH$_2$—, X=Y=thiophen-3-yl, Z=hydrogen, j=1, m=s=1, and R$^3$=R$^4$=hydrogen.

The title compound is prepared with the modified cyclic peptide precursor mesylate formed in 96C and 4,5-di(thiophen-3-yl)-2H-pyridazin-3-one by the Mitsunobu conditions elucidated in Example 158 followed by hydrolysis of the ethyl ester via the method set forth in Example 160.

Example 214

Compound of Formula II, wherein A=tBOC, G=OH, L=absent, X=Y=thiophen-3-yl, Z=hydrogen, j=3, m=s=1, and R$^3$=R$^4$=hydrogen.

214A. The saturated cyclic peptide precursor mesylate is prepared by catalytic reduction of the mesylate cyclic peptide precursor of Example 2 with Pd/C in MeOH in the presence of H$_2$.

The title compound is prepared with the saturated cyclic peptide precursor mesylate formed in 214A and 4,5-di(thiophen-3-yl)-2H-pyridazin-3-one by the Mitsunobu conditions elucidated in Example 158 followed by hydrolysis of the ethyl ester via the method set forth in Example 160.

The compounds of the present invention exhibit potent inhibitory properties against the HCV NS3 protease. The following examples elucidate exemplary assays in which the compounds of the present invention are tested for anti-HCV effects.

Example 215

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence was measured with a Molecular Devices Fluoromax (or equivalent) using an excitation wavelength of 355 nm and an emission wavelength of 485 nm.

The assay is run in Corning white half-area 96-well plates (VWR 29444-312 [Corning3693]) with full-length NS3 HCV protease 1b tethered with NS4A cofactor (final enzyme concentration 1 to 15 nM). The assay buffer is complemented with 10 µM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-$NH_2$, (SEQ ID NO. 4), AnaSpec 22991, MW 1548.6) is used as the fluorogenic peptide substrate. The assay buffer contained 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, (SEQ ID NO. 5), [−20° C.] and HCV Inh 2 (Anaspec 25346, MW 913.1) Ac-Asp-Glu-Dif-Cha-Cys-OH, (SEQ ID NO. 6), were used as reference compounds.

IC50 values were calculated using XLFit in ActivityBase (IDBS) using equation 205: $y=A+((B-A)/(1+((C/x)^\wedge D)))$.

Example 216

Cell-Based Replicon Assay

Quantification of HCV Replicon RNA in Cell Lines (HCV Cell Based Assay)

Cell lines, including Huh-1-7 or Huh 9-13, harboring HCV replicons (Lohmann, et al Science 285:110-113, 1999) are seeded at $5\times10^3$ cells/well in 96 well plates and fed media containing DMEM (high glucose), 10% fetal calf serum, penicillin-streptomycin and non-essential amino acids. Cells are incubated in a 5% $CO_2$ incubator at 37° C. At the end of the incubation period, total RNA is extracted and purified from cells using Qiagen Rneasy 96 Kit (Catalog No. 74182). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

```
HCV Forward primer "RBNS5bfor"
5'GCTGCGGCCTGTCGAGCT (SEQ ID NO. 1):

HCV Reverse primer "RBNS5Brev":
5'CAAGGTCGTCTCCGCATAC (SEQ ID NO. 2)
```

Detection of the RT-PCR product was accomplished using the Applied Biosystems (ABI) Prism 7700 Sequence Detection System (SDS) that detects the fluorescence that is emitted when the probe, which is labeled with a fluorescence reporter dye and a quencher dye, is processed during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7. The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
                                        (SEQ ID NO. 3)
5' FAM-CGAAGCTCCAGGACTGCACGATGCT-TAMRA
FAM = Fluorescence reporter dye.
TAMRA: = Quencher dye.
```

The RT reaction is performed at 48° C. for 30 minutes followed by PCR. Thermal cycler parameters used for the PCR reaction on the ABI Prism 7700 Sequence Detection System were: one cycle at 95° C., 10 minutes followed by 35 cycles each of which included one incubation at 95° C. for 15 seconds and a second incubation for 60° C. for 1 minute.

To normalize the data to an internal control molecule within the cellular RNA, RT-PCR is performed on the cellular messenger RNA glyceraldehydes-3-phosphate dehydrogenase (GAPDH). The GAPDH copy number is very stable in the cell lines used. GAPDH RT-PCR is performed on the same exact RNA sample from which the HCV copy number is determined. The GAPDH primers and probes, as well as the standards with which to determine copy number, are contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in Replicon Containing Huh-7 Cell Lines The effect of a specific anti-viral compound on HCV replicon RNA levels in Huh-11-7 or 9-13 cells was determined by comparing the amount of HCV RNA normalized to GAPDH (e.g. the ratio of HCV/GAPDH) in the cells exposed to compound versus cells exposed to the 0% inhibition and the 100% inhibition controls. Specifically, cells were seeded at $5\times10^3$ cells/well in a 96 well plate and were incubated either with: 1) media containing 1% DMSO (0% inhibition control), 2) 100 international units, IU/ml Interferon-alpha 2b in media/1% DMSO or 3) media/1% DMSO containing a fixed concentration of compound. 96 well plates as described above were then incubated at 37° C. for 3 days (primary screening assay) or 4 days ($IC_{50}$ determination). Percent inhibition was defined as:

% Inhibition=$[100-((S-C2)/C1-C2))]\times100$ where

S=the ratio of HCV RNA copy number/GAPDH RNA copy number in the sample;

C1=the ratio of HCV RNA copy number/GAPDH RNA copy number in the 0% inhibition control (media/1% DMSO); and C2=the ratio of HCV RNA copy number/GAPDH RNA copy number in the 100% inhibition control (100 IU/ml Interferon-alpha 2b).

The dose-response curve of the inhibitor was generated by adding compound in serial, three-fold dilutions over three logs to wells starting with the highest concentration of a specific compound at 10 uM and ending with the lowest concentration of 0.01 uM. Further dilution series (1 uM to 0.001 uM for example) was performed if the $IC_{50}$ value was not in the linear range of the curve. $IC_{50}$ was determined based on the IDBS Activity Base program using Microsoft Excel "XL Fit" in which A=100% inhibition value (100 IU/ml Interferon-alpha 2b), B=0% inhibition control value (media/1% DMSO) and C=midpoint of the curve as defined as C=(B−A/2)+A. A, B and C values are expressed as the ratio of HCV RNA/GAPDH RNA as determined for each sample in each well of a 96 well plate as described above. For each plate the average of 4 wells were used to define the 100% and 0% inhibition values.

Although the invention has been described with respect to various preferred embodiments, it is not intended to be limited thereto, but rather those skilled in the art will recognize that variations and modifications may be made therein which are within the spirit of the invention and the scope of the appended claims.

The invention claimed is:

1. A compound having the Formula I or a pharmaceutically acceptable salt thereof:

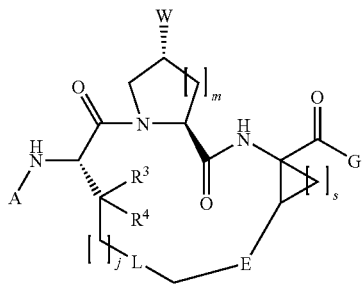

(I)

wherein:

A is selected from the group consisting of H, —(C=O)—R$^2$, —(C=O)—O—R$^1$, —C(=O)—NH—R$^2$, —C(=S)—NH—R$^2$, —S(O)$_2$—R$^2$, —(C=NR$^1$)—R$^1$, and —(C=NR$^1$)—NH—R$^1$;

G is selected from the group consisting of —OH, —O—(C$_1$-C$_{12}$ alkyl), —NHS(O)$_2$—R$^1$, —(C=O)—R$^1$, —(C=O)—O—R$^1$, and —(C=O)—NH—R$^1$;

L is selected from the group consisting of —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, —CF$_2$CH$_2$—, and —CR$_x$=CR$_x$— where R$_x$=H or halogen;

j is 0, 1, 2, 3, or 4;

m is 0, 1, or 2;

s is 0, 1 or 2;

R$^1$ is selected form the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R$^2$ is selected from the group consisting of H, C$_1$-C$_6$ alkyl, C$_3$-C$_{12}$ cycloalkyl, alkylamino, dialkylamino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R$^3$ and R$^4$ are each independently selected from the group consisting of hydrogen, OH, CH$_3$, CN, SH, halogen, NO$_2$, NH$_2$, amide, methoxy, trifluoromethoxy, and trifluoromethyl;

E is selected from —CH=CH— or —CH$_2$—CH$_2$—; and

W is a substituted or unsubstituted heterocyclic ring system; wherein the radical being joined to the rest of the molecule via a ring atom.

2. A compound according to claim 1 wherein W is substituted with one or more substituents, each of said substituents being independently selected from any of (a), (b), (c), (d) and (e):

(a) alkenyl; alkoxy; alkoxyalkyl; alkyl; alkylamino; alkylaryl; alkylsulfonyl; alkynyl; amide; amido optionally mono-substituted with C$_1$-C$_6$ alkyl; aryl; arylalkanoylalkyl; arylalkyl; arylaminoalkyl; aryloxyalkyl; arylsulfonyl; cycloalkoxy; cycloalkyl; dialkylamino; dialkylaminoalkyl; diarylaminoalkyl; haloalkyl; heteroaryl; heteroarylalkyl; heterocyclo; heterocycloalkyl; heterocycloalkylalkyl; thioalkyl; monoalkylaminoalkyl; sulfonyl; (lower alkyl)sulfonyl; haloalkyl; carboxyl; amide; (lower alkyl)amide; heterocyclo optionally substituted with C$_1$-C$_6$ alkyl; perhaloalkyl; sulfonyl; thioalkyl; urea, C(=O)—R$^{11}$; OC(=O)R$^{11}$; C(=O)O—R$^{11}$; C(=O)N(R$^{11}$)$_2$; C(=S)N(R$^{11}$)$_2$; SO$_2$R$^{11}$; NHS(O$_2$)R$^{11}$; N(R$^{12}$)$_2$; N(R$^{12}$)C(=O)R$^{11}$;

wherein each of the foregoing can be optionally be substituted with up to three groups selected from halogen, OH, alkoxy, perhaloalkyl;

(b) C$_7$-C$_{14}$ aralkyl; C$_2$-C$_7$cycloalkyl; C$_6$-C$_{10}$ aryl; heterocyclo; (lower alkyl)-heterocyclo;

wherein each aralkyl, cycloalkyl, aryl, heterocyclo or (lower alkyl)-heterocyclo may be optionally substituted with R$^6$, where R$^6$ is halogen, C$_1$-C$_6$ alkyl, C$_3$-C$_6$ cycloalkyl, C$_1$-C$_6$ alkoxy, C$_3$-C$_6$ cycloalkoxy, NO$_2$, $N(R^7)_2$, NH—C(O)—$R^7$ or NH—C(O)—$NHR^7$; where $R^7$ is H, $C_1$-$C_6$ alkyl or $C_3$-$C_6$ cycloalkyl;
or $R^6$ is NH—C(O)—$OR^8$ where $R^8$ is $C_1$-$C_6$ alkyl or $C_3$-$C_6$ cycloalkyl;
(c) $N(R^5)_2$, NH—C(O)—$R^5$, or NH—C(O)—NH—$R^5$ where $R^5$ is independently H, $C_1$-$C_6$ alkyl or $C_3$-$C_6$ cycloalkyl, $C_6$ or $C_{10}$ aryl, $C_7$-$C_{14}$ aralkyl, heterocyclo or (lower alkyl)-heterocyclo;
(d) NH—C(O)—$OR^8$ where $R^8$ is $C_1$-$C_6$ alkyl or $C_3$-$C_6$ cycloalkyl;
(e) formyl; halogen; hydroxy; $NO_2$; OH; SH; halo; CN;
wherein each $R^{11}$ is independently H, OH, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroaryl, heteroarylalkyl, arylalkanoylalkyl, heterocycloalkylalkyl aryloxyalkyl, alkylamino, dialkylamino, monoalkylaminoalkyl, dialkylaminoalkyl, arylaminoalkyl, diarylaminoalkyl, wherein any of the foregoing can be optionally be substituted with up to three groups selected from halogen, OH, alkoxy and perhaloalkyl; and
each $R^{12}$ is independently H, formyl, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroarylalkyl, heteroaryl, arylalkanoylalkyl, heterocycloalkylalkyl aryloxyalkyl, monoalkylaminoalkyl, dialkylaminoalkyl, arylaminoalkyl, or diarylaminoalkyl, wherein any of the foregoing can be optionally be substituted with up to three groups selected from halogen, OH, alkoxy and perhaloalkyl.

3. The compound of claim 1 wherein W is selected from the group consisting of:
(a) an aliphatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl, $R^{10}$ and $R^{11}$; and
(b) an aromatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl, and $R^{10}$;
wherein:
each $R^{10}$ is independently alkyl, alkenyl, alkynyl, perhaloalkyl, alkoxy, aryl, arylalkyl, alkylaryl, heterocyclo, heterocycloalkyl, alkylsulfonyl, arylsulfonyl, heretoaryl, heteroarylalkyl, arylalkanoylalkyl, heterocycloalkylalkyl aryloxyalkyl, alkylamino, dialkylamino, monoalkylaminoalkyl, dialkylaminoalkyl, arylaminoalkyl, diarylaminoalkyl, heteroaryl or urea, wherein any of the foregoing can be optionally be substituted with up to three groups selected from halogen, OH, alkoxy and perhaloalkyl; C(=O)—$R^{11}$, OC(=O)$R^{11}$, C(=O)O—$R^{11}$, C(=O)$N(R^{11})_2$, C(=S)$N(R^{11})_2$, $SO_2R^{11}$, $NHS(O_2)R^{11}$, $N(R^{12})_2$, and $N(R^{12})C(=O)R^{11}$;
each $R^{11}$ is independently H, OH, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroaryl, heteroarylalkyl, arylalkanoylalkyl, heterocycloalkylalkyl aryloxyalkyl, alkylamino, dialkylamino, monoalkylaminoalkyl, dialkylaminoalkyl, arylaminoalkyl, diarylaminoalkyl, wherein any of the foregoing can be optionally be substituted with up to three groups selected from halogen, OH, alkoxy and perhaloalkyl;
each $R^{12}$ is independently H, formyl, alkyl, alkenyl, alkynyl, perhaloalkyl, alkoxy, aryl, arylalkyl, alkylaryl, heterocyclo, heterocycloalkyl, alkylsulfonyl, arylsulfonyl, heteroarylalkyl, heteroaryl, arylalkanoylalkyl, heterocycloalkylalkyl aryloxyalkyl, monoalkylaminoalkyl, dialkylaminoalkyl, arylaminoalkyl, or diarylaminoalkyl, wherein any of the foregoing can be optionally be substituted with up to three groups selected from halogen, OH, alkoxy and perhaloalkyl.

4. The compound of claim 3 wherein W is an aliphatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl, $R_{10}$ and $R_{11}$.

5. The compound of claim 3 wherein W is an aliphatic heteromonocyclic ring system having from five to seven ring atoms and up to four ring hetero atoms selected from O, N and S, wherein said ring system is optionally substituted with up to three ring substituents selected from the group consisting of OH, CN, halogen, formyl, $R^{10}$ and $R^{11}$.

6. The compound of claim 5 herein said optionally substituted aliphatic heteromonocyclic ring system has five ring atoms and 1 or 2 ring hetero atoms selected from O, N and S.

7. The compound of claim 6 wherein said optionally substituted aliphatic heteromonocyclic ring system is selected from the group consisting of pyrrolidines, pyrazolidines, pyrrolines, tetrahydrothiophenes, dihydrothiophenes, tetrahydrofurans, dihydrofurans, imidazolines, tetrahydroimidazoles, dihydropyrazoles, tetrahydropyrazoles, and oxazolines.

8. The compound of claim 5 wherein said optionally substituted aliphatic heteromonocyclic ring system has six ring atoms and 1 or 2 ring hetero atoms selected from O, N and S.

9. The compound of claim 8 wherein said optionally substituted aliphatic heteromonocyclic ring system is selected from the group consisting of pyridines, piperidines, dihydropyridines, tetrahydropyridines, dihydropyrans, tetrahydropyrans, dioxanes, piperazines, dihydropyrimidines, tetrahydropyrimidines, perhydro pyrimidine, morpholine, thioxane, and thiomorpholine.

10. The compound of claim 5 wherein said optionally substituted aliphatic heteromonocyclic ring system has seven ring atoms and 1 or 2 ring hetero atoms selected from O, N and S.

11. The compound of claim 8 wherein said optionally substituted aliphatic heteromonocyclic ring system is selected from the group consisting of hexamethyleneimine, and hexamethylenesulfide.

12. The compound of claim 3 wherein W is an aliphatic heterobicyclic ring system having from five to sixteen ring atoms and up to four ring hetero atoms selected from O, N and S, wherein said ring system is optionally substituted with up to three ring substituents selected from the group consisting of OH, CN, halogen, formyl and $R_{10}$.

13. The compound of claim 12 wherein said optionally substituted aliphatic heterobicyclic ring system has eight to twelve ring atoms and 1 to 4 ring hetero atoms selected from O, N and S.

14. The compound of claim 13 wherein said optionally substituted aliphatic heterobicyclic ring system has eight to twelve ring atoms and 1 or 2 ring hetero atoms selected from O and N.

15. The compound of claim 3 wherein W is an aromatic heteromonocyclic, heterobicyclic or heterotricyclic ring system having from five to sixteen ring atoms and up to four ring hetero atoms selected from O, N and S, wherein said ring system is optionally substituted with up to three ring substituents selected from the group consisting of OH, CN, halogen, formyl and $R_{10}$.

16. The compound of claim 3 wherein W is an aromatic heteromonocyclic ring system having from five to seven ring atoms and up to four ring hetero atoms selected from O, N and S, wherein said ring system is optionally substituted with up to three ring substituents selected from the group consisting of OH, CN, halogen, formyl and $R_{10}$.

17. The compound of claim 15 wherein said optionally substituted aromatic heteromonocyclic ring system has five ring atoms and 1 or 2 ring hetero atoms selected from O, N and S.

18. The compound of claim 1 wherein said optionally substituted aromatic heteromonocyclic ring system is selected from the group consisting of pyrroles, pyrazoles, porphyrins, furans, thiophenes, pyrazoles, imidazoles, oxazoles, oxadiazoles, isoxazoles, thiazoles, thiadiazoles, and isothiazoles.

19. The compound of claim 16 wherein said optionally substituted aromatic heteromonocyclic ring system has six ring atoms and 1, 2 or 3 ring hetero atoms selected from O, N and S.

20. The compound of claim 19 wherein said optionally substituted aromatic heteromonocyclic ring system is selected from the group consisting of pyridines, pyrimidines, pyrazines, pyrans, and triazines.

21. The compound of claim 16 wherein said optionally substituted aromatic heteromonocyclic ring system has five ring atoms and 3 or 4 ring hetero atoms selected from O, N and S.

22. The compound of claim 21 wherein said optionally substituted aromatic heteromonocyclic ring system is triazolyl or tetrazolyl.

23. The compound of claim 3 wherein W is an aromatic heterobicyclic ring system having from eight to twelve ring atoms and up to four ring hetero atoms selected from O, N and S, wherein said ring system is optionally substituted with up to three ring substituents selected from the group consisting of OH, CN, halogen, formyl and $R_{10}$.

24. The compound of claim 23 wherein said optionally substituted aromatic heterobicyclic ring system is selected from the group consisting of adenines, azabenzimidazoles, azaindoles, benzimidazoles, benzo isothiazoles, benzofurans, benzoisoxazoles, benzooxazoles, benzothiadiazoles, benzothiazoles, benzothienes, benzothiophenes, benzoxazoles, carbazoles, cinnolines, guanines, imidazopyridines, indazoles, indoles, isoindoles, isoquinolines, phthalazines, purines, pyrrolo pyridines, quinazolines, quinolines, quinoxalines, thianaphthenes, and xanthines.

25. The compound of claim 3 wherein W is an aromatic heterotricyclic ring system having from ten to sixteen ring atoms and up to four ring hetero atoms selected from O, N and S, wherein said ring system is optionally substituted with up to three ring substituents selected from the group consisting of OH, CN, halogen, $R_{10}$ and $R_{11}$.

26. The compound of claim 25 wherein said optionally substituted aromatic heterotricyclic ring system is selected from the group consisting of carbazoles, bibenzofurans, psoralens, dibenzothiophenes, phenazines, thianthrenes, phenanthrolines, phenanthridines.

27. A compound of claim 1 represented by Formula II, or a pharmaceutically acceptable salt thereof,

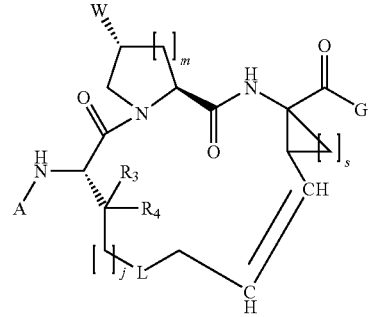

Formula II wherein:
A is selected from the group consisting of H, —(C=O)—$R^2$, —(C=O)—O—$R^1$, —C(=O)—NH—$R^1$, —C(=S)—NH—$R^1$, —S(O)$_2$—$R^1$, —(C=N$R^1$)—$R^1$, and —(C=N$R^1$)—NH—$R^1$;

G is selected from the group consisting of —OH, —O—(C$_1$-C$_{12}$ alkyl), —NHS(O)$_2$—$R^1$, —(C=O)—$R^2$, —(C=O)—O—$R^1$, and —(C=O)—NH—$R^2$;

L is selected from the group consisting of —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, —CF$_2$CH$_2$—, and —C$R_x$=C$R_x$— where $R_x$=H or halogen;

W is selected from the group consisting of

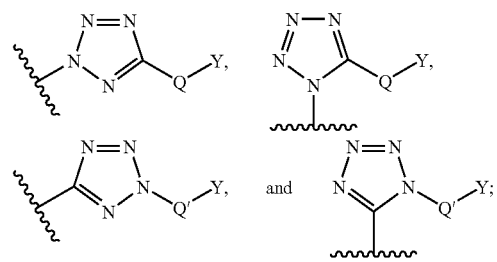

Q is selected from the group consisting of absent, —CH$_2$—, —O—, —NH—, —N($R^1$)—, —S—, —S(O)$_2$—, and —(C=O)—;

Q' is selected from the group consisting of absent, —CH$_2$—, and —NH—;

Y is selected from the group consisting of H, C$_1$-C$_6$ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

j=0, 1, 2, 3, or 4;
m=0, 1, or 2;
s=0, 1 or 2;

$R^1$ is selected from the group consisting of H, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

$R^2$ is selected from the group consisting of H, C$_1$-C$_6$ alkyl, C$_3$-C$_{12}$ cycloalkyl, substituted C$_3$-C$_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and $R^3$ and $R^4$ are each independently selected from the group consisting of hydrogen and methyl.

28. A compound according to claim 27 which is selected from the group consisting of:

| | | | | | | | | |
|---|---|---|---|---|---|---|---|---|
| m = s = 1; and | | | | | | | | |
| A | G | L | W | Q | Y | j | m, s | $R^3$, $R^4$ |
| tBOC | OH | —(C=O)CH$_2$— | tetrazole-N-Q-Y | absent | phenyl | 1 | m = 1, s = 1 | $R^3$ = $R^4$ = H; |
| tBOC | OH | —CH(CH$_3$)CH$_2$— | tetrazole-N-Q-Y | absent | phenyl | 1 | m = 1, s = 1 | $R^3$ = methyl, $R^4$ = H |
| tBOC | OH | —O— | tetrazole-N-Q-Y | absent | phenyl | 0 | m = 1, s = 1 | $R^3$ = methyl, $R^4$ = H |
| tBOC | OH | S | tetrazole-N-Q-Y | absent | phenyl | 0 | m = 1, s = 1 | $R^3$ = methyl, $R^4$ = H |
| tBOC | OH | —S(O)— | tetrazole-N-Q-Y | absent | phenyl | 0 | m = 1, s = 1 | $R^3$ = methyl, $R^4$ = H |
| tBOC | OH | —S(O)$_2$— | tetrazole-N-Q-Y | absent | phenyl | 0 | m = 1, s = 1 | $R^3$ = methyl, $R^4$ = H |
| tBOC | OH | —SCH$_2$CH$_2$— | tetrazole-N-Q-Y | absent | phenyl | 0 | m = 1, s = 1 | $R^3$ = $R^4$ = CH$_3$; |
| tBOC | OH | —CF$_2$CH$_2$— | tetrazole-N-Q-Y | absent | phenyl | 1 | m = 1, s = 1 | $R^3$ = $R^4$ = H; and |
| tBOC | OH | —CFHCH$_2$— | tetrazole-N-Q-Y | absent | phenyl | 1 | m = 1, s = 1 | $R^3$ = $R^4$ = H. |

29. A compound of claim 1 represented by Formula III, or a pharmaceutically acceptable salt thereof:

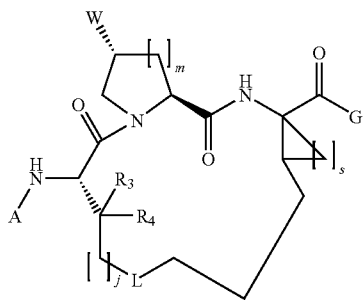

Formula III wherein:
A is selected from the group consisting of H, —(C=O)—R², —(C=O)—O—R¹, —C(=O)—NH—R², —C(=S)—NH—R², —S(O)₂—R², —(C=NR¹)—R¹, and —(C=NR¹)—NH—R¹;

G is selected from the group consisting of —OH, —O—(C₁-C₁₂ alkyl), —NHS(O)₂—R¹, —(C=O)—R², —(C=O)—O—R¹, and —(C=O)—NH—R²;

L is selected from the group consisting of —S—, —SCH₂—, —SCH₂CH₂—, —S(O)₂—, —S(O)₂CH₂CH₂—, —S(O)—, —S(O)CH₂CH₂—, —O—, —OCH₂—, —OCH₂CH₂—, —(C=O)—CH₂—, —CH(CH₃)CH₂—, —CFHCH₂—, —CF₂CH₂—, and —CRₓ=CRₓ— where Rₓ=H or halogen;

W is selected from the group consisting of

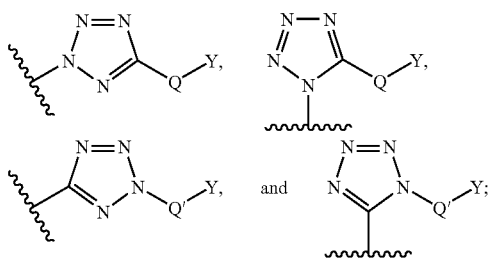

Q is selected from the group consisting of absent, —CH₂—, —O—, —NH—, —N(R¹)—, —S—, —S(O)₂—, and —(C=O)—;

Q' is selected from the group consisting of absent, —CH₂—, and —NH—;

Y is selected from the group consisting of H, C₁-C₆ alkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

j=0, 1, 2, 3, or 4;
m=0, 1, or 2;
s=0, 1 or 2;

R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R² is selected from the group consisting of H, C₁-C₆ alkyl, C₃-C₁₂ cycloalkyl, substituted C₃-C₁₂ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R³ and R⁴ are each independently selected from the group consisting of hydrogen and methyl.

30. A compound of claim 1 represented by Formula II, or a pharmaceutically acceptable salt thereof:

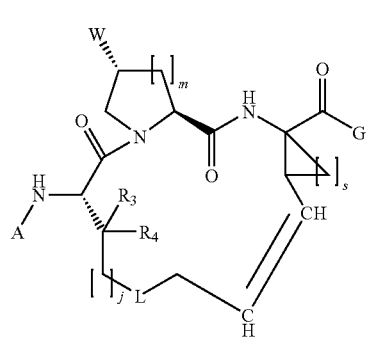

Formula II wherein:
A is selected from the group consisting of H, —(C=O)—R², —(C=O)—O—R¹, —C(=O)—NH—R², —C(=S)—NH—R², —S(O)₂—R², —(C=NR¹)—R¹, and —(C=NR¹)—NH—R¹;

G is selected from the group consisting of —OH, —O—(C₁-C₁₂ alkyl), —NHS(O)₂—R¹, —(C=O)—R², —(C=O)—O—R¹, and —(C=O)—NH—R²;

L is selected from the group consisting of —S—, —SCH₂—, —SCH₂CH₂—, S(O)₂—, —S(O)₂CH₂CH₂—, —S(O)—, —S(O)CH₂CH₂—, —O—, —OCH₂—, —OCH₂CH₂—, —(C=O)—CH₂—, —CH(CH₃)CH₂—, —CFHCH₂—, —CF₂CH₂—, and —CRₓ=CRₓ— where Rₓ=H or halogen;

W is selected from the group consisting of

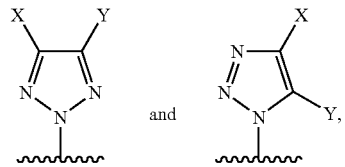

where X and Y are independently selected from the group consisting of H, halogen, C₁-C₆ alkyl, C₃-C₁₂ cycloalkyl, —CH₂-alkylamino, —CH₂-dialkylamino, —CH₂-arylamino, —CH₂-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, for a cyclic moiety selected from the group consisting of aryl, substituted aryl, heteroaryl, and substituted heteroaryl;

j=0, 1, 2, 3, or 4;
m=0, 1, or 2;
s=0, 1 or 2;

R¹ is selected from the group consisting of H, $C_1$-$C_6$ alkyl, $C_3$-$C_{12}$ cycloalkyl, substituted $C_3$-$C_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R² is selected from the group consisting of H, $C_1$-$C_6$ alkyl, $C_3$-$C_{12}$ cycloalkyl, substituted $C_3$-$C_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R³ and R⁴ are each independently selected from the group consisting of hydrogen and methyl.

31. A compound according to claim 30 which is selected from the group consisting of:

| A | G | L | W | J | m, s | R³, R⁴ |
|---|---|---|---|---|---|---|
| tBOC | OH | —(C=O)CH₂— | X—Y triazole, X=phenyl, Y=phenyl | 1 | m=, s=1 | R³ =, R⁴ = H; |
| tBOC | OH | —CH(CH₃)CH₂— | X—Y triazole, X=phenyl, Y=phenyl | 1 | m=, s=1 | R³ = methyl, R⁴ = H; |
| tBOC | OH | —O— | X—Y triazole, X=phenyl, Y=phenyl | 0 | m=, s=1 | R³ = methyl, R⁴ = H; |
| tBOC | OH | —S— | X—Y triazole, X=phenyl, Y=phenyl | 0 | m=, s=1 | R³ = methyl, R⁴ = H; |
| tBOC | OH | —S(O)— | X—Y triazole, X=phenyl, Y=phenyl | 2 | m=, s=1 | R³ = methyl, R⁴ = H; |
| tBOC | OH | —S(O)₂— | X—Y triazole, X=phenyl, Y=phenyl | 2 | m=, s=1 | R³ = methyl, R⁴ = H; |
| tBOC | OH | —SCH₂CH₂— | X—Y triazole, X=phenyl, Y=phenyl | 0 | m=, s=1 | R³ =, R⁴ = CH₃; |
| tBOC | OH | —CF₂CH₂— | X—Y triazole, X=phenyl, Y=phenyl | 1 | m=, s=1 | R³ =, R⁴ = H; and |
| tBOC | OH | —CFHCH₂— | X—Y triazole, X=phenyl, Y=phenyl | 1 | m=, s=1 | R³ =, R⁴ = H. |

32. A compound of claim 1 represented by Formula III, or a pharmaceutically acceptable salt thereof:

Formula III wherein:

A is selected from the group consisting of H, —(C=O)—R², —(C=O)—O—R¹, —C(=O)—NH—R², —C(=S)—NH—R², —S(O)₂—R², —(C=NR¹)—R¹, and —(C=NR¹)—NH—R¹;

G is selected from the group consisting of —OH, —O—(C₁-C₁₂ alkyl), —NHS(O)₂—R¹, —(C=O)—R², —(C=O)—O—R¹, and —(C=O)—NH—R²;

L is selected from the group consisting of —S—, —SCH₂—, —SCH₂CH₂—, —S(O)₂—, —S(O)₂CH2CH2—, —O—, —OCH₂—, —OCH₂CH₂—, —(C=O)—CH₂—, —CH(CH₃)CH₂—, —CFHCH₂—, —CF₂CH₂—, and —CR$_x$=CR$_x$— where R$_x$=H or halogen;

W is selected from the group consisting of

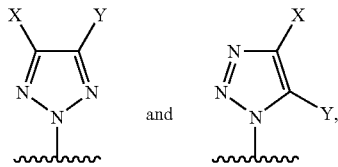

where X and Y are independently selected from the group consisting of H, halogen, C₁-C₆ alkyl, C₃-C₁₂ cycloalkyl, —CH₂-alkylamino, —CH₂-dialkylamino, —CH₂-arylamino, —CH₂-diarylamino, —(C=O)-alkylamino, —(C=O)-dialkylamino, —(C=O)-arylamino, —(C=O)-diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; in the alternative, X and Y taken together with the carbon atoms occupying the 4 and 5 positions of the triazole ring, to which X and Y are attached, for a cyclic moiety selected from the group consisting of aryl, substituted aryl, heteroaryl, and substituted heteroaryl;

j=0, 1, 2, 3, or 4;

m=0, 1, or 2;

s=0, 1 or 2;

R¹ is selected from the group consisting of H, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl;

R² is selected from the group consisting of H, C₁-C₆ alkyl, C₃-C₁₂ cycloalkyl, substituted C₃-C₁₂ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, and substituted heterocycloalkyl; and R³ and R⁴ are each independently selected from the group consisting of hydrogen and methyl.

33. A compound of claim 1 represented by Formula IV, or a pharmaceutically acceptable salt thereof:

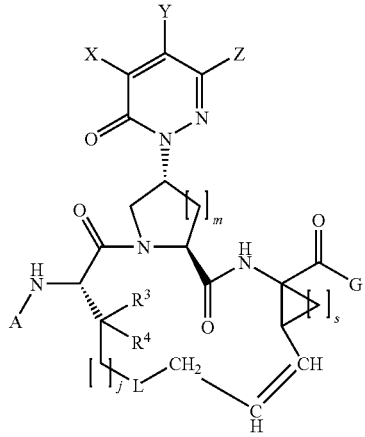

(IV)

wherein:

A is hydrogen, —(C=O)—R¹, —(C=O)—O—R¹, —C(=O)—NH—R², —C(=S)—NH—R², —S(O)₂—R², —(C=NR¹)—R¹, or —(C=NR¹)—NH—R¹;

G is —OH, —O—(C₁-C₁₂ alkyl), —NHS(O)₂—R¹, —(C=O)—R², —(C=O)—O—R¹, or —(C=O)—NH—R²;

L is selected from —S—, —SCH₂—, —SCH₂CH₂—, —S(O)²—, —S(O)²CH²CH²—, —S(O)—, —S(O)CH₂CH₂—, —O—, —OCH₂—, —OCH₂CH₂—, —(C=O)—CH₂—, —CH(CH₃)CH₂—, —CFHCH₂——CF₂CH₂—, or —CR$_x$=CR$_x$— where R$_x$=H or halogen;

X, Y, and Z are independently selected from the group consisting of hydrogen, N₃, halogen, C₁-C₆ alkyl, C₃-C₁₂ cycloalkyl, alkylamino, dialkylamino, C₁-C₆ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or, in the alternative, X and Y or Y and Z taken together with the carbon atoms to which they are attached form an aryl, substituted aryl, heteroaryl, or substituted heteroaryl cyclic moiety;

j=0, 1, 2, 3, or 4;

m=0, 1, or 2;

s=0, 1 or 2;

R¹ is hydrogen, C₁-C₆ alkyl, C₃-C₁₂ cycloalkyl, substituted C₃-C₁₂ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;

R² is hydrogen, C₁-C₆ alkyl, C₃-C₁₂ cycloalkyl, substituted C3-C12 cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; and R³ and R⁴ are each independently hydrogen or methyl.

34. A compound according to claim 33 which is selected from the group consisting of:

| A | G | L | X | Y | Z | j | m, s | R³, R⁴ |
|---|---|---|---|---|---|---|---|---|
| tBOC | OH | —(C=O)CH$_2$— | thiophen-3-yl | thiophen-3-yl | hydrogen | 1 | m = s = 1 | and R³ = R⁴ = hydrogen; |
| tBOC | OH | —CH(CH$_3$)CH$_2$— | thiophen-3-yl | thiophen-3-yl | hydrogen | 1 | m = s = 1 | R³ = methyl and R⁴ = hydrogen; |
| tBOC | OH | —O— | thiophen-3-yl | thiophen-3-yl | hydrogen | 0 | m = s = 1 | R³ = methyl and R⁴ = hydrogen; |
| tBOC | OH | —S— | thiophen-3-yl | thiophen-3-yl | hydrogen | 0 | m = s = 1 | R³ = methyl and R⁴ = hydrogen; |
| tBOC | OH | —S(O)— | thiophen-3-yl | thiophen-3-yl | hydrogen | 2 | m = s = 1 | R³ = methyl and R⁴ = hydrogen; |
| tBOC | OH | —S(O)$_2$— | thiophen-3-yl | thiophen-3-yl | hydrogen | 2 | m = s = 1 | R³ = methyl and R⁴ = hydrogen; |
| tBOC | OH | —SCH$_2$CH$_2$— | thiophen-3-yl | thiophen-3-yl | hydrogen | 0 | m = s = 1 | and R³ = R⁴ = CH$_3$; |
| tBOC | OH | —CF$_2$CH$_2$— | thiophen-3-yl | thiophen-3-yl | hydrogen | 1 | m = s = 1 | and R³ = R⁴ = hydrogen; and |
| tBOC | OH | —CFHCH$_2$— | thiophen-3-yl | thiophen-3-yl | hydrogen | 1 | m = s = 1 | and R³ = R⁴ = hydrogen. |

35. A compound of claim 1 represented by Formula V, or a pharmaceutically acceptable salt thereof:

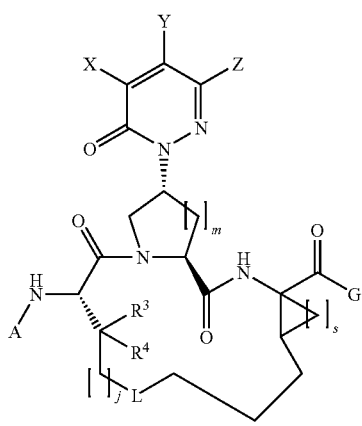

V wherein:
A is hydrogen, —(C=O)—R¹, —(C=O)—O—R¹, —C(=O)—NH—R², —C(=S)—NH—R², or —S(O)$_2$—R², —(C=NR¹)—R¹, or —(C=NR¹)—NH—R¹;
G is —OH, —O—(C$_1$-C$_{12}$ alkyl), —NHS(O)$_2$—R¹, —(C=O)—R², —(C=O)—O—R¹, or —(C=O)—NH—R²;
L is —S—, —SCH$_2$—, —SCH$_2$CH$_2$—, —S(O)$_2$—, —S(O)$_2$CH$_2$CH$_2$—, —S(O)—, —S(O)CH$_2$CH$_2$—, —O—, —OCH$_2$—, —OCH$_2$CH$_2$—, —(C=O)—CH$_2$—, —CH(CH$_3$)CH$_2$—, —CFHCH$_2$—, —CF$_2$CH$_2$—, or —CR$_x$=CR$_x$— where R$_x$=H or halogen;
X, Y, and Z are independently selected from the group consisting of hydrogen, N$_3$, halogen, C$_1$-C$_6$ alkyl, C$_3$-C$_{12}$ cycloalkyl, alkylamino, dialkylamino, C$_1$-C$_6$ alkynyl, substituted alkynyl, aryl, substituted aryl, —S-aryl, —S-substituted aryl, —O-aryl, —O-substituted aryl, NH-aryl, NH-substituted aryl, diarylamino, diheteroarylamino, arylalkyl, substituted arylalkyl, heteroaryl, substituted heteroaryl, —S-heteroaryl, —S-substituted heteroaryl, —O-heteroaryl, —O-substituted heteroaryl, —NH-heteroaryl, —NH-substituted heteroaryl, heteroarylalkyl, substituted heteroarylalkyl, heterocycloalkyl, and substituted heterocycloalkyl; or,
in the alternative, X and Y or Y and Z taken together with the carbon atoms to which they are attached form an aryl, substituted aryl, heteroaryl, and substituted heteroaryl cyclic moiety;
j=0, 1, 2, 3, or 4;
m=0, 1, or 2;
s=0, 1 or 2;
R¹ is hydrogen, C$_1$-C$_6$ alkyl, C$_3$-C$_{12}$ cycloalkyl, substituted C$_3$-C$_{12}$ cycloalkyl, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl;
R² is hydrogen, C$_1$-C$_6$ alkyl, C$_3$-C$_{12}$ cycloalkyl, substituted C$_3$-C$_{12}$ cycloalkyl, alkylamino, dialkyl amino, arylamino, diarylamino, aryl, substituted aryl, arylalkyl, substituted arylalkyl, heteroaryl, substituted heteroaryl, heteroarylalkyl, substituted heteroarylalkyl, heterocycloalkyl, or substituted heterocycloalkyl; and
R³ and R⁴ are each independently hydrogen or methyl.

36. A pharmaceutical composition comprising an anti-hepatitis C virally effective amount of a compound according to claim 1 or a pharmaceutically acceptable salt thereof, in combination with a pharmaceutically acceptable carrier or excipient.

37. A method of treating a hepatitis C viral infection in a subject, comprising administering to the subject an anti-hepatitis C virally effective amount of a pharmaceutical composition according to claim 36.

38. A method of inhibiting the replication of hepatitis C virus, the method comprising supplying a hepatitis C viral NS3 protease inhibitory amount of the pharmaceutical composition of claim 36.

39. The method of claim 37 further comprising administering concurrently an additional anti-hepatitis C virus agent.

40. The method of claim 39, wherein said additional anti-hepatitis C virus agent is selected from the group consisting of α-interferon, β-interferon, ribavarin, and adamantine.

41. A method for making a compound of Formula I in claim 1, comprising the steps of: (i) reacting a compound of formula VII:

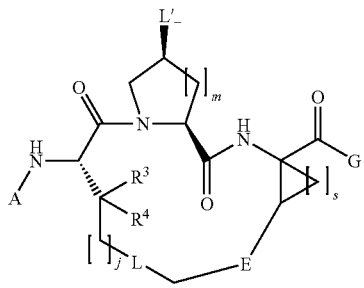

Formula VII wherein:
L' is a leaving group;
A is a nitrogen protecting group; and
the remaining variables are as defined in claim 1;
with a nucleophilic heterocyclic compound; and (ii) converting the resulting compound to a compound of Formula I in claim 1.

42. The compound of formula I in claim 1, wherein W is

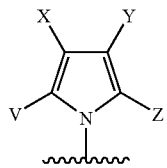

wherein V, X, Y, and Z are each independently selected from:
a) —$C_1$-$C_6$ alkyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
b) —$C_2$-$C_6$ alkenyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
c) —$C_2$-$C_6$ alkynyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
d) aryl;
e) substituted aryl;
f) heteroaryl;
g) substituted heteroaryl;
h) heterocycloalkyl; or
i) substituted heterocycloalkyl;
or in the alternative, V and X, X and Y, or Y and Z are taken together with the carbons to which they are attached to for a cyclic moiety selected from: aryl, substituted aryl, heteroaryl, substituted heteroaryl, heterocycloalkyl, or substituted heterocycloalkyl.

43. The compound of formula I in claim 1, wherein W is

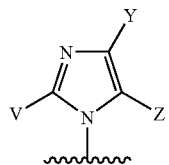

wherein X, Y, and Z are each independently selected from:
a) —$C_1$-$C_6$ alkyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
b) —$C_2$-$C_6$ alkenyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
c) —$C_2$-$C_6$ alkynyl containing 0, 1, 2, or 3 heteroatoms selected from O, S, or N, optionally substituted with one or more substituent selected from halogen, aryl, substituted aryl, heteroaryl, substituted heteroaryl, heterocycloalkyl, or substituted heterocycloalkyl;
d) aryl;
e) substituted aryl;
f) heteroaryl;
g) substituted heteroaryl;
h) heterocycloalkyl; or
i) substituted heterocycloalkyl;
or in the alternative, Y and Z are taken together with the carbons to which they are attached to for a cyclic moiety selected from: aryl, substituted aryl, heteroaryl, substituted heteroaryl, heterocycloalkyl, or substituted heterocycloalkyl.

44. The compound of claim 1
wherein:
W is a substituted or unsubstituted heteroaryl; or a substituted or unsubstituted heterocycloalkyl.

45. A compound according to claim 44, wherein W is selected from:
pyrrolidines, pyrazolidines, pyrrolines, tetrahydrothiophenes, dihydrothiophenes, tetrahydrofurans, dihydrofurans, imidazolines, tetrahydroimidazoles, dihydropyrazoles, tetrahydropyrazoles, oxazolines, pyridines, piperidines, dihydropyridines, tetrahydropyridines, dihydropyrans, tetrahydropyrans, dioxanes, piperazines, dihydropyrimidines, tetrahydropyrimidines, perhydro pyrimidine, morpholine, thioxane, thiomorpholine, hexamethyleneimine, hexamethylenesulfide, pyrroles, pyrazoles, tetrazoles, triazoles, imidazoles, porphyrins, furans, thiophenes, oxazoles, oxadiazoles, isoxazoles, thiazoles, thiadiazoles, isothiazoles, adenines, azabenzimidazoles, azaindoles, benzimidazoles, benzotriazole, benzo isothiazoles, benzofurans, benzoisoxazoles, benzooxazoles, benzothiadiazoles, benzothiazoles, benzothienes, benzothiophenes, benzoxazoles, carbazoles, cinnolines, guanines, imidazopyridines, indazoles, indoles, isoindoles, isoquinoline, phthalazines, purines, pyrrolo pyridines, quinazolines, quinolines, quinoxalines, thianaphthenes, and xanthines.

46. The compound of claim 1 wherein:

W is selected from the group consisting of: dihydro-benzoimidazol-2-one, dihydro-benzoimidazol-2-thione, dihydro-indol-2-one, indole-2,3-dione, dihydro-benzoimidazol-2-one, quinolin-2-one, quinolin-4-one, quinazolin-2-one, quinazolin-4-one, imidazolidin-2-one, imidazolidine-2-thione, pyrrolidin-2-one, pyrrolidine-2,5-dione, piperidine-2,6-dione, piperidin-2-one, piperazine-2,6-dione, piperazin-2-one, thiomorpholine-1,1-dioxide, pyrazolidin-3-one, and imidazolidine-2,4-dione.

* * * * *

UNITED STATES PATENT AND TRADEMARK OFFICE
CERTIFICATE OF CORRECTION

PATENT NO.       : 8,124,584 B2
APPLICATION NO.  : 12/351144
DATED            : February 28, 2012
INVENTOR(S)      : Zhenwei Miao et al.

It is certified that error appears in the above-identified patent and that said Letters Patent is hereby corrected as shown below:

Column 310

In Claim 27, at line 22, delete "-C(=S)-NH-$R^1$, -S(O)$_2$-$R^1$", and insert -- -C(=S)-NH-$R^2$, –S(O)$_2$-$R^2$, --.

Column 312

In the table in Claim 28, 4$^{th}$ row down under L, delete "S" and insert -- -S- --.

Signed and Sealed this
Nineteenth Day of June, 2012

David J. Kappos
*Director of the United States Patent and Trademark Office*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Forward Primer

<400> SEQUENCE: 1
gctgcggcct gtcgagct                                                 18

<210> SEQ ID NO 2
<211> LENGTH: 19
<212> TYPE: DNA
<213> ORGANISM: Artificial Sequence
<220> FEATURE:
<223> OTHER INFORMATION: Reverse Primer

<400> SEQUENCE: 2
caaggtcgtc tccgcatac                                                19

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
cgaagctcca ggactgcacg atgct                                         25

<210> SEQ ID NO 4
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 6
<223> OTHER INFORMATION: Xaa = 2-aminobutyric acid

<400> SEQUENCE: 4

Asp Glu Asp Glu Glu Xaa Ala Ser Lys
1               5

<210> SEQ ID NO 5
<211> LENGTH: 6
<212> TYPE: PRT
<213> ORGANISM: Artificial Sequence
<220> FEATURE:
```

```
<223> OTHER INFORMATION: Synthetic

<400> SEQUENCE: 5

Asp Glu Met Glu Glu Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 3
<223> OTHER INFORMATION: Xaa = 3,3-diphenyl alanine
<220> FEATURE:
<221> NAME/KEY: VARIANT
<222> LOCATION: 4
<223> OTHER INFORMATION: Xaa = beta-cyclohexyl-alanine

<400> SEQUENCE: 6

Asp Glu Xaa Xaa Cys
1               5
```